US009351972B2

(12) United States Patent
Dax et al.

(10) Patent No.: US 9,351,972 B2
(45) Date of Patent: *May 31, 2016

(54) COMPOUNDS AS RESPIRATORY STIMULANTS FOR TREATMENT OF BREATHING CONTROL DISORDERS OR DISEASES

(75) Inventors: Scott L. Dax, Landenberg, PA (US); Richard Woodward, Phoenixville, PA (US); Sean Peng, Ambler, PA (US)

(73) Assignee: Galleon Pharmaceuticals, Inc., Doylestown, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/306,349

(22) Filed: Nov. 29, 2011

(65) Prior Publication Data

US 2012/0142647 A1 Jun. 7, 2012

Related U.S. Application Data

(60) Provisional application No. 61/417,777, filed on Nov. 29, 2010, provisional application No. 61/494,268, filed on Jun. 7, 2011.

(51) Int. Cl.
*C07D 251/70* (2006.01)
*C07D 403/12* (2006.01)
(Continued)

(52) U.S. Cl.
CPC ............. *A61K 31/505* (2013.01); *A61K 31/519* (2013.01); *A61K 31/522* (2013.01);
(Continued)

(58) Field of Classification Search
CPC .. C07D 251/70; C07D 403/12; C07D 409/12;
C07D 401/14; C07D 405/14; C07D 413/04; C07D 498/08
See application file for complete search history.

(56) References Cited

U.S. PATENT DOCUMENTS 3,037,980 A 6/1962 Hitchings et al.
5,378,700 A 1/1995 Sakuma et al.
(Continued)

FOREIGN PATENT DOCUMENTS

CN 101885707 A 11/2010
GB 1001665 6/1962
(Continued)

OTHER PUBLICATIONS

Shaw et al.; "The Preparation of s-Triazine Derivatives Containing the N—O Bond. II. Hydroxylamino Derivatives of s-Triazine"; 1962; Journal of Organic Chemistry; 27: 4054-4056.*
(Continued)

*Primary Examiner* — Timothy Thomas
(74) *Attorney, Agent, or Firm* — Saul Ewing LLP; Kathryn Doyle; Domingos J. Silva

(57) ABSTRACT

The present invention includes a composition comprising a compound, such as a 2,4,6-triamino-1,3,5-triazine, 2,4,6-triaminopyrimidine, 2,4-diamino-6,7-dihydro-5H-pyrrolo[2,3-d]pyrimidine or 2,4-diamino-7H-pyrrolo[2,3-d]pyrimidine, that is useful in the treatment of breathing control diseases or disorders in a subject in need thereof. The present invention also includes a method of treating a respiratory disease or disorder in a subject in need thereof, comprising administering to the subject a therapeutically effective amount of a pharmaceutical composition of the invention. The present invention further includes a method of preventing destabilizing or stabilizing breathing rhythm in a subject in need thereof, comprising administering to the subject a therapeutically effective amount of a pharmaceutical composition of the invention.

5 Claims, 25 Drawing Sheets

(51) Int. Cl.

| | | |
|---|---|---|
| *C07D 401/12* | (2006.01) | |
| *C07D 405/14* | (2006.01) | |
| *C07D 409/12* | (2006.01) | |
| *C07D 498/08* | (2006.01) | |
| *C07D 413/04* | (2006.01) | |
| *A61K 31/505* | (2006.01) | |
| *A61K 31/519* | (2006.01) | |
| *A61K 31/522* | (2006.01) | |
| *A61K 31/53* | (2006.01) | |
| *A61K 31/5355* | (2006.01) | |
| *A61K 31/57* | (2006.01) | |
| *A61K 45/06* | (2006.01) | |
| *C07D 251/66* | (2006.01) | |
| *C07D 401/14* | (2006.01) | |
| *C07D 405/12* | (2006.01) | |
| *C07D 487/04* | (2006.01) | |
| *C07D 498/06* | (2006.01) | |

(52) U.S. Cl.
CPC ............ *A61K 31/53* (2013.01); *A61K 31/5355* (2013.01); *A61K 31/57* (2013.01); *A61K 45/06* (2013.01); *C07D 251/66* (2013.01); *C07D 401/14* (2013.01); *C07D 403/12* (2013.01); *C07D 405/12* (2013.01); *C07D 405/14* (2013.01); *C07D 409/12* (2013.01); *C07D 413/04* (2013.01); *C07D 487/04* (2013.01); *C07D 498/06* (2013.01)

(56) References Cited

U.S. PATENT DOCUMENTS

| | | | |
|---|---|---|---|
| 5,879,868 A * | 3/1999 | Uchida | ........................ 430/506 |
| 6,127,110 A | 10/2000 | Uchida | |
| 6,479,492 B1 | 11/2002 | Konradi et al. | |
| 6,525,067 B1 | 2/2003 | Chen | |
| 2003/0180287 A1 | 9/2003 | Gombotz et al. | |
| 2004/0200993 A1* | 10/2004 | Lazar et al. | ............... 252/182.13 |
| 2006/0039866 A1 | 2/2006 | Rao et al. | |
| 2007/0270588 A1 | 11/2007 | Bischoff et al. | |
| 2010/0105708 A1 | 4/2010 | Jäkel et al. | |

FOREIGN PATENT DOCUMENTS

| | | |
|---|---|---|
| JP | 38000785 | 3/1959 |
| JP | 8-272059 | 10/1996 |
| JP | 9-251197 | 9/1997 |
| JP | 9-304898 | 11/1997 |
| WO | WO01/47897 A1 | 7/2001 |
| WO | WO03/002542 A1 | 1/2003 |
| WO | WO03/024926 A2 | 3/2003 |
| WO | 03/050094 | 6/2003 |
| WO | 03/093290 | 11/2003 |
| WO | 2004/028481 | 4/2004 |
| WO | 2004/043367 | 5/2004 |
| WO | WO2005/009980 A1 | 2/2005 |
| WO | 2005090469 A1 | 9/2005 |
| WO | 2007/135380 | 11/2007 |
| WO | WO2007/136638 A2 | 11/2007 |
| WO | 2008/024978 | 2/2008 |
| WO | WO2008/016675 A1 | 2/2008 |
| WO | WO2008/105968 A1 | 9/2008 |
| WO | 2009/115084 | 9/2009 |

OTHER PUBLICATIONS

Zins; "The In Vivo Production of a Potent, Long-Acting Hypotensive Metabolite From Diallylmelamine" 1965; The Journal of Pharmacology and Experimental Therapeutics; 150(1): 109-117.*

Dovlatyan et al.; "2-(N-Alkyl-N-cyanoamino)-4-(N-alkyl-N-methoxyamino)-6-[alkyl(dialkyl)amino]-sym-triazines"; 1980; Armyanskii Khimicheskii Zhurnal; 33(3): 247-52, as evidenced by the CAPLUS abstract record of Dovlatyan; Accession No. 1980:495215; accessed Jul. 29, 2015.*

Rudakov, "Antifolic acid activity of some derivatives of 2,4,6-triaminopyrimidine and 2,6-diaminopurine in a microbiological test system," *Voprosy Onkologii*, 1975, 21(12):68, Accession No. 1976:116273.

Wang et al., "Theory study on triradicals systems with heterocycles as ferromagnetic coupling units," *Dongbei Shida Xuebao, Ziran Kexueban*, 2006, 38(2):72-75, Accession No. 2007:722440.

May et al., "Guanidine Nitrate," *Encyclopedia of Reageants for Organic Synthesis*, Oct. 2002, DOI: 10.1002/047084289X.rn00097, Abstract only.

Pudlo et al., "Synthesis, Antiproliferative, and Antiviral Activity of Certain 4-Substituted and 4,5-Disubstituted 7-[(1,3-Dihydroxy-2-propoxy)methyl]pyrrolo[2,3-*d*]pyrimidines," *J. Med. Chem.*, 1990, 33:1984-1992.

Bhattacharya et al., "Synthesis and Anti-DNA Viral Activities in Vitro of Certain 2,4-Disubstituted-7-(2-deoxy-2-fluoro-β-$_D$-arabinofuranosyl)pyrrolo[2,3-*d*]pyrimidine Nucleosides," *J. Med. Chem.*, 1995, 38:3957-3966.

Hinshaw et al., "The Synthesis of 4-Hydroxylamino-7(β-$_D$-ribofuranosyl)pyrrolo[2,3-*d*]pyrimidine (7-deaza-HAPR)(1)," *Communication to the Editor*, Dec. 1968, pp. 885.

Iwamura et al., "Plant Growth Retarding Activity of the 4-Substituted-7-(β-$_D$-ribofuranosyl)pyrrolo[2,3-d]pyrimidine Anticytokinins," *Agr. Biol. Chem.*, Mar. 1976, 40(8):1653-1654.

Iwamura et al., "Antifungal Activity of Substituted 7-(β-$_D$-Ribofuranosyl)pyrrolo-[2,3-*d*]pyrimidines," *Agr. Biol. Chem.*, Jan. 1976, 40(7):1431-1433.

Takahata et al., "Activated Lactams: New Synthesis of Azacycloalka[2,3-*d*]pyrimidine and -[2,3-*c*]pyrazole Derivatives," *Synthesis*, 1983, 3:226-228.

Liang et al., "QSAR studies for diarylpyrimidines against HIV-1 reverse transcriptase wild-type and mutant strains," *European Journal of Medicinal Chemistry*, 2009, 44:625-631.

Okide, "Synthesis of substituted five- and six-membered nitrogen heterocycles from 1-chloro-2-azapropenylium and 1-chloro-2,4-diazabutenylium salts," *Indian Journal of Chemistry*, Apr. 1993, 32B:422-426.

Supplemental European Search Report dated Mar. 31, 2014 for corresponding EP Application No. 11845815.7.

Chinese Office Action dated Aug. 1, 2014 and Search Report for copending Application No. 201180066258.6.

* cited by examiner

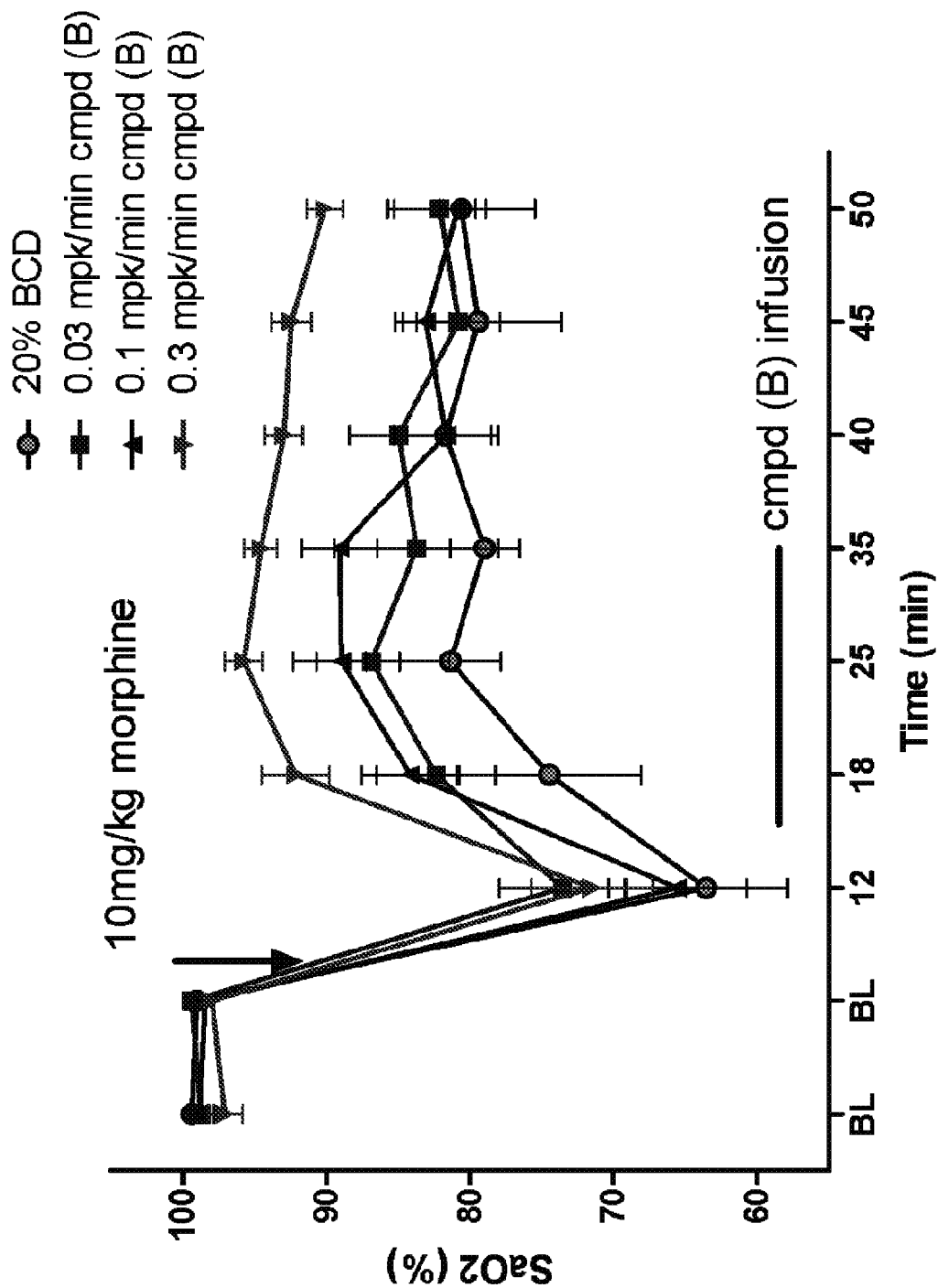

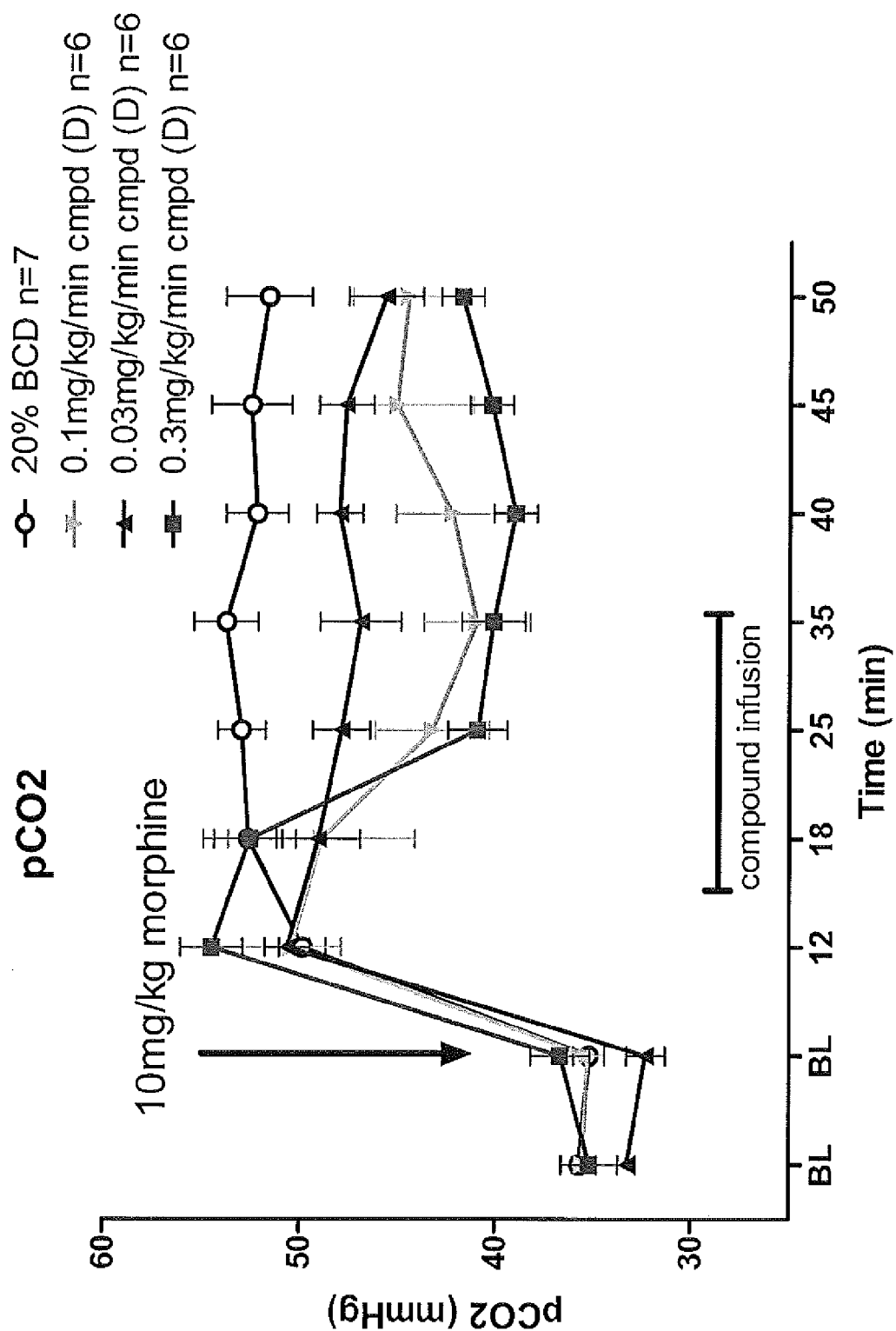

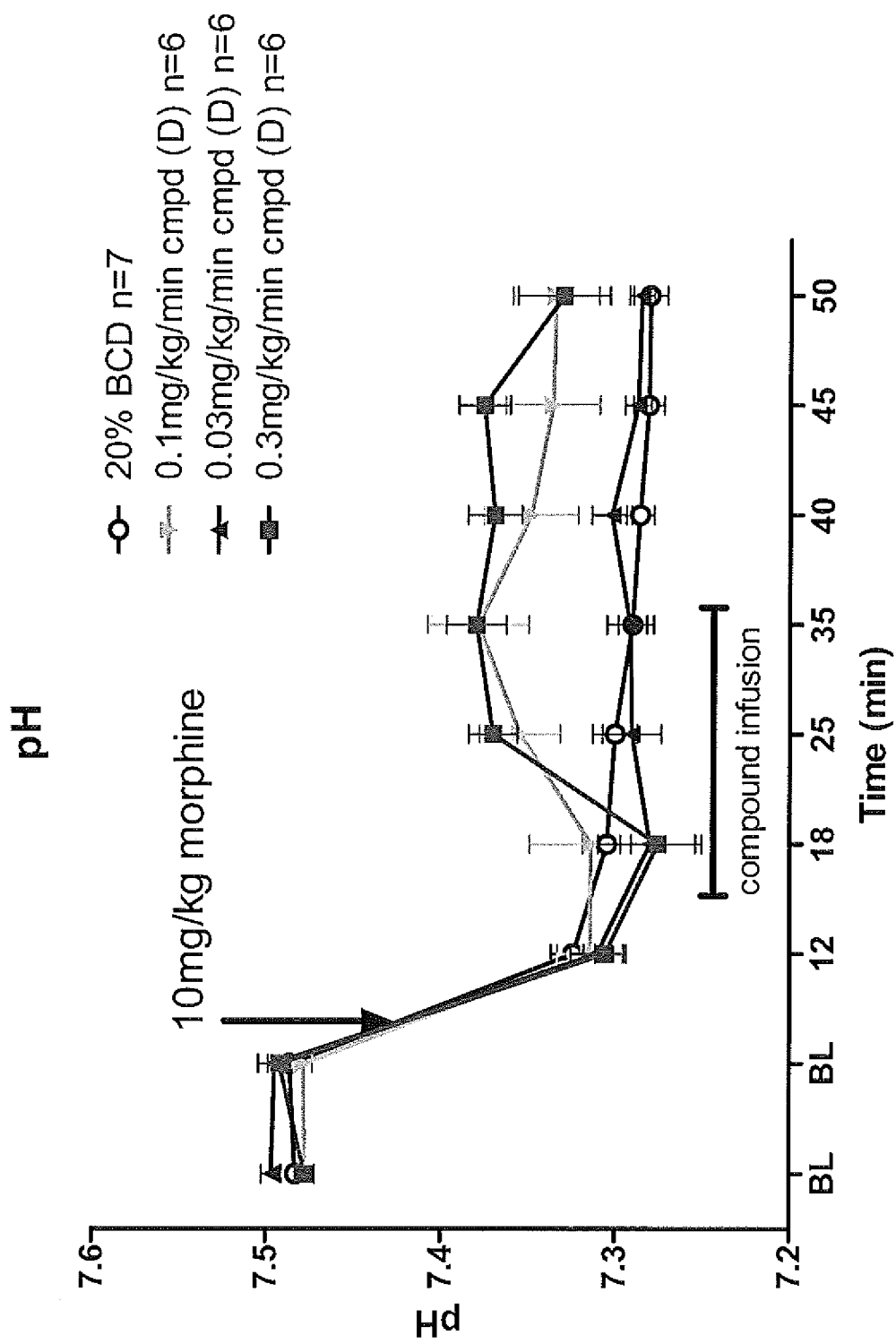

COMPOUNDS AS RESPIRATORY STIMULANTS FOR TREATMENT OF BREATHING CONTROL DISORDERS OR DISEASES

CROSS-REFERENCE TO RELATED APPLICATIONS

The present application is entitled to priority under 35 U.S.C. §119(e) to U.S. Provisional Patent Applications No. 61/417,777, filed Nov. 29, 2010, and No. 61/494,268, filed Jun. 7, 2011, all of which are hereby incorporated by reference in their entireties herein.

BACKGROUND OF THE INVENTION

Normal control of breathing is a complex process that involves the body's interpretation and response to chemical stimuli such as carbon dioxide, pH and oxygen levels in blood, tissues and the brain. Breathing control is also affected by wakefulness (i.e., whether the patient is awake or sleeping). Within the brain medulla, there is a respiratory control center that interprets the various signals that affect respiration and issues commands to the muscles that perform the work of breathing. Key muscle groups are located in the abdomen, diaphragm, pharynx and thorax. Sensors located centrally and peripherally then provide input to the brain's central respiration control areas that enables response to changing oxygen requirements.

Normal respiratory rhythm is maintained primarily by the body's rapid response to changes in carbon dioxide levels ($CO_2$). Increased $CO_2$ levels signal the body to increase breathing rate and depth, resulting in higher oxygen levels and subsequent lower $CO_2$ levels. Conversely, low $CO_2$ levels can result in periods of apnea (no breathing) since the stimulation to breathe is absent. This is what happens when a person hyperventilates.

In addition to the role of the brain, breathing control is the result of feedback from both peripheral and central chemoreceptors, but the exact contribution of each is unknown.

There are many diseases in which loss of normal breathing rhythm is a primary or secondary feature of the disease. Examples of diseases with a primary loss of breathing rhythm control are apneas (central, mixed or obstructive; where the breathing repeatedly stops for 10 to 60 seconds) and congenital central hypoventilation syndrome. Secondary loss of breathing rhythm may be due to chronic cardio-pulmonary diseases (e.g., heart failure, chronic bronchitis, emphysema, and impending respiratory failure), excessive weight (e.g., obesity-hypoventilation syndrome), certain drugs (e.g., anesthetics, sedatives, anxiolytics, hypnotics, alcohol, and narcotic analgesics and/or factors that affect the neurological system (e.g., stroke, tumor, trauma, radiation damage, and ALS). In chronic obstructive pulmonary diseases where the body is exposed to chronically low levels of oxygen, the body adapts to the lower pH by a kidney mediated retention of bicarbonate, which has the effect of partially neutralizing the $CO_2$/pH respiratory stimulation. Thus, the patient must rely on the less sensitive oxygen-based system.

In particular, loss of normal breathing rhythm during sleep is a common condition. Sleep apnea is characterized by frequent periods of no or partial breathing. Key factors that contribute to these apneas include decrease in $CO_2$ receptor sensitivity, decrease in hypoxic ventilatory response sensitivity (e.g., decreased response to low oxygen levels) and loss of "wakefulness." Normal breathing rhythm is disturbed by apnea events, resulting in hypoxia (and the associated oxidative stress) and eventually severe cardiovascular consequences (high blood pressure, stroke, heart attack). Snoring has some features in combination with sleep apnea. The upper airway muscles lose their tone resulting in the sounds associated with snoring but also inefficient airflow, which may result in hypoxia.

The ability of a mammal to breathe, and to modify breathing according to the amount of oxygen available and demands of the body, is essential for survival. There are a variety of conditions in which breathing is compromised that are characterized by, or due to, either a primary or secondary cause. Estimates for U.S. individuals afflicted with conditions wherein there is compromised respiratory control include sleep apneas (15-20 millions); obesity-hypoventilation syndrome (5-10 millions); chronic heart disease (5 millions); chronic obstructive pulmonary disease (COPD)/chronic bronchitis (10 millions); drug-induced hypoventilation (2-5 millions); and mechanical ventilation weaning (0.5 million).

There is a need in the art for novel chemical compounds that can be used to restore all or part of the body's normal breathing control system in response to changes in $CO_2$ and/or oxygen, with minimal side effects. Such compounds would be of benefit in decreasing the incidence and severity of breathing control disturbances. The present invention addresses and meets these needs.

BRIEF SUMMARY OF THE INVENTION

The invention includes a composition comprising at least one compound of formula (I):

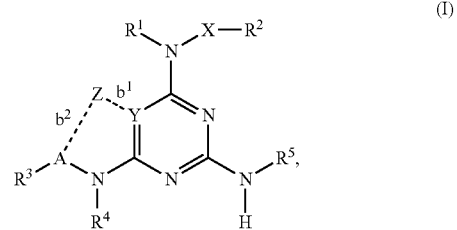

wherein:

$R^1$ and $R^2$ are independently H, alkyl, substituted alkyl, cycloalkyl, substituted cycloalkyl, alkenyl, substituted alkenyl, phenyl, substituted phenyl, phenylalkyl, substituted phenylalkyl, aryl, substituted aryl, arylalkyl, substituted arylalkyl, heteroarylalkyl, substituted heteroarylalkyl, heteroaryl or substituted heteroaryl; or $R^1$ and $R^2$ combine as to form a biradical selected from the group consisting of 3-hydroxy-pentane-1,5-diyl, 6-hydroxy-cycloheptane-1,4-diyl, propane-1,3-diyl, butane-1,4-diyl and pentane-1,5-diyl;

$R^3$ is H, alkyl, substituted alkyl, cycloalkyl, substituted cycloalkyl, alkenyl, substituted alkenyl, —$NR^1R^2$, —C(O)$OR^1$, acyl, or aryl;

$R^4$ is H, alkyl, or substituted alkyl;

$R^5$ is H, alkyl, substituted alkyl, cycloalkyl, substituted cycloalkyl, alkenyl, substituted alkenyl, —$OR^1$, —$NR^1R^2$, —C(O)$OR^1$, acyl, aryl, substituted aryl, heteroaryl, substituted heteroaryl, heterocyclic, or substituted heterocyclic; or $R^3$ and $R^5$ combine as to form a biradical selected from the group consisting of 3,6,9-trioxa-undecane-1,11-diyl and 3,6-dioxa-octane-1,8-diyl;

$R^6$ is H, alkyl, substituted alkyl or alkenyl;

X is a bond, O or $NR^4$; and,

Y is N, $CR^6$ or C; wherein:

if Y is N or CR⁶, then bond b¹ is nil and: (i) Z is H, bond b² is a single bond, and A is CH; or, (ii) Z is nil, bond b² is nil, and A is a single bond; and, if Y is C, then bond b¹ is a single bond, and: (i) Z is CH₂, bond b² is a single bond, and A is CH; or, (ii) Z is CH, bond b² is a double bond, and A is C;

or a salt thereof.

In one embodiment, R³ is H, alkyl, substituted alkyl, cycloalkyl, substituted cycloalkyl, alkenyl, or substituted alkenyl. In another embodiment, R⁵ is H, alkyl, substituted alkyl, cycloalkyl, substituted cycloalkyl, alkenyl, substituted alkenyl, or acyl.

In one embodiment, the at least one compound of formula (I) is selected from the group consisting of: (i) Y is N, bond b¹ is nil, Z is H, bond b² is a single bond, A is CH, and the at least one compound is a compound of formula (II-a) or a salt thereof:

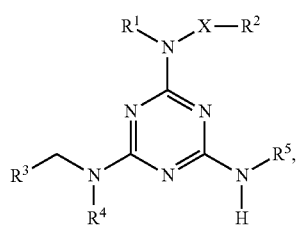

(II-a)

and
(ii) Y is N, bond b¹ is nil, Z is nil, bond b² is nil, and A is a bond, and the compound of the invention is a 1,3,5-triazine of formula (II-b) or a salt thereof:

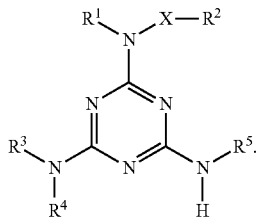

(II-b)

In one embodiment, the at least one compound of formula (I) is selected from the group consisting of: (i) Y is CR⁶, bond b¹ is nil, Z is H, bond b² is a single bond, A is CH, and the at least one compound is a compound of formula (III-a) or a salt thereof:

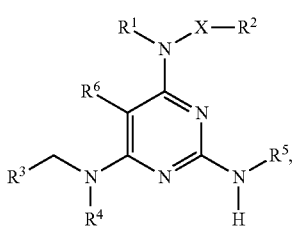

(III-a)

and
(ii) Y is CR⁶, bond b¹ is nil, Z is nil, bond b² is nil, and A is a bond, and the compound of the invention is a pyrimidine of formula (III-b) or a salt thereof:

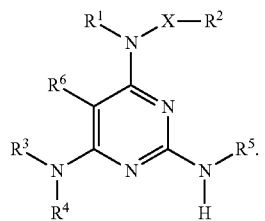

(III-b)

In one embodiment, Y is C, bond b¹ is a single bond, Z is CH₂, bond b² is a single bond, A is CH, and said at least one compound is a compound of formula (IV) or a salt thereof:

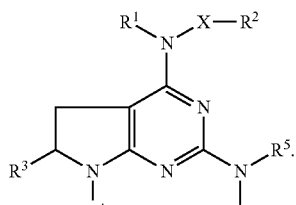

(IV)

In one embodiment, Y is C, bond b¹ is a single bond, Z is CH, bond b² is a double bond, A is C, and said at least one compound is a compound of formula (V) or a salt thereof:

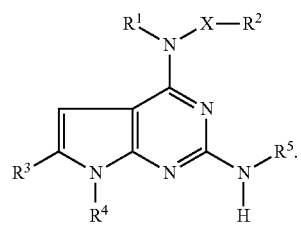

(V)

In one embodiment, the at least one compound is selected from the group consisting of: N-(4,6-Bis-methylamino-[1,3,5]triazin-2-yl)-N,O-dimethyl-hydroxylamine (XX), N-(4,6-Bis-ethylamino-[1,3,5]triazin-2-yl)-N,O-dimethyl-hydroxylamine (XXII), N-(4-Cyclopropylmethylamino)-N-(6-n-propylamino) [1,3,5]triazin-2-yl)-N,O-dimethyl-hydroxylamine (XXV), N-(4-Ethylamino)-N-(6-n-propylamino)-[1,3,5]triazin-2-yl)-N,O-dimethyl-hydroxylamine (XXVII), N-(Bis-4,6-(2-methylpropylamino)) [1,3,5]triazin-2-yl)-N,O-dimethyl-hydroxylamine (XXIX), N-(Bis-4,6-(2,2-dimethylpropylamino)) [1,3,5]triazin-2-yl)-O,N-dimethyl-hydroxylamine (XXXI), 4,6-Bis-N-cyclopropylamino-[1,3,5]triazin-2-yl)-N,O-dimethyl-hydroxylamine hydrochloride (XXXIII), N-(4,6-Bis-n-propylamino-[1,3,5]triazin-2-yl)-O,N-dimethyl-hydroxylamine (XXXV), N-(4-(Methoxy(methyl)amino)-6-(propylamino)-1,3,5-triazin-2-yl)propionamide (XL), N-(4,6-Bis-propylamino-[1,3,5]triazin-2-yl)-O-methyl-hydroxylamine (XLI), O-Allyl-N-(4,6-bis-propylamino-[1,3,5]triazin-2-yl)-hydroxylamine (XLIII), N-(4,6-Bis-propylamino-[1,3,5]triazin-2-yl)-hydroxylamine (XLV), 6-(Methoxy(methyl)amino)-N2-propyl-1,3,5-triazine-2,4-diamine (XLVII), N-(4,6-Bis-propylamino-[1,3,5]triazin-2-yl)-N-methyl-hydroxylamine (XLVIII), O-Benzyl- N-(4,6-bis-propylamino-[1,3,5]triazin-2-yl)-N-methyl-hydroxylamine (LIII), N-(4,6-Bis-propylamino-[1,3,5]triazin-2-yl)-N-isopropyl-hydroxylamine (LV), 6-[1,2]Oxazinan-2-yl-N,N'-dipropyl-[1,3,5]triazine-2,4-diamine (LVII), N-(4,6-Bis-propylamino-[1,3,5]triazin-2-yl)-O-isopropyl-N-methyl-hydroxylamine (LXIV), O-Benzyl-N-(4,6-bis-propylamino-[1,3,5]triazin-2-yl)-N-ethyl-hydroxylamine (LXVIII), N-(4,6-Bis-propylamino-[1,3,5]triazin-2-yl)-O-isopropyl-hydroxylamine (LXX), 6-((Benzyloxy)(isopropyl)amino)-$N^2,N^4$-dipropyl-1,3,5-triazine-2,4-diamine (LXXII), N-(4,6-Bis-propylamino-[1,3,5]triazin-2-yl)-N-ethyl-O-isopropyl-hydroxylamine (LXXVI), N-(4,6-Bis-propylamino-[1,3,5]triazin-2-yl)-O-isobutyl-N-methyl-hydroxylamine (LXXXII), 6-(Methyl(thiophen-2-ylmethoxy)amino)-N2,N4-dipropyl-1,3,5-triazine-2,4-diamine (LXXXIV), N-(4,6-Bis-propylamino-[1,3,5]triazin-2-yl)-O-cyclopropylmethyl-N-methyl-hydroxylamine (XCI), N-(4,6-Bis-propylamino-[1,3,5]triazin-2-yl)-O-ethyl-N-methyl-hydroxylamine (XCVI), N-(4,6-Bis-propylamino-[1,3,5]triazin-2-yl)-O-(2,2-difluoro-ethyl)-hydroxylamine (C), 4-N-(2-Dimethylaminoethyl)amino-6-N-(n-propyl)amino-[1,3,5]triazin-2-yl)-N,O-dimethyl-hydroxylamine (CIII), 4-N-(3-(1-N-Methylimidazol-2-yl)-propyl)-amino-6-N-(n-propyl)amino-[1,3,5]triazin-2-yl)-N,O-dimethyl-hydroxylamine (CV), 4-N-(1-N-Methylimidazol-2-yl)-methylamino-6-N-(n-propyl)amino-[1,3,5]triazin-2-yl)-O,N-dimethyl-hydroxylamine (CVII), 4,6-Bis-(N-(2-dimethylaminoethyl)amino)-[1,3,5]triazin-2-yl)-N,O-dimethyl-hydroxylamine (CIX), 4,6-Bis-(N-(pyridin-4-ylmethyl)amino)-[1,3,5]triazin-2-yl)-N,O-dimethyl-hydroxylamine (CXI), 4,6-Bis-[N-(3-methoxy-n-propyl)amino]-[1,3,5]triazin-2-yl)-N,O-dimethyl-hydroxylamine (CXIII), 4,6-Bis-[N-(tetrahydropyran-4-ylmethyl)amino]-[1,3,5]triazin-2-yl)-N,O-dimethyl-hydroxylamine (CXV), N-(5,8,11-Trioxa-2,14,16,18,19-pentaazabicyclo[13.3.1]nonadeca-1(18),15(19),16(17)-trien-17-yl)-N,O-dimethyl-hydroxylamine (CXVII), N-(4,6-Bis-propylamino-[1,3,5]triazin-2-yl)-N',N'-dimethylhydrazine (XLVI), N-(4,6-Bis-propylamino-[1,3,5]triazin-2-yl)-N-methyl-N'-methylhydrazine (XLIX), a salt thereof and mixtures thereof. In another embodiment, the salt is hydrogen sulfate or hydrochloride.

In one embodiment, the at least one compound is 2,6-bis-(N-n-propylamino)-[1,3]pyrimidin-4-yl)-N,O-dimethyl-hydroxylamine or a salt thereof. In another embodiment, the salt is hydrogen sulfate or hydrochloride.

In one embodiment, the at least one compound is selected from the group consisting of: 2-(n-Propyl)amino-4-(i-propylamino-7-methyl-pyrrolidino[2,3-d]pyrimidine (CXXVI), 2-(n-Propyl)amino-4-dimethylamino-7-methyl-pyrrolidino[2,3-d]pyrimidine (CXXVIII), 2-(n-Propyl)amino-4-methylamino-7-methyl-pyrrolidino[2,3-d]pyrimidine (CXXXI), 2-(n-Propyl)amino-4-(i-propyl)amino-7-i-propyl-pyrrolidino[2,3-d]pyrimidine (CXXXVI), 2,4-Bis-(n-propyl)amino-7H-pyrrolidino[2,3-d]pyrimidine (CXLIX), 2-(n-Propyl)amino-4-(4-hydroxypiperidin-1-yl)-7-methyl-pyrrolidino[2,3-d]pyrimidine (CLII), 8-(7-Methyl-2-(propylamino)-pyrrolidino[2,3-d]pyrimidin-4-yl)-8-azabicyclo[3.2.1]octan-3-ol (CLV), a salt thereof and mixtures thereof. In another embodiment, the salt is hydrogen sulfate or hydrochloride.

In one embodiment, the at least one compound is selected from the group consisting of: N-(2-Propylamino-7H-pyrrolo[2,3d]pyrimidin-4-yl)-O,N-dimethyl-hydroxylamine (CXLI), N-(2-(Propen-2-yl)amino-7-methyl-pyrrolo[2,3d]pyrimidin-4-yl)-N,O-dimethyl-hydroxylamine (CLVIII), N-(2-(Propen-2-yl)amino-7-methyl-pyrrolo[2,3d]pyrimidin-4-yl)-O-methyl-hydroxylamine (CLX), N-(2-n-Propylamino-7-methyl-pyrrolo[2,3d]pyrimidin-4-yl)-O,N-dimethyl-hydroxylamine (CLXII), N-(2-n-Propylamino-7-methyl-pyrrolo[2,3d]pyrimidin-4-yl)-O-methyl-hydroxylamine (CLXIV), N-(2-n-Propylamino-7-methyl-pyrrolo[2,3d]pyrimidin-4-yl)-hydrazine (CLXVI), N-Methyl-N-(2-n-propylamino-7-methyl-pyrrolo[2,3d]pyrimidin-4-yl)-hydrazine (CLXVIII), N,N-dimethyl-N'-(2-n-propylamino-7-methyl-pyrrolo[2,3d]pyrimidin-4-yl)-hydrazine (CLXX), a salt thereof and mixtures thereof. In another embodiment, the salt is hydrogen sulfate or hydrochloride.

In one embodiment, the composition further comprises at least one pharmaceutically acceptable carrier.

The invention also includes a method of preventing or treating a breathing control disorder or disease in a subject in need thereof. The method comprises the step of administering to the subject an effective amount of a pharmaceutical formulation comprising at least one pharmaceutically acceptable carrier and at least one compound of formula (I):

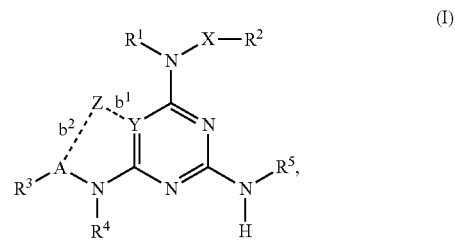

wherein
$R^1$ and $R^2$ are independently H, alkyl, substituted alkyl, cycloalkyl, substituted cycloalkyl, alkenyl, substituted alkenyl, phenyl, substituted phenyl, phenylalkyl, substituted phenylalkyl, aryl, substituted aryl, arylalkyl, substituted arylalkyl, heteroarylalkyl, substituted heteroarylalkyl, heteroaryl or substituted heteroaryl; or $R^1$ and $R^2$ combine as to form a biradical selected from the group consisting of 3-hydroxy-pentane-1,5-diyl, 6-hydroxy-cycloheptane-1,4-diyl, propane-1,3-diyl, butane-1,4-diyl and pentane-1,5-diyl;

$R^3$ is H, alkyl, substituted alkyl, cycloalkyl, substituted cycloalkyl, alkenyl, substituted alkenyl, —$NR^1R^2$, —C(O)$OR^1$, acyl, or aryl;

$R^4$ is H, alkyl, or substituted alkyl;

$R^5$ is H, alkyl, substituted alkyl, cycloalkyl, substituted cycloalkyl, alkenyl, substituted alkenyl, —$OR^1$, —$NR^1R^2$, —C(O)$OR^1$, acyl, aryl, substituted aryl, heteroaryl, substituted heteroaryl, heterocyclic, or substituted heterocyclic; or $R^3$ and $R^5$ combine as to form a biradical selected from the group consisting of 3,6,9-trioxa-undecane-1,11-diyl and 3,6-dioxa-octane-1,8-diyl;

$R^6$ is H, alkyl, substituted alkyl or alkenyl;

X is a bond, O or $NR^4$; and,

Y is N, $CR^6$ or C; wherein:
if Y is N or $CR^6$, then bond $b^1$ is nil and: (i) Z is H, bond $b^2$ is a single bond, and A is CH; or, (ii) Z is nil, bond $b^2$ is nil, and A is a single bond; and,
if Y is C, then bond $b^1$ is a single bond, and: (i) Z is $CH_2$, bond $b^2$ is a single bond, and A is CH; or, (ii) Z is CH, bond $b^2$ is a double bond, and A is C;

or a salt thereof.

In one embodiment, the breathing control disorder or disease is selected from the group consisting of respiratory depression, sleep apnea, apnea of prematurity, obesity-hypoventilation syndrome, primary alveolar hypoventilation syndrome, dyspnea, altitude sickness, hypoxia, hypercapnia and chronic obstructive pulmonary disease (COPD), wherein the respiratory depression is caused by an anesthetic, a sedative, an anxiolytic agent, a hypnotic agent, alcohol or a narcotic. In another embodiment, the subject is further administered a composition comprising at least one additional compound useful for treating said breathing disorder or disease. In yet another embodiment, the at least one additional compound is selected from the group consisting of acetazolamide, almitrine, theophylline, caffeine, methyl progesterone, a serotinergic modulator, a cannabinoid and an ampakine. In yet another embodiment, the formulation is administered in conjunction with the use of a mechanical ventilation device or positive airway pressure device on the subject. In yet another embodiment, the subject is a mammal. In yet another embodiment, the mammal is a human. In yet another embodiment, the formulation is administered to the subject by an inhalational, topical, oral, buccal, rectal, vaginal, intramuscular, subcutaneous, trans dermal, intrathecal or intravenous route.

In one embodiment, the at least one compound is selected from the group consisting of: N-(4,6-Bis-methylamino-[1,3,5]triazin-2-yl)-N,O-dimethyl-hydroxylamine, N-(4,6-Bis-ethylamino-[1,3,5]triazin-2-yl)-N,O-dimethyl-hydroxylamine, N-(4-Cyclopropylmethylamino)-N-(6-n-propylamino) [1,3,5]triazin-2-yl)-N,O-dimethyl-hydroxylamine, N-(4-Ethylamino)-N-(6-n-propylamino)-[1,3,5]triazin-2-yl)-N,O-dimethyl-hydroxylamine, N-(Bis-4,6-(2-methylpropylamino)) [1,3,5]triazin-2-yl)-N,O-dimethyl-hydroxylamine, N-(Bis-4,6-(2,2-dimethylpropylamino)) [1,3,5]triazin-2-yl)-N,O-dimethyl-hydroxylamine, N-(Bis-4,6-(2,2-dimethylpropylamino))[1,3,5]triazin-2-yl)-N,O-dimethyl-hydroxylamine, N-(4,6-Bis-n-propylamino-[1,3,5]triazin-2-yl)-N,O-dimethyl-hydroxylamine, N-(4-(Methoxy(methyl)amino)-6-(propylamino)-1,3,5-triazin-2-yl)propionamide, N-(4,6-Bis-propylamino-[1,3,5]triazin-2-yl)-O-methyl-hydroxylamine, O-Allyl-N-(4,6-bis-propylamino-[1,3,5]triazin-2-yl)-hydroxylamine, N-(4,6-Bis-propylamino-[1,3,5]triazin-2-yl)-hydroxylamine, 6-(Methoxy(methyl)amino)-N2-propyl-1,3,5-triazine-2,4-diamine, N-(4,6-Bis-propylamino-[1,3,5]triazin-2-yl)-N-methyl-hydroxylamine, O-Benzyl-N-(4,6-bis-propylamino-[1,3,5]triazin-2-yl)-N-methyl-hydroxylamine, N-(4,6-Bis-propylamino-[1,3,5]triazin-2-yl)-N-isopropyl-hydroxylamine, 6-[1,2]Oxazinan-2-yl-N,N'-dipropyl-[1,3,5]triazine-2,4-diamine, N-(4,6-Bis-propylamino-[1,3,5]triazin-2-yl)-O-isopropyl-N-methyl-hydroxylamine, O-Benzyl-N-(4,6-bis-propylamino-[1,3,5]triazin-2-yl)-N-ethyl-hydroxylamine, N-(4,6-Bis-propylamino-[1,3,5]triazin-2-yl)-O-isopropyl-hydroxylamine, 6-((Benzyloxy)(isopropyl)amino)-N2,N4-dipropyl-1,3,5-triazine-2,4-diamine, N-(4,6-Bis-propylamino-[1,3,5]triazin-2-yl)-N-ethyl-O-isopropyl-hydroxylamine, N-(4,6-Bis-propylamino-[1,3,5]triazin-2-yl)-O-isobutyl-N-methyl-hydroxylamine, 6-(Methyl(thiophen-2-ylmethoxy)amino)-N2,N4-dipropyl-1,3,5-triazine-2,4-diamine, N-(4,6-Bis-propylamino-[1,3,5]triazin-2-yl)-O-cyclopropylmethyl-N-methyl-hydroxylamine, N-(4,6-Bis-propylamino-[1,3,5]triazin-2-yl)-O-ethyl-N-methyl-hydroxylamine, N-(4,6-Bis-propylamino-[1,3,5]triazin-2-yl)-O-(2,2-difluoro-ethyl)-hydroxylamine, 4-N-(2-Dimethylaminoethyl)amino-6-N-(n-propyl)amino-[1,3,5]triazin-2-yl)-N,O-dimethyl-hydroxylamine, 4-N-(3-(1-N-Methylimidazol-2-yl)-propyl)-amino-6-N-(n-propyl)amino-[1,3,5]triazin-2-yl)-N,O-dimethyl-hydroxylamine, 4-N-(1-N-Methylimidazol-2-yl)methylamino-6-N-(n-propyl)amino-[1,3,5]triazin-2-yl)-N,O-dimethyl-hydroxylamine, 4,6-Bis-(N-(2-dimethylaminoethyl)amino)-[1,3,5]triazin-2-yl)-N,O-dimethyl-hydroxylamine, 4,6-Bis-(N-(pyridin-4-ylmethyl)amino)-[1,3,5]triazin-2-yl)-N,O-dimethyl-hydroxylamine, 4,6-Bis-[N-(3-methoxy-n-propyl)amino]-[1,3,5]triazin-2-yl)-N,O-dimethyl-hydroxylamine, 4,6-Bis-[N-(tetrahydropyran-4-ylmethyl)amino]-[1,3,5]triazin-2-yl)-N,O-dimethyl-hydroxylamine, N-(5,8,11-Trioxa-2,14,16,18,19-pentaazabicyclo[13.3.1]nonadeca-1(18),15(19),16(17)-trien-17-yl)-N,O-dimethylhydroxylamine, 2,6-Bis-(N-propylamino)-[1,3]pyrimidin-4-yl)-N,O-dimethyl-hydroxylamine, N-(4,6-Bis-propylamino-[1,3,5]triazin-2-yl)-N',N'-dimethylhydrazine, N-(4,6-Bis-propylamino-[1,3,5]triazin-2-yl)-N-methyl-N'-methylhydrazine, 2-(n-Propyl)amino-4-(i-propylamino-7-methyl-pyrrolidino[2,3-d]pyrimidine, 2-(n-Propyl)amino-4-dimethylamino-7-methyl-pyrrolidino[2,3-d]pyrimidine, 2-(n-Propyl)amino-4-methylamino-7-methyl-pyrrolidino[2,3-d]pyrimidine, 2-(n-Propyl)amino-4-(i-propyl)amino-7-i-propyl-pyrrolidino[2,3-d]pyrimidine, 2,4-Bis-(n-propyl)amino-7H-pyrrolidino[2,3-d]pyrimidine, 2-(n-Propyl)amino-4-(4-hydroxypiperidin-1-yl)-7-methyl-pyrrolidino[2,3-d]pyrimidine, 8-(7-Methyl-2-(propylamino)-pyrrolidino[2,3-d]pyrimidin-4-yl)-8-azabicyclo[3.2.1]octan-3-ol, N-(2-Propylamino-7H-pyrrolo[2,3d]pyrimidin-4-yl)-N,O-dimethyl-hydroxylamine, N-(2-(Propen-2-yl)amino-7-methyl-pyrrolo[2,3d]-pyrimidin-4-yl)-N,O-dimethyl-hydroxylamine, N-(2-(Propen-2-yl)amino-7-methyl-pyrrolo[2,3d]pyrimidin-4-yl)-O-methyl-hydroxylamine, N-(2-n-Propylamino-7-methyl-pyrrolo[2,3d]pyrimidin-4-yl)-N,O-dimethyl-hydroxylamine, N-(2-n-Propylamino-7-methyl-pyrrolo[2,3d]pyrimidin-4-yl)-O-methyl-hydroxylamine, N-(2-n-Propylamino-7-methyl-pyrrolo[2,3d]pyrimidin-4-yl)-hydrazine, N-Methyl-N-(2-n-propylamino-7-methyl-pyrrolo[2,3d]pyrimidin-4-yl)-hydrazine, N,N-Dimethyl-N'-(2-n-propylamino-7-methyl-pyrrolo[2,3d]pyrimidin-4-yl)-hydrazine, a salt thereof and mixtures thereof.

The invention also includes a method of preventing destabilization or stabilizing breathing rhythm in a subject in need thereof. The method comprises the step of administering to the subject an effective amount of a pharmaceutical formulation comprising at least one pharmaceutically acceptable carrier and at least one compound of formula (I):

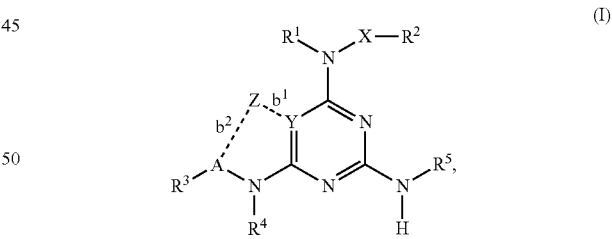

wherein $R^1$ and $R^2$ are independently H, alkyl, substituted alkyl, cycloalkyl, substituted cycloalkyl, alkenyl, substituted alkenyl, phenyl, substituted phenyl, phenylalkyl, substituted phenylalkyl, aryl, substituted aryl, arylalkyl, substituted arylalkyl, heteroarylalkyl, substituted heteroarylalkyl, heteroaryl or substituted heteroaryl; or $R^1$ and $R^2$ combine as to form a biradical selected from the group consisting of 3-hydroxy-pentane-1,5-diyl, 6-hydroxy-cycloheptane-1,4-diyl, propane-1,3-diyl, butane-1,4-diyl and pentane-1,5-diyl;

$R^3$ is H, alkyl, substituted alkyl, cycloalkyl, substituted cycloalkyl, alkenyl, substituted alkenyl, —$NR^1R^2$, —$C(O)OR^1$, acyl, or aryl;

R⁴ is H, alkyl, or substituted alkyl;

R⁵ is H, alkyl, substituted alkyl, cycloalkyl, substituted cycloalkyl, alkenyl, substituted alkenyl, —OR¹, —NR¹R², —C(O)OR¹, acyl, aryl, substituted aryl, heteroaryl, substituted heteroaryl, heterocyclic, or substituted heterocyclic; or R³ and R⁵ combine as to form a biradical selected from the group consisting of 3,6,9-trioxa-undecane-1,11-diyl and 3,6-dioxa-octane-1,8-diyl;

R⁶ is H, alkyl, substituted alkyl or alkenyl;

X is a bond, O or NR⁴; and,

Y is N, CR⁶ or C; wherein:

if Y is N or CR⁶, then bond b¹ is nil and: (i) Z is H, bond b² is a single bond, and A is CH; or, (ii) Z is nil, bond b² is nil, and A is a single bond; and, if Y is C, then bond b¹ is a single bond, and: (i) Z is CH₂, bond b² is a single bond, and A is CH; or, (ii) Z is CH, bond b² is a double bond, and A is C;

or a salt thereof.

In one embodiment, the destabilization is associated with a breathing control disorder or disease selected from the group consisting of respiratory depression, sleep apnea, apnea of prematurity, obesity-hypoventilation syndrome, primary alveolar hypoventilation syndrome, dyspnea, altitude sickness, hypoxia, hypercapnia and chronic obstructive pulmonary disease (COPD), wherein the respiratory depression is caused by an anesthetic, a sedative, an anxiolytic agent, a hypnotic agent, alcohol or a narcotic. In another embodiment, the subject is further administered a composition comprising at least one additional compound useful for treating said breathing disorder or disease. In yet another embodiment, the at least one additional compound is selected from the group consisting of acetazolamide, almitrine, theophylline, caffeine, methyl progesterone, a serotinergic modulator, a cannabinoid and an ampakine. In yet another embodiment, the formulation is administered in conjunction with the use of a mechanical ventilation device or positive airway pressure device on the subject. In yet another embodiment, the subject is a mammal. In yet another embodiment, the mammal is a human. In yet another embodiment, the formulation is administered to the subject by an inhalational, topical, oral, buccal, rectal, vaginal, intramuscular, subcutaneous, trans dermal, intrathecal or intravenous route. In yet another embodiment, the at least one compound is selected from the group consisting of: N-(4,6-Bis-methylamino-[1,3,5]triazin-2-yl)-N,O-dimethyl-hydroxylamine, N-(4,6-Bis-ethylamino-[1,3,5]triazin-2-yl)-N,O-dimethyl-hydroxylamine, N-(4-Cyclopropylmethylamino)-N-(6-n-propylamino) [1,3,5]triazin-2-yl)-N,O-dimethyl-hydroxylamine, N-(4-Ethylamino)-N-(6-n-propylamino)-[1,3,5]triazin-2-yl)-N,O-dimethyl-hydroxylamine, N-(Bis-4,6-(2-methylpropylamino)) [1,3,5]triazin-2-yl)-N,O-dimethyl-hydroxylamine, N-(Bis-4,6-(2,2-dimethylpropylamino)) [1,3,5]triazin-2-yl)-N,O-dimethyl-hydroxylamine, N-(Bis-4,6-(2,2-dimethylpropylamino))[1,3,5]triazin-2-yl)-N,O-dimethyl-hydroxylamine, N-(4,6-Bis-n-propylamino-[1,3,5]triazin-2-yl)-N,O-dimethyl-hydroxylamine, N-(4-(Methoxy(methyl)amino)-6-(propylamino)-1,3,5-triazin-2-yl) propionamide, N-(4,6-Bis-propylamino-[1,3,5]triazin-2-yl)-O-methyl-hydroxylamine, O-Allyl-N-(4,6-bis-propylamino-[1,3,5]triazin-2-yl)-hydroxylamine, N-(4,6-Bis-propylamino-[1,3,5]triazin-2-yl)-hydroxylamine, 6-(Methoxy(methyl)amino)-N2-propyl-1,3,5-triazine-2,4-diamine, N-(4,6-Bis-propylamino-[1,3,5]triazin-2-yl)-N-methyl-hydroxylamine, O-Benzyl-N-(4,6-bis-propylamino-[1,3,5]triazin-2-yl)-N-methyl-hydroxylamine, N-(4,6-Bis-propylamino-[1,3,5]triazin-2-yl)-N-isopropyl-hydroxylamine, 6-[1,2]Oxazinan-2-yl-N,N'-dipropyl-[1,3,5] triazine-2,4-diamine, N-(4,6-Bis-propylamino-[1,3,5]triazin-2-yl)-O-isopropyl-N-methyl-hydroxylamine, O-Benzyl-N-(4,6-bis-propylamino-[1,3,5]triazin-2-yl)-N-ethyl-hydroxylamine, N-(4,6-Bis-propylamino-[1,3,5]triazin-2-yl)-O-isopropyl-hydroxylamine, 6-((Benzyloxy)(isopropyl)amino)-N2,N4-dipropyl-1,3,5-triazine-2,4-diamine, N-(4,6-Bis-propylamino-[1,3,5]triazin-2-yl)-N-ethyl-O-isopropyl-hydroxylamine, N-(4,6-Bis-propylamino-[1,3,5]triazin-2-yl)-O-isobutyl-N-methyl-hydroxylamine, 6-(Methyl (thiophen-2-ylmethoxy)amino)-N2,N4-dipropyl-1,3,5-triazine-2,4-diamine, N-(4,6-Bis-propylamino-[1,3,5]triazin-2-yl)-O-cyclopropylmethyl-N-methyl-hydroxylamine, N-(4,6-Bis-propylamino-[1,3,5]triazin-2-yl)-O-ethyl-N-methyl-hydroxylamine, N-(4,6-Bis-propylamino-[1,3,5]triazin-2-yl)-O-(2,2-difluoro-ethyl)-hydroxylamine, 4-N-(2-Dimethylaminoethyl)amino-6-N-(n-propyl)amino-[1,3,5]triazin-2-yl)-N,O-dimethyl-hydroxylamine, 4-N-(3-(1-N-Methylimidazol-2-yl)-propyl)-amino-6-N-(n-propyl)amino-[1,3,5]triazin-2-yl)-N,O-dimethyl-hydroxylamine, 4-N-(1-N-Methylimidazol-2-yl)-methylamino-6-N-(n-propyl)amino-[1,3,5]triazin-2-yl)-N,O-dimethyl-hydroxylamine, 4,6-Bis-(N-(2-dimethylaminoethyl)amino)-[1,3,5]triazin-2-yl)-N,O-dimethyl-hydroxylamine, 4,6-Bis-(N-(pyridin-4-ylmethyl)amino)-[1,3,5]triazin-2-yl)-N,O-dimethyl-hydroxylamine, 4,6-Bis-[N-(3-methoxy-n-propyl)amino]-[1,3,5]triazin-2-yl)-N,O-dimethyl-hydroxylamine, 4,6-Bis-[N-(tetrahydropyran-4-ylmethyl)amino]-[1,3,5]triazin-2-yl)-N,O-dimethyl-hydroxylamine, N-(5,8,11-Trioxa-2,14,16,18,19-pentaazabicyclo[13.3.1]-nonadeca-1(18),15(19),16(17)-trien-17-yl)-N,O-dimethylhydroxylamine, 2,6-Bis-(N-propylamino)-[1,3]pyrimidin-4-yl)-N,O-dimethyl-hydroxylamine, N-(4,6-Bis-propylamino-[1,3,5]triazin-2-yl)-N',N'-dimethylhydrazine, N-(4,6-Bis-propylamino-[1,3,5]triazin-2-yl)-N-methyl-N'-methylhydrazine, 2-(n-Propyl)amino-4-(i-propylamino-7-methyl-pyrrolidino[2,3-d]pyrimidine, 2-(n-Propyl)amino-4-dimethylamino-7-methyl-pyrrolidino[2,3-d]pyrimidine, 2-(n-Propyl)amino-4-methylamino-7-methyl-pyrrolidino[2,3-d]pyrimidine, 2-(n-Propyl)amino-4-(i-propyl)amino-7-i-propyl-pyrrolidino[2,3-d]pyrimidine, 2,4-Bis-(n-propyl)amino-7H-pyrrolidino[2,3-d]pyrimidine, 2-(n-Propyl)amino-4-(4-hydroxypiperidin-1-yl)-7-methyl-pyrrolidino[2,3-d]pyrimidine, 8-(7-Methyl-2-(propylamino)-pyrrolidino[2,3-d]pyrimidin-4-yl)-8-azabicyclo[3.2.1]octan-3-ol, N-(2-Propylamino-7H-pyrrolo[2,3d]pyrimidin-4-yl)-N,O-dimethyl-hydroxylamine, N-(2-(Propen-2-yl)amino-7-methyl-pyrrolo[2,3d]pyrimidin-4-yl)-N,O-dimethyl-hydroxylamine, N-(2-(Propen-2-yl) amino-7-methyl-pyrrolo[2,3d]pyrimidin-4-yl)-O-methyl-hydroxylamine, N-(2-n-Propylamino-7-methyl-pyrrolo[2,3d]pyrimidin-4-yl)-N,O-dimethyl-hydroxylamine, N-(2-n-Propylamino-7-methyl-pyrrolo[2,3d]pyrimidin-4-yl)-O-methyl-hydroxylamine, N-(2-n-Propylamino-7-methyl-pyrrolo[2,3d]pyrimidin-4-yl)-hydrazine, N-Methyl-N-(2-n-propylamino-7-methyl-pyrrolo[2,3d]pyrimidin-4-yl)-hydrazine, N,N-Dimethyl-N'-(2-n-propylamino-7-methyl-pyrrolo[2,3d]pyrimidin-4-yl)-hydrazine, a salt thereof and mixtures thereof.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 2, comprising FIG. 2A—$PaCO_2$ (mmHg); FIG. 2B—$SaO_2$ (%).

FIG. 7, comprising FIGS. 7A-7D, illustrates the dose-dependent effect of Compound (L) [labeled as cmpd (B)] on blood gases and pH in the opioid-treated rat. FIG. 7A—pH; FIG. 7B—$SaO_2$; FIG. 7C—$pO_2$; FIG. 7D—$pCO_2$.

FIG. 8, comprising FIGS. 8A-8D, illustrates the dose-dependent effect of Compound (CXLII) [labeled as cmpd (D)] on blood gases and pH in the opioid-treated rat. FIG. 8A—$pO_2$, FIG. 8B—$SaO_2$; FIG. 8C—$pCO_2$; FIG. 8D—pH.

DETAILED DESCRIPTION OF THE INVENTION

Figure 1:
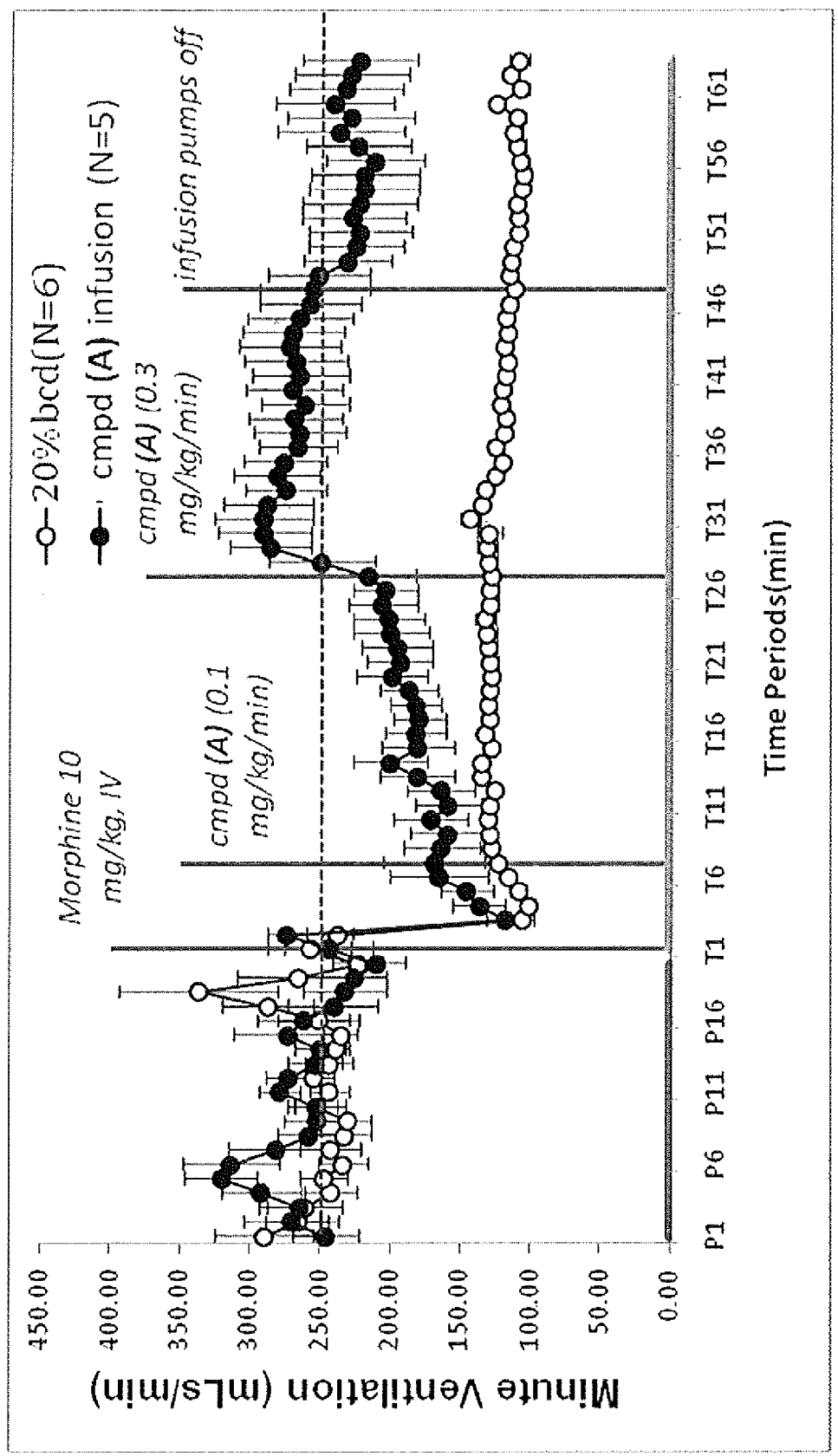
FIG. 1 is a graph illustrating results of plethysmography experiments which monitored minute ventilation in the opioid-treated rat upon administration of Compound (XXXVI) [labeled as cmpd (A)].

The present invention relates in one aspect to the unexpected discovery that the compounds of the invention are respiratory stimulants and useful in the treatment of breathing control disorders or diseases.

DEFINITIONS

As used herein, each of the following terms has the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in animal pharmacology, pharmaceutical science, separation science and organic chemistry are those well-known and commonly employed in the art.

As used herein, the articles "a" and "an" refer to one or to more than one (i.e. to at least one) of the grammatical object of the article. By way of example, "an element" means one element or more than one element.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

As used herein, a "subject" may be a human or non-human mammal. Non-human mammals include, for example, livestock and pets, such as ovine, bovine, porcine, canine, feline and murine mammals. Preferably, the subject is human.

In a non-limiting embodiment, the following terminology used to report blood gas measurements is well known to those skilled in the art and may be defined as such: minute ventilation (MV) is a measure of breathing volume per unit time and is given herein as mL/min; $pCO_2$ is partial pressure of carbon dioxide (gas) in (arterial) blood measured in mm Hg (millimeters of Hg); $pO_2$ is partial pressure of oxygen (gas) in (arterial) blood measured in mmHg (millimeters of Hg); $saO_2$ is the percentage of oxygen saturation (dissolved oxygen gas) which correlates to the percentage of hemoglobin binding sites in the bloodstream occupied by oxygen; end-tidal $CO_2$ is the measurement of exhaled carbon dioxide gas as detected using colorimetry, capnometry, or capnography techniques.

As used herein, the term $ED_{50}$ refers to the effective dose of a formulation that produces a given effect in 50% of the subjects that are administered that formulation.

As used herein, a "disease" is a state of health of an animal wherein the animal cannot maintain homeostasis, and wherein if the disease is not ameliorated then the animal's health continues to deteriorate.

As used herein, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, an "effective amount", "therapeutically effective amount" or "pharmaceutically effective amount" of a compound is that amount of compound that is sufficient to provide a beneficial effect to the subject to which the compound is administered. The term to "treat," as used herein, means reducing the frequency with which symptoms are experienced by a patient or subject or administering an agent or compound to reduce the severity with which symptoms are experienced.

As used herein, the term "pharmaceutically acceptable" refers to a material, such as a carrier or diluent, which does not abrogate the biological activity or properties of the compound useful within the invention, and is relatively non-toxic, i.e., the material may be administered to an individual without causing undesirable biological effects or interacting in a deleterious manner with any of the components of the composition in which it is contained.

As used herein, the language "pharmaceutically acceptable salt" refers to a salt of the administered compound prepared from pharmaceutically acceptable non-toxic acids and bases, including inorganic acids, inorganic bases, organic acids, inorganic bases, solvates, hydrates, and clathrates thereof.

As used herein, the term "composition" or "pharmaceutical composition" refers to a mixture of at least one compound useful within the invention with a pharmaceutically acceptable carrier. The pharmaceutical composition facilitates administration of the compound to a subject.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the subject such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the subject. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the subject. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, "treating a disease or disorder" means reducing the frequency with which a symptom of the disease or disorder is experienced by a subject. Disease and disorder are used interchangeably herein.

By the term "specifically bind" or "specifically binds," as used herein, is meant that a first molecule preferentially binds to a second molecule (e.g., a particular receptor or enzyme), but does not necessarily bind only to that second molecule.

As used herein, the term "alkyl," by itself or as part of another substituent means, unless otherwise stated, a straight or branched chain hydrocarbon having the number of carbon atoms designated (i.e. $C_1$-$C_{10}$ means one to ten carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. Most preferred is ($C_1$-$C_6$)alkyl, such as, but not limited to, ethyl, methyl, isopropyl, isobutyl, n-pentyl, n-hexyl and cyclopropylmethyl.

As used herein, the term "cycloalkyl," by itself or as part of another substituent means, unless otherwise stated, a cyclic chain hydrocarbon having the number of carbon atoms designated (i.e. $C_3$-$C_6$ means a cyclic group comprising a ring group consisting of three to six carbon atoms) and includes straight, branched chain or cyclic substituent groups. Examples include cyclopropyl, cyclobutyl, cyclopentyl, cyclohexyl, cycloheptyl, and cyclooctyl. Most preferred is ($C_3$-$C_6$)cycloalkyl, such as, but not limited to, cyclopropyl, cyclobutyl, cyclopentyl and cyclohexyl.

As used herein, the term "alkenyl," employed alone or in combination with other terms, means, unless otherwise stated, a stable mono-unsaturated or di-unsaturated straight chain or branched chain hydrocarbon group having the stated number of carbon atoms. Examples include vinyl, propenyl (or allyl), crotyl, isopentenyl, butadienyl, 1,3-pentadienyl, 1,4-pentadienyl, and the higher homologs and isomers. A functional group representing an alkene is exemplified by —$CH_2$—$CH$=$CH_2$.

As used herein, the term "alkynyl," employed alone or in combination with other terms, means, unless otherwise stated, a stable straight chain or branched chain hydrocarbon group with a triple carbon-carbon bond, having the stated number of carbon atoms. Examples include ethynyl and propynyl, and the higher homologs and isomers.

As used herein, the term "substituted alkyl," "substituted cycloalkyl," "substituted alkenyl" or "substituted alkynyl" means alkyl, cycloalkyl, alkenyl or alkynyl, as defined above, substituted by one, two or three substituents selected from the group consisting of halogen, —OH, alkoxy, tetrahydro-2-H-pyranyl, —$NH_2$, —$N(CH_3)_2$, (1-methylimidazol-2-yl), pyridin-2-yl, pyridin-3-yl, pyridin-4-yl, —C(=O)OH, trifluoromethyl, —C≡N, —C(=O)O($C_1$-$C_4$)alkyl, —C(=O)$NH_2$, —C(=O)NH($C_1$-$C_4$)alkyl, —C(=O)N(($C_1$-$C_4$)alkyl)$_2$, —$SO_2NH_2$, —C(=NH)$NH_2$, and —$NO_2$, preferably containing one or two substituents selected from halogen, —OH, alkoxy, —$NH_2$, trifluoromethyl, —$N(CH_3)_2$, and —C(=O)OH, more preferably selected from halogen, alkoxy and —OH. Examples of substituted alkyls include, but are not limited to, 2,2-difluoropropyl, 2-carboxycyclopentyl and 3-chloropropyl.

As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy(isopropoxy) and the higher homologs and isomers. Preferred are ($C_1$-$C_3$)alkoxy, such as, but not limited to, ethoxy and methoxy.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—$CH_2$—$CH_2$—$CH_3$, —$CH_2$—$CH_2$—$CH_2$—OH, —$CH_2$—$CH_2$—NH—$CH_3$, —$CH_2$—S—$CH_2$—$CH_3$, and —$CH_2CH_2$—S(=O)—$CH_3$. Up to two heteroatoms may be consecutive, such as, for example, —$CH_2$—NH—$OCH_3$, or —$CH_2$—$CH_2$—S—S—$CH_3$ As used herein, the term "heteroalkenyl" by itself or in combination with another term means, unless otherwise stated, a stable straight or branched chain monounsaturated or di-unsaturated hydrocarbon group consisting of the stated number of carbon atoms and one or two heteroatoms selected from the group consisting of O, N, and S, and wherein the nitrogen and sulfur atoms may optionally be oxidized and the nitrogen heteroatom may optionally be quaternized. Up to two heteroatoms may be placed consecutively. Examples include —CH=CH—O—$CH_3$, —CH=CH—$CH_2$—OH, —$CH_2$—CH=N—$OCH_3$, —CH=CH—N($CH_3$)—$CH_3$, and —$CH_2$—CH=CH—$CH_2$—SH.

As used herein, the term "aromatic" refers to a carbocycle or heterocycle with one or more polyunsaturated rings and having aromatic character, i.e. having (4n+2) delocalized π (pi) electrons, where n is an integer.

As used herein, the term "aryl," employed alone or in combination with other terms, means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl, anthracyl, and naphthyl. Preferred are phenyl and naphthyl, most preferred is phenyl.

As used herein, the term "aryl-($C_1$-$C_3$)alkyl" means a functional group wherein a one to three carbon alkylene chain is attached to an aryl group, e.g., —$CH_2CH_2$-phenyl or —$CH_2$-phenyl(benzyl). Preferred is aryl-$CH_2$— and aryl-CH($CH_3$)—. The term "substituted aryl-($C_1$-$C_3$)alkyl" means an aryl-($C_1$-$C_3$)alkyl functional group in which the aryl group is substituted. Preferred is substituted aryl($CH_2$)—. Similarly, the term "heteroaryl-($C_1$-$C_3$)alkyl" means a functional group wherein a one to three carbon alkylene chain is attached to a heteroaryl group, e.g., —$CH_2CH_2$-pyridyl. Preferred is heteroaryl-($CH_2$)—. The term "substituted heteroaryl-($C_1$-$C_3$) alkyl" means a heteroaryl-($C_1$-$C_3$)alkyl functional group in which the heteroaryl group is substituted. Preferred is substituted heteroaryl-($CH_2$)—.

As used herein, the term "heterocycle" or "heterocyclyl" or "heterocyclic" by itself or as part of another substituent means, unless otherwise stated, an unsubstituted or substituted, stable, mono- or multi-cyclic heterocyclic ring system that consists of carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In one embodiment, the heterocycle is a heteroaryl.

As used herein, the term "heteroaryl" or "heteroaromatic" refers to a heterocycle having aromatic character. A polycyclic heteroaryl may include one or more rings that are partially saturated. Examples include tetrahydroquinoline and 2,3-dihydrobenzofuryl.

Examples of non-aromatic heterocycles include monocyclic groups such as aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include pyridyl, pyrazinyl, pyrimidinyl (such as, but not limited to, 2- and 4-pyrimidinyl), pyridazinyl, thienyl, furyl, pyrrolyl, imidazolyl, thiazolyl, oxazolyl, pyrazolyl, isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include indolyl (such as, but not limited to, 3-, 4-, 5-, 6- and 7-indolyl), indolinyl, quinolyl, tetrahydroquinolyl, isoquinolyl (such as, but not limited to, 1- and 5-isoquinolyl), 1,2,3,4-tetrahydroisoquinolyl, cinnolinyl, quinoxalinyl (such as, but not limited to, 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (such as, but not limited to, 3-, 4-, 5-, 6- and 7-benzofuryl), 2,3-dihydrobenzofuryl, 1,2-benzisoxazolyl, benzothienyl (such as, but not limited to, 3-, 4-, 5-, 6-, and 7-benzothienyl), benzoxazolyl, benzothiazolyl (such as, but not limited to, 2-benzothiazolyl and 5-benzothiazolyl), purinyl, benzimidazolyl, benztriazolyl, thioxanthinyl, carbazolyl, carbolinyl, acridinyl, pyrrolizidinyl, and quinolizidinyl.

The aforementioned listing of heterocyclyl and heteroaryl moieties is intended to be representative and not limiting.

As used herein, the term "substituted" means that an atom or group of atoms has replaced hydrogen as the substituent attached to another group.

For aryl, aryl-($C_1$-$C_3$)alkyl and heterocyclyl groups, the term "substituted" as applied to the rings of these groups refers to any level of substitution, namely mono-, di-, tri-, tetra-, or penta-substitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two. In yet another embodiment, the substituents are independently selected from the group consisting of $C_{1-6}$ alkyl, —OH, $C_{1-6}$ alkoxy, halo, amino, acetamido and nitro. As used herein, where a substituent is an alkyl or alkoxy group, the carbon chain may be branched, straight or cyclic, with straight being preferred.

As used herein, the term "AcOH" refers to acetic acid; the term "nBuOH" refers to n-butanol; the term "$CH_2Cl_2$" refers to dichloromethane (also known as methylene dichloride); the term "DMSO" refers to dimethylsulfoxide; the term "EtOAc" refers to ethyl acetate; the term "EtOH" refers to ethanol; the term "HCl" refers to hydrochloric acid or a hydrochloride salt; the term "HPLC" refers to high pressure liquid chromatography; the term "$H_2SO_4$" refers to sulfuric acid; the term "LCMS" refers to liquid chromatography-mass spectrometry; the term "MS" refers to mass spectrometry; the term "MeOH" refers to methanol; the term "NaCl" refers to sodium chloride; the term "$NaHCO_3$" refers to sodium bicarbonate; the term "NaOH" refers to sodium hydroxide; the term "Na$_2$SO$_4$" refers to sodium sulfate; the term "mpk" refers to mg/kg; the term "NMR" refers to nuclear magnetic resonance; the term "PE" or "pet ether" refers to petroleum ether; the term "POCl$_3$" refers to phosphorous oxychloride; the term "ppm" refers to part per million; the term "xphos" refers to 2-dicyclohexylphosphino-2',4',6'-triisopropylbiphenyl; the term "dba" refers to trans,trans-dibenzylideneacetone.

"Instructional material," as that term is used herein, includes a publication, a recording, a diagram, or any other medium of expression that can be used to communicate the usefulness of the composition and/or compound of the invention in a kit. The instructional material of the kit may, for example, be affixed to a container that contains the compound and/or composition of the invention or be shipped together with a container that contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

Compounds of the Invention

The invention includes a compound of formula (I) or a salt thereof:

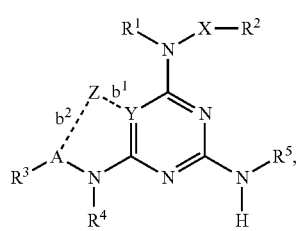

(I)

wherein

R$^1$ and R$^2$ are independently H, alkyl, substituted alkyl, cycloalkyl, substituted cycloalkyl, alkenyl, substituted alkenyl, phenyl, substituted phenyl, phenylalkyl, substituted phenylalkyl, aryl, substituted aryl, arylalkyl, substituted arylalkyl, heteroarylalkyl, substituted heteroarylalkyl, heteroaryl or substituted heteroaryl; or R$^1$ and R$^2$ combine as to form a biradical selected from the group consisting of 3-hydroxy-pentane-1,5-diyl, 6-hydroxy-cycloheptane-1,4-diyl, propane-1,3-diyl, butane-1,4-diyl and pentane-1,5-diyl;

R$^3$ is H, alkyl, substituted alkyl, cycloalkyl, substituted cycloalkyl, alkenyl, substituted alkenyl, —NR$^1$R$^2$, —C(O)OR$^1$, acyl, or aryl;

R$^4$ is H, alkyl, or substituted alkyl;

R$^5$ is H, alkyl, substituted alkyl, cycloalkyl, substituted cycloalkyl, alkenyl, substituted alkenyl, —OR$^1$, —NR$^1$R$^2$, —C(O)OR$^1$, acyl, aryl, substituted aryl, heteroaryl, substituted heteroaryl, heterocyclic, or substituted heterocyclic; or R$^3$ and R$^5$ combine as to form a biradical selected from the group consisting of 3,6,9-trioxa-undecane-1,11-diyl and 3,6-dioxa-octane-1,8-diyl;

R$^6$ is H, alkyl, substituted alkyl or alkenyl;

X is a bond, O or NR$^4$; and,

Y is N, CR$^6$ or C; wherein:

if Y is N or CR$^6$, then bond b$^1$ is nil and:

(i) Z is H, bond b$^2$ is a single bond, and A is CH; or, (ii) Z is nil, bond b$^2$ is nil, and A is a single bond; and, if Y is C, then bond b$^1$ is a single bond, and:

(i) Z is CH$_2$, bond b$^2$ is a single bond, and A is CH; or, (ii) Z is CH, bond b$^2$ is a double bond, and A is C.

In one embodiment, R$^3$ is H, alkyl, substituted alkyl, alkenyl, cycloalkyl, substituted cycloalkyl, or substituted alkenyl. In another embodiment, R$^5$ is H, alkyl, substituted alkyl, alkenyl, substituted alkenyl, acyl, cycloalkyl or substituted cycloalkyl.

In one embodiment, Y is N, bond b$^1$ is nil, Z is H, bond b$^2$ is a single bond, A is CH, and the compound of the invention is a 1,3,5-triazine of formula (II-a) or a salt thereof:

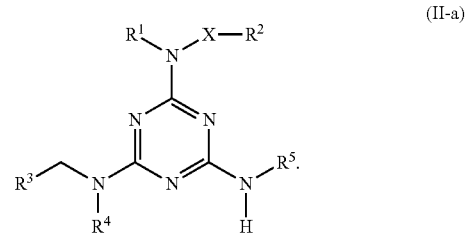

(II-a)

In one embodiment, Y is N, bond b$^1$ is nil, Z is nil, bond b$^2$ is nil, and A is a bond, and the compound of the invention is a 1,3,5-triazine of formula (II-b) or a salt thereof:

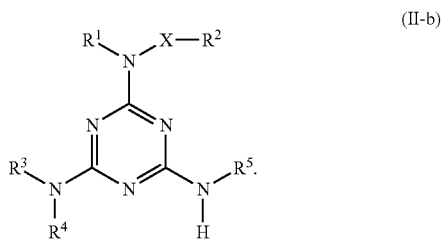

(II-b)

In one embodiment, Y is CR$^6$, bond b$^1$ is nil, Z is H, bond b$^2$ is a single bond, A is CH, and the compound of the invention is a pyrimidine of formula (III-a) or a salt thereof:

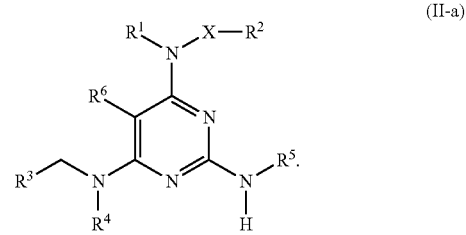

(II-a)

In one embodiment, Y is CR$^6$, bond b$^1$ is nil, Z is nil, bond b$^2$ is nil, and A is a bond, and the compound of the invention is a pyrimidine of formula (III-b) or a salt thereof:

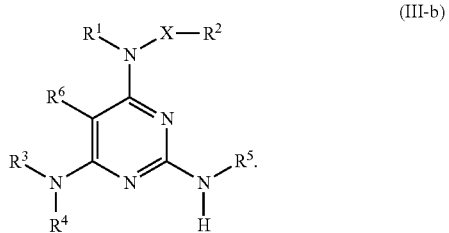

(III-b)

In one embodiment, Y is C, bond b¹ is a single bond, Z is CH₂, bond b² is a single bond, A is CH, and the compound of the invention is a pyrrolidinopyrimidine of formula (IV) or a salt thereof:

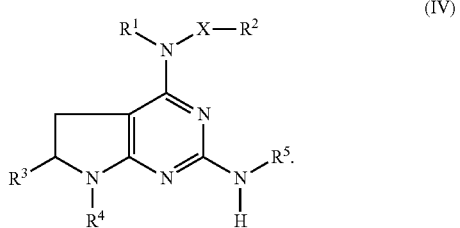

(IV)

In one embodiment, Y is C, bond b¹ is a single bond, Z is CH, bond b² is a double bond, A is C, and the compound of the invention is a pyrrolopyrimidine of formula (V) or a salt thereof:

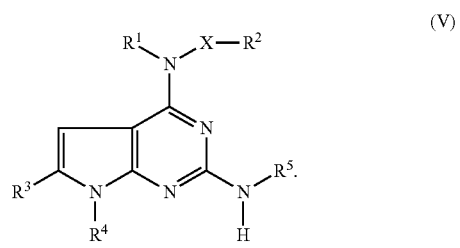

(V)

In one embodiment, the compound of formula (I) is selected from the group consisting of: N-(4,6-Bis-methylamino-[1,3,5]triazin-2-yl)-N,O-dimethyl-hydroxylamine, N-(4,6-Bis-ethylamino-[1,3,5]triazin-2-yl)-N,O-dimethyl-hydroxylamine, N-(4-Cyclopropylmethylamino)-N-(6-n-propylamino) [1,3,5]triazin-2-yl)-N,O-dimethyl-hydroxylamine, N-(4-Ethylamino)-N-(6-n-propylamino)-[1,3,5]triazin-2-yl)-N,O-dimethyl-hydroxylamine, N-(Bis-4,6-(2-methylpropylamino)) [1,3,5]triazin-2-yl)-N,O-dimethyl-hydroxylamine, N-(Bis-4,6-(2,2-dimethylpropylamino)) [1,3,5]triazin-2-yl)-N,O-dimethyl-hydroxylamine, N-(Bis-4,6-(2,2-dimethylpropylamino))[1,3,5]triazin-2-yl)-N,O-dimethyl-hydroxylamine, N-(4,6-Bis-n-propylamino-[1,3,5]triazin-2-yl)-N,O-dimethyl-hydroxylamine, N-(4-(Methoxy(methyl)amino)-6-(propylamino)-1,3,5-triazin-2-yl)propionamide, N-(4,6-Bis-propylamino-[1,3,5]triazin-2-yl)-O-methyl-hydroxylamine, O-Allyl-N-(4,6-bis-propylamino-[1,3,5]triazin-2-yl)-hydroxylamine, N-(4,6-Bis-propylamino-[1,3,5]triazin-2-yl)-hydroxylamine, 6-(Methoxy(methyl)amino)-N2-propyl-1,3,5-triazine-2,4-diamine, N-(4,6-Bis-propylamino-[1,3,5]triazin-2-yl)-N-methyl-hydroxylamine, O-Benzyl-N-(4,6-bis-propylamino-[1,3,5]triazin-2-yl)-N-methyl-hydroxylamine, N-(4,6-Bis-propylamino-[1,3,5]triazin-2-yl)-N-isopropyl-hydroxylamine, 6-[1,2]Oxazinan-2-yl-N,N'-dipropyl-[1,3,5]triazine-2,4-diamine, N-(4,6-Bis-propylamino-[1,3,5]triazin-2-yl)-O-isopropyl-N-methyl-hydroxylamine, O-Benzyl-N-(4,6-bis-propylamino-[1,3,5]triazin-2-yl)-N-ethyl-hydroxylamine, N-(4,6-Bis-propylamino-[1,3,5]triazin-2-yl)-O-isopropyl-hydroxylamine, 6-((Benzyloxy)(isopropyl)amino)-N2,N4-dipropyl-1,3,5-triazine-2,4-diamine, N-(4,6-Bis-propylamino-[1,3,5]triazin-2-yl)-N-ethyl-O-isopropyl-hydroxylamine, N-(4,6-Bis-propylamino-[1,3,5]triazin-2-yl)-O-isobutyl-N-methyl-hydroxylamine, 6-(Methyl(thiophen-2-ylmethoxy)amino)-N2,N4-dipropyl-1,3,5-triazine-2,4-diamine, N-(4,6-Bis-propylamino-[1,3,5]triazin-2-yl)-O-cyclopropylmethyl-N-methyl-hydroxylamine, N-(4,6-Bis-propylamino-[1,3,5]triazin-2-yl)-O-ethyl-N-methyl-hydroxylamine, N-(4,6-Bis-propylamino-[1,3,5]triazin-2-yl)-O-(2,2-difluoro-ethyl)-hydroxylamine, 4-N-(2-Dimethylaminoethyl)amino-6-N-(n-propyl)amino-[1,3,5]triazin-2-yl)-N,O-dimethyl-hydroxylamine, 4-N-(3-(1-N-Methylimidazol-2-yl)-propyl)-amino-6-N-(n-propyl)amino-[1,3,5]triazin-2-yl)-N,O-dimethyl-hydroxylamine, 4-N-(1-N-Methylimidazol-2-yl)-methylamino-6-N-(n-propyl)amino-[1,3,5]triazin-2-yl)-N,O-dimethyl-hydroxylamine, 4,6-Bis-(N-(2-dimethylaminoethyl)amino)-[1,3,5]triazin-2-yl)-N,O-dimethyl-hydroxylamine, 4,6-Bis-(N-(pyridin-4-ylmethyl)amino)-[1,3,5]triazin-2-yl)-N,O-dimethyl-hydroxylamine, 4,6-Bis-[N-(3-methoxy-n-propyl)amino]-[1,3,5]triazin-2-yl)-N,O-dimethyl-hydroxylamine, 4,6-Bis-[N-(tetrahydro-pyran-4-ylmethyl)amino]-[1,3,5]triazin-2-yl)-N,O-dimethyl-hydroxylamine, N-(5,8,11-Trioxa-2,14,16,18,19-pentaazabicyclo[13.3.1]nonadeca-1(18),15(19),16(17)-trien-17-yl)-N,O-dimethylhydroxylamine, 2,6-Bis-(N-propylamino)-[1,3]pyrimidin-4-yl)-N,O-dimethyl-hydroxylamine, N-(4,6-Bis-propylamino-[1,3,5]triazin-2-yl)-N',N'-dimethylhydrazine, N-(4,6-Bis-propylamino-[1,3,5]triazin-2-yl)-N-methyl-N'-methylhydrazine, 2-(n-Propyl)amino-4-(i-propylamino-7-methyl-pyrrolidino[2,3-d]pyrimidine, 2-(n-Propyl)amino-4-dimethylamino-7-methyl-pyrrolidino[2,3-d]pyrimidine, 2-(n-Propyl)amino-4-methylamino-7-methyl-pyrrolidino[2,3-d]pyrimidine, 2-(n-Propyl)amino-4-(i-propyl)amino-7-i-propyl-pyrrolidino[2,3-d]pyrimidine, 2,4-Bis-(n-propyl)amino-7H-pyrrolidino[2,3-d]pyrimidine, 2-(n-Propyl)amino-4-(4-hydroxypiperidin-1-yl)-7-methyl-pyrrolidino[2,3-d]pyrimidine, 8-(7-Methyl-2-(propylamino)-pyrrolidino[2,3-d]pyrimidin-4-yl)-8-azabicyclo[3.2.1]octan-3-ol, N-(2-Propylamino-7H-pyrrolo[2,3d]pyrimidin-4-yl)-N,O-dimethyl-hydroxylamine, N-(2-(Propen-2-yl)amino-7-methyl-pyrrolo[2,3d]pyrimidin-4-yl)-N,O-dimethyl-hydroxylamine, N-(2-(Propen-2-yl)amino-7-methyl-pyrrolo[2,3d]pyrimidin-4-yl)-O-methyl-hydroxylamine, N-(2-n-Propylamino-7-methyl-pyrrolo[2,3d]pyrimidin-4-yl)-N,O-dimethyl-hydroxylamine, N-(2-n-Propylamino-7-methyl-pyrrolo[2,3d]pyrimidin-4-yl)-O-methyl-hydroxylamine, N-(2-n-Propylamino-7-methyl-pyrrolo[2,3d]pyrimidin-4-yl)-hydrazine, N-Methyl-N-(2-n-propylamino-7-methyl-pyrrolo[2,3d]pyrimidin-4-yl)-hydrazine, N,N-Dimethyl-N'-(2-n-propylamino-7-methyl-pyrrolo[2,3d]pyrimidin-4-yl)-hydrazine, a salt thereof and mixtures thereof.

Preparation of the Compounds of the Invention

The compounds of the invention may be prepared according to the general methodology illustrated in the synthetic schemes described below. The reagents and conditions described herein may be modified to allow the preparation of the compounds of the invention, and such modifications are known to those skilled in the art. The scheme included herein are intended to illustrate but not limit the chemistry and methodologies that one skilled in the art may use to make compounds of the invention.

In one aspect, compounds of formula (I) may be prepared by the successive additions of (i) primary amines, (ii) a N-alkoxy-N-alkylamine or (iii) an appropriately substituted hydrazine ($H_2N$—$NHR^2$ or $R^1HN$—$NHR^2$) to suitably chlorinated intermediate (VI), as illustrated below in Scheme 1.

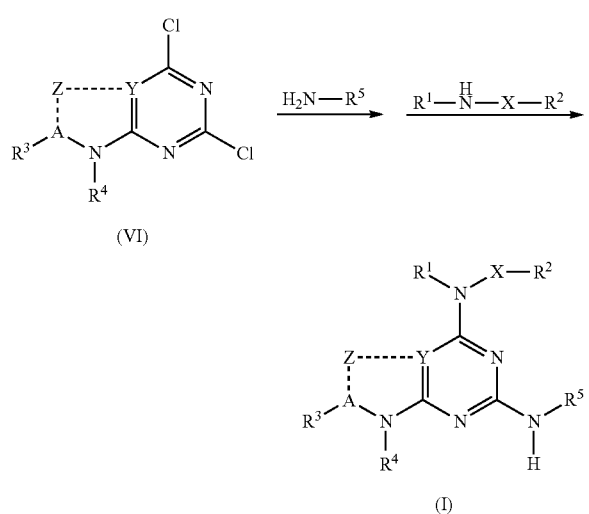

In another aspect, a compound of formula (IV) or (V) may be prepared by reductive alkylation of a suitably chlorinated amino-pyrrolidino-pyrimidine or amino-pyrrolo-pyrimidine, respectively (Scheme 2).

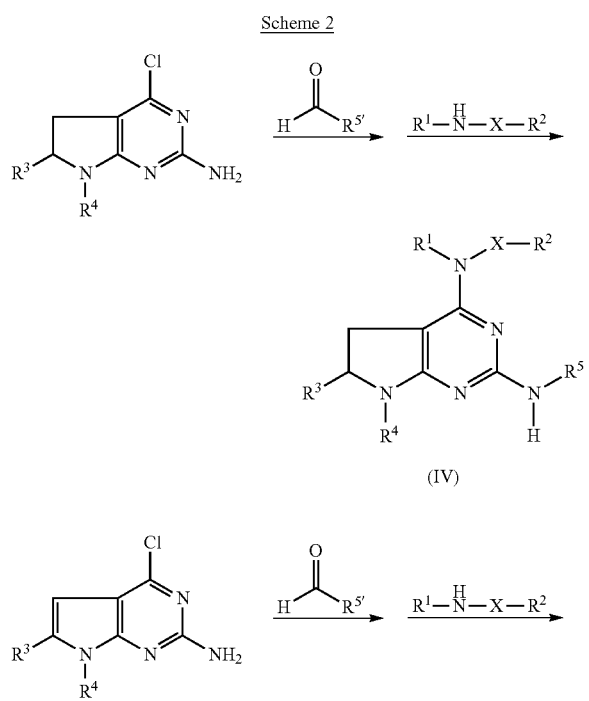

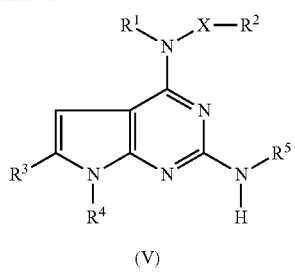

In yet another aspect, a triazine compound of formula (II) may be prepared by the successive additions of primary amines and (i) a N-alkoxy-N-alkylamine, (ii) a hydrazine $H_2N$—$NHR^2$, or (iii) a hydrazine $R^1HN$—$NHR^2$ to a suitably chlorinated triazine. Under appropriate conditions, the reaction may allow the addition of either one or two amine substituents to the triazine ring. Alternatively, first the N-alkoxy-N-alkylamine, the hydrazine $H_2N$—$NHR^2$, or the hydrazine $R^1HN$—$NHR^2$ may be added to the triazine, followed by the addition of the amines.

In a non-limiting example, to a solution of 2,4,6-trichloro-triazine in an appropriate aprotic or protic solvent containing an inorganic or organic base, is added a solution of a primary amine (VII) and the reaction is allowed to proceed at ambient temperature or heated, to isolate mono-amine adduct (VIII) or bis-amine adduct (IX).

In a subsequent reaction, mono-amine adduct (VIII) is reacted with another primary amine or a secondary amine (X) to yield the unsymmetrical monochloro-bis-amino-triazine adduct (XI). In a subsequent reaction, monochloro-bis-amino-triazine adduct (XI) is reacted with (i) a N-alkoxy-N-alkylamine, (ii) a hydrazine $H_2N$—$NHR^2$ or (iii) a hydrazine $R^1HN$—$NHR^2$ in an appropriate aprotic or protic solvent containing an inorganic or organic base to produce desired compounds of formula (II) (Scheme 3).

Alternatively, in a subsequent reaction, bis-amine adduct (IX) is reacted with (i) a N-alkoxy-N-alkylamine, (ii) a hydrazine $H_2N$—$NHR^2$ or (iii) a hydrazine $R^1HN$—$NHR^2$ in an appropriate aprotic or protic solvent containing an inorganic or organic base to produce desired compounds of formula (II), wherein $R^3CH_2$ is $R^5$ (Scheme 4).

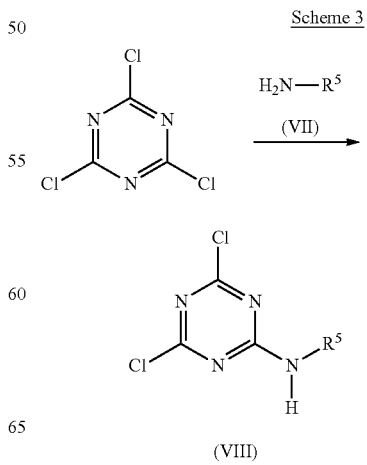

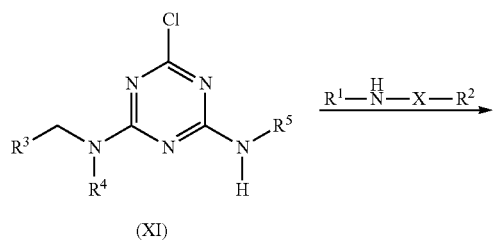

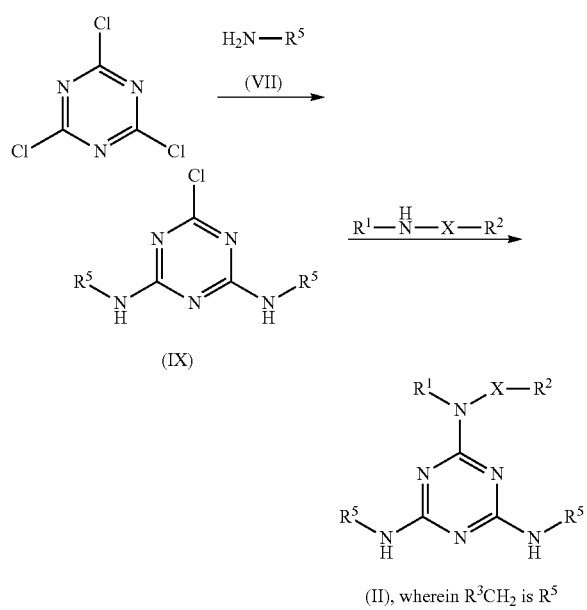

In yet another aspect, the pyrimidine compound of the formula (III) may be prepared by the successive additions of primary amines and (i) a N-alkoxy-N-alkylamine, (ii) a hydrazine $H_2N$—$NHR^2$ or (iii) a hydrazine $R^1HN$—$NHR^2$ to a suitably chlorinated pyrimidine.

In a non-limiting example, to a solution of 2,4,6-trichloropyrimidine (XII) in an appropriate aprotic or protic solvent containing an inorganic or organic base is added a solution of a primary amine (VII) and the reaction is allowed to proceed at ambient temperature or heated, yielding bis-amine adduct (XIII). In a subsequent reaction, bis-amine adduct (XIII) is reacted with (i) a N-alkoxy-N-alkylamine, (ii) a hydrazine $H_2N$—$NHR^2$, or (iii) a hydrazine $R^1HN$—$NHR^2$ in an appropriate aprotic or protic solvent containing an inorganic or organic base to produce desired compounds of formula (III) (Scheme 5).

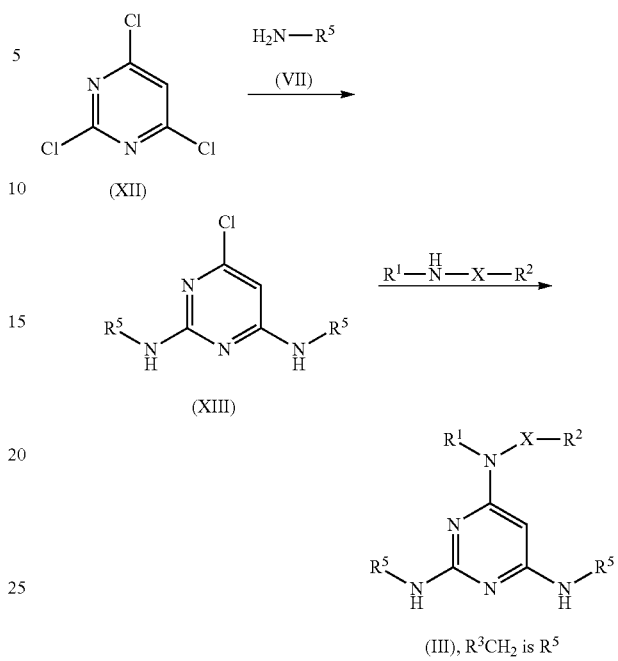

In yet another aspect, a pyrrolidino-pyrimidine of formula (IV) or a pyrrolo-pyrimidine compounds of formula (V) may be prepared from an appropriately chlorinated aminopyrrolidinopyrimidine or aminopyrrolopyrimidine intermediate, respectively.

In a non-limiting example, 2-chloroacetaldehyde may be added to a solution of 2,6-diamino-4-hydroxy-1,3-pyrimidine (XIV) in a polar protic solvent, at ambient temperature or under heating, to yield cyclized adduct (XV). Subsequent treatment with a chlorinating agent, such as, but not limited to, phosphorous oxychloride produces the chloro intermediate (XVI). Intermediate (XVI) may be submitted to reductive alkylation with an aldehyde in the presence of a reducing agent, such as a borohydride (in a non-limiting example, cyanoborohydride) in a protic solvent, at ambient temperature or elevated temperature, to produce the amino substituted adduct (XVII). In a subsequent reaction, amino substituted adduct (XVII) is reacted with (i) a N-alkoxy-N-alkylamine, (ii) a hydrazine $H_2N$—$NHR^2$, or (iii) a hydrazine $R^1HN$—$NHR^2$ in an appropriate aprotic or protic solvent containing an inorganic or organic base to produce desired compounds of formula (V), wherein $R^3$ and $R^4$ are H (Scheme 6).

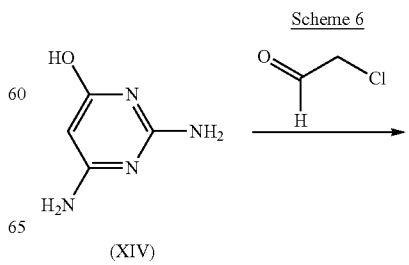

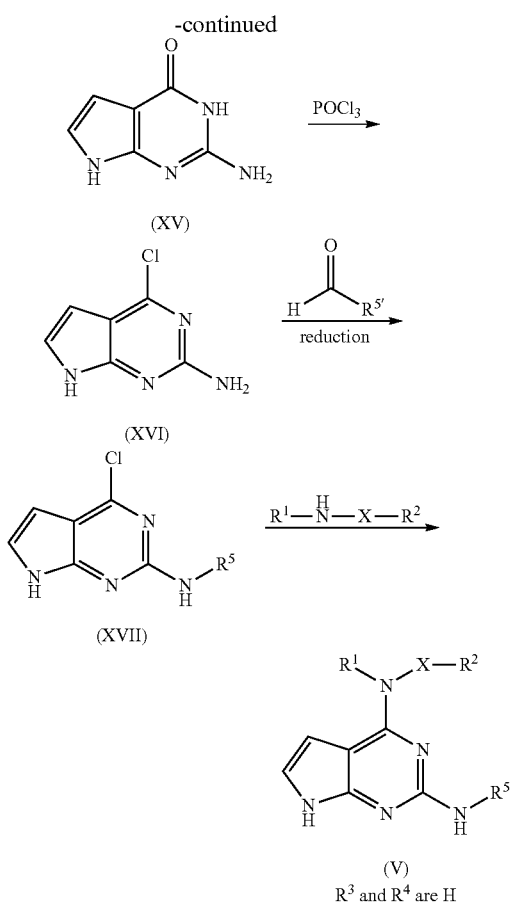

In a non-limiting example, a pyrrolidinopyrimidine compound of the formula (IV) may be prepared from the corresponding pyrrolopyrimidine analog via reduction (Scheme 7).

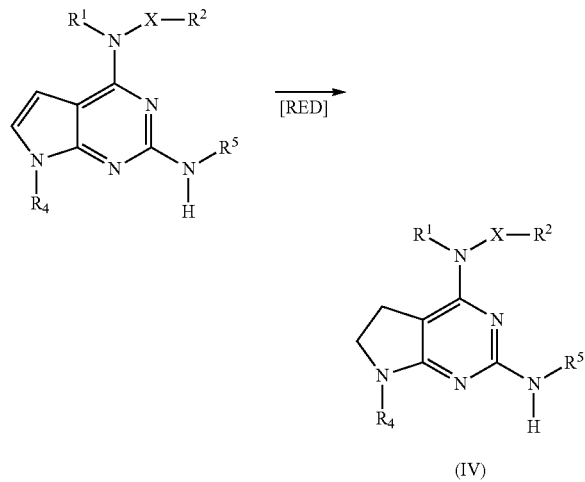

Salts

The compounds described herein may form salts with acids, and such salts are included in the present invention. In one embodiment, the salts are pharmaceutically acceptable salts. The term "salts" embraces addition salts of free acids that are useful within the methods of the invention. The term "pharmaceutically acceptable salt" refers to salts that possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds useful within the methods of the invention.

Suitable pharmaceutically acceptable acid addition salts may be prepared from an inorganic acid or from an organic acid. Examples of inorganic acids include sulfate, hydrogen sulfate, hydrochloric, hydrobromic, hydriodic, nitric, carbonic, sulfuric, and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylenediamine, chloroprocaine, choline, diethanolamine, ethylenediamine, meglumine (N-methylglucamine) and procaine. All of these salts may be prepared from the corresponding compound by reacting, for example, the appropriate acid or base with the compound.

Combination Therapies

In one embodiment, the compounds of the invention are useful in the methods of present invention in combination with at least one additional compound useful for treating breathing control disorders. These additional compounds may comprise compounds of the present invention or other compounds, such as commercially available compounds, known to treat, prevent, or reduce the symptoms of breathing disorders. In embodiment, the combination of at least one compound of the invention or a salt thereof and at least one additional compound useful for treating breathing disorders has additive, complementary or synergistic effects in the treatment of disordered breathing, and in the treatment of sleep-related breathing disorders.

In a non-limiting example, the compounds of the invention or a salt thereof may be used in combination with one or more of the following drugs: acetazolamide, almitrine, theophylline, caffeine, methylprogesterone and related compounds, serotinergic modulators, cannabinoids (such as but not limited to dronabinol), and compounds known as ampakines. Non-limiting examples of ampakines are the pyrrolidine derivative racetam drugs such as piracetam and aniracetam; the "CX-" series of drugs which encompass a range of benzoylpiperidine and benzoylpyrrolidine structures, such as CX-516 (6-(piperidin-1-yl-carbonyl)quinoxaline), CX-546 (2,3-dihydro-1,4-benzodioxin-7-yl-(1-piperidyl)-methanone), CX-614 (2H,3H,6aH-pyrrolidino(2,1-3',2')-1,3-oxazino-(6',5'-5,4)benzo(e)1,4-dioxan-10-one), CX-691 (2,1, 3-benzoxadiazol-6-yl-piperidin-1-yl-methanone), CX-717, CX-701, CX-1739, CX-1763, and CX-1837; benzothiazide derivatives such as cyclothiazide and IDRA-21 (7-chloro-3-methyl-3,4-dihydro-2H-1,2,4-benzothiadiazine 1,1-dioxide); biarylpropylsulfonamides such as LY-392,098, LY-404, 187 (N-[2-(4'-cyanobiphenyl-4-yl)propyl]propane-2-sulfonamide), LY-451,646 and LY-503,430 (4'-{(1S)-1-fluoro-2-[(isopropylsulfonyl)amino]-1-methylethyl}-N-methylbiphenyl-4-carboxamide).

A synergistic effect may be calculated, for example, using suitable methods such as, for example, the Sigmoid-$E_{max}$ equation (Holford & Scheiner, 19981, Clin. Pharmacokinet. 6: 429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22: 27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Methods of the Invention

In one aspect, the present invention includes a method of preventing or treating a breathing control disorder or disease in a subject in need thereof. The method includes the step of administering to the subject an effective amount of a pharmaceutical formulation comprising at least a pharmaceutically acceptable carrier and at least one compound of formula (I):

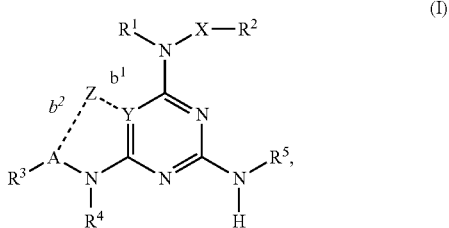

(I)

$R^1$ and $R^2$ are independently H, alkyl, substituted alkyl, cycloalkyl, substituted cycloalkyl, alkenyl, substituted alkenyl, phenyl, substituted phenyl, phenylalkyl, substituted phenylalkyl, aryl, substituted aryl, arylalkyl, substituted arylalkyl, heteroarylalkyl, substituted heteroarylalkyl, heteroaryl or substituted heteroaryl; or $R^1$ and $R^2$ combine as to form a biradical selected from the group consisting of 3-hydroxy-pentane-1,5-diyl, 6-hydroxy-cycloheptane-1,4-diyl, propane-1,3-diyl, butane-1,4-diyl and pentane-1,5-diyl;

$R^3$ is H, alkyl, substituted alkyl, cycloalkyl, substituted cycloalkyl, alkenyl, substituted alkenyl, —$NR^1R^2$, —C(O)$OR^1$, acyl, or aryl;

$R^4$ is H, alkyl, or substituted alkyl;

$R^5$ is H, alkyl, substituted alkyl, cycloalkyl, substituted cycloalkyl, alkenyl, substituted alkenyl, —$OR^1$, —$NR^1R^2$, —C(O)$OR^1$, acyl, aryl, substituted aryl, heteroaryl, substituted heteroaryl, heterocyclic, or substituted heterocyclic; or $R^3$ and $R^5$ combine as to form a biradical selected from the group consisting of 3,6,9-trioxa-undecane-1,11-diyl and 3,6-dioxa-octane-1,8-diyl;

$R^6$ is H, alkyl, substituted alkyl or alkenyl;

X is a bond, O or $NR^4$; and,

Y is N, $CR^6$ or C; wherein:

if Y is N or $CR^6$, then bond $b^1$ is nil and:

(i) Z is H, bond $b^2$ is a single bond, and A is CH; or, (ii) Z is nil, bond $b^2$ is nil, and A is a single bond; and, if Y is C, then bond $b^1$ is a single bond, and:

(i) Z is $CH_2$, bond $b^2$ is a single bond, and A is CH; or, (ii) Z is CH, bond $b^2$ is a double bond, and A is C;

or a salt thereof.

In another aspect, the present invention includes a method of preventing destabilization of or stabilizing breathing rhythm in a subject in need thereof. The method includes the step of administering to the subject an effective amount of a pharmaceutical formulation comprising at least a pharmaceutically acceptable carrier and at least one compound of formula (I) or a salt thereof.

In one embodiment, administering the formulation of the invention stabilizes the breathing rhythm of the subject. In another embodiment, administering the formulation of the invention increases minute ventilation in the subject.

In one embodiment, the destabilization is associated with a breathing control disorder or disease.

In one embodiment, the breathing disorder or disease is selected from the group consisting of narcotic-induced respiratory depression, anesthetic-induced respiratory depression, sedative-induced respiratory depression, anxiolytic-induced respiratory depression, hypnotic-induced respiratory depression, alcohol-induced respiratory depression, analgesic-induced respiratory depression, sleep apnea, apnea of prematurity, obesity-hypoventilation syndrome, primary alveolar hypoventilation syndrome, dyspnea, altitude sickness, hypoxia, hypercapnia and chronic obstructive pulmonary disease (COPD). In another embodiment, the respiratory depression is caused by an anesthetic, a sedative, an anxiolytic agent, a hypnotic agent, alcohol or a narcotic.

In one embodiment, the subject is further administered at least one additional compound useful for treating the breathing disorder or disease. In another embodiment, the at least one additional compound is selected from the group consisting of acetazolamide, almitrine, theophylline, caffeine, methylprogesterone and related compounds, a serotinergic modulator, a cannabinoid, and an ampakine. In yet another embodiment, the formulation is administered to the subject in conjunction with the use of a mechanical ventilation device or positive airway pressure device. In one embodiment, the formulation is administered to the subject by an inhalational, topical, oral, buccal, rectal, vaginal, intramuscular, subcutaneous, transdermal, intrathecal or intravenous route. In another embodiment, the subject is a mammal including but not limited to mouse, rat, ferret, guinea pig, monkey, dog, cat, horse, cow, pig and other farm animals. In one embodiment, the subject is a human. In another embodiment, the at least one compound of formula (I) is selected from the group consisting of: N-(4,6-Bis-methylamino-[1,3,5]triazin-2-yl)-N,O-dimethyl-hydroxylamine, N-(4,6-Bis-ethylamino-[1,3,5]triazin-2-yl)-N,O-dimethyl-hydroxylamine, N-(4-Cyclopropylmethylamino)-N-(6-n-propylamino) [1,3,5]triazin-2-yl)-N,O-dimethyl-hydroxylamine, N-(4-Ethylamino)-N-(6-n-propylamino)-[1,3,5]triazin-2-yl)-N,O-dimethyl-hydroxylamine, N-(Bis-4,6-(2-methylpropylamino)) [1,3,5]triazin-2-yl)-N,O-dimethyl-hydroxylamine, N-(Bis-4,6-(2,2-dimethylpropylamino)) [1,3,5]triazin-2-yl)-N,O-dimethyl-hydroxylamine, N-(Bis-4,6-(2,2-dimethylpropylamino))[1,3,5]triazin-2-yl)-N,O-dimethyl-hydroxylamine, N-(4,6-Bis-n-propylamino-[1,3,5]triazin-2-yl)-N,O-dimethyl-hydroxylamine, N-(4-(Methoxy(methyl)amino)-6-(propylamino)-1,3,5-triazin-2-yl)propionamide, N-(4,6-Bis-propylamino-[1,3,5]triazin-2-yl)-O-methyl-hydroxylamine, O-Allyl-N-(4,6-bis-propylamino-[1,3,5]triazin-2-yl)-hydroxylamine, N-(4,6-Bis-propylamino-[1,3,5]

triazin-2-yl)-hydroxylamine, 6-(Methoxy(methyl)amino)-N2-propyl-1,3,5-triazine-2,4-diamine, N-(4,6-Bis-propylamino-[1,3,5]triazin-2-yl)-N-methyl-hydroxylamine, O-Benzyl-N-(4,6-bis-propylamino-[1,3,5]triazin-2-yl)-N-methyl-hydroxylamine, N-(4,6-Bis-propylamino-[1,3,5]triazin-2-yl)-N-isopropyl-hydroxylamine, 6-[1,2]Oxazinan-2-yl-N,N'-dipropyl-[1,3,5]triazine-2,4-diamine, N-(4,6-Bis-propylamino-[1,3,5]triazin-2-yl)-O-isopropyl-N-methyl-hydroxylamine, O-Benzyl-N-(4,6-bis-propylamino-[1,3,5]triazin-2-yl)-N-ethyl-hydroxylamine, N-(4,6-Bis-propylamino-[1,3,5]triazin-2-yl)-O-isopropyl-hydroxylamine, 6-((Benzyloxy)(isopropyl)amino)-N2,N4-dipropyl-1,3,5-triazine-2,4-diamine, N-(4,6-Bis-propylamino-[1,3,5]triazin-2-yl)-N-ethyl-O-isopropyl-hydroxylamine, N-(4,6-Bis-propylamino-[1,3,5]triazin-2-yl)-O-isobutyl-N-methyl-hydroxylamine, 6-(Methyl(thiophen-2-ylmethoxy)amino)-N2,N4-dipropyl-1,3,5-triazine-2,4-diamine, N-(4,6-Bis-propylamino-[1,3,5]triazin-2-yl)-O-cyclopropylmethyl-N-methyl-hydroxylamine, N-(4,6-Bis-propylamino-[1,3,5]triazin-2-yl)-O-ethyl-N-methyl-hydroxylamine, N-(4,6-Bis-propylamino-[1,3,5]triazin-2-yl)-O-(2,2-difluoro-ethyl)-hydroxylamine, 4-N-(2-Dimethylaminoethyl)amino-6-N-(n-propyl)amino-[1,3,5]triazin-2-yl)-N,O-dimethyl-hydroxylamine, 4-N-(3-(1-N-Methylimidazol-2-yl)-propyl)-amino-6-N-(n-propyl)amino-[1,3,5]triazin-2-yl)-N,O-dimethyl-hydroxylamine, 4-N-(1-N-Methylimidazol-2-yl)-methylamino-6-N-(n-propyl)amino-[1,3,5]triazin-2-yl)-N,O-dimethyl-hydroxylamine, 4,6-Bis-(N-(2-dimethylaminoethyl)amino)-[1,3,5]triazin-2-yl)-N,O-dimethyl-hydroxylamine, 4,6-Bis-(N-(pyridin-4-yl-methyl)amino)-[1,3,5]triazin-2-yl)-N,O-dimethyl-hydroxylamine, 4,6-Bis-[N-(3-methoxy-n-propyl)amino]-[1,3,5]triazin-2-yl)-N,O-dimethyl-hydroxylamine, 4,6-Bis-[N-(tetrahydropyran-4-ylmethyl)amino]-[1,3,5]triazin-2-yl)-N,O-dimethyl-hydroxylamine, N-(5,8,11-Trioxa-2,14,16,18,19-pentaazabicyclo[13.3.1]nonadeca-1(18),15(19),16(17)-trien-17-yl)-N,O-dimethylhydroxylamine, 2,6-Bis-(N-propylamino)-[1,3]pyrimidin-4-yl)-N,O-dimethyl-hydroxylamine, N-(4,6-Bis-propylamino-[1,3,5]triazin-2-yl)-N',N'-dimethylhydrazine, N-(4,6-Bis-propylamino-[1,3,5]triazin-2-yl)-N-methyl-N'-methylhydrazine, 2-(n-Propyl)amino-4-(i-propylamino-7-methyl-pyrrolidino[2,3-d]pyrimidine, 2-(n-Propyl)amino-4-dimethylamino-7-methyl-pyrrolidino[2,3-d]pyrimidine, 2-(n-Propyl)amino-4-methylamino-7-methyl-pyrrolidino[2,3-d]pyrimidine, 2-(n-Propyl)amino-4-(i-propyl)amino-7-i-propyl-pyrrolidino[2,3-d]pyrimidine, 2,4-Bis-(n-propyl)amino-7H-pyrrolidino[2,3-d]pyrimidine, 2-(n-Propyl)amino-4-(4-hydroxypiperidin-1-yl)-7-methyl-pyrrolidino[2,3-d]pyrimidine, 8-(7-Methyl-2-(propylamino)-pyrrolidino[2,3-d]pyrimidin-4-yl)-8-azabicyclo[3.2.1]octan-3-ol, N-(2-Propylamino-7H-pyrrolo[2,3d]pyrimidin-4-yl)-N,O-dimethyl-hydroxylamine, N-(2-(Propen-2-yl)amino-7-methyl-pyrrolo[2,3d]pyrimidin-4-yl)-N,O-dimethyl-hydroxylamine, N-(2-(Propen-2-yl)amino-7-methyl-pyrrolo[2,3d]pyrimidin-4-yl)-O-methyl-hydroxylamine, N-(2-n-Propylamino-7-methyl-pyrrolo[2,3d]pyrimidin-4-yl)-N,O-dimethyl-hydroxylamine, N-(2-n-Propylamino-7-methyl-pyrrolo[2,3d]pyrimidin-4-yl)-O-methyl-hydroxylamine, N-(2-n-Propylamino-7-methyl-pyrrolo[2,3d]pyrimidin-4-yl)-hydrazine, N-Methyl-N-(2-n-propylamino-7-methyl-pyrrolo[2,3d]pyrimidin-4-yl)-hydrazine, N,N-Dimethyl-N'-(2-n-propylamino-7-methyl-pyrrolo[2,3d]pyrimidin-4-yl)-hydrazine, a salt thereof and mixtures thereof.

Pharmaceutical Compositions and Formulations

The invention also encompasses the use of pharmaceutical compositions of at least one compound of the invention or a salt thereof to practice the methods of the invention.

Such a pharmaceutical composition may consist of at least one compound of the invention or a salt thereof, in a form suitable for administration to a subject, or the pharmaceutical composition may comprise at least one compound of the invention or a salt thereof, and one or more pharmaceutically acceptable carriers, one or more additional ingredients, or some combination of these. The at least one compound of the invention may be present in the pharmaceutical composition in the form of a physiologically acceptable salt, such as in combination with a physiologically acceptable cation or anion, as is well known in the art.

In an embodiment, the pharmaceutical compositions useful for practicing the method of the invention may be administered to deliver a dose of between 1 ng/kg/day and 100 mg/kg/day. In another embodiment, the pharmaceutical compositions useful for practicing the invention may be administered to deliver a dose of between 1 ng/kg/day and 500 mg/kg/day.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

Pharmaceutical compositions that are useful in the methods of the invention may be suitably developed for inhalational, oral, rectal, vaginal, parenteral, topical, transdermal, pulmonary, intranasal, buccal, ophthalmic, intrathecal, intravenous or another route of administration. A composition useful within the methods of the invention may be directly administered to the brain, the brainstem, or any other part of the central nervous system of a mammal. Other contemplated formulations include projected nanoparticles, liposomal preparations, resealed erythrocytes containing the active ingredient, and immunologically-based formulations. The route(s) of administration will be readily apparent to the skilled artisan and will depend upon any number of factors including the type and severity of the disease being treated, the type and age of the veterinary or human patient being treated, and the like.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

As used herein, a "unit dose" is a discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage. The unit dosage form may be for a single daily dose or one of multiple daily doses (e.g., about 1 to 4 or more times per day). When multiple daily doses are used, the unit dosage form may be the same or different for each dose.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

In one embodiment, the compositions of the invention are formulated using one or more pharmaceutically acceptable excipients or carriers. In one embodiment, the pharmaceutical compositions of the invention comprise a therapeutically effective amount of at least one compound of the invention and a pharmaceutically acceptable carrier. Pharmaceutically acceptable carriers, which are useful, include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions may be brought about by including in the composition an agent that delays absorption, for example, aluminum monostearate or gelatin. In one embodiment, the pharmaceutically acceptable carrier is not DMSO alone.

Formulations may be employed in admixtures with conventional excipients, i.e., pharmaceutically acceptable organic or inorganic carrier substances suitable for oral, parenteral, nasal, inhalational, intravenous, subcutaneous, transdermal enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents. As used herein, "additional ingredients" include, but are not limited to, one or more ingredients that may be used as a pharmaceutical carrier.

The composition of the invention may comprise a preservative from about 0.005% to 2.0% by total weight of the composition. The preservative is used to prevent spoilage in the case of exposure to contaminants in the environment. Examples of preservatives useful in accordance with the invention included but are not limited to those selected from the group consisting of benzyl alcohol, sorbic acid, parabens, imidurea and combinations thereof. A particularly preferred preservative is a combination of about 0.5% to 2.0% benzyl alcohol and 0.05% to 0.5% sorbic acid.

The composition preferably includes an antioxidant and a chelating agent which inhibit the degradation of the compound. Preferred antioxidants for some compounds are BHT, BHA, alpha-tocopherol and ascorbic acid in the preferred range of about 0.01% to 0.3% and more preferably BHT in the range of 0.03% to 0.1% by weight by total weight of the composition. Preferably, the chelating agent is present in an amount of from 0.01% to 0.5% by weight by total weight of the composition. Particularly preferred chelating agents include edetate salts (e.g. disodium edetate) and citric acid in the weight range of about 0.01% to 0.20% and more preferably in the range of 0.02% to 0.10% by weight by total weight of the composition. The chelating agent is useful for chelating metal ions in the composition which may be detrimental to the shelf life of the formulation. While BHT and disodium edetate are the particularly preferred antioxidant and chelating agent respectively for some compounds, other suitable and equivalent antioxidants and chelating agents may be substituted therefore as would be known to those skilled in the art.

Liquid suspensions may be prepared using conventional methods to achieve suspension of the active ingredient in an aqueous or oily vehicle. Aqueous vehicles include, for example, water, and isotonic saline. Oily vehicles include, for example, almond oil, oily esters, ethyl alcohol, vegetable oils such as *arachis*, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. As used herein, an "oily" liquid is one which comprises a carbon-containing liquid molecule and which exhibits a less polar character than water. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water, and isotonic saline. Oily solvents include, for example, almond oil, oily esters, ethyl alcohol, vegetable oils such as *arachis*, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or *arachis* oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

Administration/Dosing

The regimen of administration may affect what constitutes an effective amount. The therapeutic formulations may be administered to the patient either prior to or after the onset of a breathing disorder event. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, preferably a mammal, more preferably a human, may be carried out using known procedures, at dosages and for periods of time effective to treat a breathing control disorder in the patient. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the patient being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 0.01 mg/kg and 50 mg/kg of body weight/per day. One of ordinary skill in the art would be able to study the relevant factors and make the determination regarding the effective amount of the therapeutic compound without undue experimentation.

The compound can be administered to an animal as frequently as several times daily, or it may be administered less frequently, such as once a day, once a week, once every two weeks, once a month, or even less frequently, such as once every several months or even once a year or less. It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on. The frequency of the dose will be readily apparent to the skilled artisan and will depend upon any number of factors, such as, but not limited to, the type and severity of the disease being treated, the type and age of the animal, etc.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of breathing disorders in a patient.

In one embodiment, the compositions of the invention are administered to the patient in dosages that range from one to five times per day or more. In another embodiment, the compositions of the invention are administered to the patient in range of dosages that include, but are not limited to, once every day, every two, days, every three days to once a week, and once every two weeks. It will be readily apparent to one skilled in the art that the frequency of administration of the various combination compositions of the invention will vary from subject to subject depending on many factors including, but not limited to, age, disease or disorder to be treated, gender, overall health, and other factors. Thus, the invention should not be construed to be limited to any particular dosage regime and the precise dosage and composition to be administered to any patient will be determined by the attending physical taking all other factors about the patient into account.

Compounds of the invention for administration may be in the range of from about 1 μg to about 7,500 mg, about 20 μg to about 7,000 mg, about 40 μg to about 6,500 mg, about 80 μg to about 6,000 mg, about 100 μg to about 5,500 mg, about 200 μg to about 5,000 mg, about 400 μg to about 4,000 mg, about 800 μg to about 3,000 mg, about 1 mg to about 2,500 mg, about 2 mg to about 2,000 mg, about 5 mg to about 1,000 mg, about 10 mg to about 750 mg, about 20 mg to about 600 mg, about 30 mg to about 500 mg, about 40 mg to about 400 mg, about 50 mg to about 300 mg, about 60 mg to about 250 mg, about 70 mg to about 200 mg, about 80 mg to about 150 mg, and any and all whole or partial increments thereinbetween.

In some embodiments, the dose of a compound of the invention is from about 0.5 μg and about 5,000 mg. In some embodiments, a dose of a compound of the invention used in compositions described herein is less than about 5,000 mg, or less than about 4,000 mg, or less than about 3,000 mg, or less than about 2,000 mg, or less than about 1,000 mg, or less than about 800 mg, or less than about 600 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In one embodiment, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of breathing disorder in a patient.

The term "container" includes any receptacle for holding the pharmaceutical composition. For example, in one embodiment, the container is the packaging that contains the pharmaceutical composition. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, e.g., treating, preventing, or reducing a breathing disorder in a patient.

Routes of Administration

Routes of administration of any of the compositions of the invention include inhalational, oral, nasal, rectal, parenteral, sublingual, transdermal, transmucosal (e.g., sublingual, lingual, (trans)buccal, (trans)urethral, vaginal (e.g., trans- and perivaginally), (intra)nasal, and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. Other formulations suitable for oral administration include, but are not limited to, a powdered or granular formulation, an aqueous or oily suspension, an aqueous or oily solution, a paste, a gel, toothpaste, a mouthwash, a coating, an oral rinse, or an emulsion. The compositions intended for oral use may be prepared according to any method known in the art and such compositions may contain one or more agents selected from the group consisting of inert, non-toxic pharmaceutically excipients which are suitable for the manufacture of tablets. Such excipients include, for example an inert diluent such as lactose; granulating and disintegrating agents such as cornstarch; binding agents such as starch; and lubricating agents such as magnesium stearate.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically controlled release tablets. Tablets may further comprise a sweetening agent, a flavoring agent, a coloring agent, a preservative, or some combination of these in order to provide for pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

For oral administration, the compounds of the invention may be in the form of tablets or capsules prepared by conventional means with pharmaceutically acceptable excipients such as binding agents; fillers; lubricants; disintegrates; or wetting agents. If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400).

Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl para-hydroxy benzoates or sorbic acid). Liquid formulations of a pharmaceutical composition of the invention which are suitable for oral administration may be prepared, packaged, and sold either in liquid form or in the form of a dry product intended for reconstitution with water or another suitable vehicle prior to use.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface-active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e. having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e. drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) will melt.

The present invention also includes a multi-layer tablet comprising a layer providing for the delayed release of one or more compounds useful within the methods of the invention, and a further layer providing for the immediate release of one or more compounds useful within the methods of the invention. Using a wax/pH-sensitive polymer mix, a gastric insoluble composition may be obtained in which the active ingredient is entrapped, ensuring its delayed release.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intravenous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

Topical Administration

An obstacle for topical administration of pharmaceuticals is the stratum corneum layer of the epidermis. The stratum corneum is a highly resistant layer comprised of protein, cholesterol, sphingolipids, free fatty acids and various other lipids, and includes cornified and living cells. One of the factors that limit the penetration rate (flux) of a compound through the stratum corneum is the amount of the active substance that can be loaded or applied onto the skin surface. The greater the amount of active substance which is applied per unit of area of the skin, the greater the concentration gradient between the skin surface and the lower layers of the skin, and in turn the greater the diffusion force of the active substance through the skin. Therefore, a formulation containing a greater concentration of the active substance is more likely to result in penetration of the active substance through the skin, and more of it, and at a more consistent rate, than a formulation having a lesser concentration, all other things being equal.

Formulations suitable for topical administration include, but are not limited to, liquid or semi-liquid preparations such as liniments, lotions, oil-in-water or water-in-oil emulsions such as creams, ointments or pastes, and solutions or suspensions. Topically administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

Enhancers of permeation may be used. These materials increase the rate of penetration of drugs across the skin. Typical enhancers in the art include ethanol, glycerol monolaurate, PGML (polyethylene glycol monolaurate), dimethylsulfoxide, and the like. Other enhancers include oleic acid, oleyl alcohol, ethoxydiglycol, laurocapram, alkanecarboxylic acids, dimethylsulfoxide, polar lipids, or N-methyl-2-pyrrolidone.

One acceptable vehicle for topical delivery of some of the compositions of the invention may contain liposomes. The composition of the liposomes and their use are known in the art (for example, see Constanza, U.S. Pat. No. 6,323,219).

In alternative embodiments, the topically active pharmaceutical composition may be optionally combined with other ingredients such as adjuvants, antioxidants, chelating agents, surfactants, foaming agents, wetting agents, emulsifying agents, viscosifiers, buffering agents, preservatives, and the like. In another embodiment, a permeation or penetration enhancer is included in the composition and is effective in improving the percutaneous penetration of the active ingredient into and through the stratum corneum with respect to a composition lacking the permeation enhancer. Various permeation enhancers, including oleic acid, oleyl alcohol, ethoxydiglycol, laurocapram, alkanecarboxylic acids, dimethylsulfoxide, polar lipids, or N-methyl-2-pyrrolidone, are known to those of skill in the art. In another aspect, the composition may further comprise a hydrotropic agent, which functions to increase disorder in the structure of the stratum corneum, and thus allows increased transport across the stratum corneum. Various hydrotropic agents such as isopropyl alcohol, propylene glycol, or sodium xylene sulfonate, are known to those of skill in the art.

The topically active pharmaceutical composition should be applied in an amount effective to affect desired changes. As used herein "amount effective" shall mean an amount sufficient to cover the region of skin surface where a change is desired. An active compound should be present in the amount of from about 0.0001% to about 15% by weight volume of the composition. More preferable, it should be present in an amount from about 0.0005% to about 5% of the composition; most preferably, it should be present in an amount of from about 0.001% to about 1% of the composition. Such compounds may be synthetically-or naturally derived.

Buccal Administration

A pharmaceutical composition of the invention may be prepared, packaged, or sold in a formulation suitable for buccal administration. Such formulations may, for example, be in the form of tablets or lozenges made using conventional methods, and may contain, for example, 0.1 to 20% (w/w) of the active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein. The examples of formulations described herein are not exhaustive and it is understood that the invention includes additional modifications of these and other formulations not described herein, but which are known to those of skill in the art.

Rectal Administration

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e., about 20° C.) and which is liquid at the rectal temperature of the subject (i.e., about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants, and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants, and preservatives.

Additional Administration Forms

Additional dosage forms of this invention include dosage forms as described in U.S. Pat. Nos. 6,340,475, 6,488,962, 6,451,808, 5,972,389, 5,582,837, and 5,007,790. Additional dosage forms of this invention also include dosage forms as described in U.S. Patent Applications Nos. 20030147952, 20030104062, 20030104053, 20030044466, 20030039688, and 20020051820. Additional dosage forms of this invention also include dosage forms as described in PCT Applications Nos. WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757.

Controlled Release Formulations and Drug Delivery Systems

Controlled- or sustained-release formulations of a pharmaceutical composition of the invention may be made using conventional technology. In some cases, the dosage forms to be used can be provided as slow or controlled-release of one or more active ingredients therein using, for example, hydropropylmethyl cellulose, other polymer matrices, gels, permeable membranes, osmotic systems, multilayer coatings, microparticles, liposomes, or microspheres or a combination thereof to provide the desired release profile in varying proportions. Suitable controlled-release formulations known to those of ordinary skill in the art, including those described herein, can be readily selected for use with the pharmaceutical compositions of the invention. Thus, single unit dosage forms suitable for oral administration, such as tablets, capsules, gelcaps, and caplets, that are adapted for controlled-release are encompassed by the present invention.

Most controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood level of the drug, and thus can affect the occurrence of side effects.

Most controlled-release formulations are designed to initially release an amount of drug that promptly produces the desired therapeutic effect, and gradually and continually release of other amounts of drug to maintain this level of therapeutic effect over an extended period of time. In order to maintain this constant level of drug in the body, the drug must be released from the dosage form at a rate that will replace the amount of drug being metabolized and excreted from the body.

Controlled-release of an active ingredient can be stimulated by various inducers, for example pH, temperature, enzymes, water, or other physiological conditions or compounds. The term "controlled-release component" in the context of the present invention is defined herein as a compound or compounds, including, but not limited to, polymers, polymer matrices, gels, permeable membranes, liposomes, or microspheres or a combination thereof that facilitates the controlled-release of the active ingredient.

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release that is longer that the same amount of agent administered in bolus form.

For sustained release, the compounds may be formulated with a suitable polymer or hydrophobic material which provides sustained release properties to the compounds. As such, the compounds for use the method of the invention may be administered in the form of microparticles, for example, by injection or in the form of wafers or discs by implantation.

In a preferred embodiment of the invention, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that may, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Mechanical Devices

In one aspect of the invention, a method of treating a patient lacking normal breathing and normal breathing control comprises administering the composition useful within the invention as described herein, and additionally treating the patient using a device for treatment of a lack of normal breathing. Such devices include, but are not limited to, ventilation devices, CPAP and BiPAP devices.

Mechanical ventilation is a method to mechanically assist or replace spontaneous breathing. Mechanical ventilation is typically used after an invasive intubation, a procedure wherein an endotracheal or tracheostomy tube is inserted into the airway. It is normally used in acute settings, such as in the ICU, for a short period of time during a serious illness. It may also be used at home or in a nursing or rehabilitation institution, if patients have chronic illnesses that require long-term ventilation assistance. The main form of mechanical ventilation is positive pressure ventilation, which works by increasing the pressure in the patient's airway and thus forcing air into the lungs. Less common today are negative pressure ventilators (for example, the "iron lung") that create a negative pressure environment around the patient's chest, thus sucking air into the lungs. Mechanical ventilation is often a life-saving intervention, but carries many potential complications including pneumothorax, airway injury, alveolar damage, and ventilator-associated pneumonia. For this reason the pressure and volume of gas used is strictly controlled, and reduced as soon as possible. Types of mechanical ventilation are: conventional ventilation, high frequency ventilation, non-invasive ventilation (non-invasive positive pressure pentilation or NIPPV), proportional assist ventilation (PAV), adaptive support ventilation (ASV) and neurally adjusted ventilatory assist (NAVA).

Non-invasive ventilation refers to all modalities that assist ventilation without the use of an endotracheal tube. Non-invasive ventilation is primarily aimed at minimizing patient discomfort and the complications associated with invasive ventilation, and is often used in cardiac disease, exacerbations of chronic pulmonary disease, sleep apnea, and neuromuscular diseases. Non-invasive ventilation refers only to the patient interface and not the mode of ventilation used; modes may include spontaneous or control modes and may be either pressure or volume modes. Some commonly used modes of NIPPV include:

(a) Continuous positive airway pressure (CPAP): This kind of machine has been used mainly by patients for the treatment of sleep apnea at home, but now is in widespread use across intensive care units as a form of ventilation. The CPAP machine stops upper airway obstruction by delivering a stream of compressed air via a hose to a nasal pillow, nose mask or full-face mask, splinting the airway (keeping it open under air pressure) so that unobstructed breathing becomes possible, reducing and/or preventing apneas and hypopneas. When the machine is turned on, but prior to the mask being placed on the head, a flow of air comes through the mask. After the mask is placed on the head, it is sealed to the face and the air stops flowing. At this point, it is only the air pressure that accomplishes the desired result. This has the additional benefit of reducing or eliminating the extremely loud snoring that sometimes accompanies sleep apnea.

(b) Bi-level positive airway pressure (BIPAP): Pressures alternate between inspiratory positive airway pressure (IPAP) and a lower expiratory positive airway pressure (EPAP), triggered by patient effort. On many such devices, backup rates may be set, which deliver IPAP pressures even if patients fail to initiate a breath.

(c) Intermittent positive pressure ventilation (IPPV), via mouthpiece or mask.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that, wherever values and ranges are provided herein, the description in range format is merely for convenience and brevity and should not be construed as an inflexible limitation on the scope of the invention. Accordingly, all values and ranges encompassed by these values and ranges are meant to be encompassed within the scope of the present invention. Moreover, all values that fall within these ranges, as well as the upper or lower limits of a range of values, are also contemplated by the present application. The description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials:

Unless otherwise noted, all remaining starting materials were obtained from commercial suppliers and used without purification. Final products are typically isolated as hydrochloride acid addition salts unless noted otherwise.

Example 1

N-(4,6-Bis-methylamino-[1,3,5]triazin-2-yl)-N,O-dimethyl-hydroxylamine hydrochloride (XX)

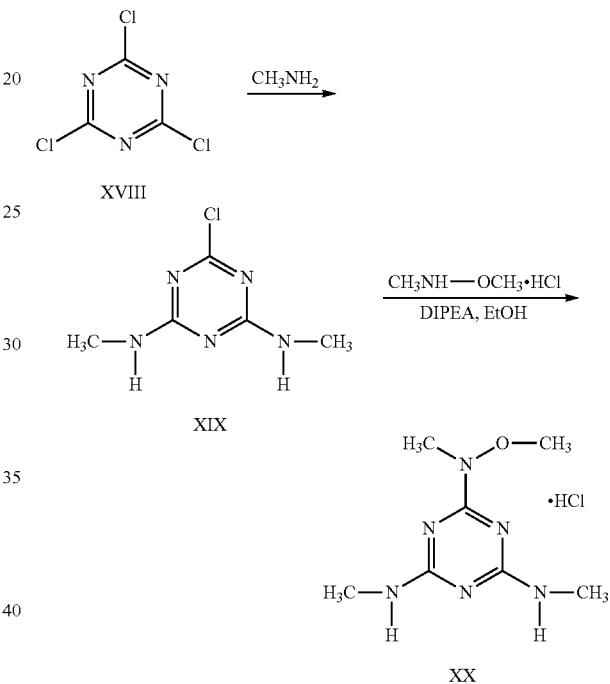

2-Chloro-N-(4,6-bis-methylamino)-[1,3,5]triazine (XIX)

2,4,6-Trichloro-1,3,5-triazine (XVIII) (5.0 g, 27 mmol) was dissolved in acetone (35 mL) and poured into ice-water (50 mL) to form a very fine suspension. A solution of N-methylamine hydrochloride (3.66 g, 54 mmol) in water (20 mL) was added and the temperature maintained at approximately 0° C. To this mixture, 2N NaOH (54 mL, 108 mmol) was added in a dropwise manner to keep the temperature between 0° C. and 5° C. The mixture was stirred 30 min at ambient temperature for an additional 60 min at 50° C. The precipitate was filtered and washed with water (3×25 mL). After drying over anhydrous calcium chloride under high vacuum, 2-chloro-N-(4,6-bis-methylamino)-[1,3,5]triazine (XIX) was isolated as a white powder (4.2 g, 89% yield). LCMS (ESI) m/z=174 (M+H)$^+$.

N-(4,6-Bis-methylamino-[1,3,5]triazin-2-yl)-N,O-dimethyl-hydroxylamine hydrochloride (XX)

A mixture of 2-chloro-N-(4,6-bis-methylamino)-[1,3,5] triazine (XIX) (1.74 g, 10 mmol), N,O-dimethylhydroxylamine hydrochloride (3.88 g, 40 mmol) and DIPEA (7.74 g, 60 mmol) in EtOH (200 mL) was heated at 100° C. for 16 h, after which the solvent was removed under reduced pressure. The residue was dissolved in EtOAc (150 mL), washed with water (100 mL) and brine solution (100 mL), and then dried over $Na_2SO_4$. The solvent was removed under reduced pressure. The crude product was purified by flash column chromatography (pet ether/ethyl acetate=5/1 to 5/3) to yield 899 mg (23%) of the desired product. The isolated free amine (380 mg, 2 mmol) was placed into $H_2O$ (10 mL) and 0.5 M aqueous HCl solution (6 mL) was added. The resultant solution was subjected to lyophilization to yield the desired product, N-(4, 6-bis-methylamino-[1,3,5]triazin-2-yl)-N,O-dimethyl-hydroxylamine hydrochloride (XX), as a white solid (468 mg). LCMS (ESI) m/z=199 (M+H)$^+$. $^1$H NMR (500 MHz, DMSO): δ (ppm) 12.20-12.50 (br, 1H), 8.48-8.62 (m, 2H), 3.76-3.86 (m, 3H), 3.29-3.39 (m, 3H), 2.76-2.93 (m, 6H).

Example 2

N-(4,6-Bis-ethylamino-[1,3,5]triazin-2-yl)-N,O-dimethyl-hydroxylamine hydrochloride (XXII)

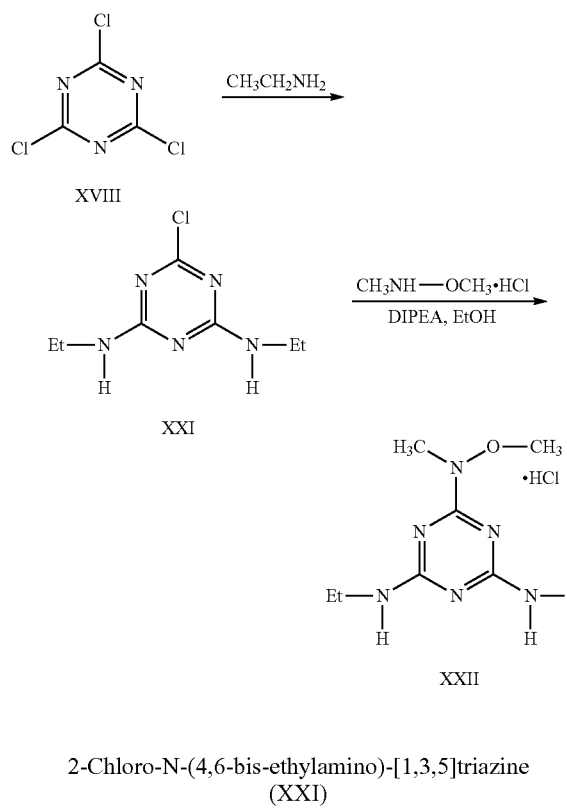

2-Chloro-N-(4,6-bis-ethylamino)-[1,3,5]triazine (XXI)

2,4,6-Trichloro-1,3,5-triazine (XVIII) (5.0 g, 27 mmol) was dissolved in acetone (35 mL) and poured into ice-water (50 mL) to form a very fine suspension. A solution of ethylamine (2.43 g, 54 mmol) in water (20 mL) was added and the temperature maintained at approximately 0° C. To this mixture, 2N NaOH (27 mL, 54 mmol) was added in a dropwise manner to keep the temperature between 0° C. and 5° C. The mixture was stirred for 30 min at ambient temperature, and for additional 60 min at 50° C. The precipitate was filtered off, washed with water (3×25 mL). After drying over anhydrous calcium chloride under high vacuum, 2-chloro-N-(4,6-bis-ethylamino)-[1,3,5]triazine (XXI) was isolated as a white powder (5.0 g, 92% yield). LCMS (ESI) m/z=202 (M+H)$^+$.

N-(4,6-Bis-ethylamino-[1,3,5]triazin-2-yl)-N,O-dimethyl-hydroxylamine hydrochloride (XXII)

A mixture of 2-chloro-N-(4,6-bis-ethylamino)-[1,3,5]triazine (XXI) (4.03 g, 20 mmol), N,O-dimethylhydroxylamine hydrochloride (9.7 g, 100 mmol) and DIPEA (1.806 g, 140 mmol) in EtOH (200 mL) was heated at 100° C. for 16 h. After this time, the solvent was removed under reduced pressure. The residue was dissolved in EtOAc (400 mL), washed with water (100 mL) and a brine solution (100 mL), then dried over $Na_2SO_4$ and concentrated. The crude product was purified by flash column chromatography (pet ether/ethyl acetate=5/1 to 5/2) to yield 811 mg (18%) of the desired product. The isolated free amine (811 mg, 3.58 mmol) was dissolved in $H_2O$ (10 mL) and 0.5 M HCl solution in $H_2O$ (7.2 mL) was added. The resultant solution was lyophilized to yield the desired product, N-(4,6-bis-ethylamino-[1,3,5]triazin-2-yl)-N,O-dimethyl-hydroxylamine hydrochloride (XXII) as a white solid (938 mg). LCMS (ESI) m/z=227 (M+H)$^+$. $^1$H NMR (500 MHz, DMSO): δ (ppm) 12.40-12.80 (br, 1H), 8.58-8.87 (m, 2H), 3.76-3.78 (m, 4H), 3.34-3.37 (m, 6H), 1.10-1.16 (m, 6H).

Example 3

N-(4-Cyclopropylmethylamino)-N-(6-n-propylamino)[1,3,5]triazin-2-yl)-N,O-dimethyl-hydroxylamine (XXV)

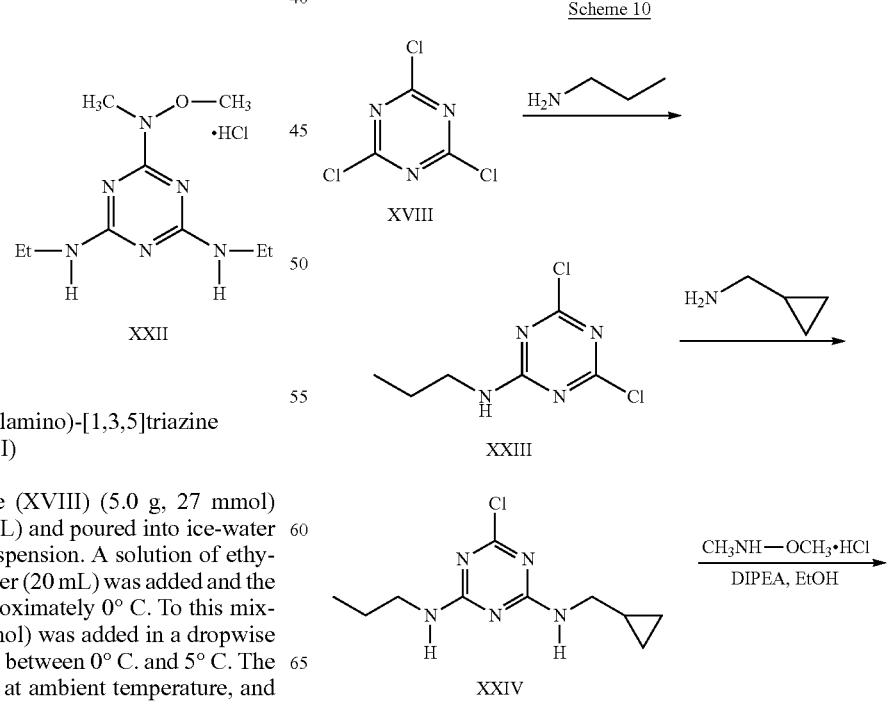

-continued

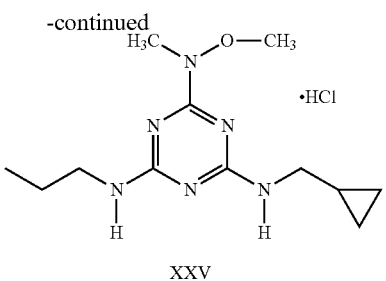

XXV

2,4-Dichloro-N-(6-n-propylamino)-[1,3,5]triazine (XXIII)

2,4,6-Trichloro-1,3,5-triazine (XVIII) (20 g, 109 mmol) was dissolved in acetone (100 mL) and poured into ice-water (50 mL) to form a very fine suspension. A solution of propan-1-amine (7.1 g, 120 mmol) in water (20 mL) was added and the temperature maintained at approximately 0° C. To this mixture, 2N NaOH (60 mL, 120 mmol) was added in a dropwise manner to keep the temperature between −5° C. and 0° C. The mixture was stirred at 0° C. for 60 min. The precipitate was filtered off and washed with water (3×25 mL). After drying over calcium chloride under high vacuum, 2,4-dichloro-N-(6-n-propylamino)-[1,3,5]triazine (XXIII) was isolated as a white powder (18 g, 80% yield). LCMS (ESI) m/z=208 (M+H)$^+$.

2-Chloro-N-(4-cyclopropylmethyl)-N-(6-n-propylamino) [1,3,5]triazine (XXIV)

2,4-Dichloro-N-(6-n-propylamino)-[1,3,5]triazine (XXIII) (18 g, 87 mmol) was dissolved in acetone (100 mL) and poured into ice-water (50 mL) to form a very fine suspension. A solution of cyclopropylmethanamine (6.7 g, 95 mmol) in acetone (30 mL) was added and the temperature was maintained at approximately 0° C. To this mixture, 2N NaOH (44 mL, 88 mmol) was added in a dropwise manner to keep the temperature between 0° C. and 5° C. The mixture was stirred for 30 min at ambient temperature and for an additional 60 min at 50° C. The precipitate was filtered off, washed with water (3×25 mL). After drying over anhydrous calcium chloride under high vacuum, 2-chloro-N-(4-cyclopropylmethyl)-N-(6-n-propylamino) [1,3,5]triazine (XXIV) was isolated as a white powder (12 g, 57% yield). LCMS (ESI) m/z=242 (M+H)$^+$.

N-(4-Cyclopropylmethylamino)-N-(6-n-propylamino) [1,3,5]triazin-2-yl)-N,O-dimethyl-hydroxylamine hydrochloride (XXV)

A mixture of 2-chloro-N-(4-cyclopropylmethyl)-N-(6-n-propylamino) [1,3,5]triazine (XXIV) (1.5 g, 6.2 mmol), N,O-dimethylhydroxylamine hydrochloride (3.0 g, 31.0 mmol) and DIPEA (6.5 g, 49.6 mmol) in EtOH (50 mL) was heated at 100° C. for 16 h, after the solvent was removed under reduced pressure. The residue was dissolved in EtOAc (400 mL), washed with water (100 mL), then with a brine solution (100 mL) and dried over Na$_2$SO$_4$. The crude was purified by flash column chromatography (pet ether/ethyl acetate=5/1 to 5/2). The solvent was removed under reduced pressure to yield 500 mg (26%) of the desired product. The isolated free amine (500 mg, 1.88 mmol) was dissolved in H$_2$O (10 mL) and 0.5 M aqueous HCl solution (4.0 mL) was added. The resultant solution was subjected was subjected to lyophilization to yield the desired product, N-(4-cyclopropylmethylamino)-N-(6-n-propylamino) [1,3,5]triazin-2-yl)-N,O-dimethyl-hydroxylamine hydrochloride (XXV, 520 mg) as a brown oil. LCMS (ESI) m/z=267 (M+H)$^+$. $^1$H NMR (500 MHz, DMSO): δ (ppm) 11.80-12.10 (br, 1H), 8.68-8.85 (m, 2H), 3.77 (s, 3H), 3.15-3.36 (m, 7H), 1.49-1.55 (m, 2H), 1.23 (s, 1H), 0.85-0.93 (m, 3H), 0.43-0.49 (m, 2H), 0.22-0.25 (m, 2H).

Example 4

N-(4-Ethylamino)-N-(6-n-propylamino)-[1,3,5]triazin-2-yl)-N,O-dimethyl-hydroxylamine (XXVII)

Scheme 11

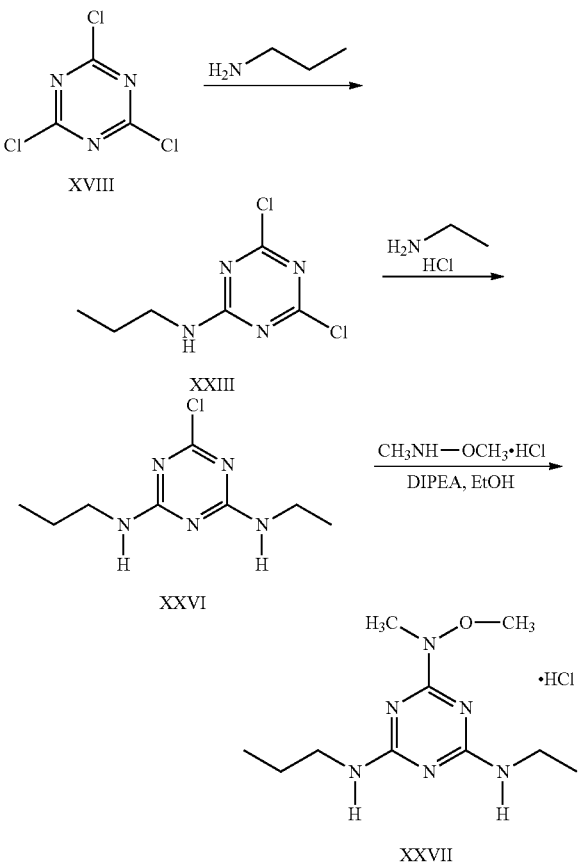

2,4-Dichloro-N-(6-n-propylamino)-[1,3,5]triazine (XXIII)

2,4,6-Trichloro-1,3,5-triazine (XVIII) (20 g, 109 mmol) was dissolved in acetone (100 mL) and poured into ice-water (50 mL) to form a very fine suspension. A solution of propan-1-amine (7.1 g, 120 mmol) in water (20 mL) was added and the temperature maintained at approximately 0° C. To this mixture was added 2 N NaOH (60 mL, 120 mmol) in a dropwise manner to keep the temperature between −5° C. and 0° C. The mixture was then stirred at 0° C. for 60 min. The precipitate was filtered off, washed with water (3×25 mL). After drying over anhydrous calcium chloride under high vacuum, 2,4-dichloro-N-(6-n-propylamino)-[1,3,5]triazine (XXIII) was isolated as a white powder (18 g, 80% yield). LCMS (ESI) m/z=208 (M+H)+.

2-Chloro-N-(4-ethylamino)-N-(6-n-propylamino)-[1,3,5]triazine (XXVI)

2,4-Dichloro-N-(6-n-propylamino)-[1,3,5]triazine (XXIII) (4.0 g, 19.5 mmol) was dissolved in acetone (40 mL) and poured into ice-water (40 mL) to form a very fine suspension. A solution of ethanamine hydrochloride (1.91 g, 23.4 mmol) in water (10 mL) was added and the temperature was maintained at approximately 0° C. A solution of NaOH (2.34 g, 58.5 mmol) in water (10 mL) was added in a dropwise manner to keep the temperature between 0° C. and 5° C. The mixture was then stirred 40 min at room temperature and concentrated. The precipitate was filtered off, washed with water (3×25 mL). After drying over calcium chloride under high vacuum, the desired product, 2-chloro-N-(4-ethylamino)-N-(6-n-propylamino)-[1,3,5]triazine (XXVI) was isolated as a white powder (3.89 g, 92% yield). LCMS (ESI) m/z=216 (M+H)+.

N-(4-Ethylamino)-N-(6-n-propylamino)[1,3,5]triazin-2-yl)-N,O-dimethyl-hydroxylamine hydrochloride (XXVII)

A mixture of 2-chloro-N-(4-ethylamino)-N-(6-n-propylamino)-[1,3,5]triazine (XXVI) (2 g, 9.3 mmol), N,O-dimethylhydroxylamine hydrochloride (4.5 g, 46.5 mmol) and DIPEA (8.4 g, 65.1 mmol) in EtOH (20 mL) was heated at 100° C. for 16 h, after which time the solvent was removed under reduced pressure. The residue was dissolved in EtOAc (150 mL), washed with water (100 mL), washed with a brine solution (100 mL) and then dried over Na$_2$SO$_4$. The solvent was removed under reduced pressure and the residue was purified by flash column chromatography (pet ether/ethyl acetate=10/1 to 2/1) to yield the desired product (820 mg, 37%). The isolated free amine (820 mg, 3.42 mmol) was dissolved in H$_2$O (10 mL), and 0.5 M aqueous HCl solution (11 mL) was added. The resultant solution was subjected to lyophilization to yield the desired product, N-(4-ethylamino)-N-(6-n-propylamino)[1,3,5]triazin-2-yl)-N,O-dimethyl-hydroxylamine hydrochloride (XXVII), as a colorless oil (944 mg). LCMS (ESI) m/z=241 (M+H)+. $^1$H NMR (500 MHz, DMSO): δ (ppm) 12.25-12.75 (br, 1H), 8.71-8.75 (m, 2H), 3.75-3.92 (m, 6H), 3.25-3.37 (m, 4H), 1.50-1.55 (m, 2H), 1.09-1.16 (m, 3H), 0.87-0.94 (m, 3H).

Example 5

N-(Bis-4,6-(2-methylpropylamino))[1,3,5]triazin-2-yl)-N,O-dimethyl-hydroxylamine (XXIX)

Scheme 12

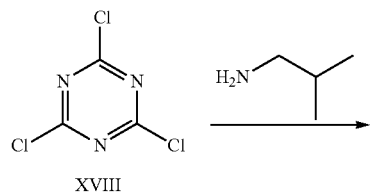

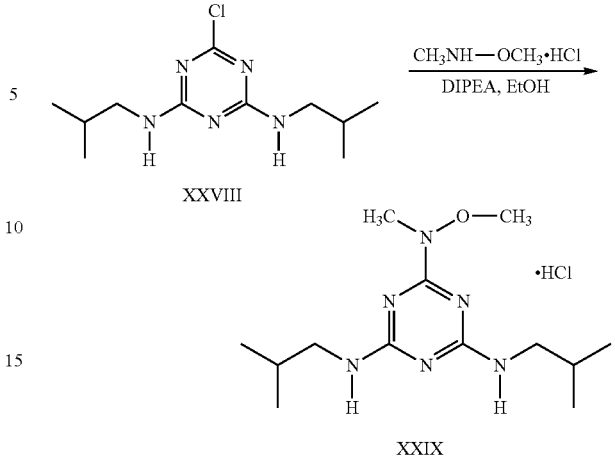

2-Chloro-N-(4,6-bis-(2-methylpropylamino)-[1,3,5]triazine (XXVIII)

2,4,6-Trichloro-1,3,5-triazine (XVIII) (5.0 g, 27 mmol) was dissolved in acetone (35 mL) and poured into ice-water (50 mL) to form a very fine suspension. A solution of 2-methylpropan-1-amine (4.0 g, 54 mmol) in acetone (20 mL) was added and the temperature was maintained at approximately 0° C. To this mixture, 2 N NaOH (27 mL, 54 mmol) was added in a dropwise manner to keep the temperature between 0° C. and 5° C. The mixture was stirred for 30 min at ambient temperature and for an additional 60 min at 50° C. The precipitate was filtered off, washed with water (3×25 mL). After drying over calcium chloride under high vacuum, 2-chloro-N-(4,6-bis-(2-methylpropylamino)-[1,3,5]triazine (XXVIII) was isolated as white powder (6.0 g, 87% yield). LCMS (ESI) m/z=258 (M+H)+.

N-(Bis-4,6-(2-methylpropylamino))[1,3,5]triazin-2-yl)-N,O-dimethyl-hydroxylamine hydrochloride (XXIX)

A mixture of 2-chloro-N-(4,6-bis-(2-methylpropylamino)-[1,3,5]triazine (XXVIII) (2.57 g, 10 mmol), N,O-dimethylhydroxylamine hydrochloride (1.94 g, 20 mmol) and DIPEA (5.16 g, 40 mmol) in EtOH (100 mL) was heated at 100° C. for 16 h, after which time the solvent was removed under reduced pressure. The residue was dissolved in EtOAc (200 mL), washed with water (2×100 mL), washed with a brine solution (100 mL) and then dried over Na$_2$SO$_4$. The solvent was removed under reduced pressure. The residue was purified by flash column chromatography (pet ether/ethyl acetate=5/1) to yield the desired product (920 mg, 33%). The isolated free amine (920 mg, 3.3 mmol) was dissolved in H$_2$O (10 mL) and 0.5 M aqueous HCl solution (6.6 mL) was added. The resultant solution was subjected to lyophilization to yield the desired product, N-(bis-4,6-(2-methylpropylamino))[1,3,5]triazin-2-yl)-N,O-dimethyl-hydroxylamine hydrochloride (XXIX) as a white solid (1.0 g). LCMS (ESI) m/z=283 (M+H)+. $^1$H NMR (500 MHz, DMSO): δ (ppm) 12.55-12.60

(br, 1H), 8.57-8.77 (br, 2H), 3.78 (s, 3H), 3.40-3.45 (m, 3H), 3.11-3.19 (m, 4H), 1.80-1.86 (m, 2H), 0.89-0.94 (m, 12H).

Example 6

N-(Bis-4,6-(2,2-dimethylpropylamino)) [1,3,5]triazin-2-yl)-N,O-dimethyl-hydroxylamine hydrochloride (XXXI)

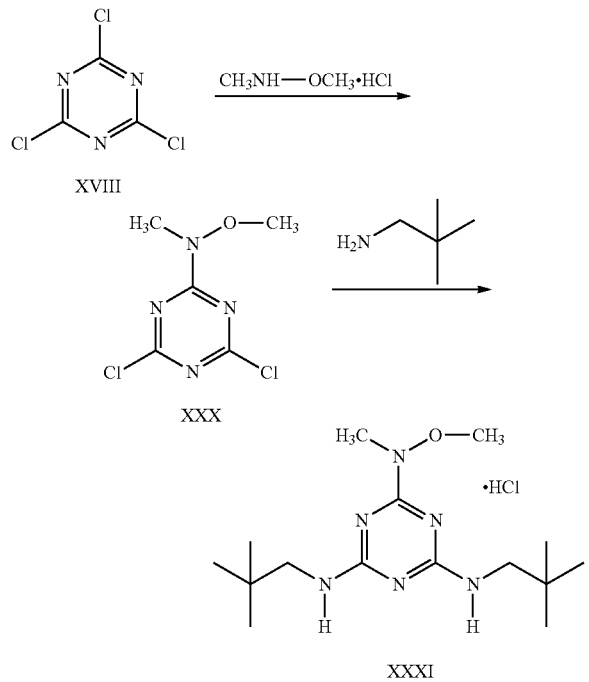

N-(4,6-Dichloro[1,3,5]triazin-2-yl)-N,O-dimethyl-hydroxylamine (XXX)

2,4,6-Trichloro-1,3,5-triazine (XVIII) (30 g, 163 mmol) was dissolved in acetone (300 mL), and N,O-dimethylhydroxylamine hydrochloride (15.8 g, 163 mmol) and DIPEA (42 g, 326 mmol) were added and the mixture then stirred at 0° C. for 1 h. The solution was concentrated and the residue was treated with EtOAc (750 mL), washed with water (100 mL), and the organic layer was dried with Na₂SO₄. The volatiles were removed in vacuo and the residue was purified by flash column chromatography (pet ether/ethyl acetate=50/1 to 10/1) to yield the desired product, N-(4,6-dichloro[1,3,5]triazin-2-yl)-N,O-dimethyl-hydroxylamine (XXX), as a white solid (25 g, 73% yield). LCMS (ESI) m/z=210 (M+H)⁺.

N-(Bis-4,6-(2,2-dimethylpropylamino)) [1,3,5]triazin-2-yl)-N,O-dimethyl-hydroxylamine (XXXI)

A mixture of N-(4,6-dichloro[1,3,5]triazin-2-yl)-N,O-dimethyl-hydroxylamine (XXX) (1 g, 4.78 mmol), 2,2-dimethylpropan-1-amine (832.5 mg, 9.57 mmol) and DIPEA (1.85 g, 14.34 mmol) in EtOH (20 mL) was heated at 100° C. for 16 h, after which time the solvent was removed under reduced pressure. The residue was dissolved in EtOAc (40 mL), washed with water (20 mL) and with a brine solution (20 mL), dried over Na₂SO₄, and then concentrated. The crude product was purified by flash column chromatography (pet ether/ethyl acetate=20/1 to 5/1) to yield the desired product (1.4 g, 95%). The isolated free amine (1.4 g, 4.52 mmol) was dissolved in H₂O (10 mL) and 0.5 M HCl solution in H₂O (14.5 mL) was added, and the resultant solution was subjected to lyophilization to yield the desired product, N-(bis-4,6-(2,2-dimethylpropylamino))[1,3,5]triazin-2-yl)-N,O-dimethyl-hydroxylamine hydrochloride, as a white solid (1.67 g). LCMS (ESI) m/z=311 (M+H)⁺. ¹H NMR (500 MHz, DMSO): δ (ppm) 12.40-12.70 (br, 1H), 8.52-8.81 (m, 2H), 3.75-3.79 (m, 3H), 3.33-3.36 (m, 3H), 3.14-3.21 (m, 4H), 0.89-0.96 (m, 18H).

Example 7

4,6-Bis-N-cyclopropylamino-[1,3,5]triazin-2-yl)-N,O-dimethyl-hydroxylamine hydrochloride (XXXIII)

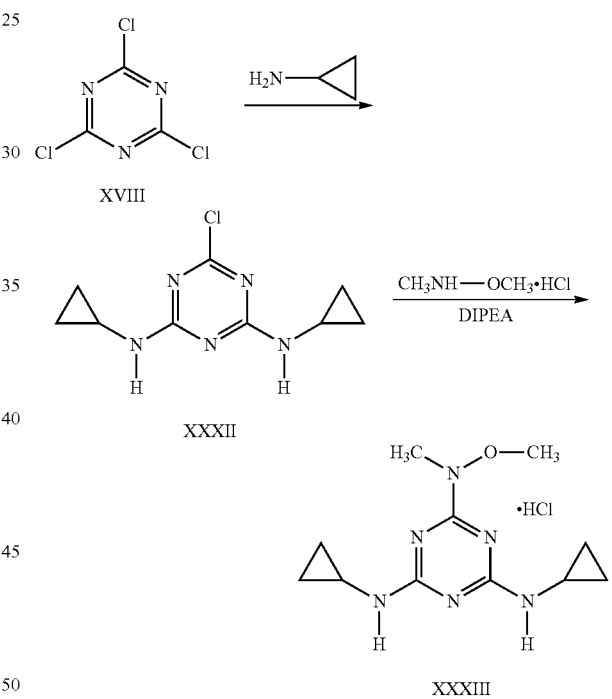

2-Chloro-N-(4,6-bis-(cyclopropylamino)-[1,3,5]triazine (XXXII)

2,4,6-Trichloro-1,3,5-triazine (XVIII) (40 g, 217 mmol) was dissolved in 200 mL of acetone and poured into ice-water (250 mL) to form a very fine suspension. A solution of cyclopropanamine (24.8 g, 435 mmol) was added with stirring at 0° C. To this mixture, 2N NaOH (218 mL, 435 mmol) was added dropwise at a rate to keep the temperature between 0° C. and 5° C. The resultant mixture was stirred for 30 min at ambient temperature and then for an additional 60 min at 50° C. The precipitate was filtered off, washed with water (3×100 mL). After drying over calcium chloride under high vacuum, chloro-N-(4,6-bis-(cyclopropylamino)-[1,3,5]triazine (XXXII) was isolated as a white powder (46 g, 93% yield). LCMS (ESI) m/z=226 (M+H)⁺.

4,6-Bis-N-cyclopropylamino-[1,3,5]triazin-2-yl)-N,O-dimethyl-hydroxylamine (XXXIII)

A mixture of chloro-N-(4,6-bis-(cyclopropylamino)-[1,3,5]triazine (XXXII) (2.25 g, 10 mmol), N,O-dimethylhydroxylamine hydrochloride (1.94 g, 20 mmol) and DIPEA (5.16 g, 40 mmol) in EtOH (100 mL) was heated at 100° C. for 16 h, and the solvent was then removed under reduced pressure. The residue was dissolved in EtOAc (200 mL), washed with water (2×100 mL) and brine (100 mL) then dried over Na₂SO₄. The solvent was removed under reduced pressure. The residue was purified by flash column chromatography (pet ether/ethyl acetate=3/1) to yield 1.0 g (40%) of the desired product. The isolated free amine (1.0 g, 4.0 mmol) was dissolved in H₂O (10 mL) and 0.5 M aqueous HCl solution (8 mL) and then the solution was lyophilized to yield N-(4,6-bis-cyclopropylamino-[1,3,5]triazin-2-yl)-N,O-dimethyl-hydroxylamine hydrochloride (XXXIII) as a white solid (1.05 g). LCMS (ESI) m/z=251 (M+H)⁺. ¹H NMR (500 MHz, DMSO): δ (ppm) 12.00-12.80 (br, 1H), 8.70-9.50 (br, 2H), 3.76 (s, 3H), 3.28-3.38 (m, 3H), 2.69-2.89 (m, 2H), 0.59-0.81 (m, 8H).

Example 8A

N-(4,6-Bis-n-propylamino-[1,3,5]triazin-2-yl)-N,O-dimethyl-hydroxylamine (XXXV)

Example 9A

N-(4,6-Bis-n-propylamino-[1,3,5]triazin-2-yl)-N,O-dimethyl-hydroxylamine hydrogen sulfate (XXXVI)

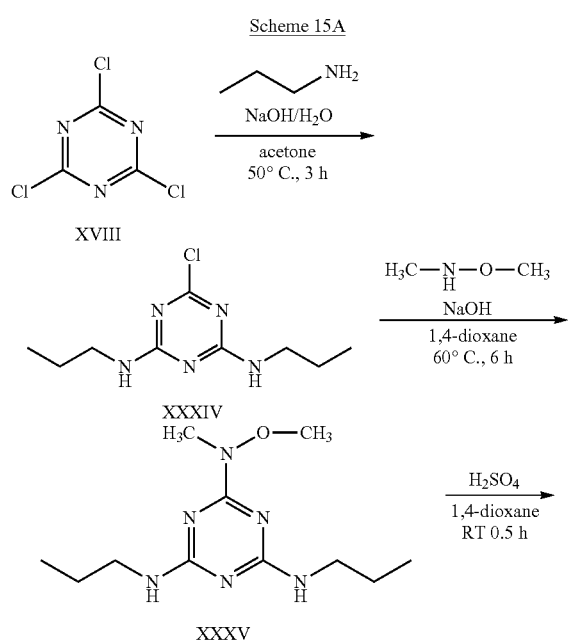

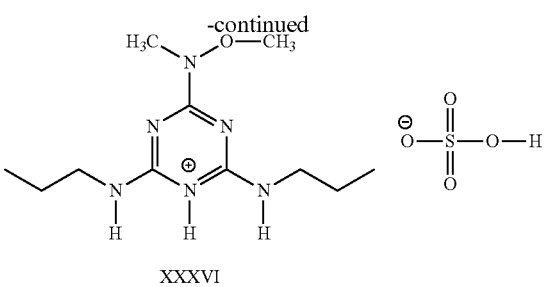

2-Chloro-N-(4,6-bis-(n-propylamino)-[1,3,5]triazine (XXXIV)

A 2 M NaOH solution (82 mL, 162.68 mmol) was added in a dropwise manner to a suspension of 2,4,6-trichloro-1,3,5-triazine (XVIII) (15.00 g, 81.34 mmol) and n-propylamine (13.4 mL, 162.68 mmol) in acetone (300 mL) and water (15 mL) at 0° C. The reaction mixture was heated at 50° C. for 3 h and then cooled. Water (100 mL) was added to the reaction mixture; the resultant precipitate was filtered, washed with water, ethyl ether and dried to yield 2-chloro-N-(4,6-bis-(n-propylamino)-[1,3,5]triazine (XXXIV) (15.88 g, 85% yield).

N-(4,6-Bis-n-propylamino-[1,3,5]triazin-2-yl)-N,O-dimethyl-hydroxylamine (XXXV)

A mixture of 2-chloro-N-(4,6-bis-(n-propylamino)-[1,3,5] triazine (XXXIV) (10.00 g, 43.53 mmol), N,O-dimethylhydroxylamine hydrochloride (8.49 g, 87.06 mmol) and NaOH (3.13 g, 78.35 mmol) in 1,4-dioxane (120 mL) and water (30 mL) was heated at 60° C. for 6 h, after which the volatiles were removed under reduced pressure. Saturated NaHCO₃ solution (500 mL) was added to the residue and the mixture was extracted with EtOAc (3×200 mL). The combined organic extracts were washed with water (300 mL), then with a brine solution (300 mL) and dried over Na₂SO₄. The solvent was removed under reduced pressure and the resultant residue was filtered through silica gel using eluent CH₂Cl₂/EtOH (9/1 v/v) to yield N-(4,6-bis-n-propylamino[1,3,5]triazine-2-yl)-N,O-dimethyl-hydroxylamine (XXXV) (9.96 g, 90% yield).

N-(4,6-Bis-n-propylamino-[1,3,5]triazin-2-yl)-N,O-dimethyl-hydroxylamine hydrogen sulfate (XXXVI)

Concentrated (95%) H₂SO₄ (0.72 mL, 12.74 mmol) was added in a dropwise manner to a solution of N-(4,6-bis-n-propylamino-[1,3,5]triazin-2-yl)-N,O-dimethyl-hydroxylamine (XXXV, 3.24 g, 12.74 mmol) in 1,4-dioxane (100 mL) at 0° C. The mixture was stirred for 0.5 h at room temperature, volatiles were removed under reduced pressure. The residue was co-evaporated with dry toluene (3×25 mL). The resulting white residue was crystallized from ethanol/ethyl ether to yield N-(4,6-bis-n-propylamino-[1,3,5]triazin-2-yl)-N,O-dimethyl-hydroxylamine, hydrogen sulfate (XXXVI, 3.86 g, 86% yield) as a white solid. ¹H NMR (400 MHz, DMSO): δ (ppm) 12.0-11.2 (1H, br s), 8.7-8.3 (0.7H, br s), 8.10 (0.3H, br s), 7.8-7.3 (1H, m), 3.78 (3H, s), 3.40-3.20 (7H, m), 1.61-1.45 (4H, m), 0.93-0.84 (6H, m). ESI-MS (m/z) 255 [M+H]$^+$; melting point: 134-135° C.

Example 8b

N-(4,6-Bis-n-propylamino-[1,3,5]triazin-2-yl)-N,O-dimethyl-hydroxylamine (XXXV)

Example 9b

N-(4,6-Bis-n-propylamino-[1,3,5]triazin-2-yl)-N,O-dimethyl-hydroxylamine hydrogen sulfate (XXXVI)

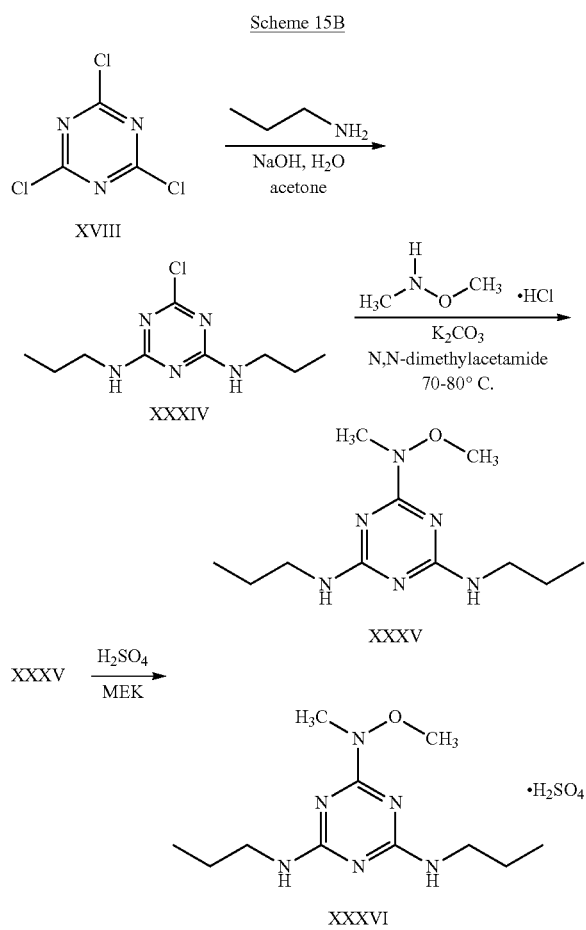

Stage 1: 2-Chloro-N-(4,6-bis-(n-propylamino)-[1,3,5]triazine (XXXIV)

Summary: Di-chloro displacement by 2 equivalents of n-propylamine. In one embodiment, two or more equivalence of n-propylamine produced only the bis-propylamine derivative of the starting material. The reaction progress was monitored by HPLC and the desired intermediate (2-chloro-4,6-bispropylamino-s-triazine) was precipitated. In-process QC Tests were performed.

A suitable glass reactor vessel equipped with a mechanical stirrer, thermocouple, condenser, addition funnel and a temperature control mantle was charged with 8 L of acetone followed by 1 kg (5.42 moles) of cyanuric chloride. The stirring mixture was pre-cooled to 15° C. and n-propylamine (at ambient temperature) was added slowly via addition funnel, to maintain the temperature below 45° C. A 2M NaOH solution was prepared and was added to the mixture at a rate to maintain the temperature below 45° C. The pH of the mixture was acidic (approximately pH=4) and 6N NaOH was added to adjust the pH to 8-9. The mixture was stirred at 40-50° C. for 0.5 h and the reaction was monitored for completion by IPC HPLC analysis. The reaction was deemed complete when <2% of cyanuric chloride was detected. Analysis was repeated every hour until reaction was complete.

After reaction was complete, WFI (sterile water) was added slowly to maintain temperature below 50° C. The resulting suspension was allowed to cool to room temperature while stirring overnight. The solids were filtered through a polypropylene filter cloth and washed with acetone/water (1:2) followed by 1.5 L of MTBE. The solids were dried on the filter (assisted by vacuum) then placed in a vacuum oven (45±5° C., >29" Hg) for a minimum of 6 h to give <0.5% in change in weight loss. A sample was collected for analytical testing (QC HPLC analysis and Karl Fisher analysis); 2 g was collected for QA retain. The product produced in Stage 1 was a white solid. This powder was transferred from drying pans to poly bag with nylon tie, double bagged and placed into fiber drum; label and submit to QA for quarantine storage.

Stage 2: N-(4,6-Bis-n-propylamino-[1,3,5]triazin-2-yl)-N,O-dimethyl-hydroxylamine (XXXV)

Summary: Chloro displacement by 1 equivalent of N-methoxymethylamine. The reaction progress was monitored by HPLC and precipitation of desired product free base was accomplished by adding water and cooling. In-process QC Tests were pre-formed. The free base was converted to the corresponding sulfate salt with crystallization and the final product was subjected to vacuum oven drying. In-process QC Tests were performed as well as finished product QC testing.

A suitable round-bottom flask equipped with a mechanical stirrer, thermocouple, condenser, and a heating mantle was charged with 6 L of N,N-dimethylacetamide (DMA) followed by 1 kg (4.35 moles) of 6-chloro-N,N-dipropyl-[1,3,5]-triazine-2,4-diamine (Stage 1 Product). Added to this stirring mixture at room temperature, was K$_2$CO$_3$ (1.2 kg, 6.53 moles, 2 eq.), with rinsing with a small quantity of additional DMA. To this, was added N,O-dimethylhydroxylamine hydrochloride (0.637 kg, 8.71 moles, 1.5 eq.) in portions over ~5-10 minutes to reduce foaming (and while maintaining the temperature below 60° C.) with rinsing using a small quantity of additional DMA. The mixture was heated to 75-80° C. and stir for a minimum of 0.5 hours. Once at 75-80° C., the reaction was monitored for completion by HPLC. The mixture was cooled to below 65° C. and water (12 L) was added. The resulting suspension was allowed to cool to room temperature while stirring overnight (18 h). The resultant solids were filtered and washed with 1.2 L of water. The filter cake to air-dry one hour and a sample for OVI amine GC analysis was obtained. The remaining solids were vacuum oven dried (45° C., >29" Hg) for a minimum of 6 hours (NMT 1% weight change). The desired product (free base) was a dense white solid. An IPC sample for testing was obtained.

Figure 10:
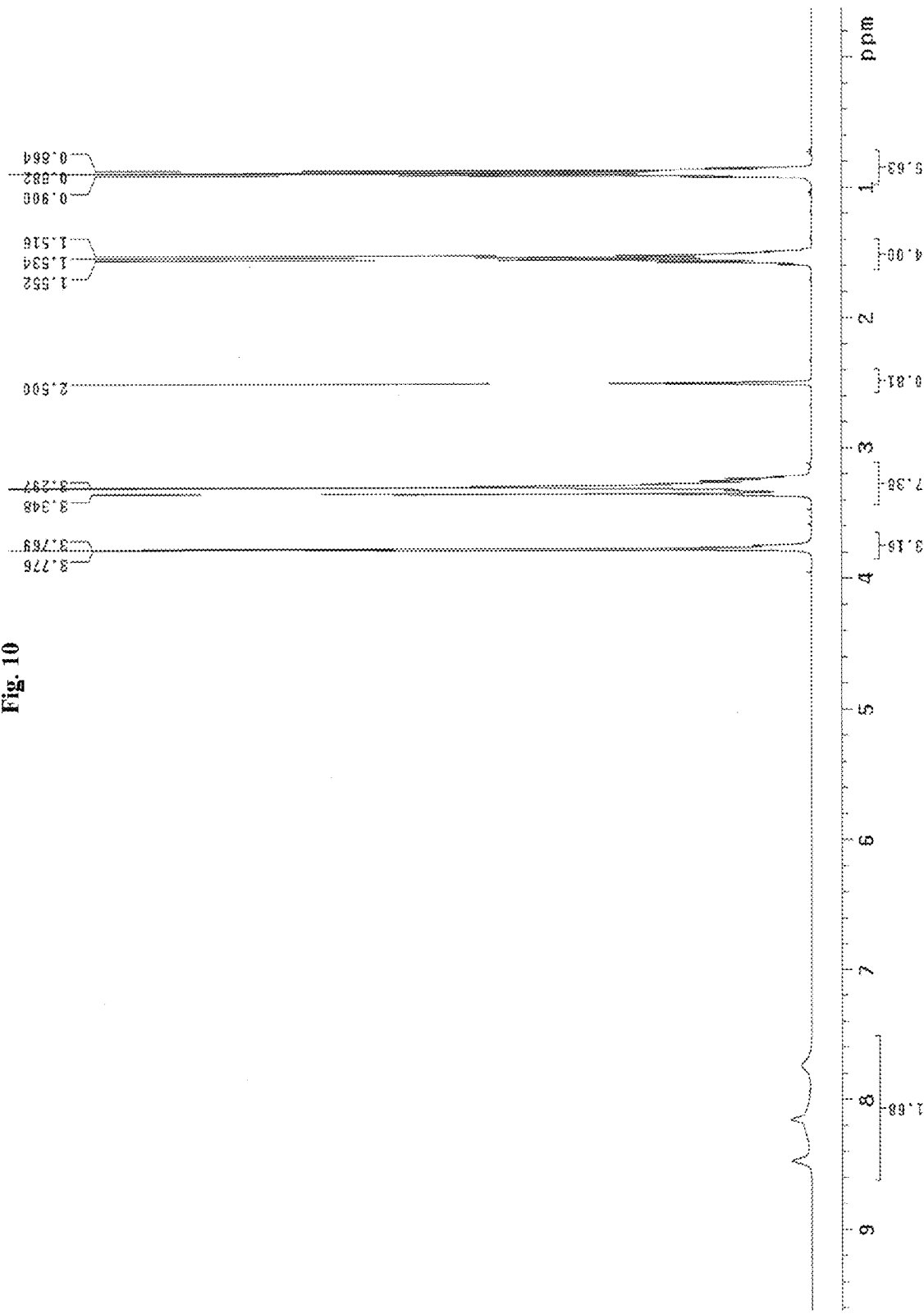
FIG. 10 illustrates the $^1$H-NMR spectrum for Compound (XXXVI) in DMSO-$d_6$ at 25° C.

MEK (14.3 L) was added to 1 kg (3.93 moles) of the free base obtained above. The mixture was stirred and heated to 45° C. then filtered through a 5μ inline filter into a suitable reactor. Concentrated H$_2$SO$_4$ (4.13 moles, 1.05 eq based on pre-filtered weight) was added slowly via addition funnel to maintain temperature below 50° C. The mixture was then cooled to 20° C. overnight. The mixture was then further cooled to 10° C., stirred for 0.5 h and then filtered. The solid product cake was washed with MEK (2 L), air dried on the filter (vacuum assisted) for a minimum of 2 h then placed in a vacuum oven (>29" Hg @ 45° C.) and dried for a minimum of 6 h to give N-(4,6-bis-n-propylamino-[1,3,5]triazin-2-yl)-N,O-dimethyl-hydroxylamine hydrogen sulfate (XXXVI) as a white solid.
Stage 1:
IPC Test 1: Temperature Chart Recording During Additions—
  Maintain temperature control specified in process steps
IPC Test 2: IPC HPLC Analysis—
  Reaction is complete when <2% of cyanuric chloride is detected.
  Repeat analysis every hour until reaction is complete.
  Contact supervisor if reaction is not complete after third sample.
Stage 1 Product QC Testing:
  QC HPLC Analysis—
  Record results of assay of cyanuric chloride and 2-chloro-4,6-bispropylamino-s-triazine
  Karl Fisher—
  Record results
Stage 2:
Step 1: Reaction:
IPC Test 1: Temperature Chart Recording During Additions—
  Maintain temperature control specified in process steps
IPC Test 2: IPC HPLC Analysis—
  Reaction is complete when <2% of 2-chloro-4,6-bispropylamino-s-triazine is detected.
  Repeat analysis every hour until reaction is complete.
  Contact supervisor if reaction is not complete after third sample.
IPC Test 3: Residual Amine Analysis (by GC)—
  n-Propylamine and N,O-dimethylhydoxylamine levels NMT 0.1%
IPC Test 4: Weight Change During Drying—
  NMT 1%
IPC Test 5: IPC HPLC Analysis—
  Purity by HPLC (AUC) record results
Step 2: Salt Formation and Crystallization
IPC Test 1: Temperature Chart Recording During Concentrated Sulfuric Acid Addition—
  Maintain temperature control specified in process step
IPC Test 2: OVI of MEK and DMAc by GC—
  NMT 800 ppm each
IPC Test 4: Weight Change During Drying—
  NMT 1%
Proton Nuclear Magnetic Resonance (NMR) Spectroscopy
  $^1$H NMR data of N-(4,6-bis-n-propylamino-[1,3,5]triazin-2-yl)-N,O-dimethyl-hydroxylamine hydrogen sulfate (XXXVI) was obtained as a solution in DMSO-$d_6$ at 400 MHz and is presented in FIG. 10 and shift assignments are presented in Table 1.

TABLE 1

$^1$H Chemical shift assignments for (XXXVI) in DMSO-d6 at 25° C.

| Resonance Peak | δ1H (ppm) | Assignment |
|---|---|---|
| 1 | 0.88 | 13, 17 |
| 2 | 1.53 | 12, 16 |
| 3 | 3.30 | 11, 15 |
| 4 | 3.35 | 18 |

TABLE 1-continued $^1$H Chemical shift assignments for (XXXVI) in DMSO-d6 at 25° C.

| Resonance Peak | δ1H (ppm) | Assignment |
|---|---|---|
| 5 | 3.77 | 9 |
| 6 | [7.42, 8.70] | 10, 14 |

Figure 11:
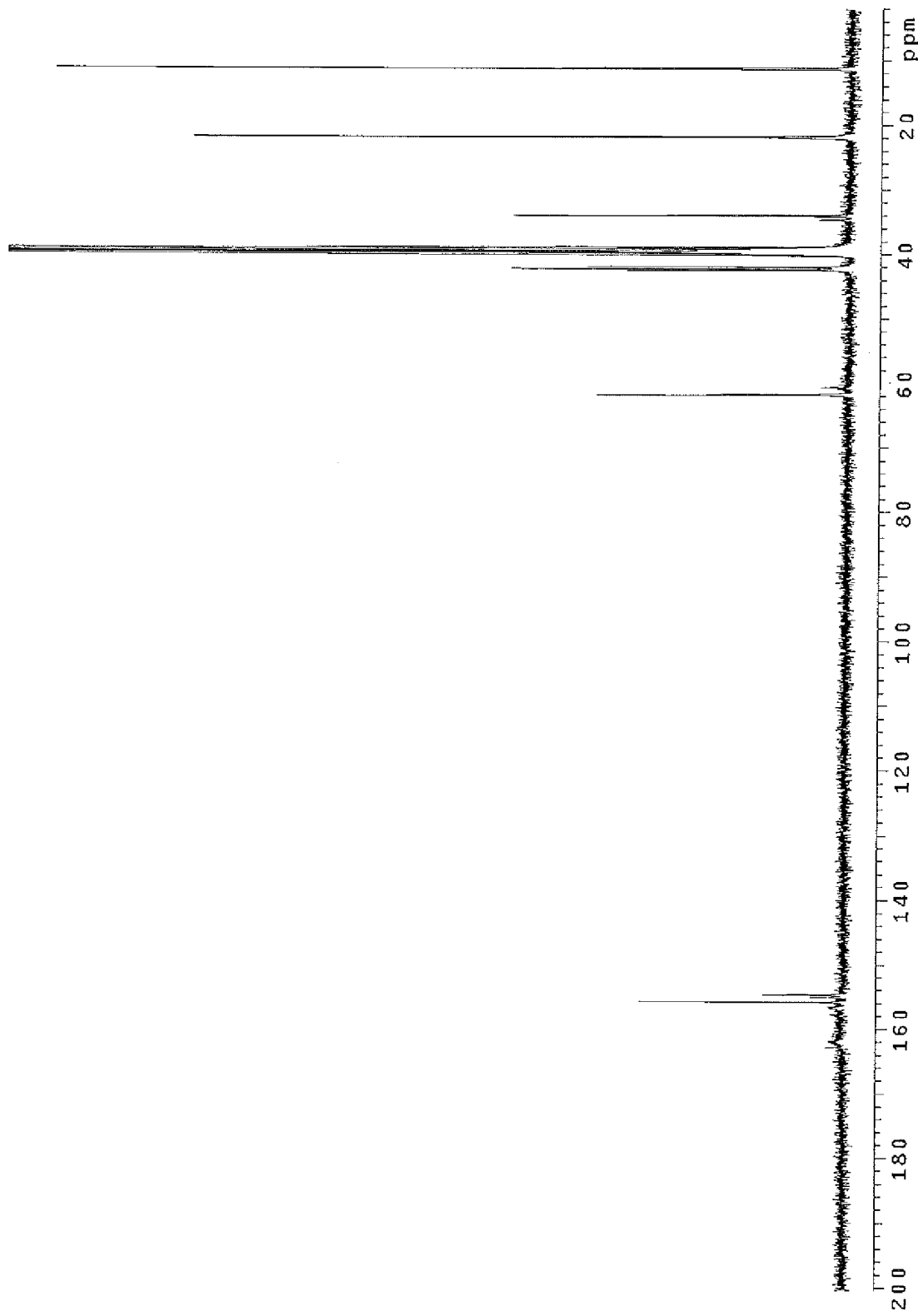
FIG. 11 illustrates the $^{13}$C-NMR spectrum for Compound (XXXVI) in DMSO-$d_6$ at 25° C.

Carbon-13 NMR Spectroscopy
  $^{13}$C NMR data of N-(4,6-bis-n-propylamino-[1,3,5]triazin-2-yl)-N,O-dimethyl-hydroxylamine hydrogen sulfate (XXXVI) was obtained as solutions in DMSO-$d_6$ at 100 MHz and is presented in FIG. 11 and shift assignments are presented in Table 2.

TABLE 2

$^{13}$C Chemical shift assignments for (XXXVI) in DMSO-d6 at 25° C.

| Resonance peak | δ13C (ppm) | Assignment |
|---|---|---|
| 1 | 11.25 | 13, 17 |
| 2 | 21.88 | 12, 16 |
| 3 | 34.08 | 18 |
| 4 | 42.24 | 11, 15 |
| 5 | 61.86 | 9 |
| 6 | 154.63 | 2 |
| 7 | 155.79 | 4, 6 |

Figure 12:
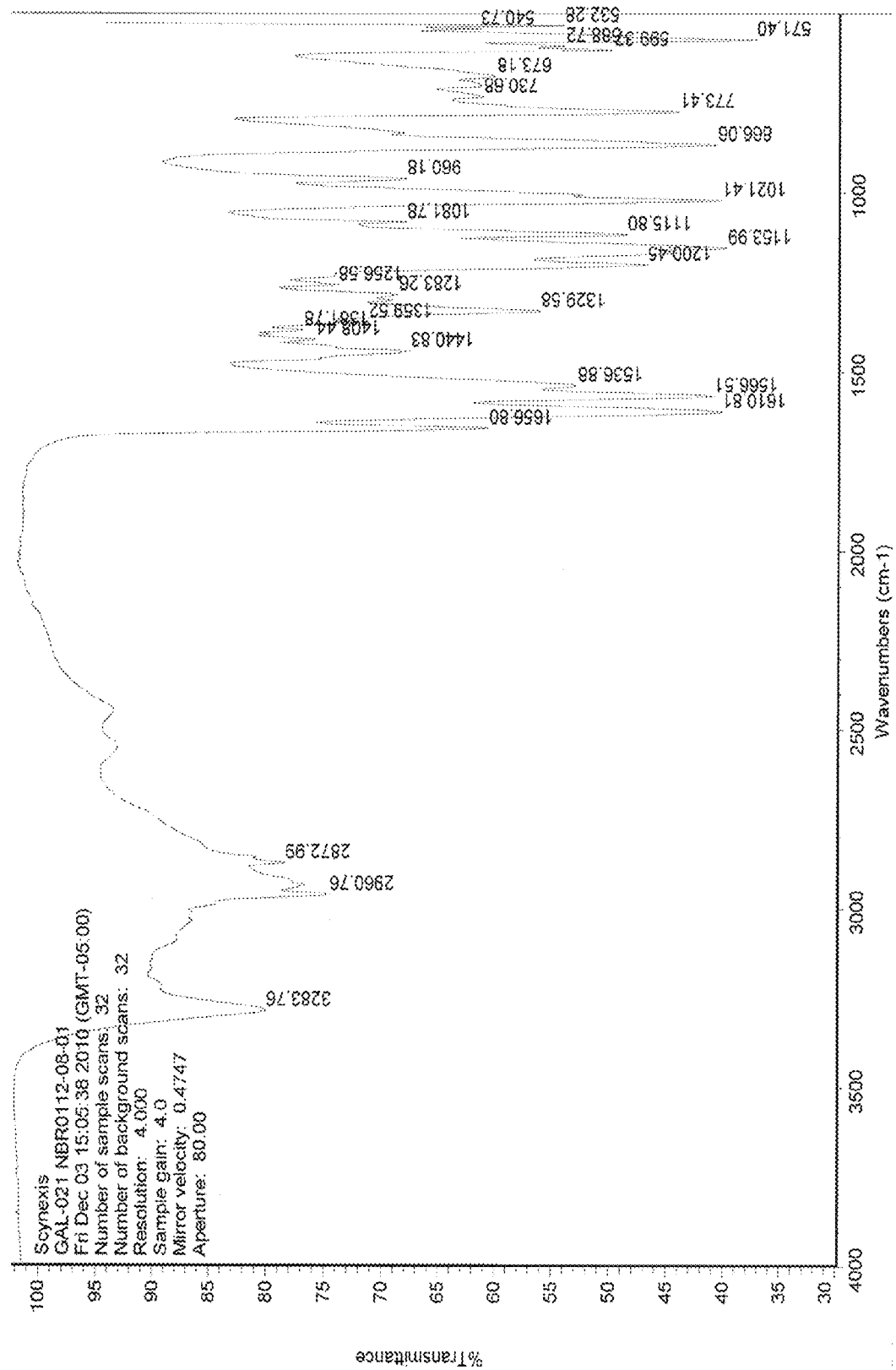
FIG. 12 illustrates the FTIR spectrum for Compound (XXXVI).

Fourier Transform Infrared (FTIR) Spectroscopy
  The FTIR spectrum of N-(4,6-bis-n-propylamino-[1,3,5]triazin-2-yl)-N,O-dimethyl-hydroxylamine hydrogen sulfate (XXXVI) is presented in Table 3 and FIG. 12.

TABLE 3

FTIR spectrum of (XXXVI)

| Wavenumber (cm−1) | Assignment |
|---|---|
| 3284 | N—H stretch |
| 2850-2960 | C—H stretch |
| 1615-1700 | C=N bend |
| 1536-1656 | N—H bend |
| 1020-1340 | C—N stretch |

High and Low Resolution Mass Spectrometry
  The mass obtained from Liquid Chromatography-Mass Spectrometry (LCMS) was 254 amu, which agrees with the theoretical mass of N-(4,6-bis-n-propylamino-[1,3,5]triazin-2-yl)-N,O-dimethyl-hydroxylamine hydrogen sulfate (XXXVI). High-resolution results obtained through direct injection are presented in Table 4.

TABLE 4

Mass spec results for (XXXVI)

| Calculated Molecular Weight | Theoretical Exact Mass | Formula |
|---|---|---|
| 254.1863 | 254.1855 | $C_{11}H_{22}N_6O$ |

Chromatographic Purity
  The HPLC chromatographic purity of the RS was determined to be 100.0% by area, with no related substances detected.
Water by Determination
  The water content was determined to be 0.04% by Karl Fischer titration.

Elemental Analysis

Elemental analysis of N-(4,6-bis-n-propylamino-[1,3,5]triazin-2-yl)-N,O-dimethyl-hydroxylamine hydrogen sulfate (XXXVI) was obtained and is presented in Table 5.

TABLE 5

Elemental analysis results for (XXXVI)

| Element | Theoretical (%) | Result (%) |
|---------|----------------|------------|
| C | 37.49 | 37.64 |
| H | 6.86 | 6.83 |
| N | 23.85 | 23.73 |

Thermal Analysis by Differential Scanning Calorimetry (DSC)

Figure 13:
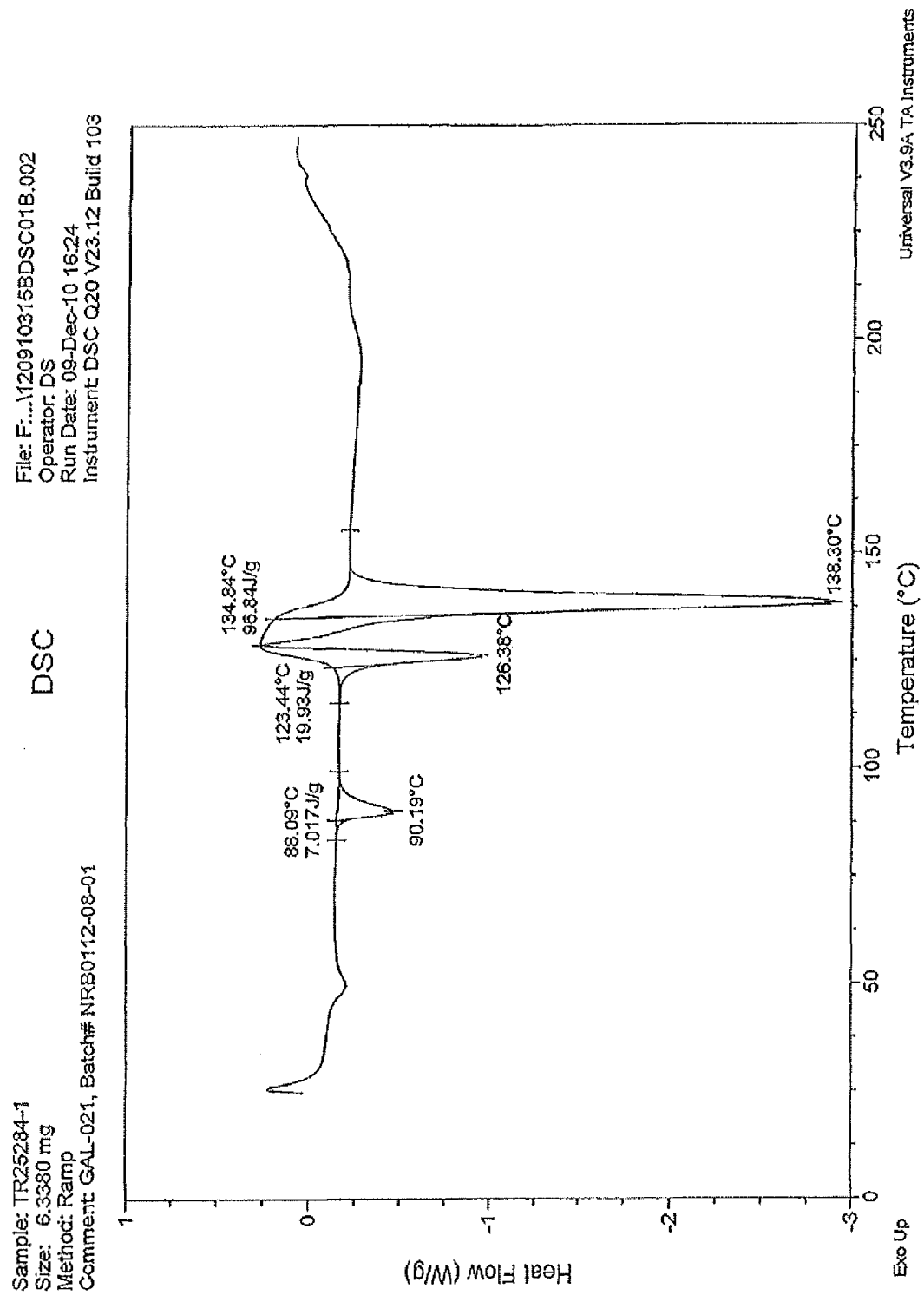
FIG. 13 illustrates the thermal analysis by DSC of N-(4,6-bis-n-propylamino-[1,3,5]triazin-2-yl)-N,O-dimethyl-hydroxylamine hydrogen sulfate (XXXVI).

N-(4,6-Bis-n-propylamino-[1,3,5]triazin-2-yl)-N,O-dimethyl-hydroxylamine hydrogen sulfate (XXXVI) was analyzed from 25° C. to 250° C., at a rate of 10° C. per minute as per cUSP <891>/EP 2.2.34 and was found to have endotherms at 90.19° C., 126.38° C., and 138.30° C. FIG. 13.

X-Ray Powder Diffraction

Figure 14:
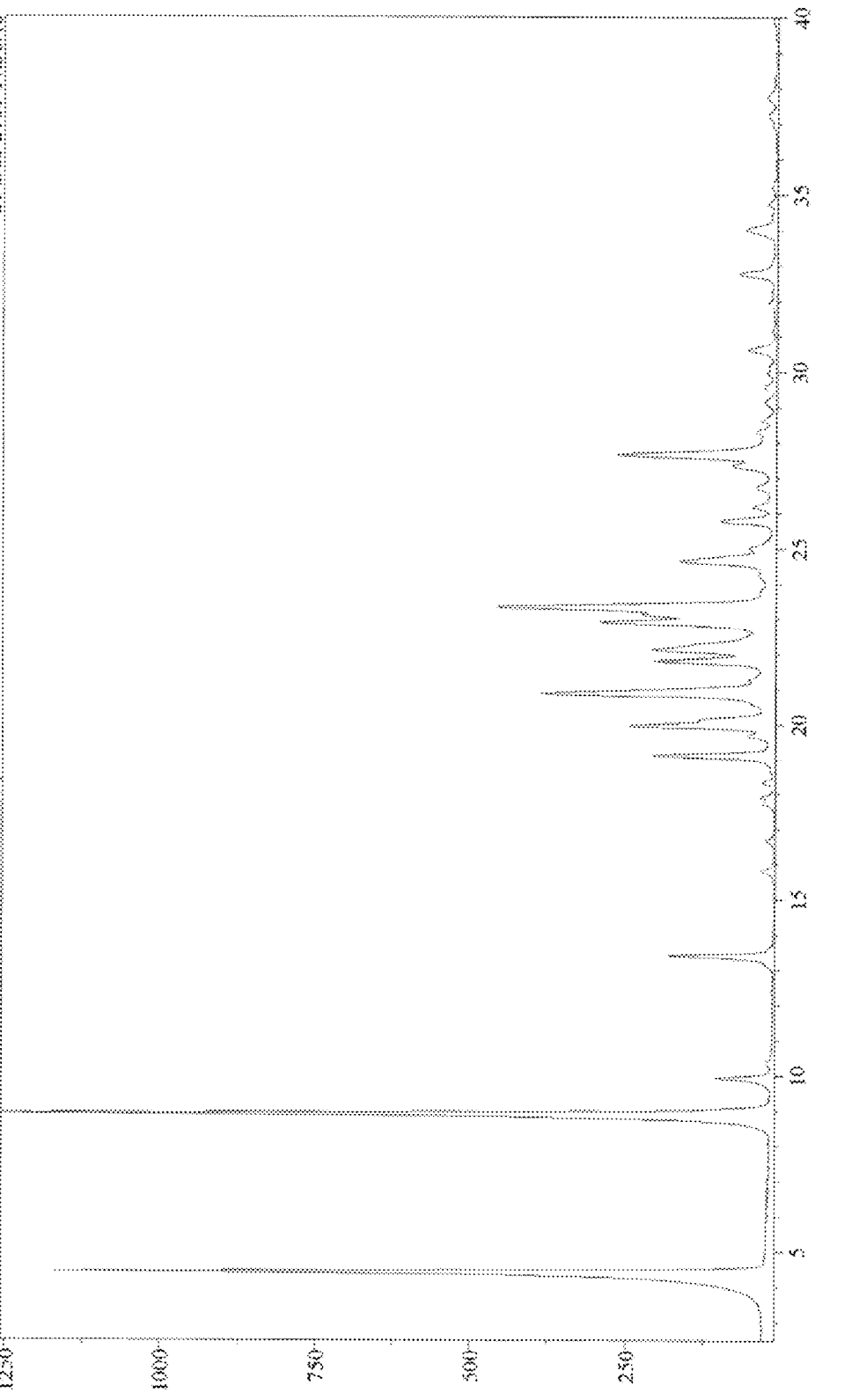
FIG. 14 illustrates the X-ray diffraction spectrum of Compound (XXXVI).

XRPD diffraction pattern of N-(4,6-bis-n-propylamino-[1,3,5]triazin-2-yl)-N,O-dimethyl-hydroxylamine hydrogen sulfate (XXXVI) was obtained and is consistent with Form A; presented in FIG. 14.

Counterion Content

N-(4,6-bis-n-propylamino-[1,3,5]triazin-2-yl)-N,O-dimethyl-hydroxylamine hydrogen sulfate (XXXVI) was found to contain 27.13% sulfate content by titration.

pH of Aqueous Solution

A 1% aqueous solution of N-(4,6-bis-n-propylamino-[1,3,5]triazin-2-yl)-N,O-dimethyl-hydroxylamine hydrogen sulfate (XXXVI) yielded a pH of 1.89.

Physical Description

N-(4,6-bis-n-propylamino-[1,3,5]triazin-2-yl)-N,O-dimethyl-hydroxylamine hydrogen sulfate (XXXVI) was determined to be a white solid.

Example 10

N-(4-(Methoxy(methyl)amino)-6-(propylamino)-1,3,5-triazin-2-yl)propionamide (XL)

Scheme 16

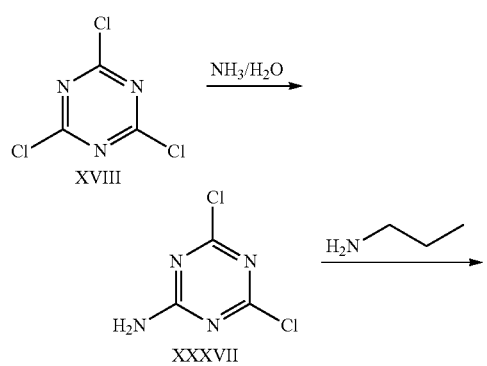

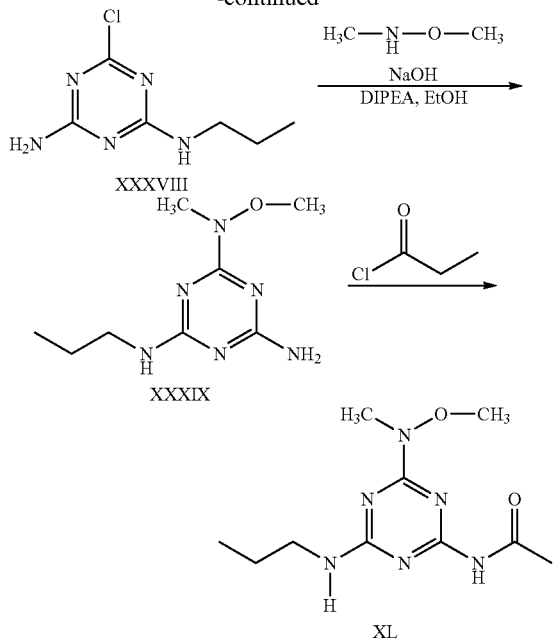

6-Amino-2,4-dichloro-[1,3,5]triazine (XXXIII)

2,4,6-Trichloro-1,3,5-triazine (XVIII) (10.0 g, 55 mmol) was dissolved in acetone (80 mL) and poured into ice-water (80 mL) to form a very fine suspension. To this mixture, 1 N ammonium hydroxide solution (108 mL, 109.4 mmol) was added at 0° C. The reaction was stirred for 30 min at ambient temperature and for additional 60 min at 25° C. The precipitate was filtered off, washed with water (3×25 mL). After drying over calcium chloride under high vacuum, 6-amino-2,4-dichloro-[1,3,5]triazine (XXXVII) was isolated as white powder (7.4 g, 82% yield). LCMS (ESI) m/z=165 (M+H)$^+$.

6-Amino-2-chloro-4-n-propylamino-[1,3,5]triazine (XXXVIII)

6-Amino-2,4-dichloro-[1,3,5]triazine (XXXVII) (30.0 g, 187 mmol) was dissolved in acetone (100 mL) and poured into ice-water (100 mL) to form a very fine suspension. To this mixture, a solution of propan-1-amine (11.0 g, 187 mmol) in acetone (20 mL) was added at 0° C. To this reaction, 2 N NaOH (94 mL, 187 mmol) was added dropwise at a rate to keep the temperature between 0° C. and 5° C. The mixture was stirred for 30 min at ambient temperature and for an additional 60 min at 50° C. The mixture was concentrated and then the precipitate was filtered off and washed with water (3×100 mL). After drying over calcium chloride under high vacuum, 6-amino-2-chloro-4-n-propylamino-[1,3,5]triazine (XXXVIII) was isolated as a white powder (35 g, 100% yield). LCMS (ESI) m/z=188 (M+H)$^+$.

N-(6-Amino-4-n-propylamino-[1,3,5]triazin-2-yl)-N,O-dimethyl-hydroxylamine (XXXIX)

A mixture of 6-amino-2-chloro-4-n-propylamino-[1,3,5]triazine (XXXVIII) (5 g, 26.65 mmol), N,O-dimethylhydroxylamine hydrochloride (13 g, 133.24 mmol) and DIPEA (27.5 g, 213.2 mmol) in EtOH (100 mL) was heated at 100° C. for 16 h, after which time the solvent was removed under reduced pressure. The residue was dissolved in EtOAc (400 mL), which was washed with water (200 mL) and then with a brine solution (200 mL) and finally dried over Na₂SO₄. The solvent was removed under reduced pressure to yield N-(6-amino-4-n-propylamino-[1,3,5]triazin-2-yl)-N,O-dimethyl-hydroxylamine (XXXIX) as a white solid (5 g, 89% yield). LCMS (ESI) m/z=213 (M+H)⁺.

N-(4-(Methoxy(methyl)amino)-6-(propylamino)-1,3,5-triazin-2-yl)propionamide (XL)

N-(6-amino-4-n-propylamino-[1,3,5]triazin-2-yl)-N,O-dimethyl-hydroxylamine (XXXIX) (5 g, 23.58 mmol) was dissolved in THF (50 mL). Propionyl chloride (3.25 g, 35.38 mmol) and DIPEA (5.47 g, 42.44 mmol) were added at 0° C. The resultant mixture was stirred at ambient temperature for 10 min, then stirred at 70° C. for 16 h, after which time the solvent was removed under reduced pressure. The residue was dissolved in EtOAc (250 mL), and this extract was washed with water (80 mL) and then with a brine solution (80 mL), and lastly dried over Na₂SO₄. The solvent was removed under reduced pressure and the crude product was purified by flash column chromatography (pet ether/ethyl acetate=5/1 to 2/1) to yield 930 mg (15%) of the desired product. The isolated free amine (930 mg, 3.47 mmol) was dissolved in H₂O (10 mL) and 0.5 M HCl solution in H₂O (10.4 mL) and then the solution was lyophilized to yield N-(4-(methoxy(methyl)amino)-6-(propylamino)-1,3,5-triazin-2-yl)propionamide (XL) as a colorless oil (1.06 g). LCMS: (ESI) m/z=269 (M+H)⁺. ¹H NMR (500 MHz, DMSO): δ (ppm) 12.23 (s, 1H), 8.25-9.45 (m, 2H), 3.76-3.84 (m, 3H), 3.30-3.44 (m, 5H), 2.55-2.56 (m, 1H), 2.21-2.22 (m, 1H), 1.53-1.58 (m, 2H), 0.88-1.08 (m, 6H).

Example 11

N-(4,6-Bis-propylamino-[1,3,5]triazin-2-yl)-O-methyl-hydroxylamine (XLI)

Example 12

N-(4,6-Bis-propylamino-[1,3,5]triazin-2-yl)-O-methyl-hydroxylamine hydrochloride (XLII)

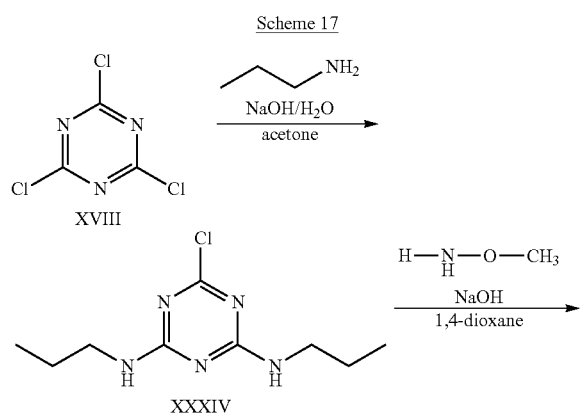

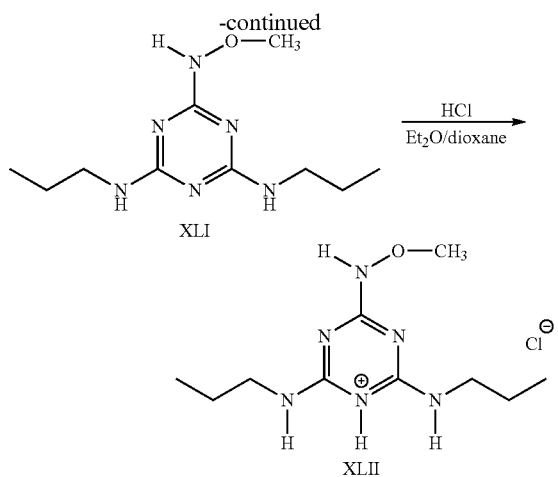

2-Chloro-N-(4,6-bis-(n-propylamino)-[1,3,5]triazine (XXXIV)

A 2 M NaOH solution (163 mL, 325.36 mmol) was added in a dropwise manner to a suspension of 2,4,6-trichloro-1,3,5-triazine (XVIII) (30.0 g, 162.68 mmol) and n-propylamine (26.8 mL, 325.36 mmol) in acetone (600 mL) and water (30 mL) at 0° C. (water-ice/NaCl bath). The ice bath was removed and the reaction mixture was heated at 50° C. for 3 h, then cooled. Water (200 mL) was added to the reaction mixture; the precipitate was filtered, washed with water (200 mL) and dried over P₂O₅ at 40° C. for 20 h to yield 2-chloro-N-(4,6-bis-(n-propylamino)-[1,3,5]triazine (XXXIV, 33.6 g, 90% yield). 400 MHz ¹H-NMR (DMSO-d₆, ppm) 7.80 (0.85H, t, J=5.5 Hz), 7.76-7.66 (1H, m), 7.49 (0.15H, t, J=5.5 Hz), 3.22-3.11 (4H, m), 1.55-1.42 (4H, m), 0.88-0.82 (6H, m). ESI-MS (m/z): 230, 232 [M+H]⁺.

N-(4,6-Bis-propylamino-[1,3,5]triazin-2-yl)-O-methyl-hydroxylamine (XLI)

A mixture of 6-chloro-N,N'-dipropyl-[1,3,5]triazine-2,4-diamine (XXXIV) (2.30 g, 10.01 mmol), O-methyl-hydroxylamine hydrochloride (1.67 g, 20.02 mmol) and NaOH (0.72 g, 18.00 mmol) in 1,4-dioxane (30 mL) and water (6 mL) was heated at 60° C. for 3 h. After this time, NaOH (0.72 g, 18.00 mmol) was added and the reaction mixture was heated for another 3 h. The volatiles were removed under reduced pressure. Saturated NaHCO₃ solution (100 mL) was added to the residue, the mixture was extracted with EtOAc (3×25 mL). The combined organic extracts were washed with water (50 mL), brine (50 mL) and dried over Na₂SO₄. The solvent was removed under reduced pressure and the crude product was purified by flash column chromatography using gradient elution from CH₂Cl₂/EtOH (99:1) to CH₂Cl₂/EtOH (95:5) to yield 2.17 g (90%) of N-(4,6-bis-propylamino-[1,3,5]triazin-2-yl)-O-methyl-hydroxylamine (XLI). ESI-MS (m/z): 241 [M+H]⁺

N-(4,6-Bis-propylamino-[1,3,5]triazin-2-yl)-O-methyl-hydroxylamine hydrochloride (XLII)

A 2M HCl/ethyl ether (4.5 mL, 9.00 mmol) was added to the solution N-(4,6-bis-propylamino-[1,3,5]triazin-2-yl)-O-methyl-hydroxylamine (XLI) (2.17 g, 9.03 mmol) in 1,4-dioxane (5 mL) at 0° C. The mixture was stirred for 0.5 h at 0°

C., volatiles were removed under reduced pressure to yield N-(4,6-bis-propylamino-[1,3,5]triazin-2-yl)-O-methyl-hydroxylamine hydrochloride (XLII) in quantitative yield. 400 MHz $^1$H NMR (DMSO-d$_6$, ppm) 12.5-11.5 (2H, br s), 8.49 (1H, br s), 8.34 (1H, br s), 3.71 (3H, s), 3.34-3.16 (4H, m), 1.59-1.46 (4H, m), 0.94-0.83 (6H, m). ESI-MS (m/z) 241 [M+H]$^+$.

Example 13

O-Allyl-N-(4,6-bis-propylamino-[1,3,5]triazin-2-yl)-hydroxylamine (XLIII)

Example 14

O-Allyl-N-(4,6-bis-propylamino-[1,3,5]triazin-2-yl)-hydroxylamine hydrochloride salt (XLIV)

Scheme 18

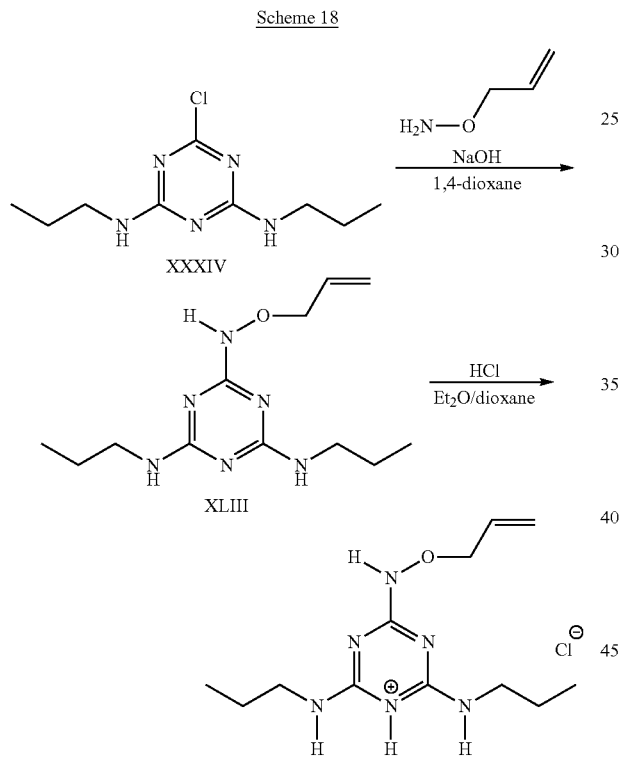

O-Allyl-N-(4,6-bis-propylamino-[1,3,5]triazin-2-yl)-hydroxylamine

A mixture of 2-chloro-N-(4,6-bis-(n-propylamino)-[1,3,5]triazine (XXXIV) (2.00 g, 8.71 mmol), 0-allyl-hydroxylamine hydrochloride (1.91 g, 17.42 mmol) and NaOH (0.70 g, 17.42 mmol) in 1,4-dioxane (25 mL) and water (5 mL) was heated at 60° C. for 4 h. The volatiles were removed under reduced pressure. Saturated NaHCO$_3$ solution (100 mL) was added to the residue and the mixture was extracted with EtOAc (3×25 mL). The combined organic extracts were washed with water (50 mL), brine (50 mL) and dried over Na$_2$SO$_4$. The solvent was removed under reduced pressure and the crude product was purified by flash column chromatography using gradient elution from CH$_2$Cl$_2$/EtOH (99:1) to CH$_2$Cl$_2$/EtOH (95:5) to yield O-allyl-N-(4,6-bis-propylamino-[1,3,5]triazin-2-yl)-hydroxylamine (XLIII, 2.05 g, 88% yield). ESI-MS (m/z) 267 [M+H]$^+$.

O-Allyl-N-(4,6-bis-propylamino-[1,3,5]triazin-2-yl)-hydroxylamine hydrochloride

O-Allyl-N-(4,6-bis-propylamino-[1,3,5]triazin-2-yl)-hydroxylamine hydrochloride (XLIV) was prepared from O-allyl-N-(4,6-bis-propylamino-[1,3,5]triazin-2-yl)-hydroxylamine (XLIII) and 2M HCl/ethyl ether as described in Example 12. 400 MHz $^1$H NMR (DMSO-d$_6$, ppm) 11.7-10.0 (1H, m), 7.9-7.1 (2H, m), 6.09-5.92 (1H, m), 5.39-5.18 (2H, m), 4.35 (2H, d, J=6.0 Hz), 3.28-3.11 (4H, m), 1.56-1.42 (4H, m), 0.91-0.81 (6H, m). ESI-MS (m/z): 267 [M+H]$^+$. MP: 130-132° C.

Example 15

N-(4,6-Bis-propylamino-[1,3,5]triazin-2-yl)-hydroxylamine (XLV)

Scheme 19

N-(4,6-Bis-propylamino-[1,3,5]triazin-2-yl)-hydroxylamine (XLV) was prepared from 2-chloro-N-(4,6-bis-(n-propylamino)-[1,3,5]triazine (XXXIV) and hydroxylamine hydrochloride as described in Example 13 (99% yield). 400 MHz $^1$H NMR (DMSO-d$_6$, ppm) 9.0-8.6 (1H, br s), 8.39-8.14 (1H, s), 6.89-6.55 (2H, m), 3.23-3.06 (4H, m), 1.54-1.40 (4H, m), 0.84 (6H, t, J=7.4 Hz). ESI-MS (m/z): 227 [M+H]$^+$. MP: 138-141° C.

Example 16

N-(4,6-Bis-propylamino-[1,3,5]triazin-2-yl)-N',N'-dimethylhydrazine (XLVI)

N-(4,6-Bis-propylamino-[1,3,5]triazin-2-yl)-N',N'-dimethylhydrazine (XLVI) may be prepared from 2-chloro-N-(4,6-bis-(n-propylamino)-[1,3,5]triazine (XXXIV) and N,N-dimethylhydrazine as described in Example 19.

Scheme 20

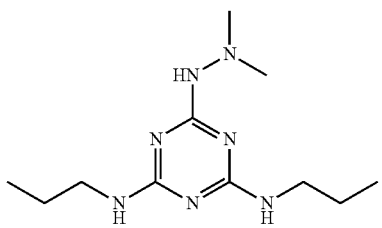

XLVI

Example 17

6-(Methoxy(methyl)amino)-N2-propyl-1,3,5-triazine-2,4-diamine (XLVII)

Scheme 21

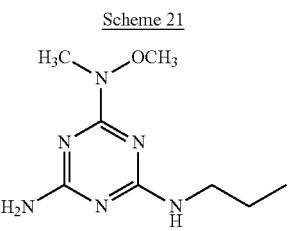

6-(Methoxy(methyl)amino)-N2-propyl-1,3,5-triazine-2,4-diamine (XLVII) may be prepared from 6-amino-2-chloro-4-n-propylamino-[1,3,5]triazine (XXXVIII) and N,O-dimethylhydroxylamine as described in Example 10.

Example 18

N-(4,6-Bis-propylamino-[1,3,5]triazin-2-yl)-N-methyl-hydroxylamine (XLVIII)

Scheme 22

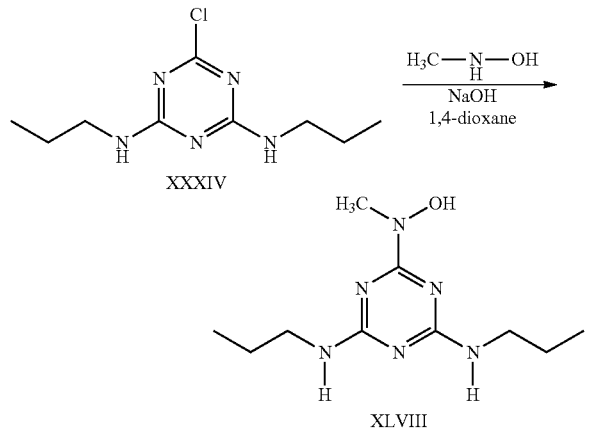

N-(4,6-Bis-propylamino-[1,3,5]triazin-2-yl)-N-methyl-hydroxylamine (XLVIII) was prepared from 2-chloro-N-(4,6-bis-(n-propylamino)-[1,3,5]triazine (XXXIV) and N-methyl-hydroxylamine hydrochloride as described in Example 13 (90% yield). 400 MHz $^1$H NMR (DMSO-$d_6$, ppm) 8.93 (1H, s), 6.92-6.43 (2H, m), 3.23-3.07 (7H, m), 1.55-1.38 (4H, m), 0.84 (6H, t, J=7.4 Hz). ESI-MS (m/z) 241 [M+H]$^+$.

Example 19

N-(4,6-Bis-propylamino-[1,3,5]triazin-2-yl)-N,N'-dimethyl-hydrazine (XLIX)

Example 20

N-(4,6-Bis-propylamino-[1,3,5]triazin-2-yl)-N,N'-dimethyl-hydrazine hydrogen sulfate (L)

Scheme 23

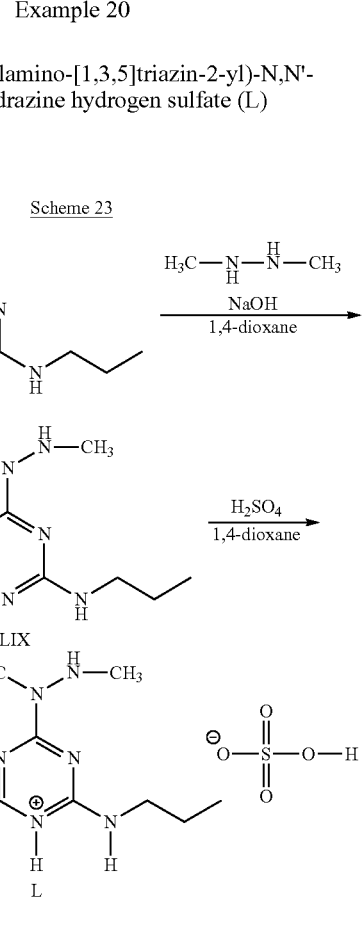

N-(4,6-Bis-propylamino-[1,3,5]triazin-2-yl)-N,N'-dimethyl-hydrazine (XLIX)

A mixture of 2-chloro-N-(4,6-bis-(n-propylamino)-[1,3,5] triazine (XXXIV) (2.50 g, 10.88 mmol), N,N'-dimethyl-hydrazine dihydrochloride (2.89 g, 21.76 mmol) and NaOH (2.18 g, 54.40 mmol) in 1,4-dioxane (40 mL) and water (20 mL) was heated at 60° C. for 18 h. The volatiles were removed under reduced pressure. Saturated NaHCO$_3$ solution (100 mL) was added to the residue, the mixture was extracted with EtOAc (3×50 mL). The combined organic extracts were washed with water (75 mL), brine (75 mL) and dried over Na$_2$SO$_4$. The solvent was removed under reduced pressure and the crude product was purified by flash column chromatography using gradient elution (CH$_2$Cl$_2$/EtOH (99:1) to CH$_2$Cl$_2$/EtOH (95:5)) to yield N-(4,6-Bis-propylamino-[1,3,5]triazin-2-yl)-N,N'-dimethyl-hydrazine (1.17 g, 42%). 200 MHz $^1$H NMR (DMSO-$d_6$, ppm): 6.81-6.44 (2H, m), 5.31 (1H, br s), 3.24-3.08 (4H, m), 3.05 (3H, s), 2.47-2.40 (3H, m), 1.57-1.37 (4H, m), 0.84 (6H, t, J=7.4 Hz). ESI-MS (m/z): 254 [M+H]$^+$.

N-(4,6-Bis-propylamino-[1,3,5]triazin-2-yl)-N,N'-dimethyl-hydrazine hydrogen sulfate (L)

95% H$_2$SO$_4$ (0.26 mL, 4.62 mmol) was added dropwise to the solution of 6-(N,N'-dimethyl-hydrazino)-N,N'-dipropyl-[1,3,5]triazine-2,4-diamine (XLIX) (1.17 g, 4.62 mmol) in 1,4-dioxane (10 mL) at 0° C. The mixture was stirred for 0.5 h at room temperature; volatiles were removed under reduced pressure. The residue was co-evaporated with dry toluene (3×25 mL) to yield N-(4,6-Bis-propylamino-[1,3,5]triazin-2-yl)-N,N'-dimethyl-hydrazine hydrogen sulfate (L) in quantitative yield. 400 MHz $^1$H NMR (DMSO-d$_6$, ppm) 8.48-8.32 (1H, m), 7.9-7.7 (0.5H, br s), 7.70-7.61 (0.5H, m), 3.34-3.20 (4H, m), 3.21 (1.5H, s), 3.17 (1.5H, s), 2.52 (1.5H, s), 2.51 (1.5H, s, overlapped with DMSO), 1.59-1.46 (4H, m), 0.93-0.82 (6H, m). ESI-MS (m/z): 254 [M+H]$^+$.

Example 21

O-Benzyl-N-(4,6-bis-propylamino-[1,3,5]triazin-2-yl)-N-methyl-hydroxylamine (LIII)

Example 22

O-Benzyl-N-(4,6-bis-propylamino-[1,3,5]triazin-2-yl)-N-methyl-hydroxylamine hydrogen sulfate salt (LIV)

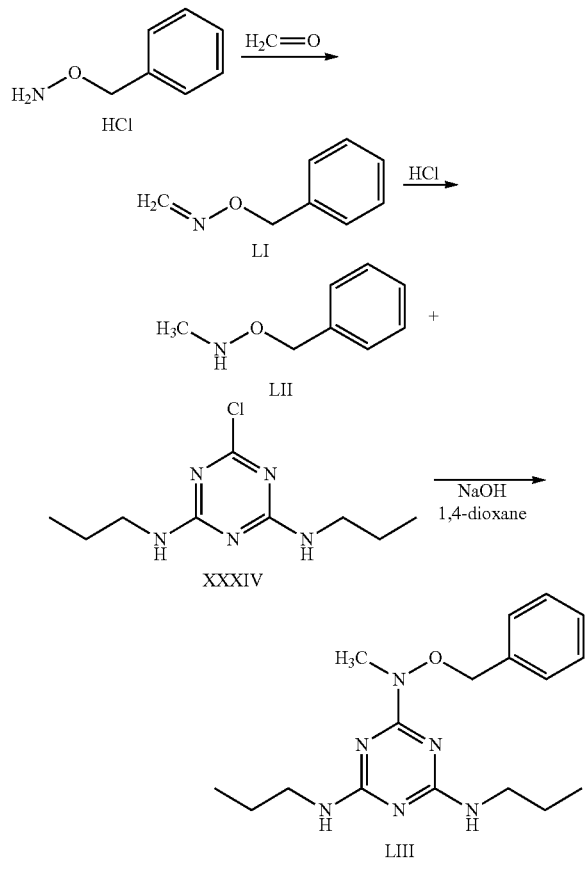

Scheme 24

Formaldehyde O-benzyl-oxime (LI)

A NaOH (1.25 g, 31.32 mmol) solution in water (6 mL) was added to the mixture of O-benzyl-hydroxylamine hydrochloride (5.00 g, 31.32 mmol) and formaldehyde (~37 wt. % in H$_2$O) (2.3 mL, 31.32 mmol) in toluene (40 mL). The reaction mixture was stirred at room temperature for 1 h. After this time, the organic phase was separated and the water phase was extracted with dichloromethane (3×30 mL). The combined organic phases were dried over Na$_2$SO$_4$, and concentrated in vacuo to yield formaldehyde O-benzyl-oxime (LI, 4.15 g, 98%). 400 MHz $^1$H NMR (CDCl$_3$, ppm) 7.40-7.29 (5H, m), 7.09 (1H, d, J=8.2 Hz), 6.47 (1H, d, J=8.2 Hz), 5.14 (2H, s).

O-Benzyl-N-methyl-hydroxylamine (LII)

A 1M HCl/EtOH solution (50 mL) was added dropwise to the solution of formaldehyde O-benzyl-oxime (3.85 g, 28.48 mmol) in EtOH at 0° C. The mixture was stirred at room temperature for 1 hour, volatiles were removed in vacuo. The residue was dissolved in dichloromethane (100 mL), washed with saturated NaHCO$_3$ solution (75 mL), water (75 mL), and dried over Na$_2$SO$_4$. The product was purified by flash column chromatography using gradient elution from petroleum ether/EtOAc (9:1) to petroleum ether/EtOAc (7:1) to yield O-benzyl-N-methyl-hydroxylamine (1.72 g, 44%). 200 MHz $^1$H NMR (CDCl$_3$, ppm) 7.40-7.27 (5H, m), 5.53 (1H, br s), 4.71 (2H, s), 2.73 (3H, s).

O-Benzyl-N-(4,6-bis-propylamino-[1,3,5]triazin-2-yl)-N-methyl-hydroxylamine (LIII)

2-Chloro-N-(4,6-bis-(n-propylamino)-[1,3,5]triazine (XXXIV) and O-benzyl-N-methyl-hydroxylamine (LII) were reacted as described in Example 13 to yield O-benzyl-N-(4,6-bis-propylamino-[1,3,5]triazin-2-yl)-N-methyl-hydroxylamine (LIII) (29% yield). 200 MHz $^1$H NMR (DMSO-d$_6$, ppm) 7.52-7.28 (5H, m), 7.07-6.67 (2H, m), 4.93 (2H, s), 3.26-3.03 (7H, m), 1.58-1.39 (4H, m), 0.85 (6H, t, J=7.2 Hz). ESI-MS (m/z): 331 [M+H]$^+$.

O-Benzyl-N-(4,6-bis-propylamino-[1,3,5]triazin-2-yl)-N-methyl-hydroxylamine hydrogen sulfate (LIV)

O-Benzyl-N-(4,6-bis-propylamino-[1,3,5]triazin-2-yl)-N-methyl-hydroxylamine (LIII) was reacted with 95% H$_2$SO$_4$ as described in Example 20 to yield O-benzyl-N-(4,6-bis-propylamino-[1,3,5]triazin-2-yl)-N-methyl-hydroxylamine hydrogen sulfate (LIV) in quantitative yield. 400 MHz $^1$H NMR (DMSO-d$_6$, ppm) 12.0-10.9 (1H, br s), 8.7-8.3 (1H, br s), 7.56-7.46 (2H, m), 7.46-7.37 (2.5H, m), 7.36-7.30 (0.5H, m), 5.07-4.95 (2H, m), 3.44-3.16 (7H, m), 1.61-1.45 (4H, m), 0.94-0.82 (6H, m). ESI-MS (m/z): 331 [M+H]$^+$.

Example 23

N-(4,6-Bis-propylamino-[1,3,5]triazin-2-yl)-N-isopropyl-hydroxylamine (LV)

Example 24

N-(4,6-Bis-propylamino-[1,3,5]triazin-2-yl)-N-isopropyl-hydroxylamine hydrogen sulfate (LVI)

Scheme 25

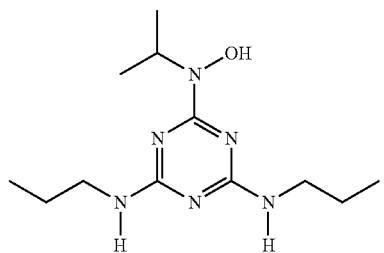

LV

N-(4,6-Bis-propylamino-[1,3,5]triazin-2-yl)-N-isopropyl-hydroxylamine (LV)

2-Chloro-N-(4,6-bis-(n-propylamino)-[1,3,5]triazine (XXXIV) and N-isopropyl-hydroxylamine hydrochloride were reacted as described in Example 13 to yield N-(4,6-bis-propylamino-[1,3,5]triazin-2-yl)-N-isopropyl-hydroxylamine (LV) (61% yield). ESI-MS (m/z): 269 [M+H]$^+$.

N-(4,6-Bis-propylamino-[1,3,5]triazin-2-yl)-N-isopropyl-hydroxylamine hydrogen sulfate (LVI)

N-(4,6-Bis-propylamino-[1,3,5]triazin-2-yl)-N-isopropyl-hydroxylamine hydrogen sulfate (LVI) was prepared from N-(4,6-bis-propylamino-[1,3,5]triazin-2-yl)-N-isopropyl-hydroxylamine (LV) and 95% H$_2$SO$_4$ as described in Example 20 (95% yield). 200 MHz $^1$H NMR (DMSO-d$_6$, ppm) 11.5-11.1 (1H, br s), 10.66-10.40 (1H, m), 8.45 (1H, s), 7.75-7.36 (1H, m), 4.77-4.55 (1H, m), 3.30-3.16 (4H, m), 1.61-1.44 (4H, m), 1.17 (6H, t, J=7.0 Hz), 0.89 (3H, t, J=7.3 Hz), 0.86 (3H, t, J=7.3 Hz). ESI-MS (m/z) 269 [M+H]$^+$. M.P.: 154-156° C.

Example 25

6-[1,2]Oxazinan-2-yl-N,N'-dipropyl-[1,3,5]triazine-2,4-diamine (LVII)

Example 26

6-[1,2]Oxazinan-2-yl-N,N'-dipropyl-[1,3,5]triazine-2,4-diamine hydrogen sulfate (LVIII)

Scheme 26

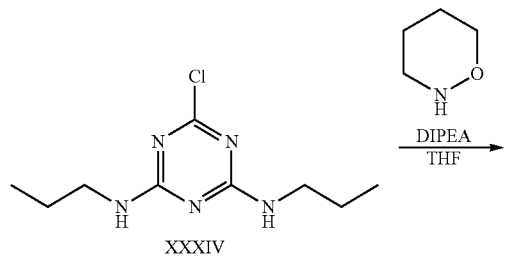

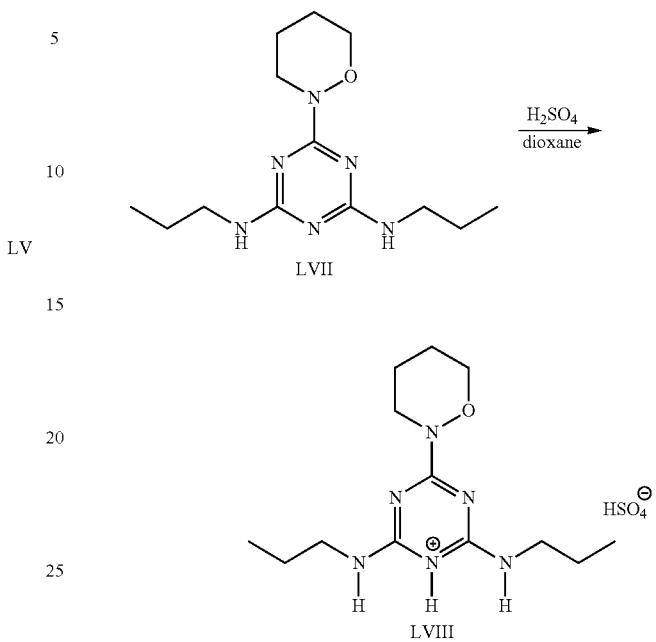

6-[1,2]Oxazinan-2-yl-N,N'-dipropyl-[1,3,5]triazine-2,4-diamine (LVII)

An ACE® pressure tube was charged with 2-chloro-N-(4,6-bis-(n-propylamino)-[1,3,5]triazine (XXXIV) (1.50 g, 6.53 mmol), N-ethyldiisopropylamine (19.59 mmol), 1,2-oxazinane hydrochloride (1.61 g, 13.06 mmol) and tetrahydrofuran. The reaction mixture was heated at 100° C. for 2 h, then cooled and poured into saturated NaHCO$_3$ solution (50 mL). The suspension was extracted with EtOAc (3×25 mL). The combined organic extracts were washed with water (50 mL), brine (50 mL) and dried over Na$_2$SO$_4$. The solvent was removed under reduced pressure and the crude product was purified by flash column chromatography using gradient elution from CH$_2$Cl$_2$/EtOH (99:1) to CH$_2$Cl$_2$/EtOH (95:5) to yield 6-[1,2]oxazinan-2-yl-N,N'-dipropyl-[1,3,5]triazine-2,4-diamine (LVII) (1.63 g, 89%). ESI-MS (m/z): 281 [M+H]$^+$.

6-[1,2]Oxazinan-2-yl-N,N'-dipropyl-[1,3,5]triazine-2,4-diamine hydrogen sulfate (LVIII)

6-[1,2]Oxazinan-2-yl-N,N'-dipropyl-[1,3,5]triazine-2,4-diamine hydrogen sulfate (LVIII) was prepared from 6-[1,2]oxazinan-2-yl-N,N'-dipropyl-[1,3,5]triazine-2,4-diamine (LVII) and 95% H$_2$SO$_4$ as described in Example 20. Quantitative yield was isolated. 400 MHz $^1$H-NMR (DMSO-d$_6$, ppm) 11.6-11.3 (1H, br s), 8.61-8.41 (0.8H, m), 8.18-8.03 (0.2H, m), 7.63-7.28 (1H, m), 4.14-4.08 (2H, m), 3.92-3.81 (2H, m, overlapped with water), 3.36-3.19 (4H, m), 1.86-1.78 (2H, m), 1.77-1.68 (2H, m), 1.6-1.45 (4H, m), 1.60-1.45 (6H, m). ESI-MS (m/z): 281 [M+H]$^+$. M.P.: 134-137° C.

Example 27

N-(4,6-Bis-propylamino-[1,3,5]triazin-2-yl)-O-isopropyl-N-methyl-hydroxylamine (LXIV)

Example 28

N-(4,6-Bis-propylamino-[1,3,5]triazin-2-yl)-O-isopropyl-N-methyl-hydroxylamine hydrogen sulfate (LXV)

2-Isopropoxy-isoindole-1,3-dione (LIX)

Diethyl azodicarboxylate (14.5 mL, 73.56 mmol) was added dropwise at 0° C. to a stirred suspension of propan-2-ol (4.7 mL, 61.30 mmol), triphenylphosphine (19.30 g, 73.56 mmol), and N-hydroxyphthalimide (10.00 g, 61.30 mmol) in THF (50 mL). The mixture was stirred at room temperature for 20 h and evaporated to dryness. The product was purified by flash column chromatography using gradient elution from petroleum ether/EtOAc (9:1) to petroleum ether/EtOAc (5:1) to yield 2-isopropoxy-isoindole-1,3-dione (LIX, 10.92 g, 87%). 400 MHz $^1$H NMR (DMSO-$d_6$, ppm): 7.86 (4H, s), 4.44 (1H, septet, J=6.2 Hz), 1.28 (6H, d, J=6.2 Hz).

Scheme 27

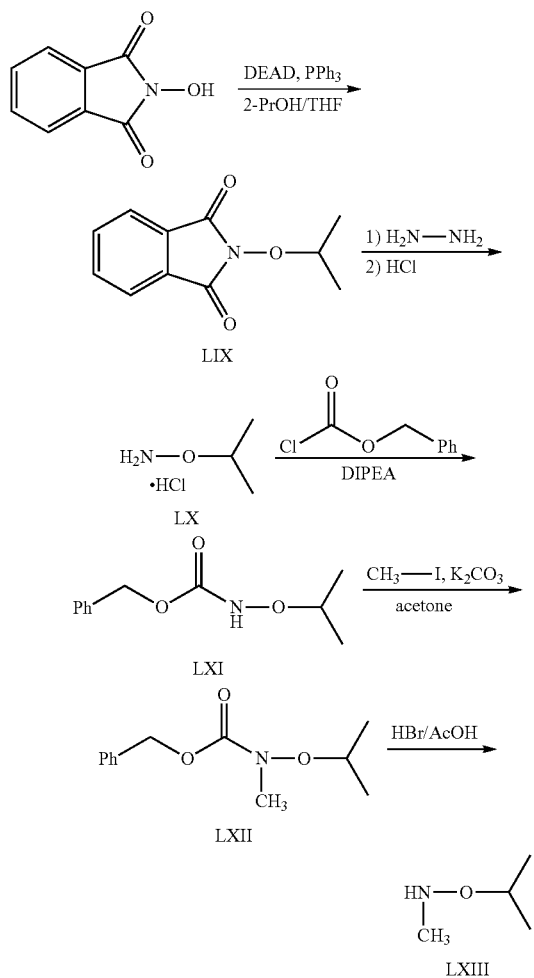

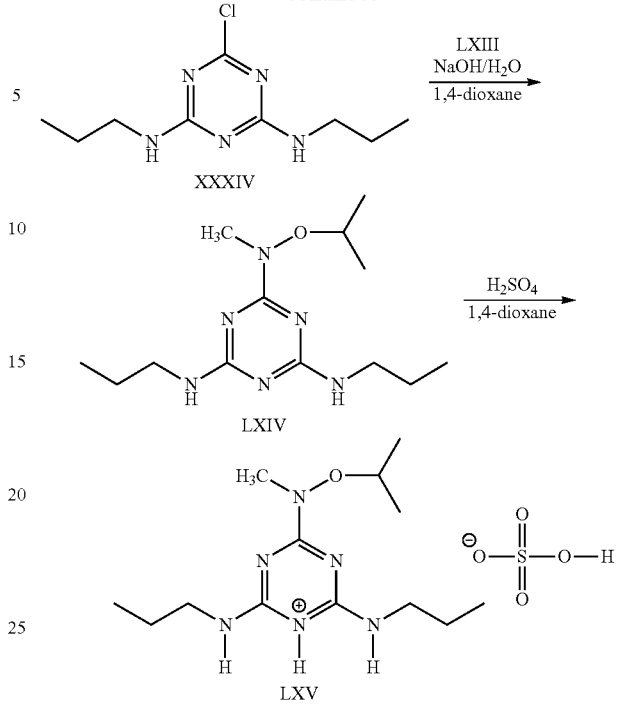

O-Isopropyl-hydroxylamine hydrochloride (LX)

A mixture of 2-isopropoxy-isoindole-1,3-dione (LIX, 10.78 g, 52.50 mmol) and hydrazine monohydrate (5.1 mL, 105.00 mmol) in $CH_2Cl_2$ (60 mL) was stirred at room temperature for 20 h. The reaction mixture was filtered. The filtrate was washed with water (70 mL), brine (70 mL) and dried over $Na_2SO_4$. After removing the drying agent via filtration, 4M HCl/1,4-dioxane (13.8 mL, 55.00 mmol) was added and the volatiles was removed under reduced pressure to yield 0-isopropyl-hydroxylamine hydrochloride (LX, 3.91 g, 67% yield). 400 MHz $^1$H NMR (DMSO-$d_6$, ppm) 11.04 (3H, br s), 4.35 (1H, septet, J=6.2 Hz), 1.21 (6H, d, J=6.2 Hz).

O-Benzyl-N-isopropoxy carbamate (LXI)

To a pre-cooled (0° C.) solution of 0-isopropyl-hydroxylamine hydrochloride (3.89 g, 34.87 mmol) in $CH_2Cl_2$ (150 mL) was added N,N-diisopropyl-ethylamine (14.4 mL, 87.18 mmol) and benzyl chloroformate (5.0 mL, 34.87 mmol). The resulting solution was stirred at room temperature for 5 h. At this time the solution was washed twice with saturated aqueous $NaHCO_3$ (30 mL) and dried over $Na_2SO_4$. The product was purified by flash column chromatography using gradient elution from petroleum ether/EtOAc (95:5) to petroleum ether/EtOAc (6:1) to yield O-benzyl-N-isopropoxycarbamate (LXI, 4.98 g, 68%). 400 MHz $^1$H NMR (DMSO-$d_6$, ppm) 10.22 (1H, s), 7.42-7.29 (5H, m), 5.07 (2H, s), 3.89 (1H, septet, J=6.2 Hz), 1.11 (6H, d, J=6.2 Hz).

O-Benzyl-N-methyl-N-isopropoxy carbamate (LXII)

An ACE® pressure tube was charged with benzyl isopropoxycarbamate (4.98 g, 23.80 mmol), anhydrous $K_2CO_3$ (4.94 g, 35.70 mmol), methyl iodide (6.7 mL, 107.10), and anhydrous acetone (30 mL). The reaction mixture was heated at 70° C. for 24 h. The reaction mixture was filtered, and the acetone was evaporated. The resulting slurry was dissolved in EtOAc, washed with water (3×50 mL), dried ($Na_2SO_4$), and filtered. The solvent was removed to yield benzyl isopropoxy (methyl)carbamate (4.96 g, 93%). 400 MHz 1H-NMR (DMSO-$d_6$, ppm) 7.41-7.30 (5H, m), 5.12 (2H, s), 4.08 (1H, septet, J=6.2 Hz), 3.08 (3H, s), 1.12 (6H, d, J=6.2 Hz).

O-Isopropyl-N-methyl-hydroxylamine hydrochloride (LXIII)

O-Benzyl-N-methyl-Nisopropoxy carbamate (4.96 g, 22.22 mmol) and 33% HBr/AcOH (45 mL) were stirred at room temperature for 20 min. Saturated solution of $NaHCO_3$ (400 mL) was added, the suspension was extracted with $CH_2Cl_2$ (3×150 mL). The combined organic extracts were dried over $Na_2SO_4$. After removal of the drying agent via filtration, 4M HCl/1,4-dioxane (6.7 mL, 26.65 mmol) was added, and the volatiles was removed under reduced pressure to yield O-isopropyl-N-methyl-hydroxylamine hydrochloride (2.09 g, 75%). 400 MHz $^1$H NMR (DMSO-$d_6$, ppm) 12.3-11.7 (2H, br s), 4.49 (1H, septet, J=6.1 Hz), 2.77 (3H, s), 1.12 (6H, d, J=6.1 Hz).

N-(4,6-Bis-propylamino-[1,3,5]triazin-2-yl)-O-isopropyl-N-methyl-hydroxylamine (LXIV)

A mixture of 2-chloro-N-(4,6-bis-(n-propylamino)-[1,3,5]triazine (XXXIV) (1.65 g, 16.61 mmol), O-isopropyl-N-methyl-hydroxylamine hydrochloride (LXIII, 2.09 g, 16.61 mmol) and NaOH (0.66 g, 16.61 mmol) in 1,4-dioxane (50 mL) and water (5 mL) was heated at 100° C. for 16 h. The volatiles were then removed under reduced pressure. Saturated $NaHCO_3$ solution (50 mL) was added to the residue and the mixture was extracted with EtOAc (3×50 mL). The combined organic extracts were washed with water (50 mL), brine (50 mL) and dried over $Na_2SO_4$. The solvent was removed under reduced pressure and the crude product was purified by flash column chromatography using gradient elution from $CH_2Cl_2$/EtOH (99:1) to $CH_2Cl_2$/EtOH (95:5) to yield N-(4,6-bis-propylamino-[1,3,5]triazin-2-yl)-O-isopropyl-N-methyl-hydroxylamine (LXIV, 1.93 g, 95%). ESI-MS (m/z): 283 [M+H]$^+$.

N-(4,6-Bis-propylamino-[1,3,5]triazin-2-yl)-O-isopropyl-N-methyl-hydroxylamine hydrogen sulfate (LXV)

To a solution N-(4,6-bis-propylamino-[1,3,5]triazin-2-yl)-O-isopropyl-N-methyl-hydroxylamine (LXIV, 1.93 g, 6.83 mmol) in 1,4-dioxane (6 mL) at 0° C. was added 95% $H_2SO_4$ (0.36 mL, 6.83 mmol) in a drop-wise manner. The mixture was stirred for 0.5 h at room temperature and then the volatiles were removed under reduced pressure. The residue was co-evaporated with dry toluene (3×25 mL) to yield N-(4,6-bis-propylamino-[1,3,5]triazin-2-yl)-O-isopropyl-N-methyl-hydroxylamine hydrogen sulfate (quantitative yield). 400 MHz $^1$H-NMR (DMSO-$d_6$, ppm) 11.3-10.7 (1H, br s), 8.8-8.4 (1H, br s), 8.2-8.0 (0.3H, br s), 8.04-7.65 (0.7H, m), 4.43-4.28 (1H, m), 3.42-3.18 (7H, m), 1.64-1.44 (4H, m), 1.25 (6H, d, J=6.1 Hz), 0.94-0.82 (6H, m). ESI-MS (m/z): 283 [M+H]$^+$.

Example 29

O-Benzyl-N-(4,6-bis-propylamino-[1,3,5]triazin-2-yl)-N-ethyl-hydroxylamine (LXVIII)

Example 30

O-Benzyl-N-(4,6-bis-propylamino-[1,3,5]triazin-2-yl)-N-ethyl-hydroxylamine hydrogen sulfate (LXIX)

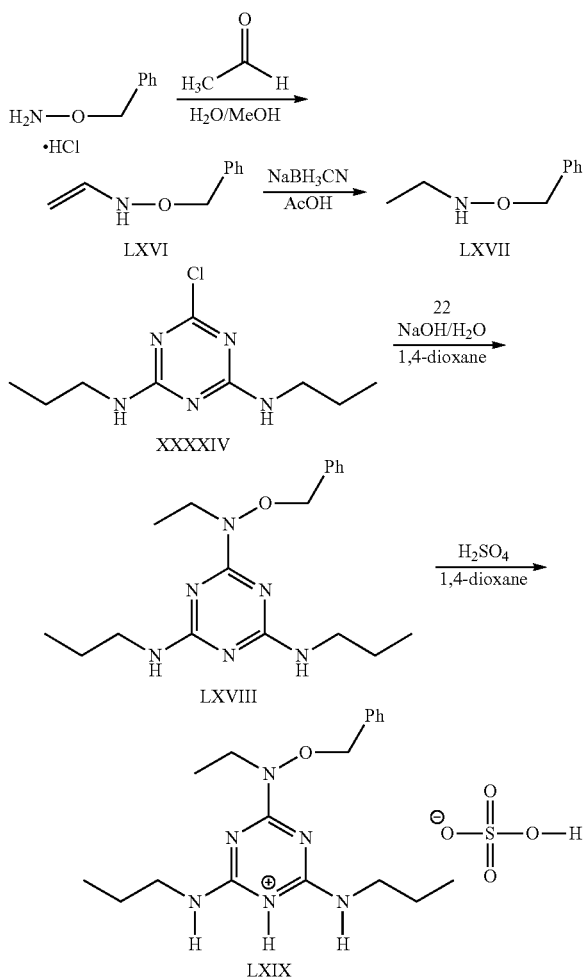

Scheme 28

O-Benzyl-N-vinyl-hydroxylamine (LXVI)

Acetaldehyde (24.7 mL, 44.2 mmol) was added dropwise to the cooled solution (0° C.) of O-benzyl-hydroxylamine hydrochloride (7.00 g, 43.85 mmol) in water (100 mL) and MeOH (20 mL). The reaction mixture was stirred for 16 h. The volatiles were removed under reduced pressure, and the water suspension was extracted with EtOAc (2×75 mL). The combined organic extracts were washed with brine, and then dried over $Na_2SO_4$ and evaporated to yield O-benzyl-N-vinyl-hydroxylamine (LXVI) in quantitative yield. 400 MHz $^1$H NMR (DMSO-d$_6$, ppm) 7.48 (0.5H, q, J=5.8 Hz), 7.39-7.26 (5H, m), 6.86 (0.5H, q, J=5.5 Hz), 5.06 (1H, s), 4.97 (1H, s), 1.78 (1.5H, d, J=5.5 Hz), 1.76 (1.5H, d, J=5.8 Hz).

O-Benzyl-N-ethyl-hydroxylamine (LXVII)

To a solution of O-benzyl-N-vinyl-hydroxylamine (LXVI, 6.52 g, 43.70 mmol) in AcOH (10 mL), NaCNBH$_3$ (11.00 g, 175.05 mmol) was added in portions. The reaction mixture was stirred at room temperature for 1 h. The mixture was neutralized (pH 7) with 1N NaOH and extracted with EtOAc (3×75 mL). The combined organic extracts were washed with saturated NaHCO$_3$ solution (2×100 mL), dried over Na$_2$SO$_4$, and purified by flash column chromatography (eluent: petroleum ether/EtOAc (9:1) to petroleum ether/EtOAc (1:4)) to yield O-benzyl-N-ethyl-hydroxylamine (LXVII, 2.10 g, 32%). 400 MHz $^1$H NMR (DMSO-d$_6$, ppm) 7.36-7.24 (5H, m), 6.50 (1H, t, J=6.4 Hz), 4.60 (2H, s), 2.81 (2H, qd, J=7.0, 6.4 Hz), 0.98 (3H, t, J=7.0 Hz).

O-Benzyl-N-(4,6-bis-propylamino-[1,3,5]triazin-2-yl)-N-ethyl-hydroxylamine (LXVIII)

2-Chloro-N-(4,6-bis-(n-propylamino)-[1,3,5]triazine (XXXIV) and O-benzyl-N-ethyl-hydroxylamine (LXVII) were reacted as described in Example 13 to afford O-benzyl-N-(4,6-bis-propylamino-[1,3,5]triazin-2-yl)-N-ethyl-hydroxylamine (LXVIII, 38% yield). 400 MHz $^1$H NMR (DMSO-d$_6$, ppm) 7.51-7.45 (2H, m), 7.40-7.30 (3H, s), 6.97-6.85 (1H, m), 6.79-6.67 (1H, m), 4.97-4.87 (1H, m), 3.72-3.53 (2H, m), 3.23-3.11 (4H, m), 1.56-1.43 (4H, m), 1.13-1.00 (3H, m), 0.89-0.80 (6H, m). ESI-MS (m/z): 345 [M+H]$^+$.

O-Benzyl-N-(4,6-bis-propylamino-[1,3,5]triazin-2-yl)-N-ethyl-hydroxylamine hydrogen sulfate (LXIX)

O-Benzyl-N-(4,6-bis-propylamino-[1,3,5]triazin-2-yl)-N-ethyl-hydroxylamine (LXVIII) was reacted with 95% H$_2$SO$_4$ as described in Example 9 to yield O-benzyl-N-(4,6-bis-propylamino-[1,3,5]triazin-2-yl)-N-methyl-hydroxylamine hydrogen sulfate (LXIX) in quantitative yield. 400 MHz $^1$H NMR (DMSO-d$_6$, ppm) 12.0-11.0 (1H, br s), 8.7-8.0 (1H, m), 7.57-7.30 (5H, m), 5.07-4.95 (2H, m), 3.89-3.68 (2H, m), 3.39-3.14 (4H, m), 1.63-1.42 (4H, m), 1.23-1.07 (3H, m), 0.94-0.77 (6H, m). ESI-MS (m/z): 345 [M+H]$^+$.

Example 31

N-(4,6-Bis-propylamino-[1,3,5]triazin-2-yl)-O-isopropyl-hydroxylamine (LXX)

Example 32

N-(4,6-Bis-propylamino-[1,3,5]triazin-2-yl)-O-isopropyl-hydroxylamine hydrogen sulfate (LXXI)

Scheme 29

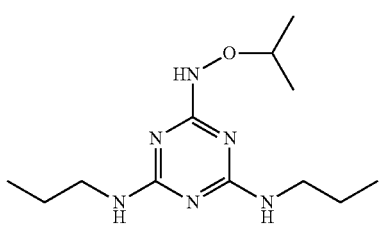

LXX

N-(4,6-Bis-propylamino-[1,3,5]triazin-2-yl)-O-isopropyl-hydroxylamine (LXX)

2-Chloro-N-(4,6-bis-(n-propylamino)-[1,3,5]triazine (XXXIV) and 0-isopropyl-hydroxylamine hydrochloride were reacted as described in Example 13 (80% yield). ESI-MS (m/z): 269 [M+H]$^+$.

N-(4,6-Bis-propylamino-[1,3,5]triazin-2-yl)-O-isopropyl-hydroxylamine hydrogen sulfate (LXXI)

N-(4,6-Bis-propylamino-[1,3,5]triazin-2-yl)-O-isopropyl-hydroxylamine (LXX) was reacted with 95% H$_2$SO$_4$ as described in Example 20 (quantitative yield). 400 MHz $^1$H NMR (DMSO-d$_6$, ppm) 11.5-10.7 (1H, m), 8.6-7.5 (3H, m), 4.08 (1H, septet, J=6.2 Hz), 3.38-3.13 (4H, m), 1.61-1.44 (4H, m), 1.21 (6H, d, J=6.2 Hz), 0.94-0.81 (6H, m). ESI-MS (m/z): 269 [M+H]$^+$.

Example 33

6-((Benzyloxy)(isopropyl)amino)-N$^2$,N$^4$-dipropyl-1,3,5-triazine-2,4-diamine (LXXII)

Example 34

6-((Benzyloxy)(isopropyl)amino)-N$^2$,N$^4$-dipropyl-1,3,5-triazine-2,4-diamine hydrogen sulfate (LXXIII)

Scheme 30

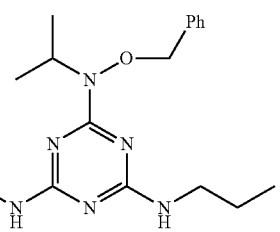

LXXII 6-((Benzyloxy)(isopropyl)amino)-N$^2$,N$^4$-dipropyl-1,3,5-triazine-2,4-diamine (LXXII) was prepared by reacting 2-chloro-N-(4,6-bis-(n-propylamino)-[1,3,5]triazine (XXXIV) and O-benzyl-N-isopropyl-hydroxylamine as exemplified in Example 13. The corresponding hydrogen sulfate (LXXIII) was prepared as described in Example 20.

Example 35

N-(4,6-Bis-propylamino-[1,3,5]triazin-2-yl)-N-ethyl-O-isopropyl-hydroxylamine (LXXVI)

Example 36

N-(4,6-Bis-propylamino-[1,3,5]triazin-2-yl)-N-ethyl-O-isopropyl-hydroxylamine hydrogen sulfate (LXXVII)

Scheme 31

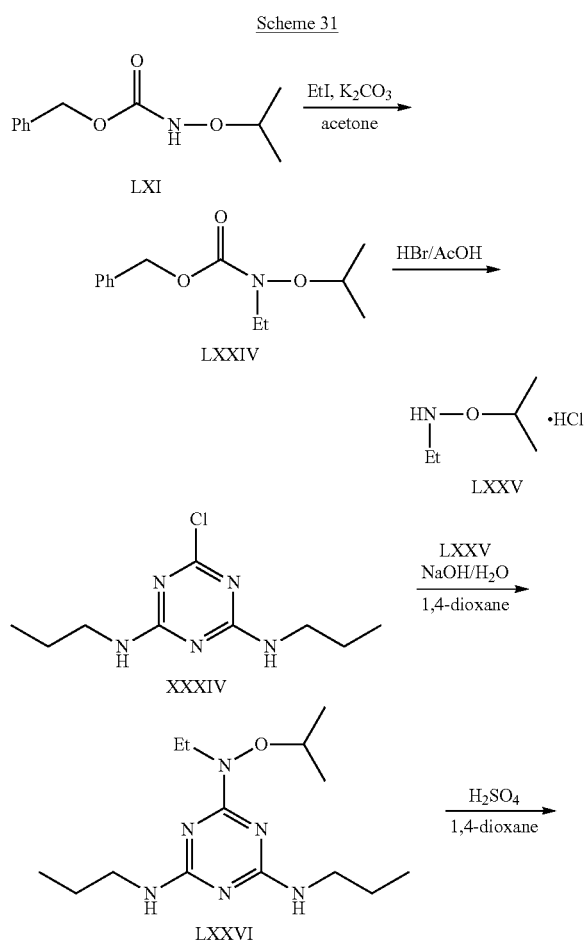

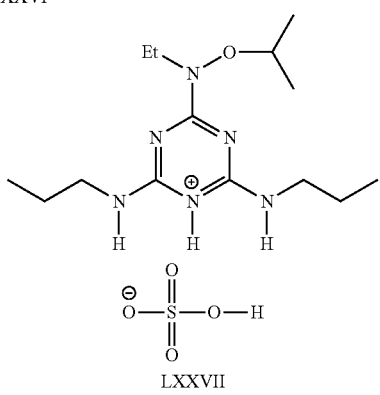

O-Benzyl-N-ethyl-N-isopropoxy-carbamate (LXXIV)

An ACE® pressure tube was charged with benzyl isopropoxycarbamate (4.08 g, 19.50 mmol), anhydrous $K_2CO_3$ (4.04 g, 29.25 mmol), ethyl iodide (7.0 mL, 87.75 mmol), and anhydrous acetone (30 mL). The reaction mixture was heated at 70° C. for 24 h. Ethyl iodide (7.0 mL, 87.75 mmol) and $K_2CO_3$ (4.04 g, 29.25 mmol) were added and the reaction mixture was heated for 24 h. The reaction mixture was filtered, and the acetone was evaporated. The resulting slurry was dissolved in EtOAc (150 mL), washed with water (3×50 mL), dried ($Na_2SO_4$), and filtered. The solvent was removed to yield O-benzyl-N-ethyl-N-isopropoxy-carbamate (3.86 g, 83%). 400 MHz $^1$H NMR (DMSO-$d_6$, ppm) 7.41-7.30 (5H, m), 5.12 (2H, s), 4.05 (1H, septet, J=6.2 Hz), 3.46 (2H, q, J=7.0 Hz), 1.12 (6H, d, J=6.2 Hz), 1.06 (3H, t, J=7.0 Hz).

N-Ethyl-O-isopropyl-hydroxylamine hydrochloride (LXXV)

O-Benzyl-N-ethyl-N-isopropoxy-carbamate was reacted with HBr/AcOH as described for the preparation of compound LXIII in Example 27 (yield 71%). 400 MHz $^1$H NMR (DMSO-$d_6$, ppm) 11.7-11.2 (2H, br s), 4.41 (1H, septet, J=6.1 Hz), 3.16 (2H, q, J=7.2 Hz), 1.24 (6H, d, J=6.1 Hz), 1.19 (3H, t, J=7.2 Hz).

N-(4,6-Bis-propylamino-[1,3,5]triazin-2-yl)-N-ethyl-O-isopropyl-hydroxylamine (LXXVI)

2-Chloro-N-(4,6-bis-(n-propylamino)-[1,3,5]triazine (XXXIV) was reacted with N-ethyl-O-isopropyl-hydroxylamine hydrochloride (LXXV) as described in Example 13, yielding N-(4,6-bis-propylamino-[1,3,5]triazin-2-yl)-N-ethyl-O-isopropyl-hydroxylamine (LXXVI) (88% yield). ESI-MS (m/z): 297 [M+H]$^+$.

N-(4,6-Bis-propylamino-[1,3,5]triazin-2-yl)-N-ethyl-O-isopropyl-hydroxylamine hydrogen sulfate (LXXVII)

N-(4,6-bis-propylamino-[1,3,5]triazin-2-yl)-N-ethyl-O-isopropyl-hydroxylamine (LXXVI) was reacted with 95% $H_2SO_4$ as described in Example 20 (quantitative yield). 400 MHz $^1$H NMR (DMSO-$d_6$, ppm) 12.0-10.8 (1H, m), 8.7-8.4 (1H, br s), 8.27-7.78 (1H, m), 4.39-4.25 (1H, m), 3.90-3.76 (2H, m), 3.39-3.15 (4H, m), 1.62-1.45 (4H, m), 1.25 (6H, d, J=6.1 Hz), 1.18-1.10 (3H, m), 0.95-0.82 (6H, m). ESI-MS (m/z): 297 [M+H]$^+$.

Example 37

N-(4,6-Bis-propylamino-[1,3,5]triazin-2-yl)-O-isobutyl-N-methyl-hydroxylamine (LXXXII)

Example 38

N-(4,6-Bis-propylamino-[1,3,5]triazin-2-yl)-O-isobutyl-N-methyl-hydroxylamine hydrogen sulfate (LXXXIII)

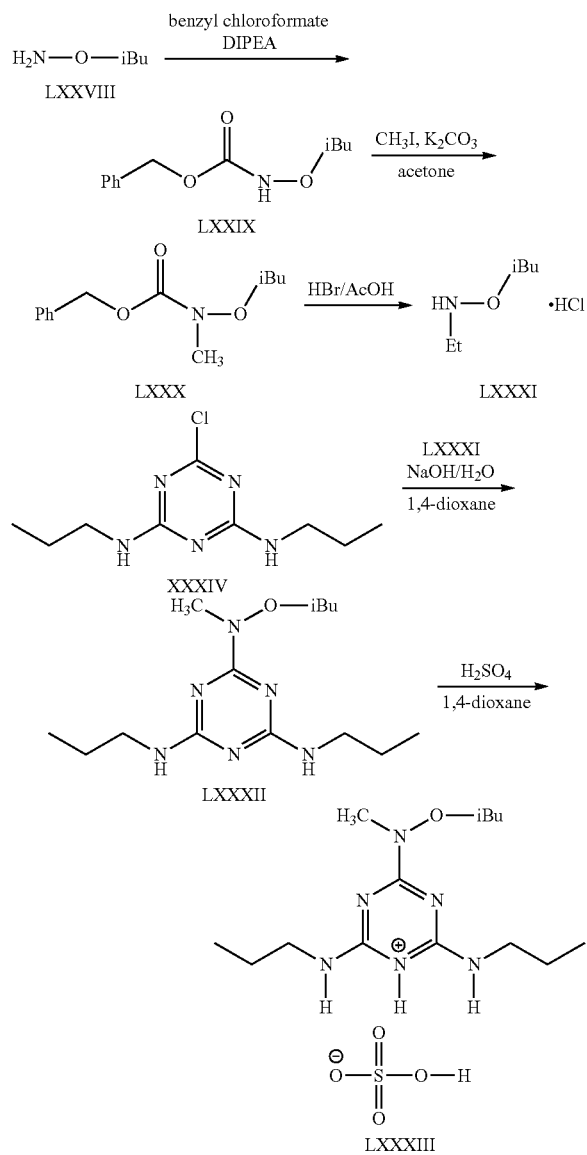

Scheme 32

O-Benzyl-N-isobutoxy carbamate (LXXIX)

O-isobutyl-hydroxylamine hydrochloride (LXXVIII) was reacted with benzyl chloroformate as described for the preparation of compound LXI in Example 27, yielding O-benzyl-N-isobutoxy carbamate (LXXIX) (87% yield). 400 MHz $^1$H NMR (CDCl$_3$, ppm) 7.36-7.23 (5H, m), 5.11 (2H, s), 3.58 (2H, d, J=6.6 Hz), 1.89 (1H, septet, J=6.7 Hz), 0.86 (6H, d, J=6.7 Hz).

O-Benzyl-N-methyl-N-isobutoxy carbamate (LXXX)

O-Benzyl-N-isobutoxycarbamate was reacted with methyl iodide, as described for the preparation of compound LXII in Example 27, affording O-benzyl-N-methyl-N-isobutoxycarbamate in 78% yield. 400 MHz $^1$H-NMR (DMSO-d$_6$, ppm) 7.41-7.30 (5H, m), 5.12 (2H, s), 3.59 (2H, d, J=6.6 Hz), 3.09 (3H, s), 1.80 (1H, septet, J=6.7 Hz), 0.87 (6H, d, J=6.7 Hz).

O-Isobutyl-N-methyl-hydroxylamine hydrochloride (LXXXI)

O-Benzyl-N-methyl-N-isobutoxycarbamate was reacted with HBr/AcOH as described for the preparation of compound LXIII in Example 27 (38% yield). 200 MHz $^1$H NMR (DMSO-d$_6$, ppm) 12.5-11.4 (2H, br s), 3.84 (2H, d, J=6.6 Hz), 2.81 (3H, s), 1.90 (1H, septet, J=6.7 Hz), 0.89 (6H, d, J=6.7 Hz).

N-(4,6-Bis-propylamino-[1,3,5]triazin-2-yl)-O-isobutyl-N-methyl-hydroxylamine (LXXXII)

2-Chloro-N-(4,6-bis-(n-propylamino)-[1,3,5]triazine (XXXIV) was reacted with O-isobutyl-N-methyl-hydroxylamine hydrochloride as described in Example 13, affording LXXXII in 82% yield. ESI-MS (m/z) 297 [M+H]$^+$.

N-(4,6-Bis-propylamino-[1,3,5]triazin-2-yl)-O-isobutyl-N-methyl-hydroxylamine hydrogen sulfate (LXXXIII)

N-(4,6-bis-propylamino-[1,3,5]triazin-2-yl)-O-isobutyl-N-methyl-hydroxylamine (LXXXII) was reacted with 95% H$_2$SO$_4$ as described in Example 20 (quantitative yield). 400 MHz $^1$H-NMR (DMSO-d$_6$, ppm) 12.0-10.7 (1H, br s), 8.7-7.6 (2H, m), 3.82-3.72 (2H, m), 3.41-3.20 (7H, m), 2.11-1.82 (1H, m), 1.62-1.44 (4H, m), 1.00-0.82 (12H, m). ESI-MS (m/z): 297 [M+H]$^+$.

Example 39

6-(Methyl(thiophen-2-ylmethoxy)amino)-N2,N4-dipropyl-1,3,5-triazine-2,4-diamine (LXXXIV)

Example 40

6-(Methyl(thiophen-2-ylmethoxy)amino)-N2,N4-dipropyl-1,3,5-triazine-2,4-diamine hydrogen sulfate (LXXXV)

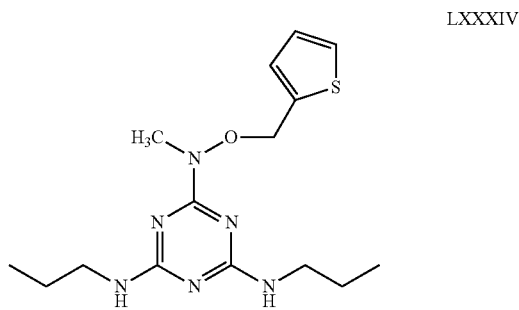

Scheme 33

81

6-(Methyl(thiophen-2-ylmethoxy)amino)-N2,N4-dipropyl-1,3,5-triazine-2,4-diamine (LXXXIV) may be prepared by reacting 2-chloro-N-(4,6-bis-(n-propylamino)-[1,3,5]triazine (XXXIV) and O-(thiophen-2-yl-methyl)-N-methyl-hydroxylamine as exemplified in Example 13.

Example 41

N-(4,6-Bis-propylamino-[1,3,5]triazin-2-yl)-O-cyclopropylmethyl-N-methyl-hydroxylamine (XCI)

Example 42

N-(4,6-Bis-propylamino-[1,3,5]triazin-2-yl)-O-cyclopropylmethyl-N-methyl-hydroxylamine hydrogen sulfate (XCII)

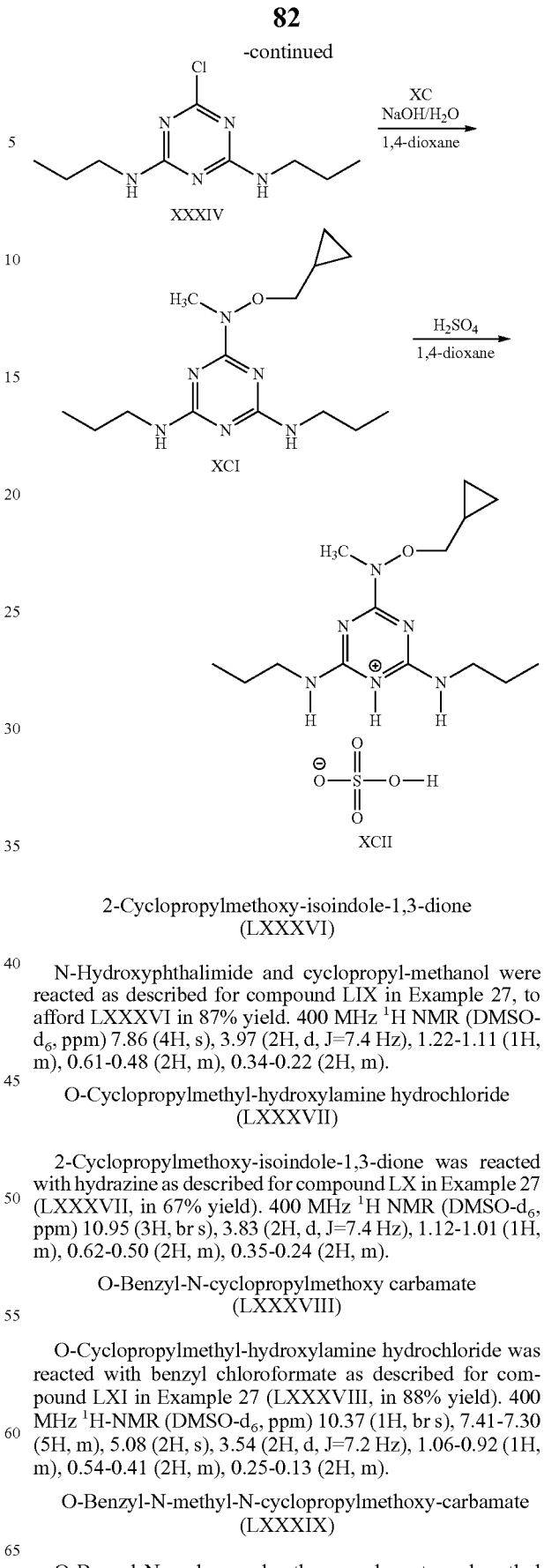

2-Cyclopropylmethoxy-isoindole-1,3-dione (LXXXVI)

N-Hydroxyphthalimide and cyclopropyl-methanol were reacted as described for compound LIX in Example 27, to afford LXXXVI in 87% yield. 400 MHz $^1$H NMR (DMSO-$d_6$, ppm) 7.86 (4H, s), 3.97 (2H, d, J=7.4 Hz), 1.22-1.11 (1H, m), 0.61-0.48 (2H, m), 0.34-0.22 (2H, m).

O-Cyclopropylmethyl-hydroxylamine hydrochloride (LXXXVII)

2-Cyclopropylmethoxy-isoindole-1,3-dione was reacted with hydrazine as described for compound LX in Example 27 (LXXXVII, in 67% yield). 400 MHz $^1$H NMR (DMSO-$d_6$, ppm) 10.95 (3H, br s), 3.83 (2H, d, J=7.4 Hz), 1.12-1.01 (1H, m), 0.62-0.50 (2H, m), 0.35-0.24 (2H, m).

O-Benzyl-N-cyclopropylmethoxy carbamate (LXXXVIII)

O-Cyclopropylmethyl-hydroxylamine hydrochloride was reacted with benzyl chloroformate as described for compound LXI in Example 27 (LXXXVIII, in 88% yield). 400 MHz $^1$H-NMR (DMSO-$d_6$, ppm) 10.37 (1H, br s), 7.41-7.30 (5H, m), 5.08 (2H, s), 3.54 (2H, d, J=7.2 Hz), 1.06-0.92 (1H, m), 0.54-0.41 (2H, m), 0.25-0.13 (2H, m).

O-Benzyl-N-methyl-N-cyclopropylmethoxy-carbamate (LXXXIX)

O-Benzyl N-cyclopropylmethoxy carbamate and methyl iodide were reacted as described for compound LXII in Example 27 (LXXXIX, in 95% yield). 400 MHz $^1$H NMR (DMSO-$d_6$, ppm) 7.42-7.30 (5H, m), 5.11 (2H, s), 3.62 (2H, d, J=7.2 Hz), 3.11 (3H, s), 1.06-0.93 (1H, m), 0.54-0.41 (2H, m), 0.26-0.13 (2H, m).

O-Cyclopropylmethyl-N-methyl-hydroxylamine hydrochloride (XC)

O-Benzyl-N-methyl-N-cyclopropylmethoxy carbamate was reacted with HBr/AcOH as described for compound LXIII in Example 27, yielding XC in 77% yield. 400 MHz $^1$H NMR (DMSO-$d_6$, ppm) 11.96 (2H, br s), 3.91 (2H, d, J=7.4 Hz), 2.80 (3H, s), 1.13-1.01 (1H, m), 0.63-0.50 (2H, m), 0.37-0.25 (2H, m).

N-(4,6-Bis-propylamino-[1,3,5]triazin-2-yl)-O-cyclopropylmethyl-N-methyl-hydroxylamine (XCI)

2-Chloro-N-(4,6-bis-(n-propylamino)-[1,3,5]triazine (XXXIV) was reacted with O-cyclopropylmethyl-N-methyl-hydroxylamine hydrochloride (XC) as described in Example 13, yielding (XCI) in 99% yield. 400 MHz $^1$H NMR (DMSO-$d_6$, ppm) 6.91-6.77 (1H, m), 6.75-6.58 (1H, m), 3.77-3.64 (2H, m), 3.21-3.09 (7H, m), 1.54-1.41 (4H, m), 1.11-1.00 (1H, m), 0.88-0.80 (6H, m), 0.56-0.44 (2H, m), 0.32-0.20 (2H, m). ESI-MS (m/z) 295 [M+H]$^+$.

N-(4,6-Bis-propylamino-[1,3,5]triazin-2-yl)-O-cyclopropylmethyl-N-methyl-hydroxylamine hydrogen sulfate (XCII)

N-(4,6-bis-propylamino-[1,3,5]triazin-2-yl)-O-cyclopropylmethyl-N-methyl-hydroxylamine (XCI) was reacted with 95% $H_2SO_4$ as described in Example 20, yielding (XCII) in quantitative yield. 400 MHz $^1$H-NMR (DMSO-$d_6$, ppm) 11.6-11.0 (1H, br s), 8.7-8.4 (0.7H, br s), 8.2-8.0 (0.3H, br s), 7.89-7.42 (1H, m), 3.88-3.77 (2H, m), 3.42-3.18 (7H, m), 1.62-1.45 (4H, m), 1.24-1.13 (1H, m), 0.95-0.82 (6H, m), 0.61-0.52 (2H, m), 0.38-0.28 (2H, m). ESI-MS (m/z) 295 [M+H]$^+$.

Example 43

N-(4,6-Bis-propylamino-[1,3,5]triazin-2-yl)-O-ethyl-N-methyl-hydroxylamine (XCVI)

Example 44

N-(4,6-Bis-propylamino-[1,3,5]triazin-2-yl)-O-ethyl-N-methyl-hydroxylamine hydrogen sulfate (XCVII)

Scheme 35

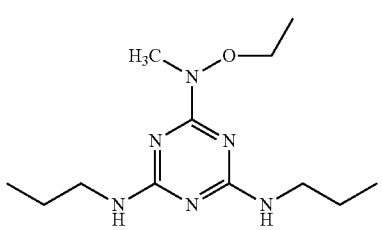

XCVI tert-Butyl ethoxycarbamate (XCIII)

A solution of saturated $Na_2CO_3$ solution (45.0 mL) was added dropwise at room temperature to a solution of O-ethylhydroxylamine (1.76 g, 18.0 mmol) and di-tert-butyl dicarbonate (5.13 g, 23.67 mmol) in dichloromethane (45.0 mL) and stirred for 24 h. Water was added, the mixture pH was adjusted to 2 by adding 6N HCl, and the resulting system was extracted with dichloromethane (3×50 mL). The combined organic extracts were dried over $Na_2SO_4$ and evaporated. The crude product was purified by flash column chromatography using gradient elution from petroleum ether/EtOAc (98:2) to petroleum ether/EtOAc (95:5) to yield tert-butyl ethoxycarbamate (XCIII) (2.62 g, 90%). 400 MHz $^1$H NMR (DMSO-$d_6$, ppm) 9.89 (1H, s) 3.72 (2H, q, J=7.0 Hz) 1.40 (9H, s) 1.10 (3H, t, J=7.0 Hz).

tert-Butyl ethoxy(methyl)carbamate (XCIV)

A solution of tert-butyl ethoxycarbamate (XCIII, 2.48 g, 15.38 mmol) in DMF (10 mL) was added dropwise to the suspension of 60% sodium hydride (0.66 g, 16.92 mmol) in DMF (5 mL) at 0° C. After 30 min. methyl iodide (1.95 mL, 31.32 mmol) in DMF (10 mL) was added, and the reaction mixture was stirred at room temperature for 24 h. Water (100 mL) was added and the product was extracted with ethyl acetate (3×50 mL), dried over $Na_2SO_4$, and concentrated in vacuo to yield tert-butyl ethoxy(methyl)carbamate (XCIV, 2.34 g, 87%). 400 MHz $^1$H NMR (DMSO-$d_6$, ppm) 3.81 (2H, q, J=7.0 Hz), 3.00 (3H, s), 1.41 (9H, s), 1.12 (3H, t, J=7.0 Hz).

O-Ethyl-N-methyl-hydroxylamine hydrochloride (XCV)

A solution of 4M HCl/1,4-dioxane (25 mL) was added in portions to tert-butyl ethoxy(methyl)carbamate (XCIV, 2.34 g, 13.35 mmol) at 0° C. The mixture was stirred at room temperature for 4 h. The volatiles removed in vacuo and the residue was triturated with ethyl ether and filtered to yield a solid (O-ethyl-N-methyl-hydroxylamine hydrochloride, XCV, 1.35 g, 91%).

N-(4,6-Bis-propylamino-[1,3,5]triazin-2-yl)-O-ethyl-N-methyl-hydroxylamine (XCVI)

2-Chloro-N-(4,6-bis-(n-propylamino)-[1,3,5]triazine (XXXIV) was reacted with O-ethyl-N-methyl-hydroxylamine hydrochloride as described in Example 13, to yield XCVI in 93% yield. ESI-MS (m/z) 269 [M+H]$^+$.

N-(4,6-Bis-propylamino-[1,3,5]triazin-2-yl)-O-ethyl-N-methyl-hydroxylamine hydrogen sulfate (XCVII)

N-(4,6-bis-propylamino-[1,3,5]triazin-2-yl)-O-ethyl-N-methyl-hydroxylamine (XCVI) was reacted with 95% $H_2SO_4$ as described in Example 20, to afford (XCVII) in 91% yield. 400 MHz $^1$H NMR (DMSO-$d_6$, ppm) 11.7-10.8 (1H, br s), 8.79-7.34 (2H, m), 4.09-3.98 (2H, m), 3.40-3.20 (7H, m), 1.61-1.46 9 (4H, m), 1.27 (3H, t, J=7.1 Hz), 0.94-0.84 (6H, m). 400 MHz $^1$H NMR ($D_2O$, ppm) 3.99-3.88 (2H, m), 3.34-

3.13 (7H, m), 1.52-1.39 (4H, m), 1.14 (3H, t, J=7.1 Hz), 0.76 (6H, t, J=7.5 Hz). ESI-MS (m/z): 269 [M+H]⁺. M.P.: 84-86° C.

Example 45

N-(4,6-Bis-propylamino-[1,3,5]triazin-2-yl)-O-(2,2-difluoro-ethyl)-hydroxylamine (C)

Example 46

N-(4,6-Bis-propylamino-[1,3,5]triazin-2-yl)-O-(2,2-difluoro-ethyl)-hydroxylamine hydrogen sulfate (CI)

Scheme 36

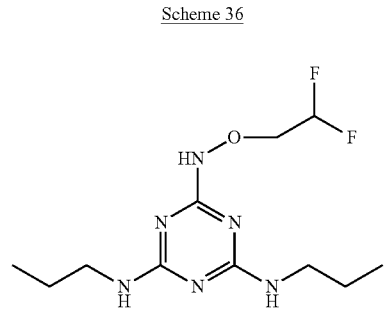

C 2-(2,2-Difluoro-ethoxy)-isoindole-1,3-dione (XCVIII)

N-Hydroxyphthalimide and 2,2-difluoro-ethanol were reacted as described for compound LXI in Example 27, affording XCVIII in 52% yield. 400 MHz $^1$H NMR (DMSO-$d_6$, ppm) 7.92-7.85 (4H, m), 6.34 (1H, tt, J=54.4, 3.9 Hz), 4.46 (2H, td, J=14.1, 3.9 Hz).

O-(2,2-Difluoro-ethyl)-hydroxylamine hydrochloride (XCIX)

2-(2,2-Difluoro-ethoxy)-isoindole-1,3-dione was reacted with hydrazine as described for compound LX in Example 27, affording XCIX in 73% yield. 400 MHz $^1$H NMR (DMSO-$d_6$, ppm) 12.3-10.3 (3H, br s), 6.38 (1H, tt, J=54.0, 3.3 Hz), 4.34 (2H, td, J=14.7, 3.3 Hz).

N-(4,6-Bis-propylamino-[1,3,5]triazin-2-yl)-O-(2,2-difluoro-ethyl)-hydroxylamine (C)

2-Chloro-N-(4,6-bis-(n-propylamino)-[1,3,5]triazine (XXXIV) was reacted with O-(2,2-difluoro-ethyl)-hydroxylamine hydrochloride as described in Example 13, affording C in 59% yield. 400 MHz $^1$H NMR (DMSO-$d_6$, ppm) 9.91-9.56 (1H, m), 7.00-6.90 (1H, m), 6.89-6.67 (1H, m), 6.48-6.13 (1H, m, 4.12-3.98 (2H, m), 3.20-3.09 (4H, m), 1.53-1.41 (4H, m), 0.88-0.80 (6H, m). ESI-MS (m/z) 291 [M+H]⁺.

N-(4,6-Bis-propylamino-[1,3,5]triazin-2 yl)-O-(2,2-difluoro-ethyl)-hydroxylamine hydrogen sulfate (CI)

N-(4,6-bis-propylamino-[1,3,5]triazin-2-yl)-O-(2,2-difluoro-ethyl)-hydroxylamine (C, 1.02 g, 3.51 mmol) was reacted with 95% $H_2SO_4$ (0.19 mL, 3.51 mmol) in diethyl ether (3 mL) at 0° C. Two drops of EtOH were added, and the resultant crystals were filtered, washed with diethyl ether, and dried to yield N-(4,6-bis-propylamino-[1,3,5]triazin-2-yl)-O-(2,2-difluoro-ethyl)-hydroxylamine hydrogen sulfate (CI) (1.26 g, 93%). 400 MHz $^1$H NMR (DMSO-$d_6$, ppm) 11.8-10.5 (1H, m) 8.8-8.4 (0.3H, br s) 8.36-7.53 (1.7H, m) 6.50-6.08 (1H, m) 4.28-4.07 (2H, m) 3.39-3.13 (4H, m) 1.64-1.42 (4H, m) 0.97-0.78 (6H, m). ESI-MS (m/z) 291 [M±H]⁺. M.P.: 91-93° C.

Example 47

4-N-(2-Dimethylaminoethyl)amino-6-N-(n-propyl)amino-[1,3,5]triazin-2-yl)-N,O-dimethyl-hydroxylamine (CIII)

Example 48

4-N-(2-Dimethylaminoethyl)amino-6-N-(n-propyl)amino-[1,3,5]triazin-2-yl)-N,O-dimethyl-hydroxylamine hydrochloride (CIV)

Scheme 37

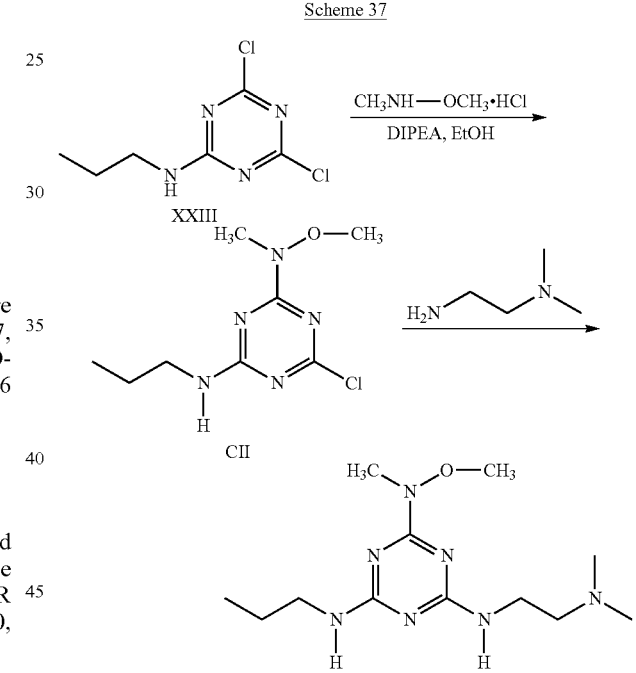

2-Chloro-6-N-(n-propyl)amino-[1,3,5]triazin-2-yl)-N,O-dimethyl-hydroxylamine (CII)

2,4-Dichloro-N-(6-n-propylamino)-[1,3,5]triazine (XXIII) (18 g, 87 mmol) was dissolved in acetone (100 mL) and poured into ice-water (50 mL) to form a very fine suspension. A solution of N,O-dimethylhydroxylamine hydrochloride (9.3 g, 95 mmol) in water (30 mL) was added, while keeping the temperature at 0° C. (ice bath). To this mixture, 2N NaOH (44 mL, 88 mmol) was added dropwise at a rate adjusted to keep the temperature between 0° C. and 5° C. The reaction was stirred for 30 min at ambient temperature and for additional 60 min at 50° C. The resultant precipitate was filtered off, and washed with water (3×25 mL). After drying over calcium chloride under high vacuum, 2-chloro-N-(6-n-propylamino)-[1,3,5]triazin-2-yl)-N,O-dimethyl-hydroxylamine (CII, 12 g, 60%) was isolated as a white powder. LCMS (ESI) m/z=232 (M+H)+.

4-N-(2-Dimethylaminoethyl)amino-6-N-(n-propyl) amino-[1,3,5]triazin-2-yl)-N,O-dimethyl-hydroxylamine (CIII)

A mixture of 2-chloro-6-N-(n-propyl)amino-[1,3,5]triazin-2-yl)-N,O-dimethyl-hydroxylamine (CII, 1.5 g, 6.5 mmol), N,N-dimethylethane-1,2-diamine (3.5 g, 39 mmol) and DIPEA (2.5 g, 20 mmol) in EtOH (30 mL) was heated at 100° C. for 16 h. The solvent was then removed under reduced pressure. The residue was dissolved in EtOAc (80 mL), washed with water (2×50 mL) and then with a brine solution (50 mL) and lastly, dried over Na$_2$SO$_4$. The solvent was removed under reduced pressure. The residue was purified by flash column chromatography (DCM/MeOH=20/1 to 5/1) to yield 4-N-(2-dimethylaminoethyl)amino-6-N-(n-propyl)amino-[1,3,5]triazin-2-yl)-N,O-dimethyl-hydroxylamine (620 mg, 33%).

4-N-(2-Dimethylaminoethyl)amino-6-N-(n-propyl) amino-[1,3,5]triazin-2-yl)-N,O-dimethyl-hydroxylamine hydrochloride (CIV)

4-N-(2-dimethylaminoethyl)amino-6-N-(n-propyl) amino-[1,3,5]triazin-2-yl)-N,O-dimethyl-hydroxylamine (610 mg, 2.1 mmol) was dissolved in H$_2$O (10 mL) and 0.5 M aqueous HCl solution (6.6 mL) and the solution was lyophilized to yield 4-N-(2-dimethylaminoethyl)amino-6-N-(n-propyl)amino-[1,3,5]triazin-2-yl)-N,O-dimethyl-hydroxylamine hydrochloride (CIV, 630 mg) as a colorless oil. LCMS (ESI) m/z=284 (M+H)+. $^1$H NMR (500 MHz, DMSO) δ (ppm) 10.55-10.88 (br, 1H), 8.70-9.10 (m, 2H), 4.37-4.43 (m, 5H), 3.76-3.87 (m, 7H), 2.84-2.88 (m, 6H), 1.60-1.64 (m, 2H), 0.94-1.02 (m, 3H).

Example 49

4-N-(3-(1-N-Methylimidazol-2-yl)-propyl)-amino-6-N-(n-propyl)amino-[1,3,5]triazin-2-yl)-N,O-dimethyl-hydroxylamine (CV)

Example 50

4-N-(3-(1-N-Methylimidazol-2-yl)-propyl)-amino-6-N-(n-propyl)amino-[1,3,5]triazin-2-yl)-N,O-dimethyl-hydroxylamine hydrochloride (CVI)

Scheme 38

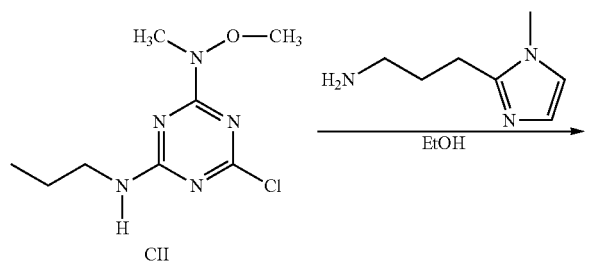

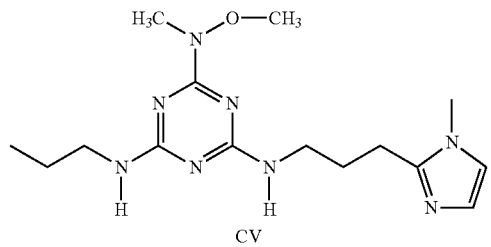

4-N-(3-(1-N-Methylimidazol-2-yl)-propyl)-amino-6-N-(n-propyl)amino-[1,3,5]triazin-2-yl)-N,O-dimethyl-hydroxylamine (CV)

2-Chloro-6-N-(n-propylamino)-[1,3,5]triazin-2-yl)-N,O-dimethyl-hydroxylamine (CII) (400 mg, 2.9 mmol), DIPEA (5.16 g, 40 mmol) and 3-(1-methyl-1H-imidazol-2-yl)propan-1-amine (J. Heterocyclic Chem., 2005, 42:1011-15) (732 mg, 3.2 mmol) in EtOH (50 mL) were heated at 100° C. for 16 h. After this time, the solvent was removed under reduced pressure. The residue was dissolved in DCM/MeOH (400 mL/200 mL), washed with water (50 mL) then dried over Na$_2$SO$_4$. The solvent was removed under reduced pressure. The crude product was purified by flash column chromatography (DCM/MeOH=50/1 to 10/1) to yield 4-N-(3-(1-N-methylimidazol-2-yl)-propyl)-amino-6-N-(n-propyl)amino-[1,3,5]triazin-2-yl)-N,O-dimethyl-hydroxylamine (CV, 210 mg, 22%).

4-N-(3-(1-N-Methylimidazol-2-yl)-propyl)-amino-6-N-(n-propyl)amino-[1,3,5]triazin-2-yl)-N,O-dimethyl-hydroxylamine hydrochloride (CVI)

4-N-(3-(1-N-methylimidazol-2-yl)-propyl)-amino-6-N-(n-propyl)amino-[1,3,5]triazin-2-yl)-N,O-dimethyl-hydroxylamine (CV) (210 mg, 0.63 mmol) was dissolved in H$_2$O (10 mL) and 0.5 M aqueous HCl solution (1.3 mL), and the solution was lyophilized to yield 4-N-(3-(1-N-methylimidazol-2-yl)-propyl)-amino-6-N-(n-propyl)amino-[1,3,5]triazin-2-yl)-N,O-dimethyl-hydroxylamine hydrochloride (CVI, 210 mg) as a yellow oil. LCMS (ESI) m/z=335 (M+H)+. $^1$H NMR (500 MHz, DMSO) δ (ppm) 14.40-14.55 (br, 1H), 8.60-8.80 (m, 2H), 7.57-7.62 (m, 2H), 3.77-3.83 (m, 6H), 3.28-3.42 (m, 7H), 2.80-2.84 (m, 2H), 1.95-2.10 (m, 2H), 1.53-1.56 (m, 2H), 0.89-0.93 (m, 3H).

Example 51

4-N-(1-N-Methylimidazol-2-yl)-methylamino-6-N-(n-propyl)amino-[1,3,5]triazin-2-yl)-N,O-dimethyl-hydroxylamine (CVII)

Example 52

4-N-(1-N-Methylimidazol-2-yl)-methylamino-6-N-(n-propyl)amino-[1,3,5]triazin-2-yl)-N,O-dimethyl-hydroxylamine hydrochloride (CVIII)

Scheme 39

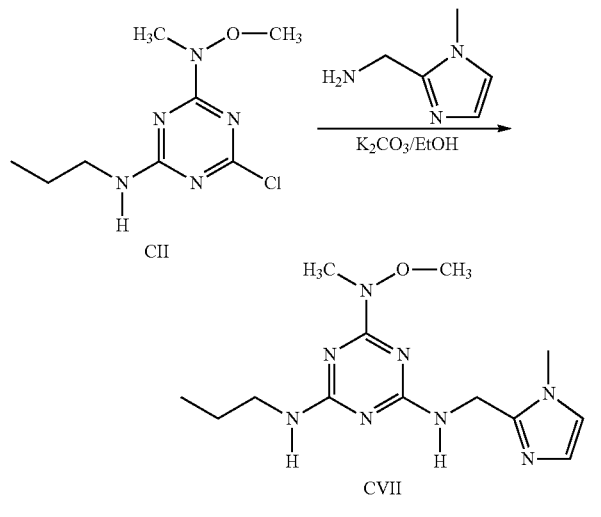

4-N-(1-N-Methylimidazol-2-yl)-methylamino-6-N-(n-propyl)amino-[1,3,5]triazin-2-yl)-N,O-dimethyl-hydroxylamine (CVII)

2-Chloro-6-N-(n-propyl)amino-[1,3,5]triazin-2-yl)-N,O-dimethyl-hydroxylamine (CII) (1 g, 4.5 mmol), (1-methyl-1H-imidazol-2-yl)methanamine (600 mg, 5.4 mmol) and $K_2CO_3$ (1.24 g, 9 mmol) in EtOH (50 mL) were heated at 100° C. for 16 h. The reaction mixture was filtered, and the volatiles were removed under reduced pressure. The residue was dissolved in EtOAc (100 mL), washed with water (30 mL) and then with a brine solution (30 mL), and lastly dried over $Na_2SO_4$. The solvent was removed under reduced pressure. The crude product was purified by flash column chromatography (DCM/MeOH=20/1 to 8/1) to yield 4-N-(1-N-methylimidazol-2-yl)-methylamino-6-N-(n-propyl)amino-[1,3,5]triazin-2-yl)-N,O-dimethyl-hydroxylamine (CVII, 650 mg, 47%).

4-N-(1-N-Methylimidazol-2-yl)-methylamino-6-N-(n-propyl)amino-[1,3,5]triazin-2-yl)-N,O-dimethyl-hydroxylamine hydrochloride (CVIII)

4-N-(1-N-methylimidazol-2-yl)-methylamino-6-N-(n-propyl)amino-[1,3,5]triazin-2-yl)-N,O-dimethyl-hydroxylamine (CVII, 650 mg, 2.1 mmol) was dissolved in $H_2O$ (10 mL) and 0.5 M aqueous HCl solution (6.3 mL). The resultant solution was subjected to lyophilization to yield 4-N-(1-N-methylimidazol-2-yl)-methylamino-6-N-(n-propyl)amino-[1,3,5]triazin-2-yl)-N,O-dimethyl-hydroxylamine hydrochloride (CVIII, 389 mg) as a colorless oil. LCMS (ESI) m/z=307 (M+H)$^+$. $^1$H NMR (500 MHz, DMSO) δ (ppm) 14.65-14.85 (br, 1H), 8.70-9.20 (m, 2H), 7.62-7.70 (m, 2H), 4.87-4.91 (m, 2H), 3.75-3.89 (m, 9H), 3.31-3.40 (m, 3H), 1.55-1.56 (m, 2H), 0.85-0.96 (m, 3H).

Example 53

4,6-Bis-(N-(2-dimethylaminoethyl)amino)-[1,3,5]triazin-2-yl)-N,O-dimethyl-hydroxylamine (CIX)

Example 54

4,6-Bis-(N-(2-dimethylaminoethyl)amino)-[1,3,5]triazin-2-yl)-N,O-dimethyl-hydroxylamine hydrochloride (CX)

Scheme 40

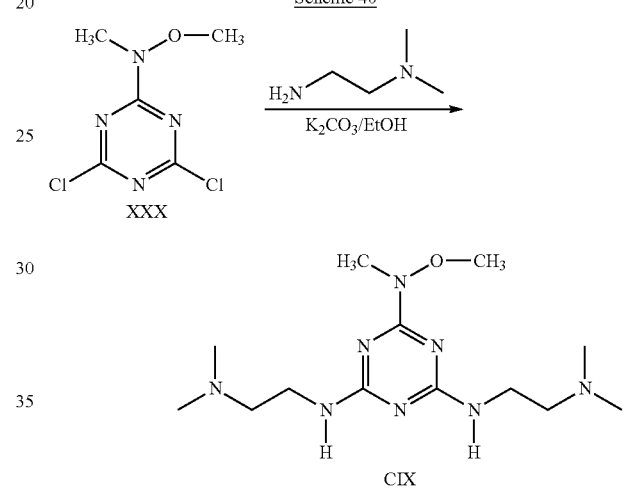

4,6-Bis-(N-(2-dimethylaminoethyl)amino)-[1,3,5]triazin-2-yl)-N,O-dimethyl-hydroxylamine (CIX)

N-(4,6-Dichloro[1,3,5]triazin-2-yl)-N,O-dimethyl-hydroxylamine (XXX) (7 g, 33.5 mmol), N,N-dimethyl-ethane-1,2-diamine (6.05 g, 68.7 mmol) and $K_2CO_3$ (10.2 g, 73.7 mmol) in THF (250 mL) were heated at 70° C. for 5 h, after which time the solvent was removed under reduced pressure. The residue was purified by reverse flash column chromatography to yield 4,6-bis-(N-(2-dimethylaminoethyl)amino)-[1,3,5]triazin-2-yl)-N,O-dimethyl-hydroxylamine (270 mg, 3%).

4,6-Bis-(N-(2-dimethylaminoethyl)amino)-[1,3,5]triazin-2-yl)-N,O-dimethyl-hydroxylamine hydrochloride (CX)

4,6-Bis-(N-(2-dimethylaminoethyl)amino)-[1,3,5]triazin-2-yl)-N,O-dimethyl-hydroxylamine (270 mg, 0.86 mmol) was dissolved in $H_2O$ (10 mL) and 0.5 M aqueous HCl solution (2 mL), and the resultant solution was lyophilized to yield 4,6-bis-(N-(2-dimethylaminoethyl)amino)-[1,3,5]triazin-2-yl)-N,O-dimethyl-hydroxylamine hydrochloride (290 mg) as a colorless oil. LCMS (ESI) m/z=313 (M+H)$^+$. $^1$H NMR (500 MHz, DMSO) δ (ppm) 10.20-10.60 (br, 1H), 7.17-7.25 (m, 2H), 3.54-3.76 (m, 7H), 3.01-3.25 (m, 7H), 2.72 (s, 12H).

Example 55

4,6-Bis-(N-(pyridin-4-ylmethyl)amino)-[1,3,5]triazin-2-yl)-N,O-dimethyl-hydroxylamine (CXI)

Example 56

4,6-Bis-(N-(pyridin-4-ylmethyl)amino)-[1,3,5]triazin-2-yl)-N,O-dimethyl-hydroxylamine hydrochloride (CXII)

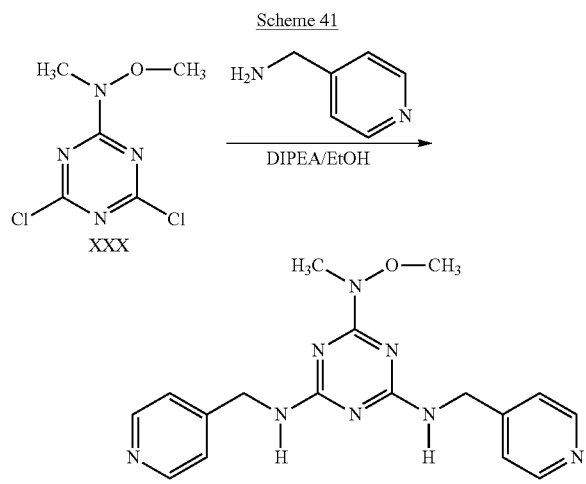

Scheme 41

4,6-Bis-(N-(pyridin-4-ylmethyl)amino)-[1,3,5]triazin-2-yl)-N,O-dimethyl-hydroxylamine (CXI)

N-(4,6-Dichloro[1,3,5]triazin-2-yl)-N,O-dimethyl-hydroxylamine (XXX) (1 g, 4.78 mmol), pyridin-4-ylmethanamine (1.14, 10.52 mmol) and DIPEA (1.85 g, 14.34 mmol) in EtOH (80 mL) were heated at 100° C. for 16 h, after which the solvent was removed under reduced pressure. The crude product was purified by flash chromatography to yield 4,6-bis-(N-(pyridin-4-ylmethyl)amino)-[1,3,5]triazin-2-yl)-N,O-dimethyl-hydroxylamine (CXI) (450 mg, 27%).

4,6-Bis-(N-(pyridin-4-ylmethyl)amino)-[1,3,5]triazin-2-yl)-N,O-dimethyl-hydroxylamine hydrochloride (CXII)

4,6-Bis-(N-(pyridin-4-ylmethyl)amino)-[1,3,5]triazin-2-yl)-N,O-dimethyl-hydroxylamine (CXI) (450 mg, 1.28 mmol) was dissolved in $H_2O$ (10 mL) and 0.5 M aqueous HCl solution (3.84 mL), and the resultant solution was lyophilized to yield 4,6-bis-(N-(pyridin-4-ylmethyl)amino)-[1,3,5]triazin-2-yl)-N,O-dimethyl-hydroxylamine hydrochloride (497 mg) as a yellow solid. LCMS (ESI) m/z=353 (M+H)$^+$. $^1$H NMR (500 MHz, MeOD) δ (ppm) 8.79-8.89 (m, 4H), 7.98-8.20 (m, 4H), 5.04 (s, 2H), 4.85 (s, 2H), 3.90-3.95 (m, 3H), 3.50 (s, 1H), 3.33 (s, 2H).

Example 57

4,6-Bis-[N-(3-methoxy-n-propyl)amino]-[1,3,5]triazin-2-yl)-N,O-dimethyl-hydroxylamine (CXIII)

Example 58

4,6-Bis-[N-(3-methoxy-n-propyl)amino]-[1,3,5]triazin-2-yl)-N,O-dimethyl-hydroxylamine hydrochloride salt (CXIV)

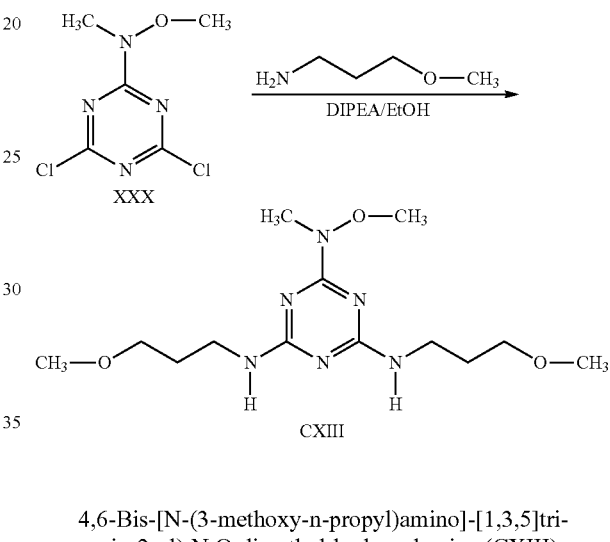

Scheme 42

4,6-Bis-[N-(3-methoxy-n-propyl)amino]-[1,3,5]triazin-2-yl)-N,O-dimethyl-hydroxylamine (CXIII)

N-(4,6-Dichloro[1,3,5]triazin-2-yl)-N,O-dimethyl-hydroxylamine (XXX) (1 g, 4.78 mmol), 3-methoxypropan-1-amine (936 mg, 10.52 mmol) and DIPEA (1.85 g, 14.34 mmol) in EtOH (50 mL) were heated at 100° C. for 16 h, after which time the solvent was removed under reduced pressure. The residue was dissolved in EtOAc (200 mL), washed with water (50 mL) and then with a brine solution (50 mL) and lastly dried over $Na_2SO_4$. The solvent was removed under reduced pressure. The crude product was purified by flash column chromatography (pet ether/ethyl acetate=5/1 to 1/2) to yield 4,6-bis-[N-(3-methoxy-n-propyl)amino]-[1,3,5]triazin-2-yl)-N,O-dimethyl-hydroxylamine (CXIII) (1.4 g, 93%).

4,6-Bis-[N-(3-methoxy-n-propyl)amino]-[1,3,5]triazin-2-yl)-N,O-dimethyl-hydroxylamine hydrochloride (CXIV)

4,6-Bis-[N-(3-methoxy-n-propyl)amino]-[1,3,5]triazin-2-yl)-N,O-dimethyl-hydroxylamine (CXIII, 1.4 g, 4.46 mmol) was dissolved in $H_2O$ (10 mL) and 0.5 M aqueous HCl solution (13.4 mL), and the resultant solution was lyophilized to yield 4,6-bis-[N-(3-methoxy-n-propyl)amino]-[1,3,5]triazin-2-yl)-N,O-dimethyl-hydroxylamine hydrochloride (1.56 g) as a colorless oil. LCMS (ESI) m/z=315 (M+H)$^+$. $^1$H NMR (500 MHz, DMSO) δ (ppm) 12.10-12.60 (br, 1H), 8.55-8.74 (m, 2H), 3.75-3.86 (m, 3H), 3.35-3.45 (m, 11H), 3.22-3.25 (m, 5H), 2.77 (s, 1H), 1.72-1.76 (m, 4H).

Example 59

4,6-Bis-[N-(tetrahydropyran-4-ylmethyl)amino]-[1,3,5]triazin-2-yl)-N,O-dimethyl-hydroxylamine (CXV)

Example 60

4,6-Bis-[N-(tetrahydropyran-4-ylmethyl)amino]-[1,3,5]triazin-2-yl)-N,O-dimethyl-hydroxylamine hydrochloride (CXVI)

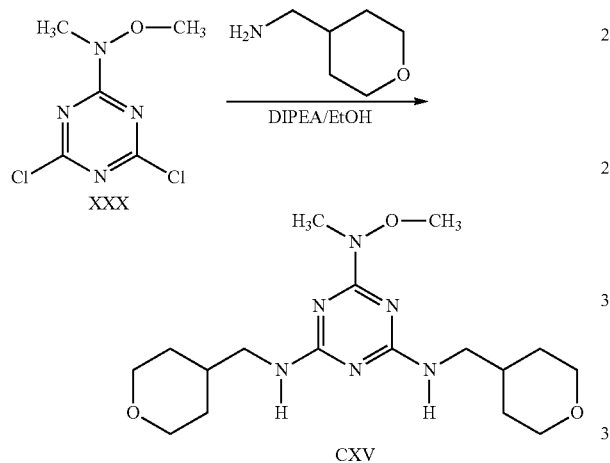

4,6-Bis-[N-(tetrahydropyran-4-ylmethyl)amino]-[1,3,5]triazin-2-yl)-N,O-dimethyl-hydroxylamine (CXV)

N-(4,6-Dichloro[1,3,5]triazin-2-yl)-N,O-dimethyl-hydroxylamine (XXX) (1 g, 4.78 mmol), (tetrahydro-2H-pyran-4-yl)methanamine (1.21 g, 10.52 mmol) and DIPEA (1.85 g, 14.34 mmol) in EtOH (50 mL) were heated at 100° C. for 16 h, after which time the solvent was removed under reduced pressure. The residue was dissolved in EtOAc (200 mL), washed with water (50 mL) and then with a brine solution (50 mL) and lastly dried over Na₂SO₄. The solvent was removed under reduced pressure. The crude product was purified by flash column chromatography (PE/EA=5/1 to 1/1) to afford 4,6-bis-[N-(tetrahydropyran-4-ylmethyl)amino]-[1,3,5]triazin-2-yl)-N,O-dimethyl-hydroxylamine (CXV) (1.5 g, 85%).

4,6-Bis-[N-(tetrahydropyran-4-ylmethyl)amino]-[1,3,5]triazin-2-yl)-N,O-dimethyl-hydroxylamine hydrochloride (CXVI)

4,6-Bis-[N-(tetrahydropyran-4-ylmethyl)amino]-[1,3,5]triazin-2-yl)-N,O-dimethyl-hydroxylamine (CXV) (1.5 g, 4.1 mmol) was dissolved in H₂O (10 mL) and 0.5 M aqueous HCl solution (12.3 mL), and the resultant solution was lyophilized to yield 4,6-bis-[N-(tetrahydropyran-4-ylmethyl)amino]-[1,3,5]triazin-2-yl)-N,O-dimethyl-hydroxylamine (CXVI) hydrochloride (1.65 g) as a white solid. LCM: (ESI) m/z=367 (M+H)⁺. ¹H NMR (500 MHz, DMSO) δ (ppm) 12.30-12.70 (br, 1H), 8.65-8.80 (m, 2H), 3.77-3.86 (m, 7H), 3.20-3.35 (m, 11H), 1.75-1.78 (m, 2H), 1.56-1.58 (m, 4H), 1.20-1.23 (m, 4H).

Example 61

N-(5,8,11-Trioxa-2,14,16,18,19-pentaazabicyclo[13.3.1]nonadeca-1(18),15(19),16(17)-trien-17-yl)-N,O-dimethylhydroxylamine (CXVII)

Example 62

N-(5,8,11-Trioxa-2,14,16,18,19-pentaazabicyclo[13.3.1]nonadeca-1(18),15(19),16(17)-trien-17-yl)-N,O-dimethylhydroxylamine hydrochloride (CXVIII)

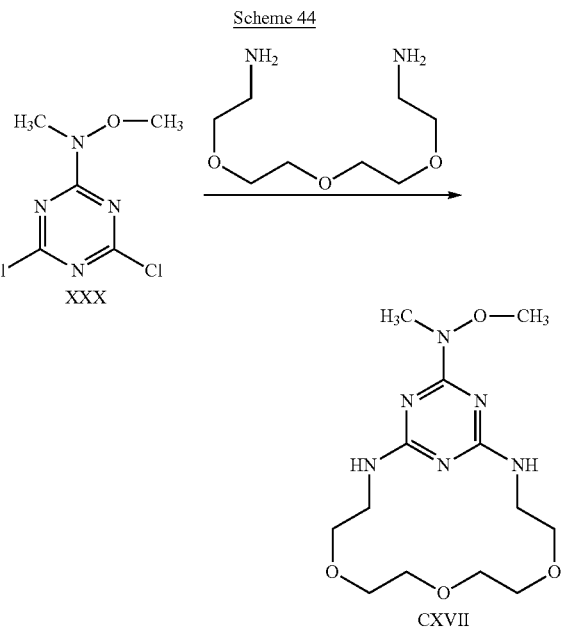

N-(5,8,11-Trioxa-2,14,16,18,19-pentaazabicyclo[13.3.1]nonadeca-1(18),15(19),16(17)-trien-17-yl)-N,O-dimethylhydroxylamine (CXVII)

N-(4,6-Dichloro[1,3,5]triazin-2-yl)-N,O-dimethyl-hydroxylamine (XXX) (1.63 g, 7.8 mmol) in EtOH (100 mL) was added to 2,2'-(2,2'-oxybis(ethane-2,1-diyl)bis(oxy))diethanamine (Org. Biomol. Chem. 2005, 3:2255-61) (1.5 g, 7.8 mmol) and DIPEA (2.01 g, 15.6 mmol). The reaction was heated at 100° C. for 3 h, after which time the solvent was removed under reduced pressure. The residue was dissolved in EtOAc (200 mL), washed with water (2×100 mL) and then with a brine solution (100 mL) and lastly dried over Na₂SO₄. The solvent was removed under reduced pressure and the residue was purified by flash column chromatography (DCM/MeOH=50/1 to 20/1) to yield N-(5,8,11-trioxa-2,14,16,18,19-pentaazabicyclo[13.3.1]nonadeca-1(18),15(19),16(17)-trien-17-yl)-N,O-dimethylhydroxylamine (CXVII) (700 mg) as a colourless oil (yield 27%).

N-(5,8,11-Trioxa-2,14,16,18,19-pentaazabicyclo [13.3.1]nonadeca-1(18),15(19),16(17)-trien-17-yl)-N,O-dimethylhydroxylamine hydrochloride (CXVIII)

N-(5,8,11-Trioxa-2,14,16,18,19-pentaazabicyclo[13.3.1] nonadeca-1(18),15(19),16(17)-trien-17-yl)-N,O-dimethyl-hydroxylamine (CXVII) (700 mg, 2.1 mmol) was dissolved in $H_2O$ (10 mL) and 0.5 M aqueous HCl solution (4.3 mL), and the resultant solution was lyophilized to yield N-(5,8,11-trioxa-2,14,16,18,19-pentaazabicyclo[13.3.1]nonadeca-1 (18),15(19),16(17)-trien-17-yl)-N,O-dimethylhydroxylamine hydrochloride (CXVIII) (750) mg as a colorless oil. LCMS: (ESI) m/z=329 (M+H)$^+$. $^1$H NMR (500 MHz, DMSO) δ (ppm) 11.50-12.60 (br, 1H), 8.61 (s, 2H), 3.77 (s, 3H), 3.30-3.62 (m, 16H), 3.30 (s, 3H).

Example 63

2,6-Bis-(N-propylamino)-[1,3]pyrimidin-4-yl)-N,O-dimethyl-hydroxylamine (CXX)

Example 64

2,6-Bis-(N-propylamino)-[1,3]pyrimidin-4-yl)-N,O-dimethyl-hydroxylamine hydrogen sulfate (CXXI)

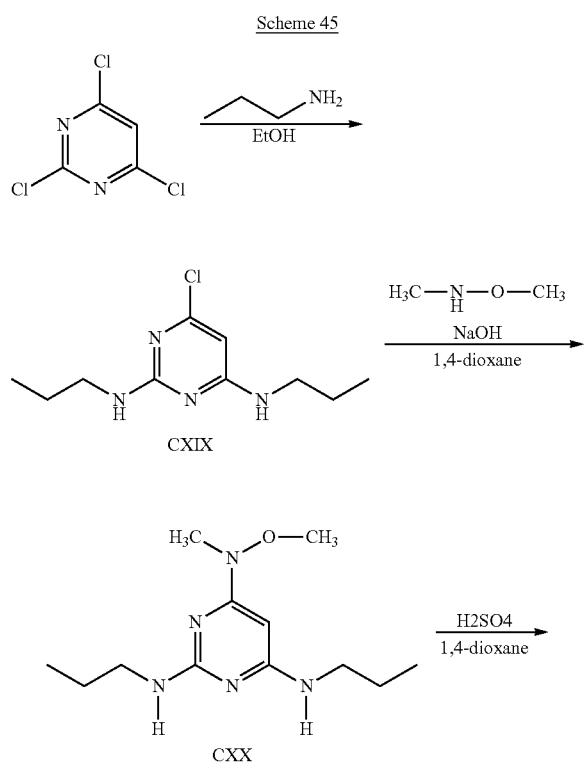

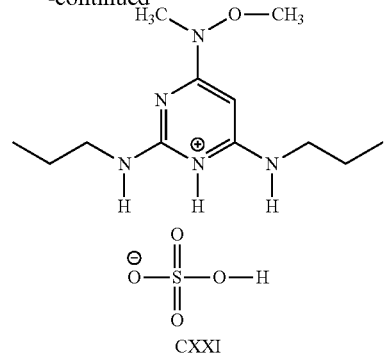

4-Chloro-2,6-bis-[N-n-propylamino]-1,3-pyrimidine (CXIX)

2,4,6-Trichloro-pyrimidine (5.00 g, 27.26 mmol) and n-propylamine (13.5 mL, 163.56 mmol) in EtOH were heated at 60° C. for 24 h and then cooled. The volatiles were removed under reduced pressure. Water (100 mL) was added and the resulting suspension was extracted with $CH_2Cl_2$ (3×75 mL). The combined organic extracts were washed with water (150 mL), then with a brine solution (100 mL) and dried over $Na_2SO_4$. The solvent was removed under reduced pressure to yield 4-chloro-2,6-bis-[N-n-propylamino]-1,3-pyrimidine (CXIX) (5.78 g, 93%). 200 MHz $^1$H-NMR (DMSO-$d_6$, ppm) 7.26-7.04 (1H, m) 7.04-6.81 (1H, m) 5.69 (1H, s) 3.26-3.01 (4H, m) 1.60-1.36 (4H, m) 0.87 (3H, t, J=7.4 Hz) 0.85 (3H, t, J=7.4 Hz); ESI-MS (m/z) 229, 231 [M+H]$^+$.

(2,6-Bis-N-[n-propylamino]-pyrimidin-4-yl)-N,O-dimethyl-hydroxylamine (CXX)

4-Chloro-2,6-bis-[N-n-propylamino]-1,3-pyrimidine (CXIX) (5.78 g, 25.27 mmol), N,O-dimethylhydroxylamine hydrochloride (4.93 g, 50.54 mmol) and NaOH (2.02 g, 50.54 mmol) in 1,4-dioxane (400 mL) and water (20 mL) were heated at 60° C. for 24 h. N,O-Dimethylhydroxylamine hydrochloride (4.93 g, 50.54 mmol) and NaOH (3.03 g, 75.81 mmol) were added to the reaction mixture and heating was continued for 3 days at 110° C. The volatiles were removed under reduced pressure. Saturated $NaHCO_3$ solution (50 mL) was added to the residue and the mixture was extracted with $CH_2Cl_2$ (3×75 mL). The combined organic extracts were washed with water (150 mL) and dried over $Na_2SO_4$. The solvent was removed under reduced pressure, and the residue was purified by flash column chromatography ($CH_2Cl_2$/ EtOH (25/1)) to yield (2,6-bis-N-[n-propylamino]-pyrimidin-4-yl)-N,O-dimethyl-hydroxylamine (CXX) (1.2 g, 19%). 200 MHz $^1$H-NMR (DMSO-$d_6$, ppm) 6.57-6.45 (1H, m) 6.13 (1H, t, J=5.5 Hz) 5.34 (1H, s) 3.59 (3H, s) 3.20-3.04 (4H, m) 3.03 (3H, s) 1.58-1.37 (4H, m) 0.87 (3H, t, J=7.1 Hz) 0.84 (3H, t, J=7.1 Hz).

(2,6-Bis-N-[n-propylamino]-pyrimidin-4-yl)-N,O-dimethyl-hydroxylamine hydrogen sulfate (CXXI)

(2,6-Bis-N-[n-propylamino]-pyrimidin-4-yl)-N,O-dimethyl-hydroxylamine (1.20 g, 4.74 mmol) in 1,4-dioxane (15 mL) was treated with 95% $H_2SO_4$ (0.27 mL, 4.74 mmol) in a dropwise manner at 0° C. The mixture was stirred at room temperature for 0.5 h and then the volatiles were removed under reduced pressure. The resulting residue was co-evaporated with dry toluene (3×5 mL) to yield (2,6-bis-N-[n-propylamino]-pyrimidin-4-yl)-N,O-dimethyl-hydroxylamine hydrogen sulfate (CXXI) in quantitative yield. 400 MHz H-NMR (DMSO-d$_6$, ppm) 11.3-10.5 (1H, m), 8.29 (0.4H, br s), 7.38 (0.6H, br s), 5.48-5.20 (1H, m), 3.70 (3H, s), 3.36-3.21 (5H, m), 3.20-3.08 (2H, m), 1.61-1.48 (4H, m), 0.9 (6H, t, J=7.4 Hz). ESI-MS (m/z) 254 [M+H]$^+$; melting point: 123-126° C.

Example 65

2-(n-Propyl)amino-4-(i-propylamino-7-methyl-pyrrolidino[2,3-d]pyrimidine (CXXVI)

Example 66

2-(n-Propyl)amino-4-(i-propylamino-7-methyl-pyrrolidino[2,3-d]pyrimidine hydrochloride (CXXVII)

Scheme 46

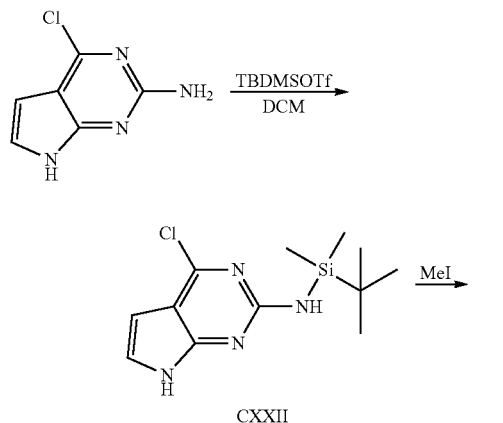

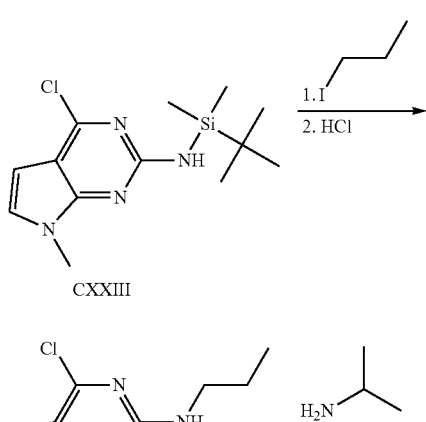

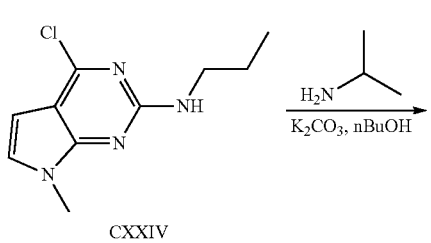

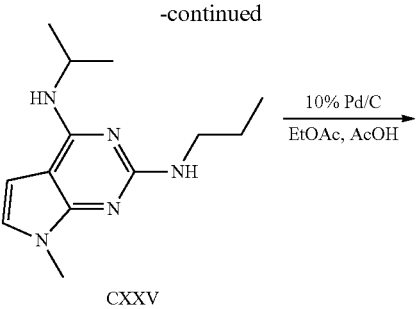

CXXV

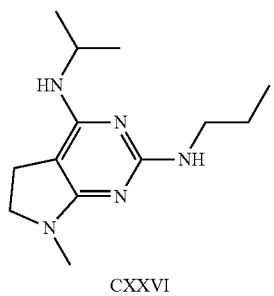

CXXVI 2-(t-Butyl-dimethylsilyl)amino-4-chloro-7H-pyrrolo[2,3-d]pyrimidine (CXXII)

To a dichloromethane solution (100 mL) of 2-amino-4-chloro-7H-pyrrolo[2,3-d]pyrimidine (8.7 g, 52 mmol) was added Et$_3$N (26 g, 260 mmol) and the mixture was stirred at −30° C. After this time, TBDMSOTf (15.1 g, 57.2 mmol) was added in a slow dropwise manner and the resultant reaction was stirred at ambient temperature for 1.5 h. The observed solid material completely dissolved to form a light brown solution. The mixture was then quenched with 1 N NaOH (100 mL) and extracted with DCM (250 mL). The organic layer was washed with H$_2$O (150 mL) and then with a brine solution (150 mL) and dried over Na$_2$SO$_4$. The solvents were removed in vacuo and the residue was purified by flash column chromatography (PE/EtOAc=10/1 to 5/1) to afford 2-(t-butyl-dimethylsilyl)amino-4-chloro-7H-pyrrolo[2,3-d]pyrimidine (CXXII, 11.4 g, 79%) as a light yellow solid. LCMS: (ESI) m/z=283 (M+H)$^+$.

2-(t-Butyl-dimethylsilyl)amino-4-chloro-7-methyl-pyrrolo[2,3-d]pyrimidine (CXXIII)

2-(t-Butyl-dimethyl silyl)amino-4-chloro-7H-pyrrolo[2,3-d]pyrimidine (CXXII) (700 mg, 2.5 mmol), 0.18 mL (3.5 mmol) of methyl iodide in DMF (10 mL), and K$_2$CO$_3$ (552 mg, 4 mmol) were reacted at ambient temperature for 15 h. After addition of H$_2$O (10 mL), the reaction was extracted with EtOAc (100 mL), and the organic layer was washed with a brine solution (10 mL), and dried over Na$_2$SO$_4$. The solvents were removed in vacuo, and the residue was purified by flash column chromatography (PE/EtOAc=10/1 to 5/1) to afford 2-(t-butyl-dimethylsilyl)amino-4-chloro-7-methyl-pyrrolo[2,3-d]pyrimidine (CXXIII) (750 mg, 100%) as a light yellow oil. LCMS (ESI) m/z=297 (M+H)$^+$.

2-(n-Propyl)amino-4-chloro-7-methyl-pyrrolo[2,3-d]pyrimidine (CXXIV)

Under a nitrogen atmosphere 2-(t-butyl-dimethyl silyl)amino-4-chloro-7-methyl-pyrrolo[2,3-d]pyrimidine (CXXIII, 5.0 g, 17 mmol) and 1-iodopropane (4.3 g, 25 mmol) were dissolved in DMF (20 mL). The reaction mixture was cooled to 0° C. with vigorous stirring, then NaH (1 g of a 60% dispersion in mineral oil, 21 mmol) was added. The mixture was stirred for 10 min. and water (50 mL) was slowly added to quench the reaction. The aqueous solution was extracted with EtOAc (200 mL), and the organic layer was washed with water (50 mL) and with a brine solution (50 mL), and lastly, dried over anhydrous $Na_2SO_4$. After evaporation of volatiles, a yellow oily residue (5.7 g) was isolated. The residue was dissolved in $Et_2O$ (50 mL) and concentrated hydrochloric acid (10 mL) was added at 0° C. with stirring. The mixture was reacted for an additional 10 min. After this time, the solution was extracted with EtOAc (200 mL) and 1N NaOH (200 mL). The organic layer was washed with $H_2O$ (150 mL) and then with a brine solution (150 mL) and lastly, dried over $Na_2SO_4$. The solvents were removed in vacuo and the resultant residue was purified by flash column chromatography (PE/EtOAc=10/1 to 5/1) to afford 2-(n-propyl)amino-4-chloro-7-methyl-pyrrolo[2,3-d]pyrimidine (3.78 g, 100%) of the desired product as a yellow solid. LCMS: (ESI) m/z=225 (M+H)$^+$.

2-(n-Propyl)amino-4-(i-propyl)amino-7-methyl-pyrrolo[2,3-d]pyrimidine (CXXV)

To a solution of 2-(n-propyl)amino-4-chloro-7-methyl-pyrrolo[2,3-d]pyrimidine (1.6 g, 7.1 mmol) in n-butanol (10 mL) was added potassium carbonate (4.9 g, 35.5 mmol), followed by propan-2-amine (632 mg, 10.7 mmol). The mixture was stirred in an autoclave equipped with a stirrer at 140° C. for 16 h. After cooling to room temperature, water was added (20 mL), and the mixture was extracted with EtOAc (3×50 mL). The combined organic layers were washed with water and then with a brine solution, and lastly dried over anhydrous $Na_2SO_4$. The volatiles were removed in vacuo and the residue was purified by flash column chromatography (PE/EtOAc=3/1) to yield 2-(n-propyl)amino-4-(i-propyl)amino-7-methyl-pyrrolo[2,3-d]pyrimidine (1.2 g, 75%) as a yellow solid. LCMS: (ESI) m/z=248 (M+H)$^+$.

2-(n-Propyl)amino-4-(i-propylamino-7-methyl-pyrrolidino[2,3-d]pyrimidine (CXXVI)

To the solution of 2-(n-propyl)amino-4-(i-propyl)amino-7-methyl-pyrrolo[2,3-d]pyrimidine (CXXV, 1.0 g, 4 mmol) in EtOAc (50 mL) were added 10% Pd/C (1.0 g) and AcOH (2.43 g, 40 mmol). The mixture was attached to a hydrogenation apparatus and the system was evacuated and then refilled with hydrogen. The reaction was stirred at ambient temperature for 48 h. After this time, the mixture was filtered over 10 g of silica-gel on a glass-filter. The filtrate was concentrated and the residue was purified by flash column chromatography (DCM/MeOH=50/1 to 10/1) to yield 2-(n-propyl)amino-4-(i-propylamino-7-methyl-pyrrolidino[2,3-d]pyrimidine (CXXVI, 500 mg, 50%) as a yellow solid.

2-(n-Propyl)amino-4-(i-propylamino-7-methyl-pyrrolidino[2,3-d]pyrimidine hydrochloride (CXXVII)

The isolated free amine (CXXVI, 500 mg, 2 mmol) was dissolved in $H_2O$ (10 mL) and 0.5 M aqueous HCl solution (4 mL), and the solution was lyophilized to yield 2-(n-propyl)amino-4-(i-propylamino-7-methyl-pyrrolidino[2,3-d]pyrimidine hydrochloride (CXXVII, 525 mg) as a brown solid. LCMS (ESI) m/z=250 (M+H)$^+$. $^1$H NMR (500 MHz, MeOD) δ (ppm) 3.80 (s, 1H), 3.58 (t, J=8.5 Hz, 2H), 3.23-3.29 (m, 2H), 2.88 (s, 3H), 2.77 (t, J=8.5 Hz, 2H), 1.52-1.56 (m, 2H), 1.15 (d, J=6.5 Hz, 6H), 0.89 (d, J=7.5 Hz, 3H).

Example 67

2-(n-Propyl)amino-4-dimethylamino-7-methyl-pyrrolidino[2,3-d]pyrimidine (CXXVIII)

Example 68

2-(n-Propyl)amino-4-dimethylamino-7-methyl-pyrrolidino[2,3-d]pyrimidine hydrochloride (CXXIX)

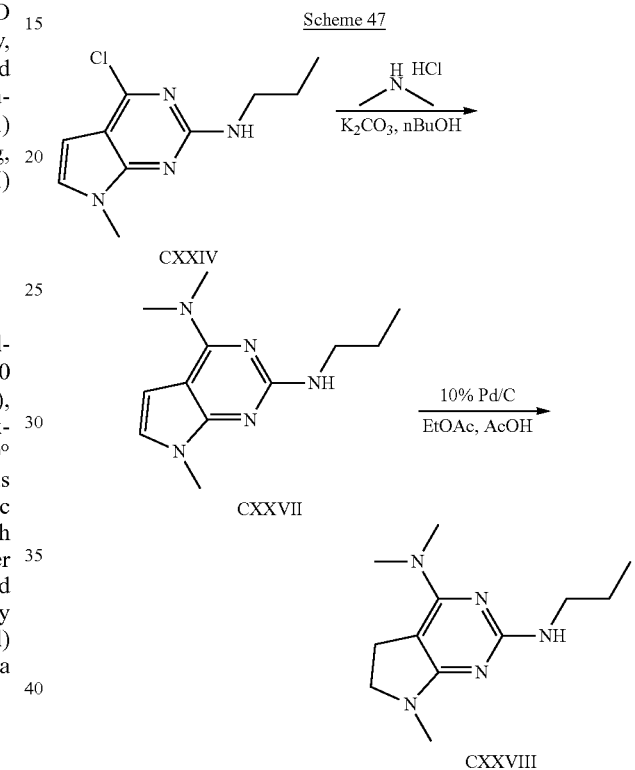

Scheme 47

2-(n-Propyl)amino-4-dimethylamino-7-methyl-pyrrolo[2,3-d]pyrimidine (CXXVII)

To 2-(n-propyl)amino-4-chloro-7-methyl-pyrrolo[2,3-d]pyrimidine (1.0 g, 4.5 mmol) (CXXIV) in n-butanol (20 mL) was added potassium carbonate (3.7 g, 27 mmol) and dimethylamine hydrochloride (1.0 g, 22 mmol). The mixture was stirred in an autoclave equipped with a stirrer at 120° C. for 16 h. After cooling to room temperature, water was added (20 mL), and the mixture was extracted with EtOAc (3×50 mL). The combined organic layers were washed with water and then with a brine solution, and dried over anhydrous $Na_2SO_4$. The solvents were removed in vacuo and the residue was purified by flash column chromatography (PE/EtOAc=6/1) to yield 2-(n-propyl)amino-4-dimethylamino-7-methyl-pyrrolo[2,3-d]pyrimidine (CXXVII, 800 mg, 76%) as a yellow solid. LCMS (ESI) m/z=234 (M+H)$^+$.

2-(n-Propyl)amino-4-dimethylamino-7-methyl-pyrrolidino[2,3-d]pyrimidine (CXXVIII)

To the solution of 2-(n-propyl)amino-4-dimethylamino-7-methyl-pyrrolo[2,3-d]pyrimidine (CXXVII, 800 mg, 3.4 mmol) in EtOAc (30 mL) was added 10% Pd/C (1.0 g) and AcOH (3 mL), and the mixture was attached to a hydrogenation apparatus. The system was evacuated and then refilled with hydrogen. The mixture was stirred at ambient temperature for 48 h. The mixture was filtered through 10 g of silica-gel on a glass-filter. The filtrate was concentrated and the residue was purified by flash column chromatography (EtOAc/MeOH=25/1) to yield 2-(n-propyl)amino-4-dimethylamino-7-methyl-pyrrolidino[2,3-d]pyrimidine (CXXVIII, 600 mg, 75%).

2-(n-Propyl)amino-4-dimethylamino-7-methyl-pyrrolidino[2,3-d]pyrimidine hydrochloride (CXXIX)

2-(n-Propyl)amino-4-dimethylamino-7-methyl-pyrrolidino[2,3-d]pyrimidine (CXXVIII, 600 mg, 2.6 mmol) was dissolved in H$_2$O (10 mL) and 0.5 M aqueous HCl solution (5.2 mL), and the solution was lyophilized to yield 2-(n-propyl)amino-4-dimethylamino-7-methyl-pyrrolidino[2,3-d]pyrimidine hydrochloride (CXXIX, 600 mg) as a yellow solid. LCMS (ESI) m/z=236 (M+H)$^+$. $^1$H NMR (500 MHz, MeOD) δ (ppm) 3.66 (t, J=9.0 Hz, 2H), 3.40 (t, J=7.0 Hz, 2H), 3.33 (s, 1H), 3.23 (t, J=9.5 Hz, 2H), 3.17 (s, 5H), 3.00 (s, 3H), 1.63-1.67 (m, 2H), 1.00 (t, J=7 Hz, 3H).

Example 69

2-(n-Propyl)amino-4-methylamino-7-methyl-pyrrolidino[2,3-d]pyrimidine (CXXXI)

Example 70

2-(n-Propyl)amino-4-methylamino-7-methyl-pyrrolidino[2,3-d]pyrimidine hydrochloride (CXXXII)

2-(n-Propyl)amino-4-methylamino-7-methyl-pyrrolidino[2,3-d]pyrimidine (CXXXI)

To a solution of 2-(n-propyl)amino-4-methylamino-7-methyl-pyrrolo[2,3-d]pyrimidine (CXXX) (2.0 g, 9.13 mmol) in EtOAc (50 mL) was added 10% Pd/C (2.1 g) and AcOH (8 mL), and the mixture was attached to a hydrogenation apparatus. The system was evacuated and refilled with hydrogen. The mixture was stirred at ambient temperature for 48 h. The mixture was filtered through 10 g of silica-gel on a glass-filter. The filtrate was concentrated and the residue was purified by flash column chromatography (DCM/MeOH=60/1 to 10/1) to yield 2-(n-propyl)amino-4-methylamino-7-methyl-pyrrolidino[2,3-d]pyrimidine (CXXXI, 700 mg, 43%) as a yellow solid.

2-(n-Propyl)amino-4-methylamino-7-methyl-pyrrolidino[2,3-d]pyrimidine hydrochloride (CXXXII)

2-(n-Propyl)amino-4-methylamino-7-methyl-pyrrolidino[2,3-d]pyrimidine (CXXX, 700 mg, 3.2 mmol) was dissolved in H$_2$O (10 mL) and 0.5 M aqueous HCl solution (7 mL), and the solution was lyophilized to yield 2-(n-propyl)amino-4-methylamino-7-methyl-pyrrolidino[2,3-d]pyrimidine (717 mg) as a brown solid. LCMS: (ESI) m/z=222 (M+H)$^+$. $^1$H NMR (500 MHz, MeOD) δ (ppm) 3.50 (t, J=8.5, 2H), 3.22 (t, J=7.0 Hz, 2H), 2.79 (s, 6H), 2.68 (t, J=9.0 Hz, 2H), 1.43-1.51 (m, 2H), 0.81 (t, J=8.0 Hz, 3H).

Example 71

2-(n-Propyl)amino-4-(i-propyl)amino-7-i-propyl-pyrrolidino[2,3-d]pyrimidine (CXXXVI)

Example 72

2-(n-Propyl)amino-4-(i-propyl)amino-7-i-propyl-pyrrolidino[2,3-d]pyrimidine hydrochloride salt (CXXXVII)

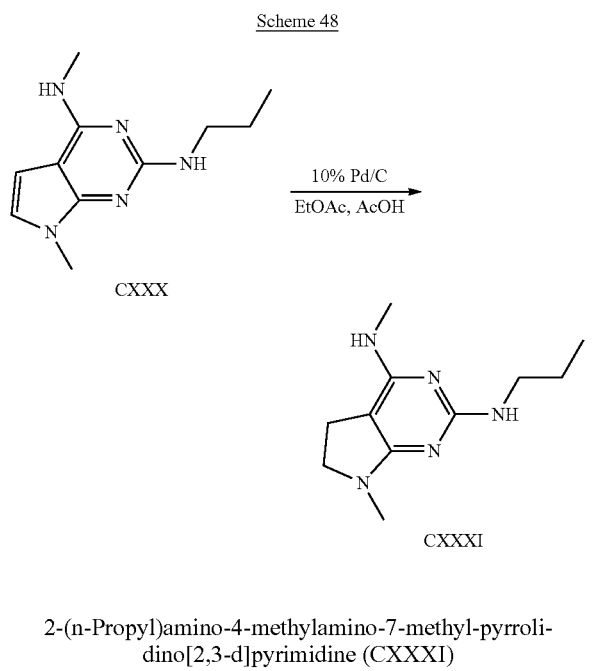

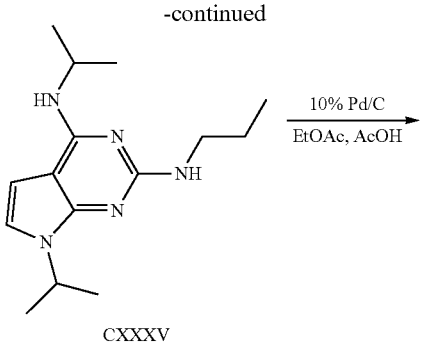

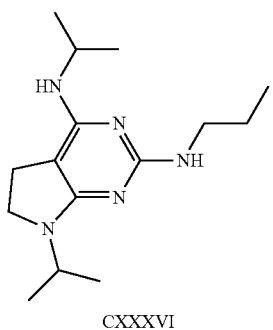

2-(t-Butyl-dimethylsilyl)amino-4-chloro-7-i-propyl-pyrrolo[2,3-d]pyrimidine (CXXXIII)

2-(t-Butyl-dimethylsilanyl)amino-4-chloro-7H-pyrrolo[2,3-d]pyrimidine (CXXII) (5 g, 17.7 mmol), 2-iodopropane (4.5 g, 26.6 mmol) and K$_2$CO$_3$ (4.3 g, 26.6 mmol) in DMF (20 mL) were reacted at ambient temperature for 15 h. After addition of H$_2$O (50 mL) to the reaction mixture, the aqueous solution was extracted with EtOAc (300 mL) and the organic layer was washed with a brine solution (50 mL) and dried with Na$_2$SO$_4$. The solvents were removed in vacuo and the residue was purified by flash column chromatography (pet ether/EtOAc=10/1 to 5/1) to afford 2-(t-butyl-dimethylsilyl)amino-4-chloro-7-i-propyl-pyrrolo[2,3-d]pyrimidine (CXXXIII, 5.7 g, 100%) as a light yellow oil. LCMS: (ESI) m/z=325 (M+H)$^+$.

2-(n-Propyl)amino-4-chloro-7-i-propyl-pyrrolo[2,3-d]pyrimidine (CXXXIV)

Under nitrogen atmosphere, 2-(t-butyl-dimethylsilanyl)amino-4-chloro-7-i-propyl-pyrrolo[2,3-d]pyrimidine (5.7 g, 17.6 mmol) and 1-iodopropane (4.5 g (26.4 mmol) were dissolved in DMF (20 mL). The reaction mixture was cooled to 0° C. with vigorous stirring, and NaH (1.06 g of a 60% dispersion in mineral oil, 26.4 mmol) of (60%) was added. The mixture was stirred for 10 min, and then water (50 mL) was slowly added to quench the reaction. The mixture was extracted with EtOAc (300 mL) and the organic layer was washed with water (50 mL) and then with a brine solution (50 mL), and lastly, dried over anhydrous Na$_2$SO$_4$. After evaporation of the solvents, a yellow oily residue was isolated (6.5 g). The residue was dissolved in Et$_2$O (50 mL), concentrated hydrochloric acid (10 mL) was added at 0° C. with stirring, and the mixture was stirred for an additional 10 min. After the reaction was completed, the solution was extracted with EtOAc (200 mL) and 1N NaOH (200 mL). The organic layer was washed with H$_2$O (150 mL) and then with a brine solution (150 mL) and dried over Na$_2$SO$_4$. The solvents in vacuo and the residue was purified by flash column chromatography (PE/EtOAc=10/1 to 5/1) to yield 2-(n-propyl)amino-4-chloro-7-i-propyl-pyrrolo[2,3-d]pyrimidine (CXXXIV, 4.5 g, !00%) as a yellow solid. LCMS (ESI) m/z=253 (M+H)$^+$.

2-(n-Propyl)amino-4-(i-propyl)amino-7-i-propyl-pyrrolo[2,3-d]pyrimidine (CXXXV)

To 2-(n-propyl)amino-4-chloro-7-i-propyl-pyrrolo[2,3-d]pyrimidine (CXXXIV, 3.0 g, 12 mmol) in n-butanol (10 mL) was added propan-2-amine (1.05 g, 18 mmol) and potassium carbonate (2.5 g, 18 mmol). The resulting mixture was stirred in an autoclave equipped with a stirrer at 140° C. for 16 h. After cooling to room temperature, water was added (20 mL), and the mixture was extracted with EtOAc (3×50 mL). The combined organic layers were washed with water and then with a brine solution and dried over anhydrous Na$_2$SO$_4$. After the solvents were removed in vacuo, the residue was purified by flash column chromatography (PE/EtOAc=5/1 to 3/1) to yield 2-(n-propyl)amino-4-(i-propyl)amino-7-i-propyl-pyrrolo[2,3-d]pyrimidine (CXXXV, 1.2 g, 36%) as a yellow solid. LCMS: (ESI) m/z=276 (M+H)$^+$.

2-(n-Propyl)amino-4-(i-propyl)amino-7-i-propyl-pyrrolidino[2,3-d]pyrimidine (CXXXVI)

To a solution of 2-(n-propyl)amino-4-(i-propyl)amino-7-i-propyl-pyrrolo[2,3-d]pyrimidine (1.0 g, 3.6 mmol) in EtOAc (10 mL) were added 10% Pd/C (1.0 g) and AcOH (2.43 g, 40 mmol). The mixture was attached to a hydrogenation apparatus. The system was evacuated and refilled with hydrogen gas. The mixture was stirred at ambient temperature for 48 h, and filtered through 10 g of silica-gel on a glass-filter. The filtrate was concentrated and the residue was purified by flash column chromatography (DCM/MeOH=100/1 to 20/1) to yield 2-(n-propyl)amino-4-(i-propyl)amino-7-i-propyl-pyrrolidino[2,3-d]pyrimidine (CXXXVI) (800 mg, 79%) as a yellow solid.

2-(n-Propyl)amino-4-(i-propyl)amino-7-i-propyl-pyrrolidino[2,3-d]pyrimidine hydrochloride (CXXXVII)

2-(n-Propyl)amino-4-(i-propyl)amino-7-i-propyl-pyrrolo[2,3-d]pyrimidine (200 mg, 0.72 mmol) was dissolved in H$_2$O (10 mL) and 0.5 M aqueous HCl solution (1.5 mL) and then the solution was lyophilized to yield 2-(n-propyl)amino-4-(i-propyl)amino-7-i-propyl-pyrrolidino[2,3-d]pyrimidine hydrochloride (225 mg, 95%) as a yellow solid. LCMS (ESI) m/z=278 (M+H)$^+$. $^1$H NMR (500 MHz, MeOD) δ (ppm) 4.36 (s, 1H), 3.90 (s, 1H), 3.67 (t, J=8.5 Hz, 2H), 3.30 (t, J=7.5 Hz, 2H), 2.84 (t, J=8.5 Hz, 2H), 1.60-1.66 (m, 2H), 1.24 (d, J=6.0 Hz, 6H), 1.21 (d, J=6.0 Hz, 6H), 0.98 (t, J=7.5 Hz, 3H).

Example 73

N-(2-Propylamino-7H-pyrrolo[2,3d]pyrimidin-4-yl)-N,O-dimethyl-hydroxylamine (CXLI)

Example 74

N-(2-Propylamino-7H-pyrrolo[2,3d]pyrimidin-4-yl)-N,O-dimethyl-hydroxylamine hydrochloride (CXLII)

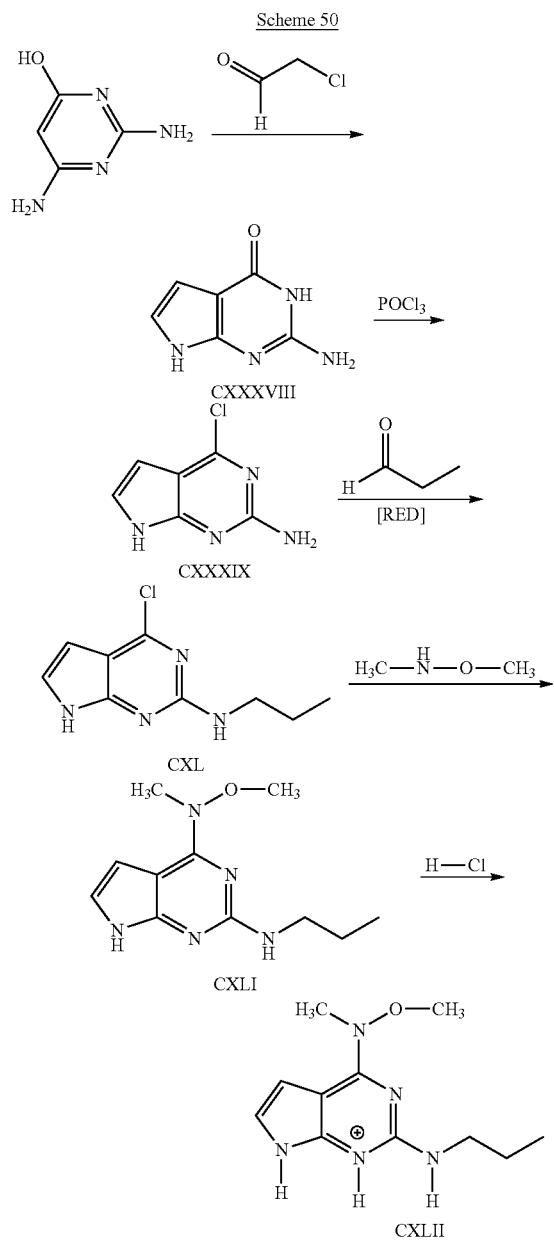

2-Amino-4-oxo-4,7-dihydro-3H-pyrrolo[2,3d]pyrimidine (CXXXVIII)

To the solution of 2,4-diamino-6-hydroxypyrimidine (50 g, 397 mmol) in H₂O (750 mL) was added 2-chloroacetaldehyde (40% in H₂O, 85 g, 437 mmol) in a dropwise manner at 0° C. The mixture was stirred at 65° C. for 2 h and then heated at 100° C. until the reaction was complete. The resultant solids were filtered and the remaining residue was heated at reflux in EtOH (750 mL). The additional solids were filtered and the mother liquor was concentrated to afford 2-amino-4-oxo-4,7-dihydro-3H-pyrrolo[2,3d]pyrimidine (CXXXVIII) as a yellow solid 40 g (~67%, ~70% purity). LCMS (ESI) m/z=151 (M+H)⁺.

2-Amino-4-chloro-7H-pyrrolo[2,3d]pyrimidine (CXXXIX)

2-Amino-4-oxo-4,7-dihydro-3H-pyrrolo[2,3d]pyrimidine (CXXXVIII, 25 g, 167 mmol) was suspended in POCl₃ (200 mL) and cooled in an ice bath. The mixture was slowly warmed and heated up to 120° C. for 3 h. After this time, the volatiles (excess POCl₃) were evaporated the under vacuum. To this residue was added ice water (200 mL) and the resultant solid was filtered to afford 2-amino-4-chloro-7H-pyrrolo[2,3d]pyrimidine (CXXXIX) as a yellow solid (20 g, ~71%, ~75% purity). LCMS (ESI) m/z=169 (M+H)⁺.

4-Chloro-2-n-propylamino-7H-pyrrolo[2,3d]pyrimidine (CXL)

To a solution of 2-amino-4-chloro-7H-pyrrolo[2,3d]pyrimidine (CXXXIX, 26 g, 155 mmol) and n-propionaldehyde (27 g, 464 mmol) in MeOH (600 mL) was added AcOH (50 mL). The reaction was stirred at ambient temperature for 30 min. After this time, NaBH₃CN (49 g, 775 mmol) was added in portions at −20° C. for 30 min. The resultant mixture was stirred at 80° C. for 3 h and the volatiles were removed. The resultant residue was extracted with EtOAc (3×300 mL) and the combined organics were washed with a brine solution (2×100 mL). The organic layer was dried over Na₂SO₄, concentrated and purified via silica-gel column chromatography (pet ether/EtOAc (5/1)) to afford 4-chloro-2-propylamino-7H-pyrrolo[2,3d]pyrimidine (CXL) as a yellow solid (6 g, 18%). LCMS (ESI) m/z=211 (M+H)⁺.

N-(2-Propylamino-7H-pyrrolo[2,3d]pyrimidin-4-yl)-N,O-dimethyl-hydroxylamine (CXLI)

To a solution of 4-chloro-2-propylamino-7H-pyrrolo[2,3d]pyrimidine (CXL, 1.0 g, 4.8 mmol) in n-BuOH (5 mL) was added potassium carbonate (3.3 g, 5.0 eq.) and N,O-dimethylhydroxylamine hydrochloride (1.1 g, 4.0 eq.). The mixture was stirred in an autoclave equipped with a stirrer at 100° C. for 8 h. After cooling to ambient temperature, water was added (20 mL) and the mixture was extracted with EtOAc (3×25 mL). The combined organic layers were washed with water and then with a brine solution, and dried over anhydrous Na₂SO₄. The solvents were removed in vacuo and the resultant residue was purified by flash column chromatography (pet ether/EtOAc=5/1) to yield N-(2-propylamino-7H-pyrrolo[2,3d]pyrimidin-4-yl)-N,O-dimethyl-hydroxylamine (CXLI, 500 mg, 45%).

N-(2-Propylamino-7H-pyrrolo[2,3d]pyrimidin-4-yl)-N,O-dimethyl-hydroxylamine hydrochloride (CXLII)

N-(2-propylamino-7H-pyrrolo[2,3d]pyrimidin-4-yl)-N,O-dimethyl-hydroxylamine (CXLI, 500 mg, 2.1 mmol) was dissolved in H₂O (10 mL) and 0.5 M aqueous HCl solution (5 mL). The solution was then lyophilized to yield N-(2-propylamino-7H-pyrrolo[2,3d]pyrimidin-4-yl)-N,O-dimethyl-hydroxylamine hydrochloride as a white solid (CXLII, 550 mg). LCMS (ESI) m/z=236 (M+H)⁺. ¹H NMR (500 MHz, MeOD) δ (ppm) 6.74 (d, J=3.5 Hz, 1H), 6.41 (d, J=4.0 Hz, 1H), 3.80 (s, 3H), 3.35 (s, 3H), 3.28-3.35 (m, 2H), 1.59-1.62 (m, 2H), 0.97 (t, J=7.0 Hz, 3H).

Example 75

2,4-Bis-(n-propyl)amino-7H-pyrrolidino[2,3-d]pyrimidine (CXLIX)

Example 76

2,4-Bis-(n-propyl)amino-7H-pyrrolidino[2,3-d]pyrimidine hydrochloride (CL)

5-Allyl-2-amino-4,6-dihydroxypyrimidine (CXLIII)

Guanidine hydrochloride (27 g, 0.28 mol) was added to cold absolute EtOH (200 mL) and NaOEt (30% in ethanol) (200 mL), and the mixture was stirred at 0° C. for 10 min. After this time, diethyl allylmalonate (55 g, 0.28 mol) was added. The reaction mixture was then stirred at room temperature for 18 h. Acidification with 3N HCl precipitated the crude product (pH=6). The solid was collected by filtration and washed with ethanol. Recrystallization from water afforded 29 g (62%) of pure 5-allyl-2-amino-4,6-dihydroxypyrimidine (CXLIII). LCMS (ESI) m/z=168 (M+H)⁺.

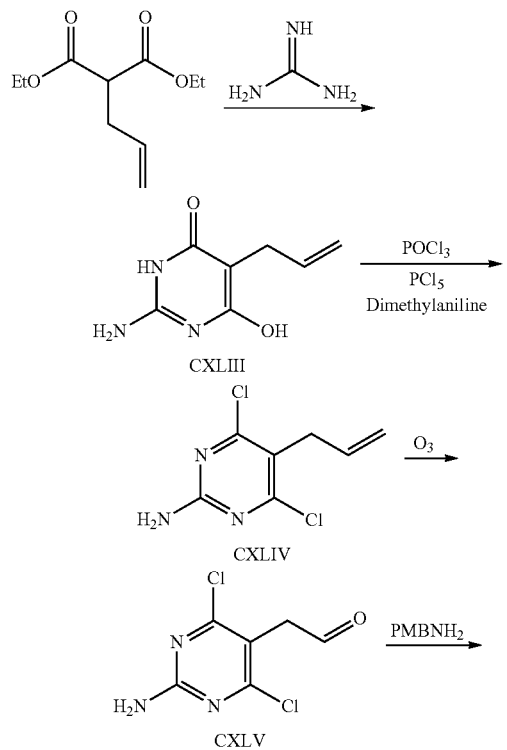

Scheme 51

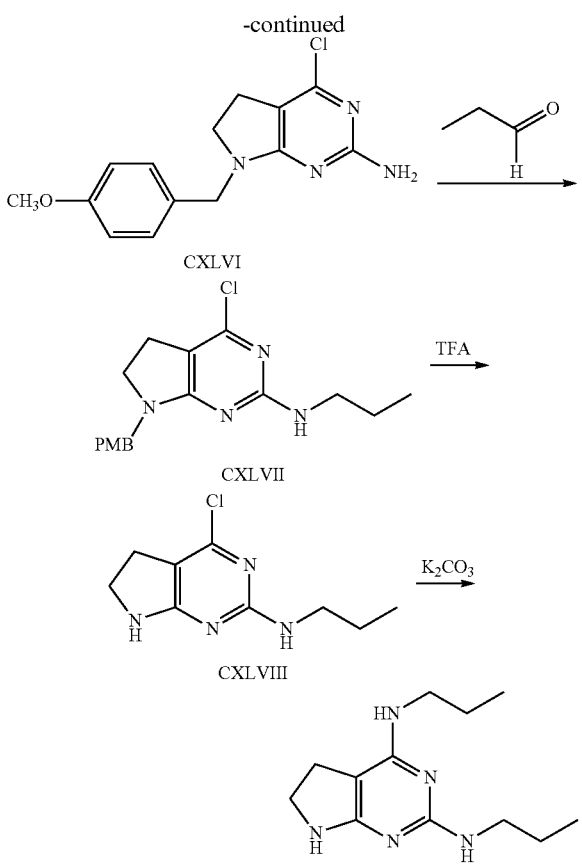

5-Allyl-2-amino-4,6-chloropyrimidine (CXLIV)

5-Allyl-2-amino-4,6-dihydroxypyrimidine (4.9 g, 28.0 mmol) was added in small portions to a solution of PCl₅ (6.6 g, 29.5 mmol) in POCl₃ (180 mL) at 60° C., and diethylaniline (3 g) was added dropwise. The temperature was raised to 120° C. The reaction mixture was heated at reflux overnight before it was evaporated to dryness. Hot water (100° C.) (100 mL) was added slowly to the residue, and the resulting suspension was cooled and extracted with CH₂Cl₂ (2×100 mL). The combined organic layers were washed with cold water three times until the aqueous extract was above pH=5. The organic layer was dried (Na₂SO₄) and evaporated to dryness in vacuo. The resultant residue was purified by column chromatography (EtOAc/pet ether=1:10) to afford 5-allyl-2-amino-4,6-chloropyrimidine (CXLIV, 2.5 g, 42%). LCMS (ESI) m/z=204 (M+H)⁺.

2-(2-Amino-4,6-chloropyrimidin-5-yl)ethanal (CXLV)

5-Allyl-2-amino-4,6-chloropyrimidine (1 g, 4.9 mmol) was dissolved in ethyl acetate (40 mL) and reacted with ozone gas at −78° C. for about 1 h (about 5% ozone at a rate of 1 L/min). The reaction was monitored by TLC (pet ether/AcOEt=3/1 (v/v)), and once the starting material was consumed, the reaction mixture was flushed with oxygen for 10 min. At this time, NaI (3 g) and glacial acetic acid (3 mL) were added simultaneously to the cold reaction mixture, and the temperature was allowed to warm up to 20° C. with continuous stirring over a 60-min period. Sodium thiosulfate solution (67 g/100 mL of H$_2$O) was added to the reaction mixture until it became colorless. The resulting mixture was diluted with water (30 mL) and extracted with CH$_2$Cl$_2$ (4×70 mL). The combined organic extracts were washed successively with H$_2$O (4×30 mL), a saturated NaHCO$_3$ solution (30 mL) and with a brine solution (30 mL) and lastly, dried over anhydrous Na$_2$SO$_4$). After filtration and evaporation, 2-(2-amino-4,6-chloropyrimidin-5-yl)ethanal (CXLV, 1.1 g, 87%) was isolated as a white solid with ~80% purity. LCMS (ESI) m/z=207 (M+H)$^+$.

2-Amino-4-chloro-7-(4-methoxy)benzyl-pyrrolidino [2,3-d]pyrimidine (CXLVI)

A solution of 2-(2-amino-4,6-chloropyrimidin-5-yl)ethanal (CXLV, 1.2 g, 5.8 mmol) and para-methoxybenzylamine (PMBNH$_2$) (1.6 g, 11.6 mmol) in THF (20 mL) and AcOH (2 mL) was stirred at ambient temperature for 30 min. To this mixture was added NaBH(OAc)$_3$ (6.2 g, 29 mmol) in portions and the reaction was stirred overnight. The mixture was concentrated in vacuo, and extracted with EtOAc (3×80 mL). The combined organic extracts were then washed with a brine solution (2×50 mL), dried over anhydrous Na$_2$SO$_4$, filtered and concentrated in vacuum. The resultant residue was purified by flash column chromatography (pet ether/EtOAc=10/1) to afford 2-amino-4-chloro-7-(4-methoxy)benzyl-pyrrolidino[2,3-d]pyrimidine (CXLVI, 950 mg, 52%) as a yellow solid (52%). LCMS (ESI) m/z=291 (M+H)$^+$.

2-n-Propylamino-4-chloro-7-(4-methoxy)benzyl-pyrrolidino[2,3-d]pyrimidine (CXLVII)

2-Amino-4-chloro-7-(4-methoxy)benzyl-pyrrolidino[2,3-d]pyrimidine (CXLVI, 950 mg, 3.3 mmol) and propionaldehyde (575 mg, 16.5 mmol) in MeOH (30 mL) and AcOH (3 mL) were stirred at ambient temperature for 30 min. At this time, NaBH$_3$CN (1.0 g, 16.5 mmol) was added in portions and the reaction was then heated at 85° C. for 16 h. After cooling, the mixture was evaporated, and extracted with EtOAc (2×50 mL). The combined organics were then washed with a brine solution (2×50 mL). The organic layer was dried over anhydrous Na$_2$SO$_4$, filtered and concentrated in vacuum. The resultant residue was purified by flash column chromatography (PE/EtOAc=10/1) to afford 2-n-propylamino-4-chloro-7-(4-methoxy)benzyl-pyrrolidino[2,3-d]pyrimidine (CXLVII, 920 mg, 85%). LCMS (ESI) m/z=333 (M+H)$^+$.

2-n-Propylamino-4-chloro-7H-pyrrolidino[2,3-d] pyrimidine (CXLVIII)

A solution of 2-n-propylamino-4-chloro-7-(4-methoxy)benzyl-pyrrolidino[2,3-d]pyrimidine (CXLVII, 920 mg, 3.2 mmol) in TFA (5 mL) was heated at 85° C. for 3 h. After cooling the mixture was evaporated and extracted with EtOAc (2×50 mL). The combined organics were washed with a brine solution (2×50 mL), dried over Na$_2$SO$_4$, filtered and concentrated in vacuum. The resultant residue was purified by flash column chromatography (pet ether/EtOAc=5/1) to afford 2-n-propylamino-4-chloro-7H-pyrrolidino[2,3-d]pyrimidine (CXLVIII, 500 mg, 85%) as a colorless solid. LCMS (ESI) m/z=213 (M+H)$^+$.

2,4-Bis-(n-propyl)amino-7H-pyrrolidino[2,3-d]pyrimidine (CXLIX)

2-n-Propylamino-4-chloro-7H-pyrrolidino[2,3-d]pyrimidine (CXLVIII, 500 mg, 2.38 mmol) was dissolved in n-butanol (5 mL), and potassium carbonate (1.64 g, 5.0 eq.) and propan-1-amine (923 mg, 4.0 eq.) were added. The mixture was stirred in an autoclave equipped with a stirrer at 100° C. for 72 h. After cooling to room temperature, 20 mL of water was added, and the mixture was extracted with EtOAc (3×20 mL). The combined organic layers were washed with water and with a brine solution, and dried over anhydrous Na$_2$SO$_4$. After removal of the solvents in vacuo, the resultant residue was purified by preparative HPLC to yield 2-n-propylamino-4-chloro-7H-pyrrolidino[2,3-d]pyrimidine (CXLIX, 210 mg, 37% yield).

2,4-Bis-(n-propyl)amino-7H-pyrrolidino[2,3-d]pyrimidine hydrochloride (CL)

2-n-Propylamino-4-chloro-7H-pyrrolidino[2,3-d]pyrimidine (CXLIX, 210 mg, 0.89 mmol) was dissolved in H$_2$O (5 mL) and 0.5 M aqueous HCl solution (2.0 mL), and the solution was lyophilized to yield 2,4-bis-(n-propyl)amino-7H-pyrrolidino[2,3-d]pyrimidine hydrochloride (CL, 242 mg, 95% yield) as an orange solid. LCMS (ESI) m/z=236 (M+H)$^+$. $^1$H NMR (500 MHz, MeOD) δ (ppm) 3.72 (t, J=9.0 Hz, 2H), 3.30-3.34 (m, 4H), 2.90 (t, J=9.0 Hz, 2H), 1.61-1.65 (m, 4H), 0.96-0.99 (m, 6H).

Example 77

2-(n-Propyl)amino-4-(4-hydroxypiperidin-1-yl)-7-methyl-pyrrolidino[2,3-d]pyrimidine (CLII)

Example 78

2-(n-Propyl)amino-4-(4-hydroxypiperidin-1-yl)-7-methyl-pyrrolidino[2,3-d]pyrimidine hydrochloride (CLIII)

Scheme 52

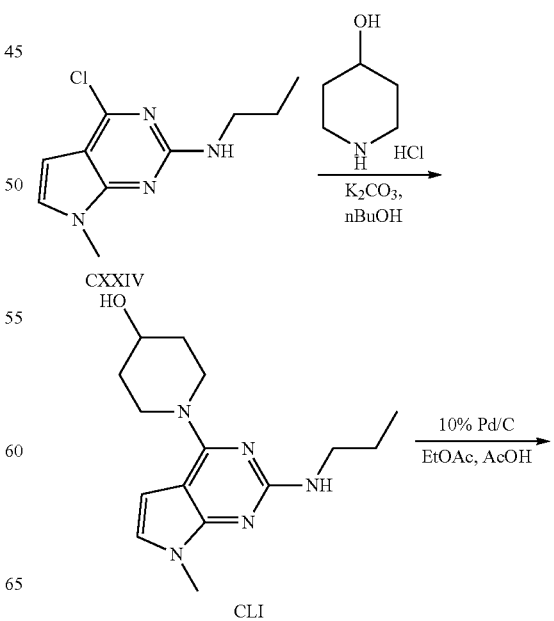

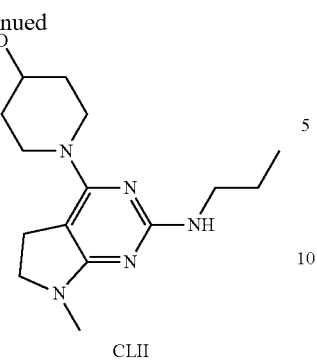

CLII

2-(n-Propyl)amino-4-(4-hydroxypiperidin-1-yl)-7-methyl-pyrrolo[2,3-d]pyrimidine (CLI)

2-(n-Propyl)amino-4-chloro-7-methyl-pyrrolo[2,3-d]pyrimidine (CXXIV) (1.6 g, 7.1 mmol) was added to n-butanol (10 mL) followed by potassium carbonate (4.9 g, 35.5 mmol) and piperidin-4-ol hydrochloride (632 mg, 10.7 mmol). The mixture was stirred in an autoclave equipped with a stirrer at 130° C. for 16 h. After cooling to room temperature, water was added (20 mL), and the mixture was extracted with EtOAc (3×50 mL). The combined organic layers were washed with water and then with a brine solution, and dried over anhydrous $Na_2SO_4$. The solvents were removed in vacuo and the residue was purified by flash column chromatography (pet ether/EtOAc=3/1) to yield 2-(n-propyl)amino-4-(4-hydroxypiperidin-1-yl)-7-methyl-pyrrolo[2,3-d]pyrimidine (1.2 g, 75%) as a yellow solid. LCMS (ESI) m/z=290 $(M+H)^+$.

2-(n-Propyl)amino-4-(4-hydroxypiperidin-1-yl)-7-methyl-pyrrolidino[2,3-d]pyrimidine (CLII)

To the solution of 2-(n-propyl)amino-4-(4-hydroxypiperidin-1-yl)-7-methyl-pyrrolo[2,3-d]pyrimidine (CLI, 1.0 g, 4 mmol) in EtOAc (50 mL) were added 10% Pd/C (1.0 g) and AcOH (2.43 g, 40 mmol). The mixture was attached to a hydrogenation apparatus. The system was evacuated and refilled with hydrogen gas. The mixture was stirred at ambient temperature for 48 h. The mixture was filtered through 10 g of silica-gel on a glass-filter. The filtrate was concentrated and the residue was purified by flash column chromatography (DCM/MeOH=50/1 to 10/1) to yield 2-(n-propyl)amino-4-(4-hydroxypiperidin-1-yl)-7-methyl-pyrrolidino[2,3-d]pyrimidine (CLII, 500 mg, 50% yield) as a yellow solid.

2-(n-Propyl)amino-4-(4-hydroxypiperidin-1-yl)-7-methyl-pyrrolidino[2,3-d]pyrimidine hydrochloride (CLIII)

2-(n-Propyl)amino-4-(4-hydroxypiperidin-1-yl)-7-methyl-pyrrolidino[2,3-d]pyrimidine (CLII, 500 mg, 2 mmol) was dissolved in $H_2O$ (10 mL) and 0.5 M HCl solution in $H_2O$ (4 mL) and the solution was lyophilized to yield 2-(n-propyl)amino-4-(4-hydroxypiperidin-1-yl)-7-methyl-pyrrolidino[2,3-d]pyrimidine hydrochloride (525 mg) as a yellow solid. LCMS (ESI) m/z=292 $(M+H)^+$. $^1$H NMR (500 MHz, MeOD) δ (ppm) 4.12-4.15 (m, 2H), 3.80-3.82 (m, 1H), 3.40 (t, J=8.0 Hz, 2H), 3.29 (t, J=7.0 Hz, 2H), 3.08-3.14 (m, 2H), 3.02 (t, J=8.0 Hz, 2H), 2.84 (s, 3H), 1.86-1.90 (m, 2H), 1.58-1.62 (m, 2H), 1.46-1.51 (m, 2H), 0.97 (t, J=4.0 Hz, 3H).

Example 79

8-(7-methyl-2-(propylamino)-pyrrolidino[2,3-d]pyrimidin-4-yl)-8-azabicyclo[3.2.1]octan-3-ol (CLV)

Example 80

8-(7-methyl-2-(propylamino)-pyrrolidino[2,3-d]pyrimidin-4-yl)-8-azabicyclo[3.2.1]octan-3-ol hydrochloride (CLVI)

Scheme 53

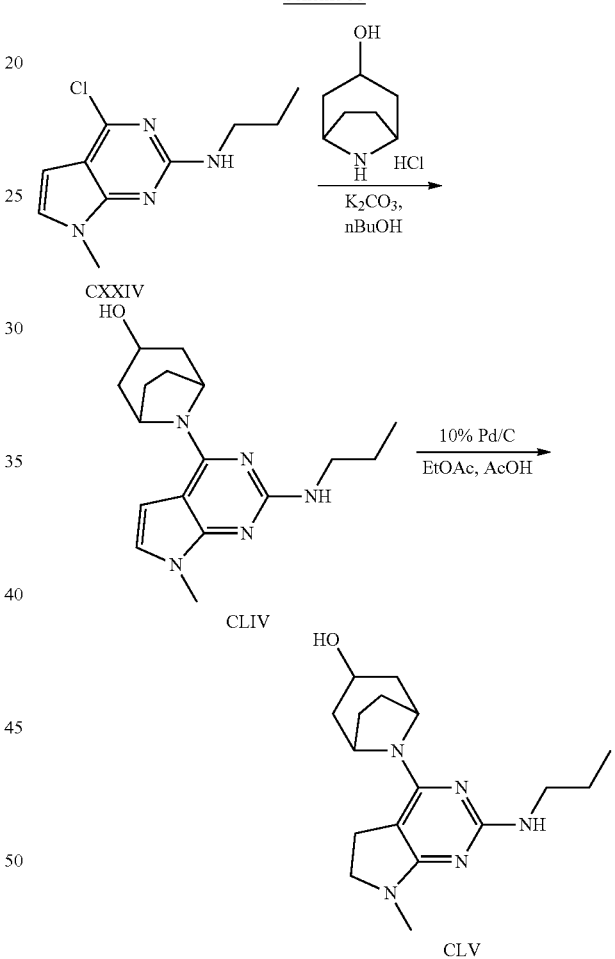

8-(7-Methyl-2-(propylamino)-7H-pyrrolo[2,3-d]pyrimidin-4-yl)-8-azabicyclo[3.2.1]octan-3-ol (CLIV)

To a solution of 2-(n-propyl)amino-4-chloro-7-methyl-pyrrolo[2,3-d]pyrimidine (CXXIV) (1.0 g, 4.5 mmol) in n-butanol (10 mL) were added DIPEA (1.0 g, 7.8 mmol) and 8-aza-bicyclo[3.2.1]octan-3-ol hydrochloride (1.1 g, 6.7 mmol). The mixture was stirred at 125° C. for 16 h. After cooling to room temperature, water (20 mL) was added, and the mixture was extracted with EtOAc (3×50 mL). The combined organic layers were washed with water and then with a brine solution, and dried over anhydrous Na$_2$SO$_4$. The solvents were removed in vacuo and the resultant residue was purified by flash column chromatography (pet ether/EtOAc=6/1) to yield 8-(7-methyl-2-(propylamino)-7H-pyrrolo[2,3-d]pyrimidin-4-yl)-8-azabicyclo[3.2.1]octan-3-ol (CLIV) (800 mg, 57% yield) as a yellow solid. LCMS (ESI) m/z=316 (M+H)$^+$.

8-(7-Methyl-2-(propylamino)-pyrrolidino[2,3-d]pyrimidin-4-yl)-8-azabicyclo[3.2.1]octan-3-ol (CLV)

To a solution of 2-(n-propyl)amino-4-(4-hydroxy-1-azabicyclo[3.2.1]octan-1-yl)-7-methyl-pyrrolo[2,3-d]pyrimidine (CLIV, 1.00 g, 3.2 mmol) in EtOAc (10 mL) were added 10% Pd/C (1.0 g) and AcOH (3 mL). The mixture was attached to a hydrogenation apparatus. The system was evacuated and refilled with hydrogen. The mixture was stirred at ambient temperature for 48 h. The mixture was filtered through 10 g of silica-gel on a glass-filter. The filtrate was concentrated and the residue was purified by flash column chromatography (EtOAc/MeOH=50/1) to yield 8-(7-methyl-2-(propylamino)-pyrrolidino[2,3-d]pyrimidin-4-yl)-8-azabicyclo[3.2.1]octan-3-01 (CLV) (500 mg, 49% yield) as a yellow solid.

8-(7-Methyl-2-(propylamino)-pyrrolidino[2,3-c]pyrimidin-4-yl)-8-azabicyclo[3.2.1]octan-3-ol hydrochloride (CLVI)

8-(7-Methyl-2-(propylamino)-pyrrolidino[2,3-d]pyrimidin-4-yl)-8-azabicyclo[3.2.1]octan-3-ol (CLV, 200 mg, 0.63 mmol) was dissolved in H$_2$O (10 mL) and 0.5 M aqueous HCl solution (1.3 mL), and the solution was lyophilized to yield 8-(7-methyl-2-(propylamino)-pyrrolidino[2,3-d]pyrimidin-4-yl)-8-azabicyclo[3.2.1]octan-3-ol hydrochloride (CLVI) (224 mg) as a yellow solid. LCMS (ESI) m/z=318 (M+H)$^+$.
$^1$H NMR (500 MHz, DMSO) δ (ppm) 4.55 (br, 2H), 3.90 (s, 1H), 3.60 (t, J=8.0 Hz, 2H), 3.27 (t, J=6.5 Hz, 2H), 3.00 (t, J=9.0 Hz, 2H), 2.92 (s, 3H), 2.27 (d, J=7.0 Hz, 2H), 1.90-1.95 (m, 4H), 1.69 (s, 1H), 1.66 (s, 1H), 1.49-1.54 (m, 2H), 0.92 (t, J=7.0 Hz, 3H).

Example 81

N-(2-(Propen-2-yl)amino-7-methyl-pyrrolo[2,3d]pyrimidin-4-yl)-N,O-dimethyl-hydroxylamine (CLVIII)

Example 82

N-(2-(Propen-2-yl)amino-7-methyl-pyrrolo[2,3d]pyrimidin-4-yl)-N,O-dimethyl-hydroxylamine hydrochloride (CLIX)

Scheme 54

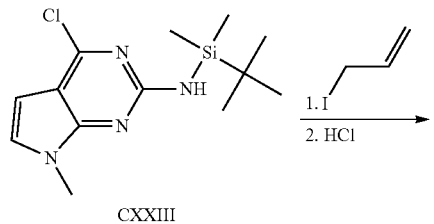

CXXIII

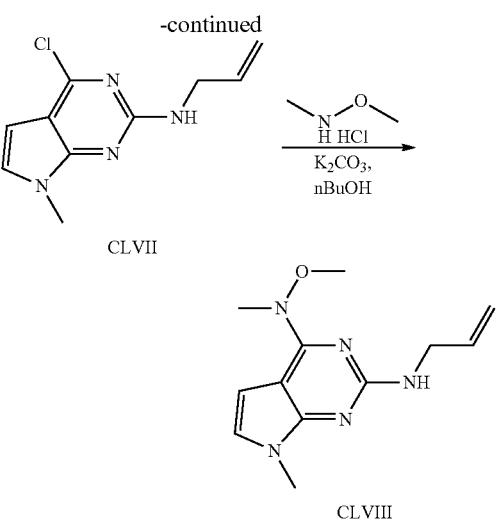

2-(Propen-2-yl)amino-4-chloro-7-methyl-pyrrolo[2,3-d]pyrimidine (CLVII)

Under a nitrogen atmosphere, 2-(t-butyl-dimethyl silanyl)amino-4-chloro-7-methyl-pyrrolo[2,3-d]pyrimidine (CXXIII) (7.5 g, 25 mmol) was dissolved in DMF (100 ml) and 3-iodoprop-1-ene (6.38 g, 38 mmol) was added. The mixture was cooled to 0° C. with vigorous stirring, then NaH (1.5 g of a 60% dispersion in mineral oil, 38 mmol) was added. The mixture was stirred for 30 min, and water (50 mL) was slowly added to quench the reaction. The aqueous mixture was extracted with EtOAc (300 mL) and the organic layer was washed with water (100 mL) and then with a brine solution (100 mL), and dried over anhydrous Na$_2$SO$_4$. After evaporation, 8.6 g of a yellow oily residue was isolated. This material was dissolved in Et$_2$O (100 mL), and concentrated hydrochloric acid (20 mL) was added at 0° C. with stirring. The mixture was then stirred for an additional 10 min. The mixture was extracted with EtOAc (200 mL) and 1N NaOH (200 mL). The organic layer was separated and washed with H$_2$O (150 mL) and with a brine solution (150 mL) and dried over anhydrous Na$_2$SO$_4$. The solvents were removed in vacuo and the resultant residue was purified by flash column chromatography (pet ether/EtOAc=10/1 to 5/1) to yield 2-(propen-2-yl)amino-4-chloro-7-methyl-pyrrolo[2,3-d]pyrimidine (6 g, 100% yield) as a yellow solid. LCMS: (ESI) m/z=223 (M+H)$^+$.

N-(2-(Propen-2-yl)amino-7-methyl-pyrrolo[2,3d]pyrimidin-4-yl)-N,O-dimethyl-hydroxylamine (CLVIII)

To 2-(propen-2-yl)amino-4-chloro-7-methyl-pyrrolo[2,3-d]pyrimidine (CLVII, 500 mg, 2.38 mmol) were added n-butanol (5 mL), potassium carbonate (1.64 g, 5.0 eq.) and N,O-dimethylhydroxylamine hydrochloride (923 mg, 4.0 eq.). The mixture was stirred in an autoclave equipped with a stirrer at 100° C. for 8 h. After cooling to room temperature, water (20 mL) was added, and the mixture was extracted with EtOAc (3×20 mL). The combined organic layers were washed with water and with a brine solution and dried over anhydrous Na$_2$SO$_4$. The solvents were then removed in vacuo and the resultant residue was purified by flash column chromatography (pet ether/EtOAc=3/1) to yield N-(2-(propen-2- yl)amino-7-methyl-pyrrolo[2,3d]pyrimidin-4-yl)-N,O-dimethyl-hydroxylamine (CLVIII, 310 mg, 55% yield).

N-(2-(Propen-2-yl)amino-7-methyl-pyrrolo[2,3d]pyrimidin-4-yl)-N,O-dimethyl-hydroxylamine hydrochloride (CLIX)

N-(2-(Propen-2-yl)amino-7-methyl-pyrrolo[2,3d]pyrimidin-4-yl)-N,O-dimethyl-hydroxylamine (310 mg, 1.32 mmol) was dissolved in H$_2$O (5 mL) and 0.5 M aqueous HCl solution (2.7 mL), and the solution was lyophilized to yield N-(2-(propen-2-yl)amino-7-methyl-pyrrolo[2,3d]pyrimidin-4-yl)-N,O-dimethyl-hydroxylamine hydrochloride (CLIX, 325 mg) as a white solid. LCMS (ESI) m/z=248 (M+H)$^+$. $^1$H NMR (500 MHz, DMSO) δ (ppm) 12.60-14.80 (br, 1H), 7.70-8.70 (br, 1H), 7.06 (s, 1H), 6.55 (s, 1H), 5.90-5.94 (m, 1H), 5.31 (d, J=17.0 Hz, 1H), 5.17 (d, J=10.5 Hz, 1H), 4.06 (s, 2H), 3.84 (s, 3H), 3.70 (s, 3H), 3.53 (s, 3H).

Example 83

N-(2-(Propen-2-yl)amino-7-methyl-pyrrolo[2,3d]pyrimidin-4-yl)-O-methyl-hydroxylamine (CLX)

Example 84

N-(2-(Propen-2-yl)amino-7-methyl-pyrrolo[2,3d]pyrimidin-4-yl)-O-methyl-hydroxylamine hydrochloride (CLXI)

Scheme 55

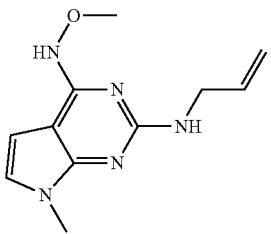

CLX

N-(2-(Propen-2-yl)amino-7-methyl-pyrrolo[2,3d]pyrimidin-4-yl)-O-methyl-hydroxylamine (CLX)

2-(2-Propen-2-yl)amino-4-chloro-7-methyl-pyrrolo[2,3-d]pyrimidine (CLVII) (700 mg, 3.15 mmol) was dissolved in n-butanol, and potassium carbonate (2.2 g, 5.0 eq.) and O-methylhydroxylamine hydrochloride (768 mg, 4.0 eq.) were added. The mixture was stirred in an autoclave equipped with a stirrer at 100° C. for 12 h. After cooling to room temperature, water (20 mL) was added, and the mixture was extracted with EtOAc (3×25 mL). The combined organic layers were washed with water and a brine solution, and dried over anhydrous Na$_2$SO$_4$. The solvents were removed in vacuo and the resultant residue was purified by flash column chromatography (pet ether/EtOAc=5/1) to yield N-(2-(propen-2-yl)amino-7-methyl-pyrrolo[2,3d]pyrimidin-4-yl)-O-methyl-hydroxylamine (370 mg, 46% yield).

N-(2-(Propen-2-yl)amino-7-methyl-pyrrolo[2,3d]pyrimidin-4-yl)-O-methyl-hydroxylamine hydrochloride (CLXI)

N-(2-(propen-2-yl)amino-7-methyl-pyrrolo[2,3d]pyrimidin-4-yl)-O-methyl-hydroxylamine (370 mg, 1.59 mmol) was dissolved in H$_2$O (5 mL) and 0.5 M aqueous HCl solution (2 mL), and the solution was lyophilized to yield N-(2-(propen-2-yl)amino-7-methyl-pyrrolo[2,3d]pyrimidin-4-yl)-O-methyl-hydroxylamine hydrochloride (383 mg) as a white solid. LCMS (ESI) m/z=234 (M+H)$^+$. $^1$H NMR (500 MHz, DMSO) δ (ppm) 12.40-13.00 (br, 1H), 7.70-8.10 (br, 1H), 7.04 (d, J=3.5 Hz, 1H), 6.49 (d, J=3.0 Hz, 1H), 5.94-5.99 (m, 1H), 5.32 (d, J=17.0 Hz, 1H), 5.17 (d, J=10.5 Hz, 1H), 4.04 (s, 2H), 3.85 (s, 3H), 3.61 (s, 3H).

Example 85

N-(2-n-Propylamino-7-methyl-pyrrolo[2,3d]pyrimidin-4-yl)-N,O-dimethyl-hydroxylamine (CLXII)

Example 86

N-(2-n-Propylamino-7-methyl-pyrrolo[2,3d]pyrimidin-4-yl)-N,O-dimethyl-hydroxylamine hydrochloride (CLXIII)

Scheme 56

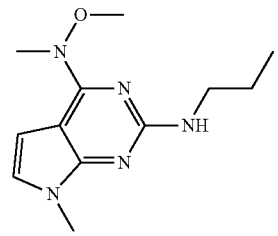

CLXII

N-(2-n-Propylamino-7-methyl-pyrrolo[2,3d]pyrimidin-4-yl)-N,O-dimethyl-hydroxylamine (CLXII)

The desired compound was prepared from 4-chloro-2-n-propylamino-7-methyl-pyrrolo[2,3d]pyrimidine and N,O-dimethyl-hydroxylamine as described in Example 73. LCMS: (ESI) m/z=250 (M+H)$^+$. $^1$H NMR (500 MHz, CDCl$_3$) δ (ppm) 7.70 (s, 1H), 7.02 (s, 1H), 6.52 (s, 1H), 3.82 (s, 3H), 3.67 (s, 3H), 3.53 (s, 3H), 3.34 (t, J=8.5 Hz, 2H), 1.54-1.59 (m, 2H), 0.93 (t, J=8.5 Hz, 3H).

Example 87

N-(2-n-Propylamino-7-methyl-pyrrolo[2,3d]pyrimidin-4-yl)-O-methyl-hydroxylamine (CLXIV)

Example 88

N-(2-n-Propylamino-7-methyl-pyrrolo[2,3d]pyrimidin-4-yl)-O-methyl-hydroxylamine hydrochloride (CLXV)

Scheme 57

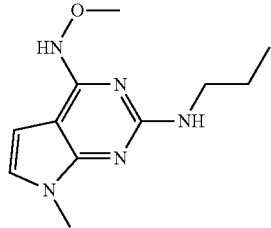

CLXIV

N-(2-n-Propylamino-7-methyl-pyrrolo[2,3d]pyrimidin-4-yl)-O-methyl-hydroxylamine (CLXIV)

The desired compound was prepared from 4-chloro-2-n-propylamino-7-methyl-pyrrolo[2,3d]pyrimidine and O-methyl-hydroxylamine as described in Example 73. LCMS (ESI) m/z=236 (M+H)$^+$. $^1$H NMR (500 MHz, DMSO) δ (ppm) 12.50 (s, 1H), 8.10 (s, 1H), 7.05 (s, 1H), 6.01 (s, 1H), 3.85 (s, 3H), 3.60 (s, 3H), 3.36 (s, 1H), 3.34 (t, J=6.5 Hz, 2H), 1.58-1.62 (m, 2H), 0.96 (t, J=7.5 Hz, 3H).

Example 89

N-(2-n-Propylamino-7-methyl-pyrrolo[2,3d]pyrimidin-4-yl)-hydrazine (CLXVI)

Example 90

N-(2-n-Propylamino-7-methyl-pyrrolo[2,3d]pyrimidin-4-yl)-hydrazine hydrochloride (CLXVII)

Scheme 58

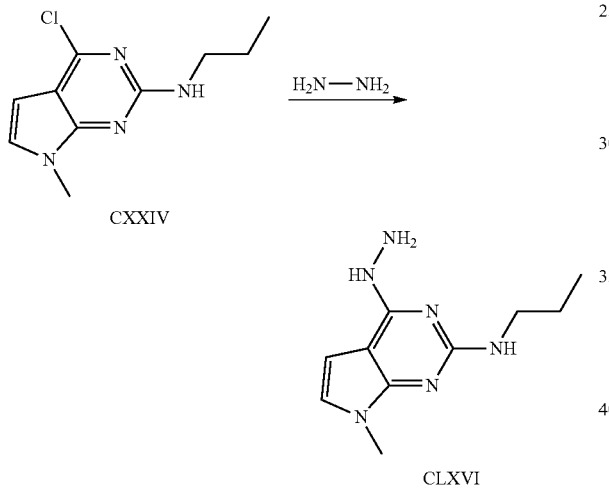

CLXVI

N-(2-n-Propylamino-7-methyl-pyrrolo[2,3d]pyrimidin-4-yl)-hydrazine (CLXVI)

To a solution of 4-chloro-2-n-propylamino-7-methyl-pyrrolo[2,3d]pyrimidine (CXXIV, 1.0 g, 4.5 mmol) in ethanol (70 mL) was added hydrazine (14 mL) and the mixture was heated at refluxed for 3 h. After cooling to room temperature, the solvents were removed in vacuo. The residue was purified by flash column chromatography (CH$_2$Cl$_2$/MeOH=30/1) to yield N-(2-n-propylamino-7-methyl-pyrrolo[2,3d]pyrimidin-4-yl)-hydrazine (CLXVI, 1.0 g, 80% yield).

N-(2-n-Propylamino-7-methyl-pyrrolo[2,3d]pyrimidin-4-yl)-hydrazine hydrochloride (CLXVII)

N-(2-n-Propylamino-7-methyl-pyrrolo[2,3d]pyrimidin-4-yl)-hydrazine (460 mg, 2.0 mmol) was dissolved in H$_2$O (10 mL) and 0.5 M aqueous HCl solution (4 mL), and the solution was lyophilized to yield N-(2-n-propylamino-7-methyl-pyrrolo[2,3d]pyrimidin-4-yl)-hydrazine hydrochloride (440 mg) as a brown solid. LCMS (ESI) m/z=221 (M+H)$^+$. $^1$H NMR (500 MHz, DMSO) δ (ppm) 10.63 (s, 1H), 7.56 (s, 2H), 6.97 (d, J=3.0 Hz, 1H), 6.54 (d, J=3.5 Hz, 1H), 3.58 (s, 3H), 3.33 (s, 2H), 1.56-1.61 (m, 2H), 0.95 (t, J=8.0 Hz, 3H).

Example 91

N-Methyl-N-(2-n-propylamino-7-methyl-pyrrolo[2,3d]pyrimidin-4-yl)-hydrazine (CLXVIII)

Example 92

N-Methyl-N-(2-n-propylamino-7-methyl-pyrrolo[2,3d]pyrimidin-4-yl)-hydrazine hydrochloride (CLXIX)

Scheme 59

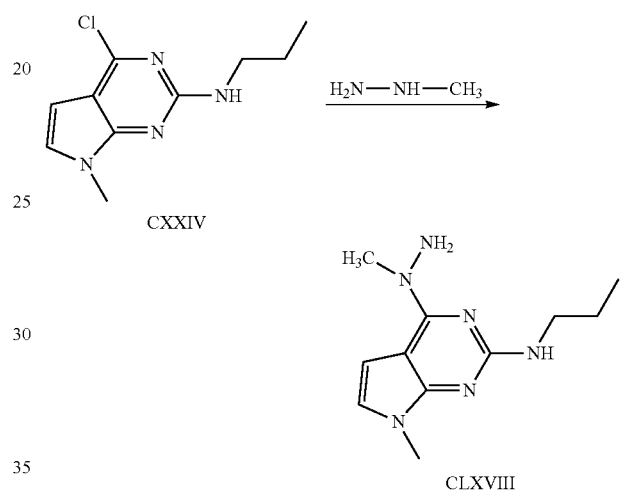

N-Methyl-N-(2-n-propylamino-7-methyl-pyrrolo[2,3d]pyrimidin-4-yl)-hydrazine (CLXVIII)

To a solution of 4-chloro-2-n-propylamino-7-methyl-pyrrolo[2,3d]pyrimidine (CXXIV, 800 mg, 3.42 mmol) in n-butanol (5 mL) was added potassium carbonate (2.36 g, 5.0 eq.) and methylhydrazine (630 mg, 4.0 eq.). The mixture was stirred in an autoclave equipped with a stirrer at 100° C. for 15 h. After cooling to room temperature, water was added (20 mL), and the mixture was extracted with EtOAc (3×25 mL). The combined organic layers were washed with water and with a brine solution, and dried over anhydrous Na$_2$SO$_4$. The solvents were removed in vacuo and the resultant residue was purified by flash column chromatography (pet ether/EtOAc=3/1 to DCM/MeOH=10/1) to yield N-methyl-N-(2-n-propylamino-7-methyl-pyrrolo[2,3d]pyrimidin-4-yl)-hydrazine (CLXVIII, 220 mg, 36% yield).

N-Methyl-N-(2-n-propylamino-7-methyl-pyrrolo[2,3d]pyrimidin-4-yl)-hydrazine hydrochloride (CLXIX)

N-methyl-N-(2-n-propylamino-7-methyl-pyrrolo[2,3d]pyrimidin-4-yl)-hydrazine (220 mg, 0.94 mmol) was dissolved in H$_2$O (10 mL) and 0.5 M aqueous HCl solution (2 mL), and the solution was lyophilized to yield N-methyl-N-(2-n-propylamino-7-methyl-pyrrolo[2,3d]pyrimidin-4-yl)-hydrazine hydrochloride (CLXIX, 238 mg) as a brown solid. LCMS (ESI) m/z=235 (M+H)$^+$. $^1$H NMR (500 MHz, DMSO)

δ (ppm) 7.50-8.10 (br, 4H), 7.05 (s, 1H), 6.67 (s, 1H), 3.60 (s, 3H), 3.58 (s, 3H), 3.33 (s, 2H), 1.55-1.62 (m, 2H), 0.95 (t, J=7.5 Hz, 3H).

Example 93

N,N-Dimethyl-N'-(2-n-propylamino-7-methyl-pyrrolo[2,3d]pyrimidin-4-yl)-hydrazine (CLXX)

Example 94

N,N-Dimethyl-N'-(2-n-propylamino-7-methyl-pyrrolo[2,3d]pyrimidin-4-yl)-hydrazine hydrochloride (CLXXI)

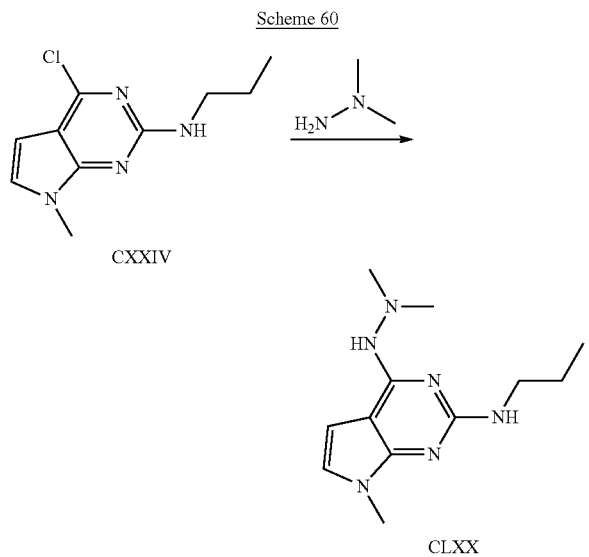

N,N-Dimethyl-N'-(2-n-propylamino-7-methyl-pyrrolo[2,3d]pyrimidin-4-yl)-hydrazine (CLXX)

To a solution of 4-chloro-2-n-propylamino-7-methyl-pyrrolo[2,3d]-pyrimidine (1.1 g, 5 mmol) and 1,1-dimethylhydrazine (450 mg, 7.5 mmol) in dioxane (30 mL) was added xphos (622 mg, 1 mmol), Pd$_2$(dba)$_3$ (458 mg, 0.5 mmol) and Cs$_2$CO$_3$ (2.45 g, 7.5 mmo). The solution was degassed by bubbling argon through it for 10 min using a syringe needle. The mixture was then stirred at 80° C. for 2 h. After cooling to room temperature, water was added (20 mL) and the mixture was extracted with EtOAc (3×40 mL). The combined organic layers were washed with water and with a brine solution, and dried over anhydrous Na$_2$SO$_4$. The solvents were removed in vacuo and the resultant residue was purified by flash column chromatography (DCM/MeOH=30/1 to 5/1) to yield N,N-dimethyl-N'-(2-n-propylamino-7-methyl-pyrrolo[2,3d]pyrimidin-4-yl)-hydrazine (CLXX, 100 mg, 8% yield, ~85% purity).

N,N-Dimethyl-N'-(2-n-propylamino-7-methyl-pyrrolo[2,3d]pyrimidin-4-yl)-hydrazine hydrochloride (CLXXI)

N,N-dimethyl-N'-(2-n-propylamino-7-methyl-pyrrolo[2,3d]pyrimidin-4-yl)-hydrazine (100 mg, 0.4 mmol) was dissolved in H$_2$O (5 mL) and 0.5 M aqueous HCl solution (1 mL) and the solution was lyophilized to yield N, N-dimethyl-N'-(2-n-propylamino-7-methyl-pyrrolo[2,3-d]pyrimidin-4-yl)-hydrazine hydrochloride (110 mg) as a yellow oil. LCMS (ESI) m/z=249 (M+H)$^+$. $^1$H NMR (500 MHz, MeOD) δ (ppm) 6.92 (d, J=4.0 Hz, 1H), 6.50 (d, J=3.0 Hz, 1H), 3.66 (s, 3H), 3.45 (t, J=7.5 Hz, 2H), 2.79 (s, 6H), 1.67-1.72 (m, 2H), 1.01-1.04 (m, 3H).

Example 95

Effect of Compound (XXXVI) on Opioid-Induced Respiratory Depression in the Rat

All animal experiments were carried out according to the U.S. law on animal care and use approved by Galleon Pharmaceuticals Institutional Animal Care and Use Committee (IACUC). Rats with pre-cannulated jugular vein (for administrating drugs) were acclimated to plethysmography chambers for a minimum of 60 minutes, or until animals were no longer restless. Each animal was dosed with morphine sulfate (10 mg/kg), dissolved in sterile water at a concentration of 10 mg/mL (supplied by Baxter Healthcare Corporation), via injection into the jugular vein catheter over a period of 5-10 seconds.

Compound (XXXVI) was dissolved in 20% hydroxypropyl β-cyclodextran (20% bcd on graph) at a concentration of 0.45 mg/mL at pH 5. After a period of 5 min, compound (XXXVI), labeled as cmpd (A), was administered via infusion into the jugular vein at a dose of 0.10 mg/kg/min for 20 min and then at a dose of 0.30 mg/kg/min for 20 min (e.g., 20 µL/min/0.3 kg rat to yield 0.03 mpk/min).

After 20 minutes of infusion at this dose, the infusion pumps were turned off, and all animals were given a 20 minute recovery period, followed by a post-study analysis of rat health and behavior. The minute ventilation data indicate that compound (XXXVI) significantly reversed opioid-induced respiratory depression in rat compared to vehicle. Results are illustrated in FIG. 1.

Example 96

Effects of Morphine and Compound (XXXVI) on Blood Gases in the Rat

Rats with pre-cannulated jugular vein and femoral arterial catheters (for administrating drugs and obtaining blood samples respectively) were obtained from Harlan laboratories and kept at the animal facility at Galleon Pharmaceuticals until the experimental procedures. All animals experiments were carried out according to the US law on animal care and use approved by Galleon Pharmaceuticals IACUC. Each animal was dosed with morphine sulfate (10 mg/kg), dissolved in saline at a concentration of 10 mg/ml, via injection into the jugular vein over a period of 20 seconds with a 20 second flush of 0.9% NaCl saline. Prior to morphine administration, two 250 µL samples of arterial blood were aspirated from the femoral artery into a pre-heparinized syringe. The samples were analyzed on Radiometer's ABL Flex 800, where pO$_2$, pCO$_2$, pH, saO$_2$ and other parameters were recorded. Aspirated volumes of arterial blood were replaced by room temperature sterile saline (~300 µL) slowly flushed back into the femoral arterial catheter of the rodent to prevent anemia and/or dehydration. Morphine was then administered and 2 minutes later another blood sample was taken.

Figure 2A:
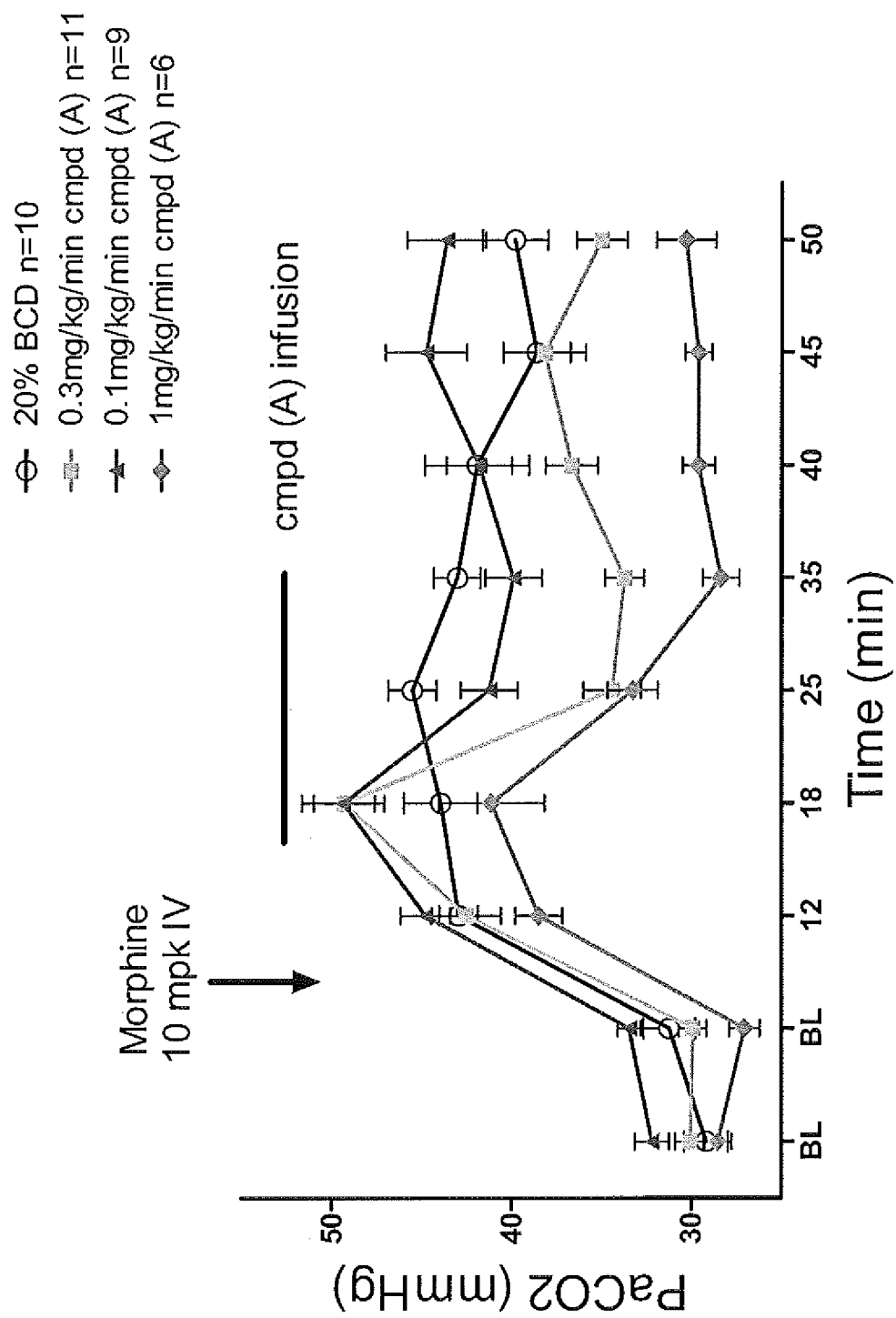
FIGS. 2A-2B, illustrates arterial blood gas analysis results for administration of Compound (XXXVI) [labeled as cmpd (A)] in the opioid-treated rat.
Figure 2B:
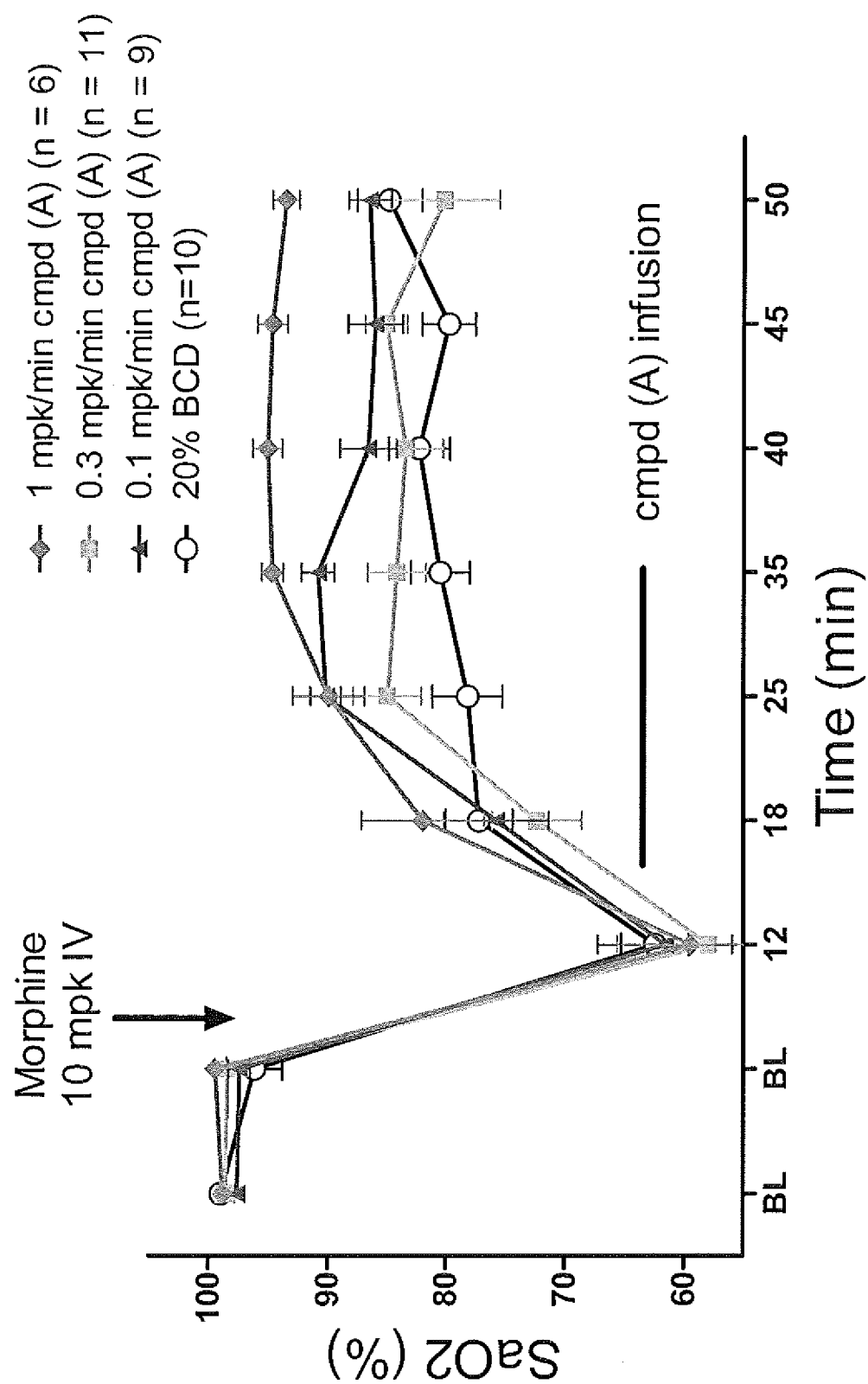

After a period of 5 min from the administration of morphine, compound (XXXVI), labeled as cmpd (A), was administered via infusion into the jugular vein at a dose of 0.1, 0.3 and 1.0 mg/kg/min (dissolved in PBS buffer). The infusion started at t=15 minutes and ended at t=35 minutes. Arterial blood gas analysis occurred at time points t=12, 18, 25, 35, 40, 45, and 50 minutes. The data show that compound (XXXVI) significantly reverses opioid-induced respiratory depression in rat compared to vehicle. Results are illustrated in FIG. 2a and FIG. 2b and the accompanying Table 6.

TABLE 6

| Cmpd | n | Dose (mpk/min) | pH (% reversal) | $PaCO_2$ (% reversal) | $PaO_2$ (% reversal) | $SaO_2$ (% reversal) |
|---|---|---|---|---|---|---|
| XXXVI | 6 | 1 | 60 | 94 | 26 | 62 |
| XXXVI | 11 | 0.3 | 55 | 72 | −16 | 43 |
| XXXVI | 10 | 0.1 | 37 | 47 | 16 | 51 |
| XXXVI | 6 | 0.03 | 20 | 18 | −2.0 | 42 |

Example 97

Figure 3:
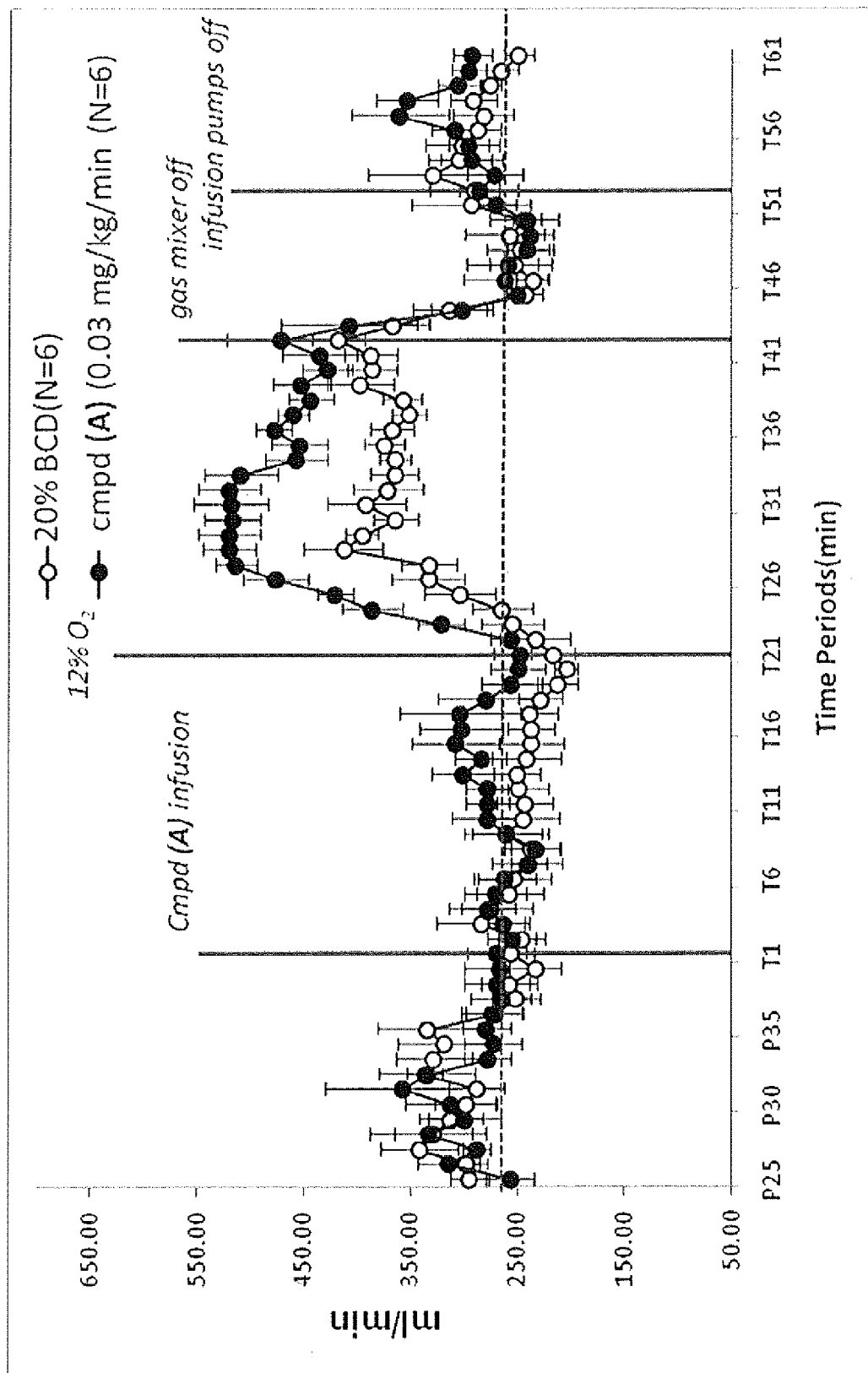
FIG. 3 is a graph illustrating results of plethysmography experiments monitoring minute ventilation in the rat upon administration of Compound (XXXVI) [labeled as cmpd (A)] under conditions of hypoxia.

Hypoxic Ventilatory Response (HVR) and Effect of Compound (XXXVI) on HVR in the Rat Rats with a pre-cannulated jugular vein (for administrating drugs) were acclimated to plethysmography chambers for a minimum of 60 minutes, or until animals were no longer restless. Each animal was dosed with compound (XXXVI), labeled as cmpd (A), at 0.03 mg/kg/min via infusion into the jugular vein catheter for a period of 50 minutes. After a period of 20 minutes, an isocapnic hypoxic mixture (12% $O_2$ balanced $N_2$) was administered into all chambers using a gas mixer (CWE inc. GSM-3 gas mixer) for 20 minutes. After this time, the gas mixer was turned off, resulting in normal room air pumped into the chambers. Ten minutes later, the infusion pumps were turned off, and all animals were given a 20 minute recovery period, followed by a post-study analysis of rat health and behavior. The minute ventilation data show that compound (XXXVI) significantly potentiates the hypoxic ventilatory response in the rat compared to vehicle. Results are illustrated in FIG. 3.

Example 98

Effect of Compound (XXXVI) on Opioid-Induced Respiratory Depression in the Monkey Juvenile macaques (four-year-old *Macaca fascicularis*, 2 to 5 kg, n=13) were used for the study. Animal husbandry was conducted under USDA guidelines and the protocols were approved by the Institutional Animal Care and Use Committee of East Carolina University.

Anesthesia was induced with 5% isoflurane and then maintained with 1.5 to 2% isoflurane (100% $O_2$, 2 L/min). Antebrachial veins were cannulated. Vivometrics Lifeshirts (Ventura, Calif.) were fitted to the animals for monitoring respiratory function by inductance plethysmography. Abdomen and rib cage deflections were calibrated using the Qualitative Diagnostic Calibration (QDC) procedure, and tidal volume was normalized to 15 mL, which represented a typical tidal volume for these animals as previously measured using conventional techniques. Heart rate was monitored continuously by 3-lead ECG.

$ETCO_2$ was measured via a neonatal nasal cannula connected to a microstream $CO_2$ sensor (Cardell monitor, Model 9405). $SpO_2$ and HR were monitored by pulse oximetry using a reflectance probe (Nelcor Max-Fast) positioned on the inner aspect of the upper arm. HR was also determined from the ECG allowing measurement when animal activity compromised the integrity of pulse oximetry signals. BP was measured in anesthetized animals using a cuff positioned on the ankle.

Figure 4:
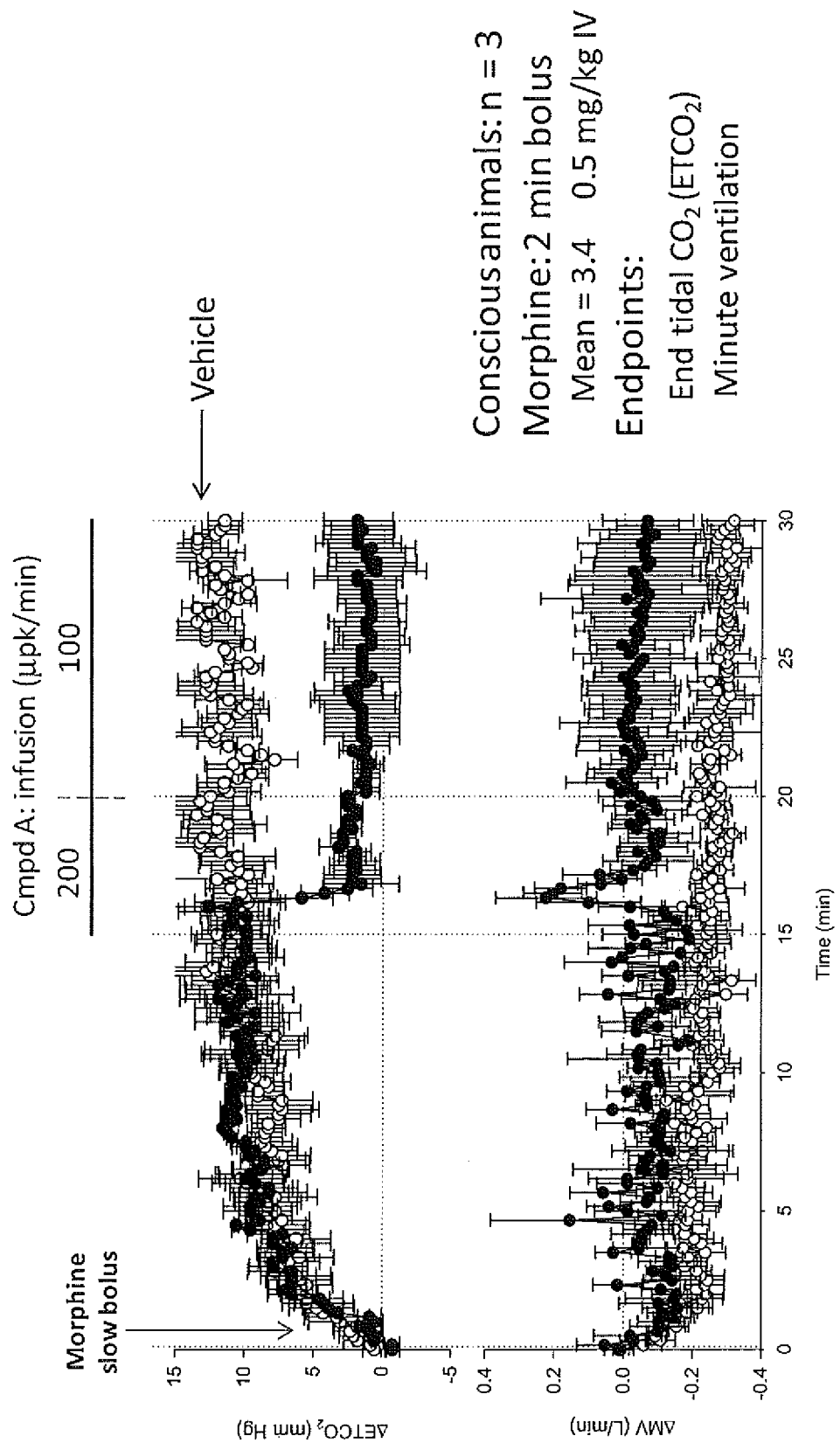
FIG. 4 is a graph illustrating end-tidal $CO_2$ and minute ventilation in the opioid-treated monkey upon administration of Compound (XXXVI) [labeled as cmpd (A)].

Compound (XXXVI) was dissolved in 20% hydroxypropyl β-cyclodextran (HPBCD) and sterile filtered using a 2μ syringe filter. Compound (XXXVI), labeled as cmpd (A), was then delivered at a rate of 0.20 mg/kg/min for 5 minutes, followed by reduction of the infusion rate to 0.10 mg/kg/min for 10 minutes. Minute Ventilation and end-tidal $CO_2$ was monitored. Naloxone HCl (0.05 mg/kg intravenous) was delivered to reverse morphine effects and conclude the experiment. The data showed that cmpd (A) produced a full reversal of end-tidal carbon dioxide increases caused by the opioid, and also increased minute ventilation (FIG. 4).

Example 99

Effect of Compound (XXXVI) and (L) on Dose-Dependent Minute Ventilation (MV) in Naive Rats All surgical procedures were performed under anesthesia induced by 2% isoflurane in compressed medical grade air. With rats in supine position, the right femoral vein was catheterized using polyethylene tubing (PE-50). This catheter was used for fluid and drug administration. Simultaneously, the right femoral artery was also catheterized for monitoring blood pressure. In order to measure the respiratory parameters in spontaneously breathing rats, trachea was intubated using 13 gauge tracheal tube (2.5 mm ID, Instech Solomon, Pa.).

Figure 5:
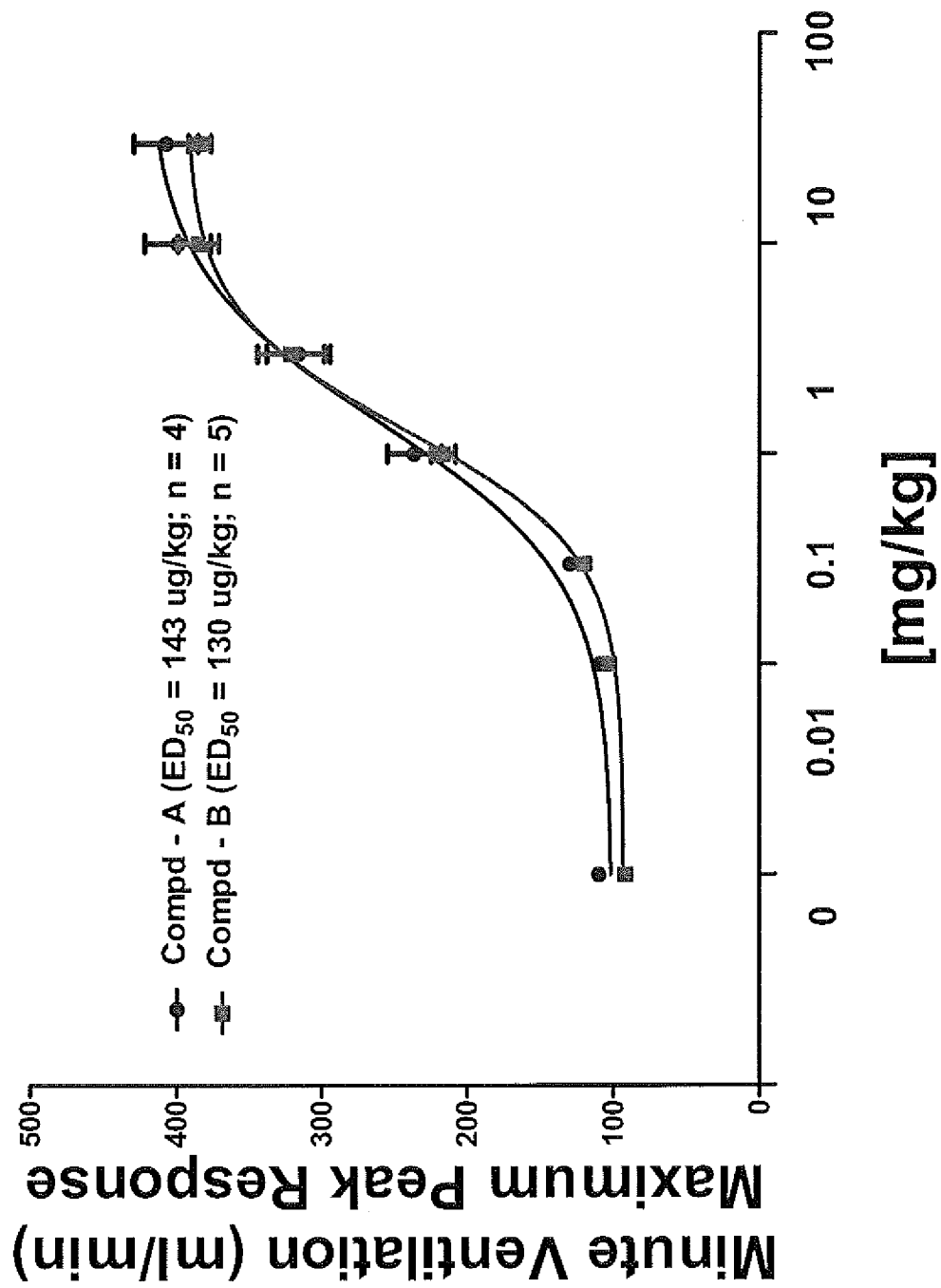
FIG. 5 is a graph illustrating the dose-dependent effect of Compound (XXXVI) [labeled as cmpd (A)] and Compound (L) [labeled as cmpd (B)] on minute ventilation, in terms of maximum peak response, in the rat.

After establishing a stable base-line at 1.5% isoflurane, cumulative dose-dependent (0.01, 0.03, 0.1, 0.3, 1, 3, 10 mg/kg) ventilatory responses to compounds (XXXVI) and (L), labeled as cmpd (A) and cmpd (B) respectively, were generated from spontaneously breathing rats. Maximum peak minute ventilatory (MV) values at each dose from corresponding drug were calculated and used for generating $ED_{50}$ values. The results are shown in FIG. 5. Both compounds (XXXVI) and (L) increased minute ventilation in a dose-dependent manner with calculated $ED_{50}$ values of 0.14 and 0.13 mg/kg respectively.

Example 100

Figure 6:
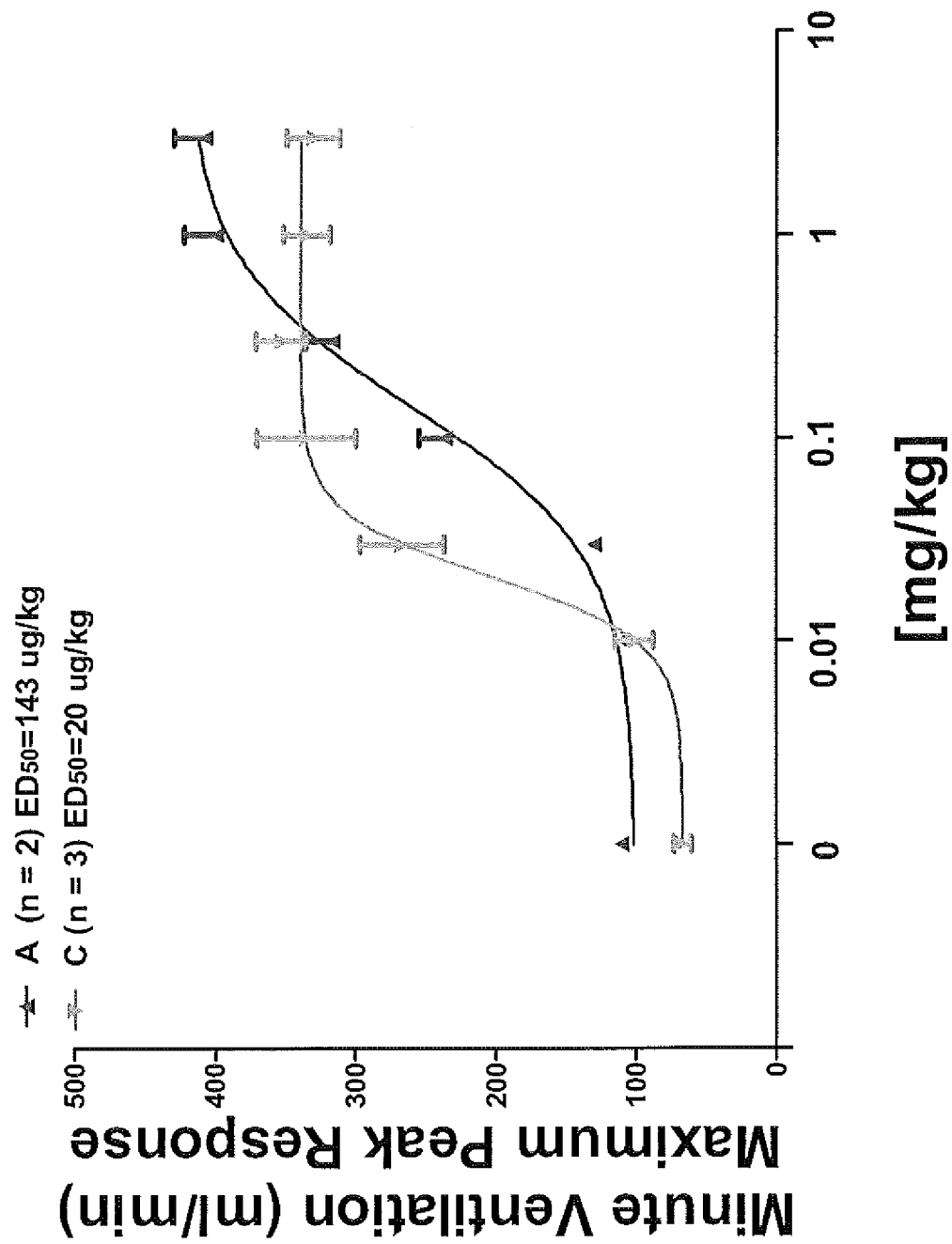
FIG. 6 is a graph illustrating the dose-dependent effect of Compound (XXXVI) [labeled as cmpd (A)] and Compound (CXXI) [labeled as cmpd (C)] on minute ventilation, in terms of maximum peak response, in the rat.
Figure 7A:
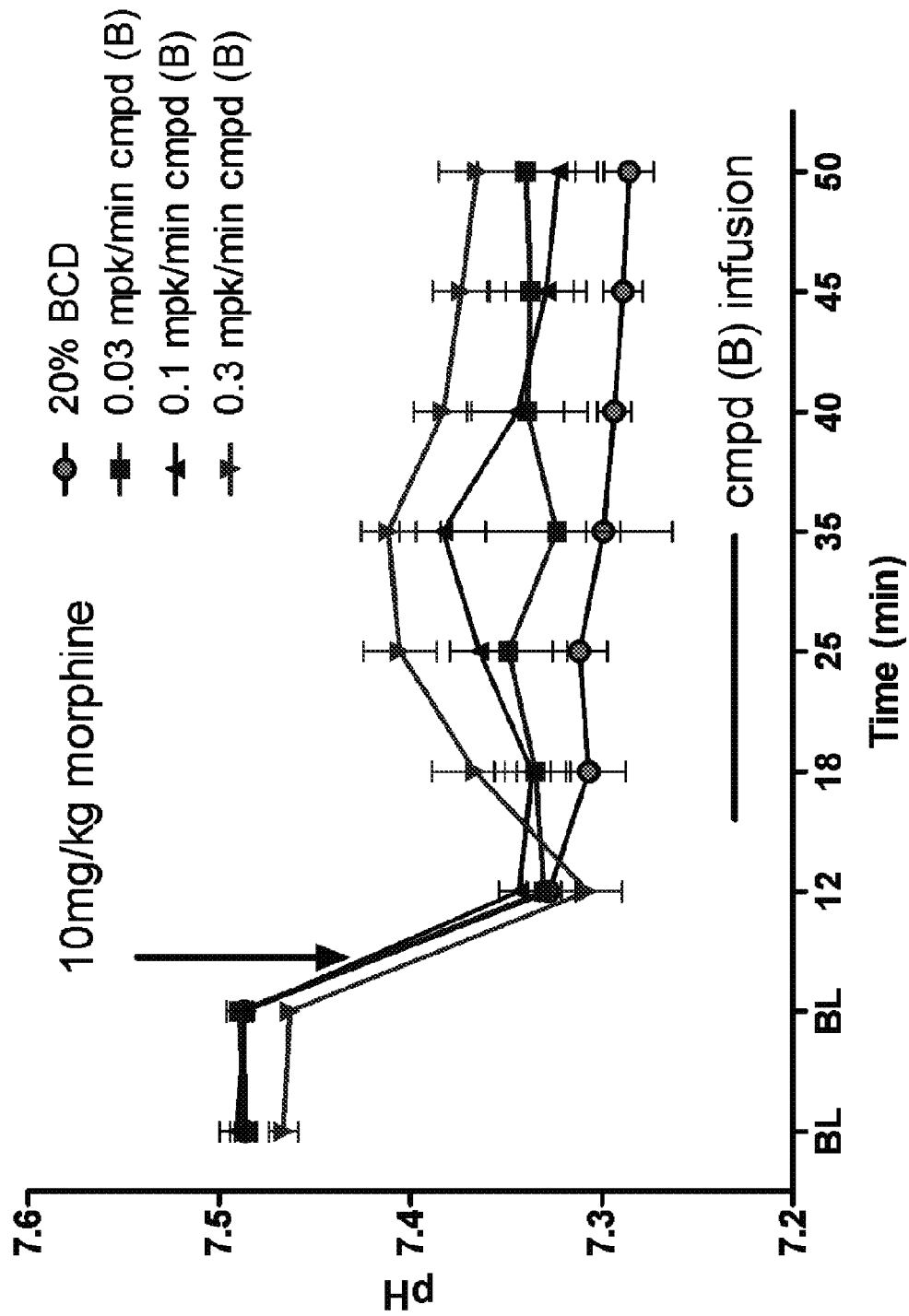
Figure 7C:
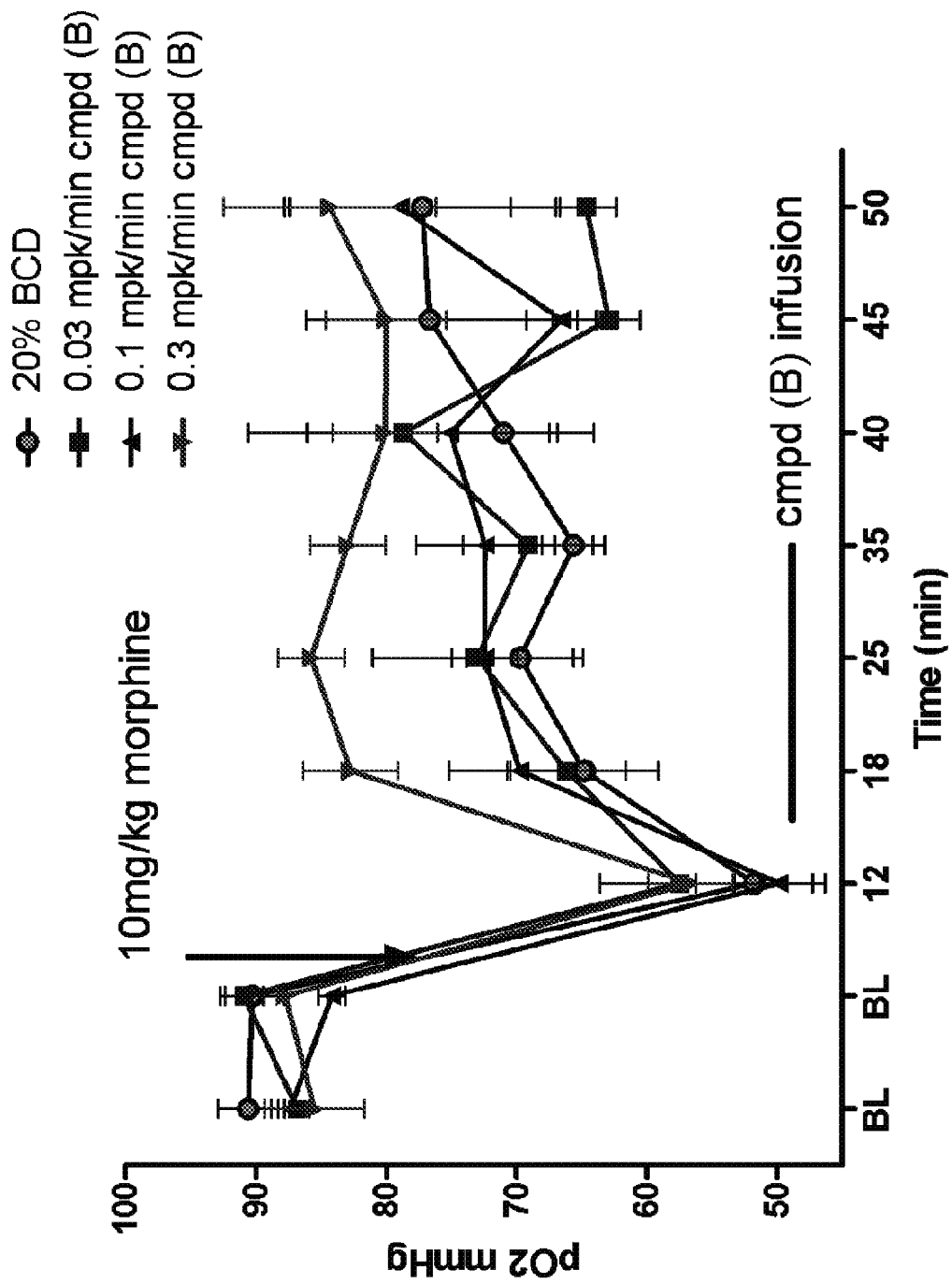
Figure 7D:
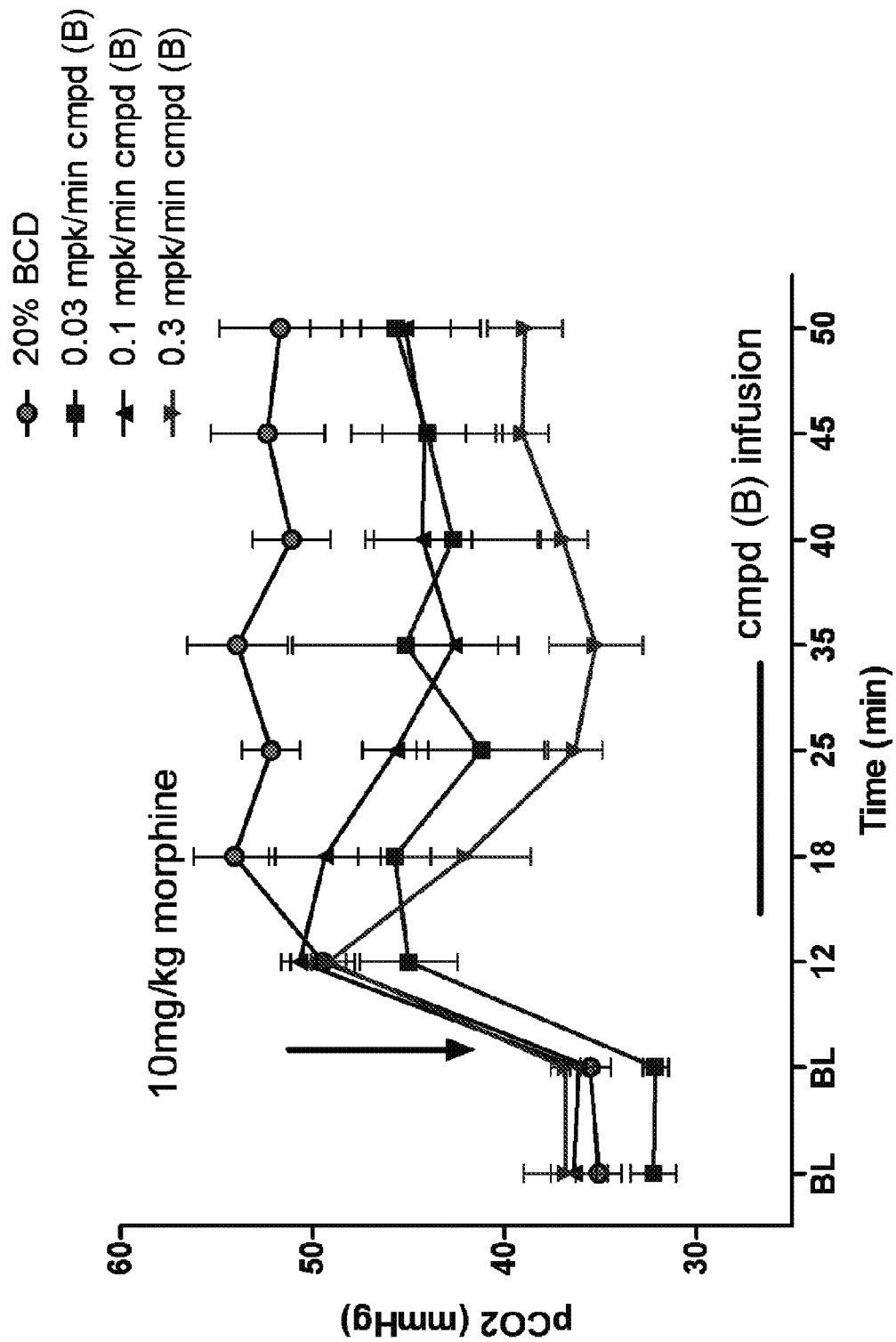
Figure 8A:
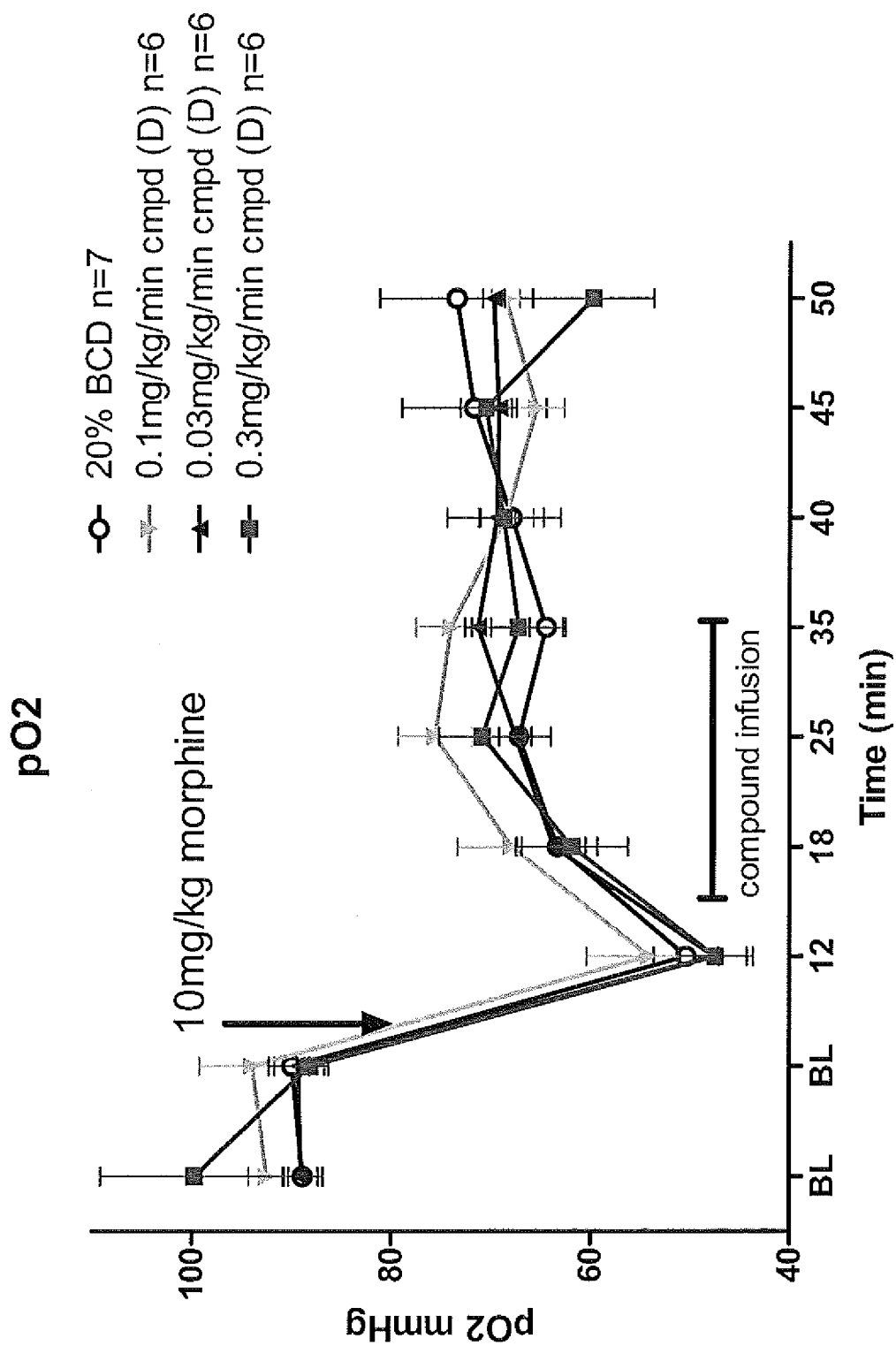
Figure 8B:
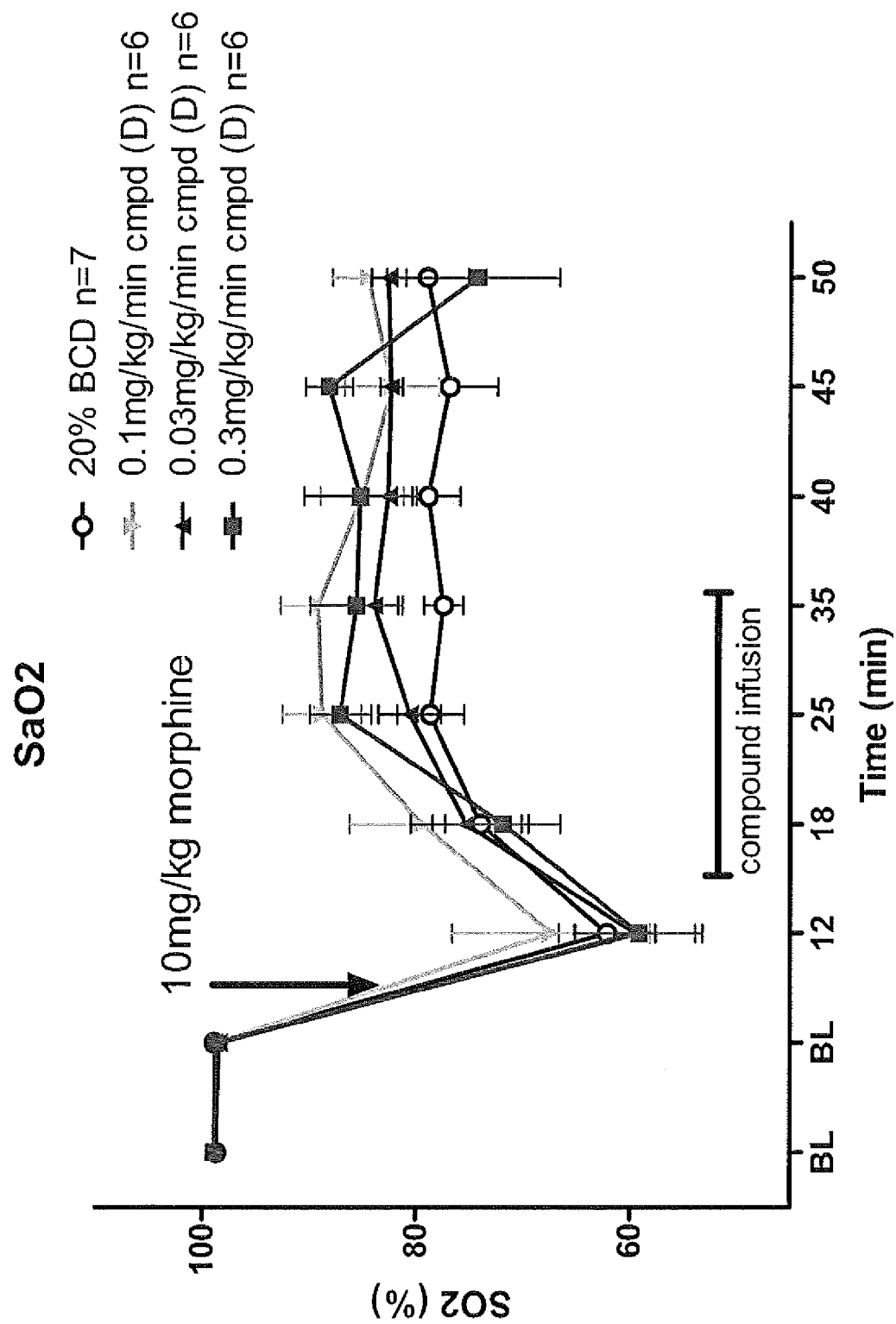

Effect of Compound (CXXI) on Dose-Dependent Minute Ventilation (MV) in Naive Rats Compound (CXXI), labeled as cmpd (C), was shown to increase minute ventilation in a dose-dependent manner following the procedure above. Results are shown in FIG. 6.

Example 101

Effects of Compound (L) in the Opioid-Treated Rat

Following the procedure in Example 6, Compound (L), labeled as cmpd (B), was shown to reverse the effects of opioid on blood gases and pH in the rat by increasing pH, $SaO_2$ and $pO_2$ and by decreasing $pCO_2$ levels, as illustrated in FIGS. 7A-7D.

Example 102

Effects of Compound (CXLII) in the Opioid-Treated Rat

Following the procedure in Example 6, Compound (CXLII), labeled as cmpd (D), was shown to reverse the effects of opioid on blood gases and pH in the rat by increasing $pO_2$ levels, increasing ($SaO_2$) oxygen saturation, decreasing $pCO_2$ levels and raising pH, as illustrated in FIGS. 8A-8D.

Example 103

Figure 9:
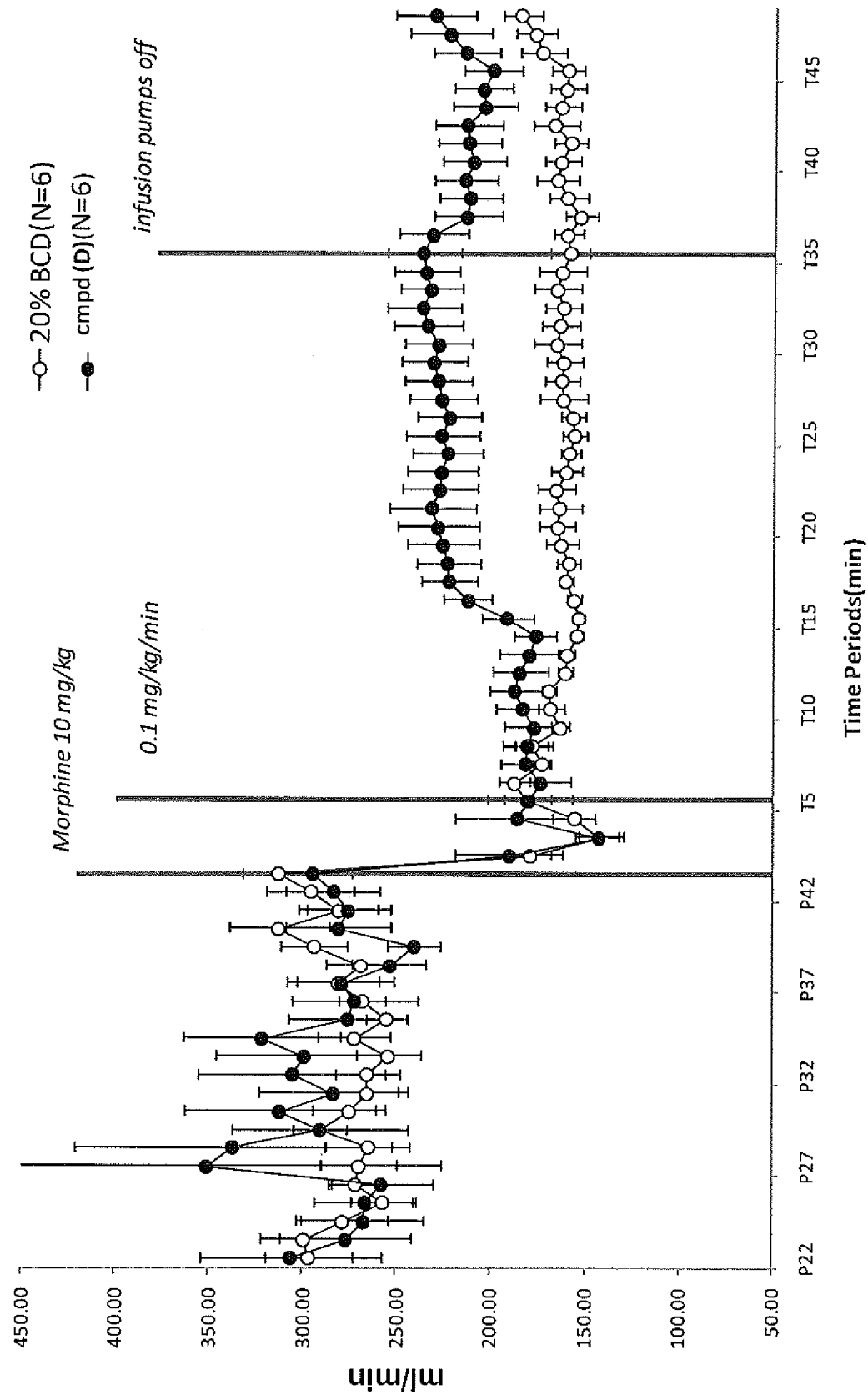
FIG. 9 is a graph illustrating the effect of Compound (CXLII) [labeled as cmpd (D)] in the minute ventilation of the opioid-treated rat.

Effects of Compound (CXLII) on Opioid-Induced Respiratory Depression in the Rat Following the procedure in Example 5, Compound (CXLII), labeled as cmpd (D), was shown to reverse opioid-induced respiratory depression in the rat by increasing minute ventilation (MV) as determined by plethysmography. The results are illustrated in FIG. 9.

Example 104

Effect of Compounds on Minute Ventilation (MV) and Cardiovascular Parameters in Naive Rats All surgical procedures were performed under anesthesia induced by 2% isoflurane in compressed medical grade air. With rats in supine position, the right femoral vein was catheterized using polyethylene tubing (PE-50). This catheter was used for fluid and drug administration. Simultaneously, the right femoral artery was also catheterized for monitoring blood pressure and heart rate. In order to measure the respiratory parameters in spontaneously breathing rats, trachea was intubated using 13 gauge tracheal tube (2.5 mm ID, Instech Solomon, Pa.).

After establishing a stable base-line at 1.5% isoflurane, compounds (typically at a dose of 1 mpk) were administered IV, and ventilatory parameters were generated from spontaneously breathing rats, along with cardiovascular output (mean arterial pressure (MAP) and heart rate). Maximum peak minute ventilatory (MV) responses (MPR), along with changes in minute ventilation versus baseline (DMV) were obtained as shown in the tables below.

TABLE 7

| Cmpd | Structure | Formulation | Dose | pH | MV MPR | MV ΔMV | CV MAP (mm Hg) | CV Heart Rate (B/min) |
|---|---|---|---|---|---|---|---|---|
| (1,5)-8-(4,6-bis(propylamino)-1,3,5-triazin-2-yl)-8-azabicyclo[3.2.1]octan-3-one | [structure] | 20% HPβCD | 1 mpk | 5 | 213 | 98 | 114 | 308 |
| (1,5)-8-(4,6-bis(isobutylamino)-1,3,5-triazin-2-yl)-8-azabicyclo[3.2.1]octan-3-one | [structure] | 20% HPβCD | 1 mpk | 5 | 237 | 137 | 117 | 345 |
| $N^4$-isopropyl-7-methyl-N-propyl-7H-pyrrolo[2,3-d]pyrimidine-2,4-diamine | [structure] | 20% HPβCD | 1 mpk | 5 | 402 | 320 | 118 | 340 |

TABLE 7-continued

| Cmpd | Structure | Formulation | Dose | pH | MV | | CV | |
|---|---|---|---|---|---|---|---|---|
| | | | | | MPR | ΔMV | MAP (mm Hg) | Heart Rate (B/min) |
| 6-(1-(2-(allylamino)-7-methyl-7H-pyrrolo[2,3-d]pyrimidin-4-yl)piperidin-4-yl)-$N^2,N^4$-dipropyl-1,3,5-triazine-2,4-diamine | 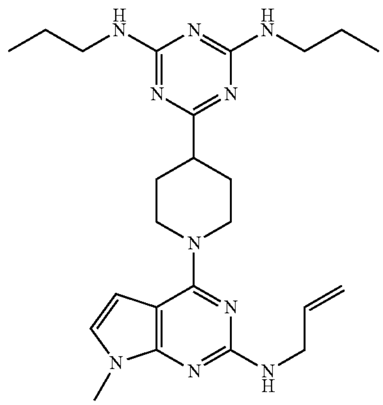 [SMILES: C=CCNc1nc(N2CCC(c3nc(NCCC)nc(NCCC)n3)CC2)c2ccn(C)c2n1] | 20% HPβCD | 1 mpk | 5 | 154 | 60 | 114 | 350 |
| $N^4$-isopropyl-7-methyl-$N^2$-propyl-6,7-dihydro-5H-pyrrolo[2,3-d]pyrimidine-2,4-diamine | | 20% HPβCD | 1 mpk | 5 | 327 | 224 | 93 | 318 |
| CLX, CLXI | 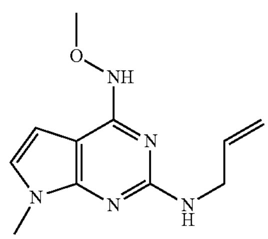 [SMILES: C=CCNc1nc(NOC)c2ccn(C)c2n1] | 20% HPβCD | 1 mpk | 5 | 182 | 103 | 96 | 336 |
| CXXXI, CXXXII | 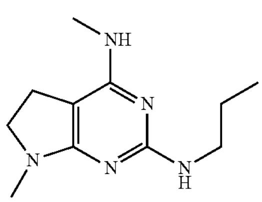 [SMILES: CCCNc1nc(NC)c2c(n1)N(C)CC2] | 20% HPβCD | 1 mpk | 4 | 204 | 130 | 101 | 348 |
| $N^4$,7-diisopropyl-$N^2$-propyl-7H-pyrrolo[2,3-d]pyrimidine-2,4-diamine | 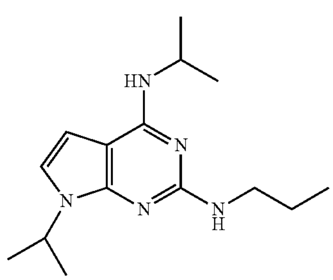 [SMILES: CCCNc1nc(NC(C)C)c2ccn(C(C)C)c2n1] | 20% HPβCD | 1 mpk | 6 | 250 | 155 | 103 | 356 |

TABLE 7-continued

| Cmpd | Structure | Formulation | Dose | pH | MV MPR | MV ΔMV | CV MAP (mm Hg) | CV Heart Rate (B/min) |
|---|---|---|---|---|---|---|---|---|
| CXXXVI, CXXXVII | 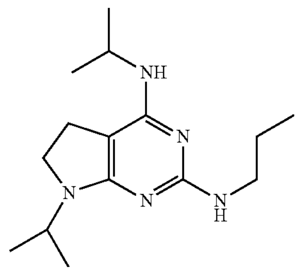 [SMILES: CCCNc1nc(NC(C)C)c2c(n1)N(C(C)C)CC2] | 20% HPβCD | 1 mpk | 4 | 238 | 143 | 98 | 389 |
| $N^4$-isopropyl-$N^2$-propyl-7H-pyrrolo[2,3-d]pyrimidine-2,4-diamine | 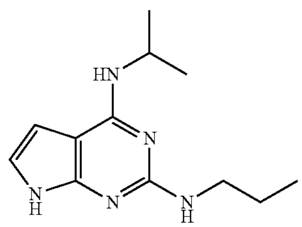 [SMILES: CCCNc1nc(NC(C)C)c2cc[nH]c2n1] | 20% HPβCD | 1 mpk | 4 | 259 | 172 | 96 | 387 |
| XXIX | 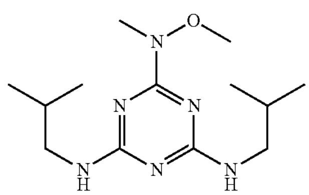 [SMILES: CON(C)c1nc(NCC(C)C)nc(NCC(C)C)n1] | 20% HPβCD | 1 mpk | 4-6 | 253 | 161 | 92 | 371 |
| CXLI, CXLII | 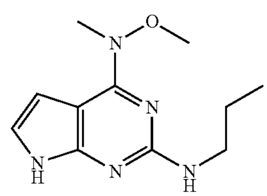 [SMILES: CCCNc1nc(N(C)OC)c2cc[nH]c2n1] | 20% HPβCD | 1 mpk | 4-6 | 264 | 163 | 93 | 336 |
| XX | 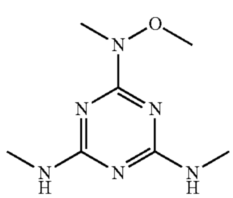 | 20% HPβCD | 1 mpk | 4-6 | 213 | 60 | 92 | 432 |
| XXII | 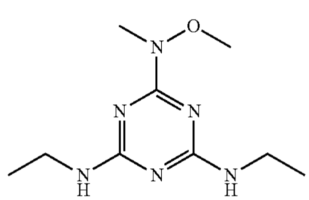 [SMILES: CCNc1nc(NCC)nc(N(C)OC)n1] | 20% HPβCD | 1 mpk | 4-6 | 252 | 130 | 95 | 415 |

TABLE 7-continued

| Cmpd | Structure | Formulation | Dose | pH | MV MPR | MV ΔMV | CV MAP (mm Hg) | CV Heart Rate (B/min) |
|---|---|---|---|---|---|---|---|---|
| N²,N⁴-dipropyl-7H-pyrrolo[2,3-d]pyrimidine-2,4-diamine | | 20% HPβCD | 1 mpk | 4-6 | 336 | 164 | 94 | 427 |
| XXV | | 20% HPβCD | 1 mpk | 4-6 | 257 | 126 | 98 | 430 |
| N²-ethyl-6-(methoxyamino)-N⁴-propyl-1,3,5-triazine-2,4-diamine | | 20% HPβCD | 1 mpk | 4-6 | 208 | 117 | 95 | 445 |
| 7-methyl-N-propyl-4-(1,2,2-trimethyl-hydrazinyl)-7H-pyrrolo[2,3-d]pyrimidin-2-amine | | 20% HPβCD 15/65/20 | 1 mpk 1 mpk | 4 5 | 175 167 | 83 89 | 93 87 | 372 376 |
| N²,N⁴-dipropyl-6,7-dihydro-5H-pyrrolo[2,3-d]pyrimidine-2,4-diamine | | 20% HPβCD 20% HPβCD | 1 mpk 1 mpk | 4 6 | 175 263 | 93 167 | 93 99 | 385 381 |
| N²-methyl-N⁴,N⁶-dipropyl-1,3,5-triazine-2,4,6-triamine | | 15/65/20 | 1 mpk | 5 | 145 | 106 | 92 | 285 |

TABLE 7-continued

| Cmpd | Structure | Formulation | Dose | pH | MV MPR | MV ΔMV | CV MAP (mm Hg) | CV Heart Rate (B/min) |
|---|---|---|---|---|---|---|---|---|
| 6-(1,2-dimethylhydrazinyl)-N²,N⁴-dipropyl-1,3,5-triazine-2,4-diamine | | 20% HPβCD | 1 mpk | 5 | 338 | 216 | 97 | 329 |
| LIII, LIV | | 20% HPβCD | 1 mpk | 4-6 | 288 | 179 | 96 | 403 |
| 6-(methoxy(methyl)amino)-N²,N⁴-dipropylpyrimidine-2,4-diamine | | 20% HPβCD | 1 mpk | 4-6 | 355 | 243 | 90 | 356 |
| 6-(isopropoxy(methyl)amino)-N²,N⁴-dipropyl-1,3,5-triazine-2,4-diamine | | 20% HPβCD | 1 mpk | | 271 | 209 | 98 | 378 |
| 6-(ethyl(isopropoxy)amino)-N²,N⁴-dipropyl-1,3,5-triazine-2,4-diamine | | 20% HPβCD | 1 mpk | 4 | 308 | 191 | 89 | 351 |
| 6-(isobutoxy(methyl)amino)-N²,N⁴-dipropyl-1,3,5-triazine-2,4-diamine | | 20% HPβCD | 1 mpk | 4 | 248 | 133 | 87 | 351 |

TABLE 7-continued

| Cmpd | Structure | Formulation | Dose | pH | MV MPR | MV ΔMV | CV MAP (mm Hg) | CV Heart Rate (B/min) |
|---|---|---|---|---|---|---|---|---|
| 6-(methyl(thiophen-2-ylmethoxy)amino)-N²,N⁴-dipropyl-1,3,5-triazine-2,4-diamine | | 20% HPβCD | 1 mpk | 4 | 213 | 110 | 112 | 411 |
| 6-((cyclopropyl methoxy)(methyl)amino)-N²,N⁴-dipropyl-1,3,5-triazine-2,4-diamine | | 20% HPβCD | 1 mpk | 4 | 261 | 152 | 98 | 362 |
| CLII, CLIII | | 20% HPβCD | 1 mpk | 4 | 49 | 0.33 | 79 | 245 |
| XXXV, XXXVI | | 15% DMA 85% D5W | 1 mpk | 5-6 | 207 | 135 | 87 | 268 |
| XLVII | | 20% HPβCD | 1 mpk | 5 | 150.73 | 61.48 | 109.6 | 350.52 |
| XLVIII | | 15/65/20 | 1 mpk | 5 | 114 | 30.13 | 98 | 300 |

TABLE 7-continued

| Cmpd | Structure | Formulation | Dose | pH | MV MPR | MV ΔMV | CV MAP (mm Hg) | CV Heart Rate (B/min) |
|---|---|---|---|---|---|---|---|---|
| XXXV, XXXVI | (triazine with N(CH₃)(OCH₃) and two NH-propyl groups) | 20% HPβCD | 1 mpk | 4-5 | 344 | 210 | 90 | 321 |
| CLV, CLVI | (hydroxy-azabicyclic pyrrolopyrimidine with NH-propyl) | 20% HPβCD | 1 mpk | 4 | 170 | 57 | 111 | 349 |
| XXXIII | (triazine with N(CH₃)(OCH₃) and two NH-cyclopropyl groups) | 20% HPβCD | 1 mpk | 4-6 | 147 | 53 | 89 | 480 |
| LIII, LIV | (triazine with N(CH₃)(OCH₂Ph) and two NH-propyl groups) | 20% HPβCD | 1 mpk | 4-6 | 288 | 179 | 96 | 403 |

TABLE 8

| Compound | Formulation | Dose | pH | MV MPR | MV DMV | CV MAP (mmHg) BL | CV MAP (mmHg) DE | CV HR (B/min) BL | CV HR (B/min) DE |
|---|---|---|---|---|---|---|---|---|---|
| CXX, CXXI | 20% HPβCD | 1 mpk | 4.5 | 355 | 243 | 107 | 2.3 | 293 | 17 |
| CLXX, CLXXI | 20% HPβCD | 1 mpk | 4 | 175 | 83 | 93 | −1.0 | 372 | −9.0 |
| CXLIX, CL | 20% HPβCD | 1 mpk | 4 | 175 | 93 | 93 | −1.7 | 385 | −28 |
| CLXX, CLXXI | 15/65/20 | 1 mpk | 5 | 167 | 89 | 87 | 1.0 | 376 | −3.8 |
| XXXV, XXXVI | 20% HPβCD | 1 mpk | 5 | 267 | 164 | 101 | −1.7 | 335 | 43 |
| CXLIX, CL | 20% HPβCD | 1 mpk | 6 | 263 | 167 | 99 | −3 | 381 | −18 |
| XXXI | 20% HPβCD | 1 mpk | 4 | 140 | 43 | 101 | 2.6 | 372 | 2.5 |
| CXIII, CXIV | 20% HPβCD | 1 mpk | 4 | 167.1 | 46 | 101 | −4 | 368 | 23 |
| CXV, CXVI | 15/65/20 | 1 mpk | 4 | 155.7 | 33.8 | 97 | −5 | 374 | −5 |
| CXVII, CXVIII | 20% HPβCD | 1 mpk | 4.5 | 143.8 | 15 | 92 | −8 | 365 | −2 |
| LXXII, LXXIII | 20% HPβCD | 1 mpk | 4 | 176 | 82 | 358 | 8 | 108 | −4 |
| LXXVI, LXXVII | 20% HPβCD | 1 mpk | 4 | 308 | 191 | 351 | 15 | 89 | −2 |
| LXXXII, LXXXIII | 20% HPβCD | 1 mpk | 4 | 248 | 133 | 351 | 19 | 87 | 10 |
| LXXXIV, LXXXV | 20% HPβCD | 1 mpk | 4 | 213 | 110 | 411 | 15 | 112 | −1 |

TABLE 8-continued

| Compound | Formulation | Dose | pH | MPR | DMV | MAP (mmHg) BL | MAP (mmHg) DE | HR (B/min) BL | HR (B/min) DE |
|---|---|---|---|---|---|---|---|---|---|
| XCI, XCII | 20% HPβCD | 1 mpk | 4 | 261 | 152 | 362 | 63 | 98 | −2 |

Example 105

Effect of Compound (XXXVI) on Benzodiazepine-Induced Respiratory Depression (BIRD)

In one aspect, the objective of the current study was to evaluate the effects of an intravenous infusion of compound (XXXVI) on respiratory depression, induced by midazolam in rats.

Procedures:

Compound (XXXVI) was dissolved in 20% hydroxypropyl-beta-cyclodextran in sterile water, and titrated to a pH of 4-8 using pH paper and NaOH or HCl, resulting in a clear, stable solution at a concentration of 1.5 mg/mL. Other compounds: morphine sulfate, supplied as 10 mg/ml solution by (Baxter, Inc) and midazolam, supplied as 5 mg/mL solution (Hospira, Inc.)

Materials:

Male Sprague-Dawley rats (Harlan, Inc.), 250-350 g at time of dosing, surgically prepared by Harlan with jugular vein cannulas. 12 Chamber Plethysmography System with temperature/humidity compensation (Epstein et al., 1980, J. Apply Physiol. 49:1107-1115); From Buxco, Inc. (PLY 3223; Buxco, Inc, Wilmington, N.C., USA) Biosystem XA, software, v2.11.1. Customized 12 site automated infusion system (Harvard Apparatus; Instech, Inc)

Methods:

Rat whole body plethysmography was used to evaluate and quantify minute ventilation and the pattern of breathing. A respiratory waveform was generated from the exchange of air between the animal and the chamber. This exchange induced changes in air volume that were measured with a pressure transducer, constituting the respiratory waveform. Atmospheric temperature and humidity were also measured using temperature and humidity probes which sampled chamber conditions. A compensation factor was then determined and applied to the respiratory waveform using a standardized algorithm (Epstein et al., 1980, J. Apply Physiol. 49:1107-1115) to compensate for respiratory conditioning, which was reported as the parameter COMP (see appendix).

All animals were acclimated to plethysmography chambers for at least 1 hour, or until animals were no longer restless (up to 2 hours) prior to data collection. Bolus intravenous (IV) dosing was administered at a rate of 5-10 seconds per dose, and catheters were flushed with 350 μL of sterile saline to be sure of complete drug delivery. All 12 animals (6 vehicle; 6 drug treated) were dosed simultaneously within one 60 second period. For intravenous infusions, vehicle or test compound was prepared at a 0.1 mg/mL stock as described, and administered with Harvard apparatus infusion pumps. Compound (XXXVI) was given via infusion over a 30 minute period at a rate of 20 μL/min/0.3 kg, to give a dose of 0.1 mg/kg/min, beginning 5 minutes after the bolus IV administration of midazolam. None of the included studies were performed blinded, due to the logistics of simultaneously dosing multiple animals. All plethysmography data was recorded automatically by the Buxco equipment.

Statistical Analysis:

Respiratory data was collected on a breath-by-breath basis and averaged into 1 min time bins for data analysis. For each designated acquisition phase, which is the time between doses, percent change from pre-treatment baseline values were calculated for each cohort on multiple ventilatory parameters including respiratory frequency (f), tidal volume (TV), accumulated volume (AV), minute ventilation (MV), inspiratory time (Ti), expiratory time (Te), peak inspiratory flow (PIF), peak expiratory flow (PEF), relaxation time (RT), end inspiratory pause (EIP), end expiratory pause (EEP), delta volume (DV), expiratory flow at 50% TV (EF50), rejection index (Rinx), compensation (Comp), enhanced pause (Penh), pause (PAU), PEF rate (Rpef), relative humidity (RH), and atmospheric temperature (Temp).

Each parameter was compared to vehicle in order to calculate percent difference, using area under the curve (AUC) and peak response values for each defined acquisition period using a customized visual basic restructure analysis macro. Additionally, percent reversal of drug induced respiratory depression by compound was calculated using the mean respiratory depression derived from all vehicle (or untreated) animals, compared to the mean pre-treatment baselines of all animals in the study.

Figure 15:
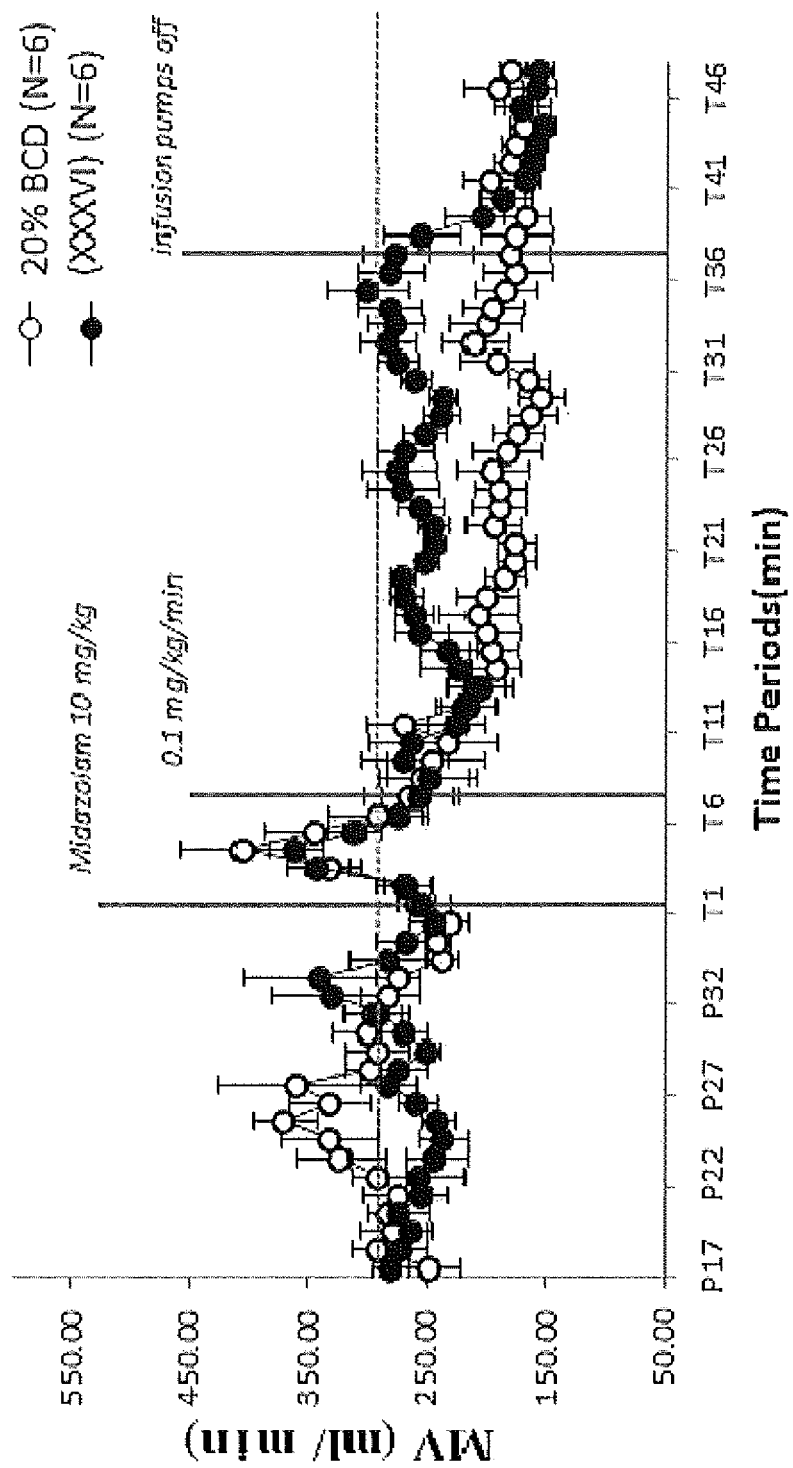
FIG. 15 is a graph illustrating the effect of Compound (XXXVI) on reversing the effects of midazolam on minute ventilation (MV) in the rat.
Figure 16:
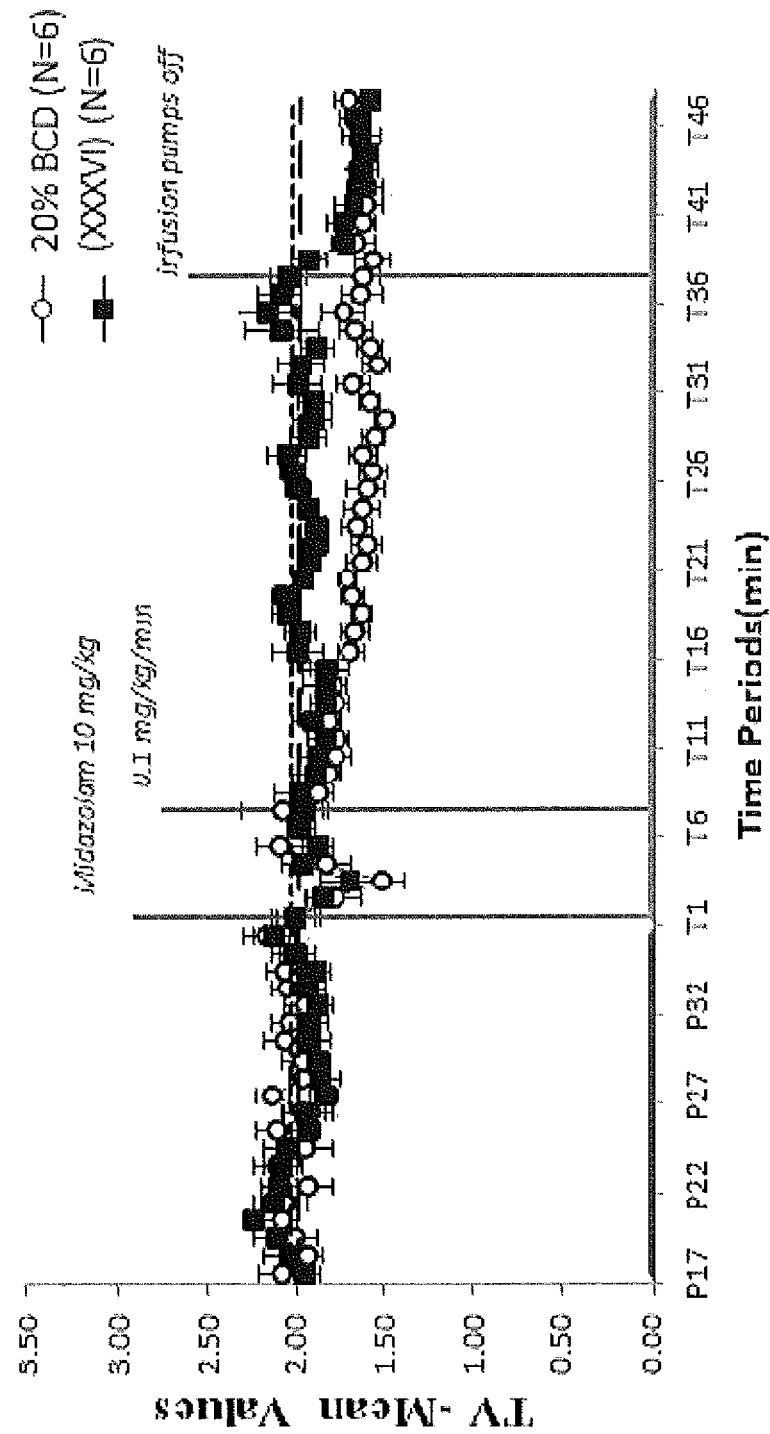
FIG. 16 is a graph illustrating the effect of Compound (XXXVI) on reversing the effects of midazolam on tidal volume (TV) in the rat.
Figure 17:
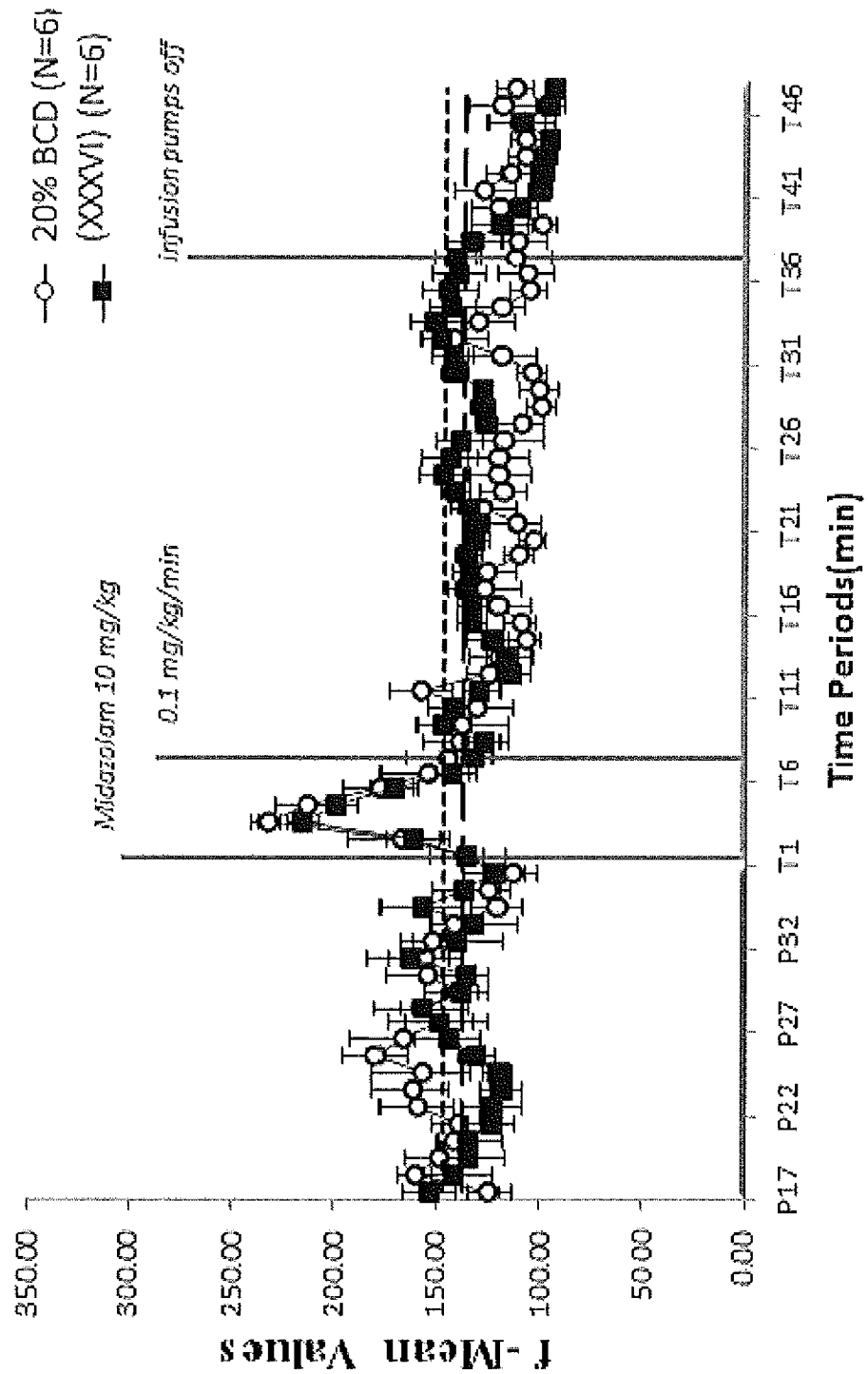
FIG. 17 is a graph illustrating the effect of Compound (XXXVI) on reversing the effects of midazolam on respiratory frequency (f) in the rat.
Figure 18:
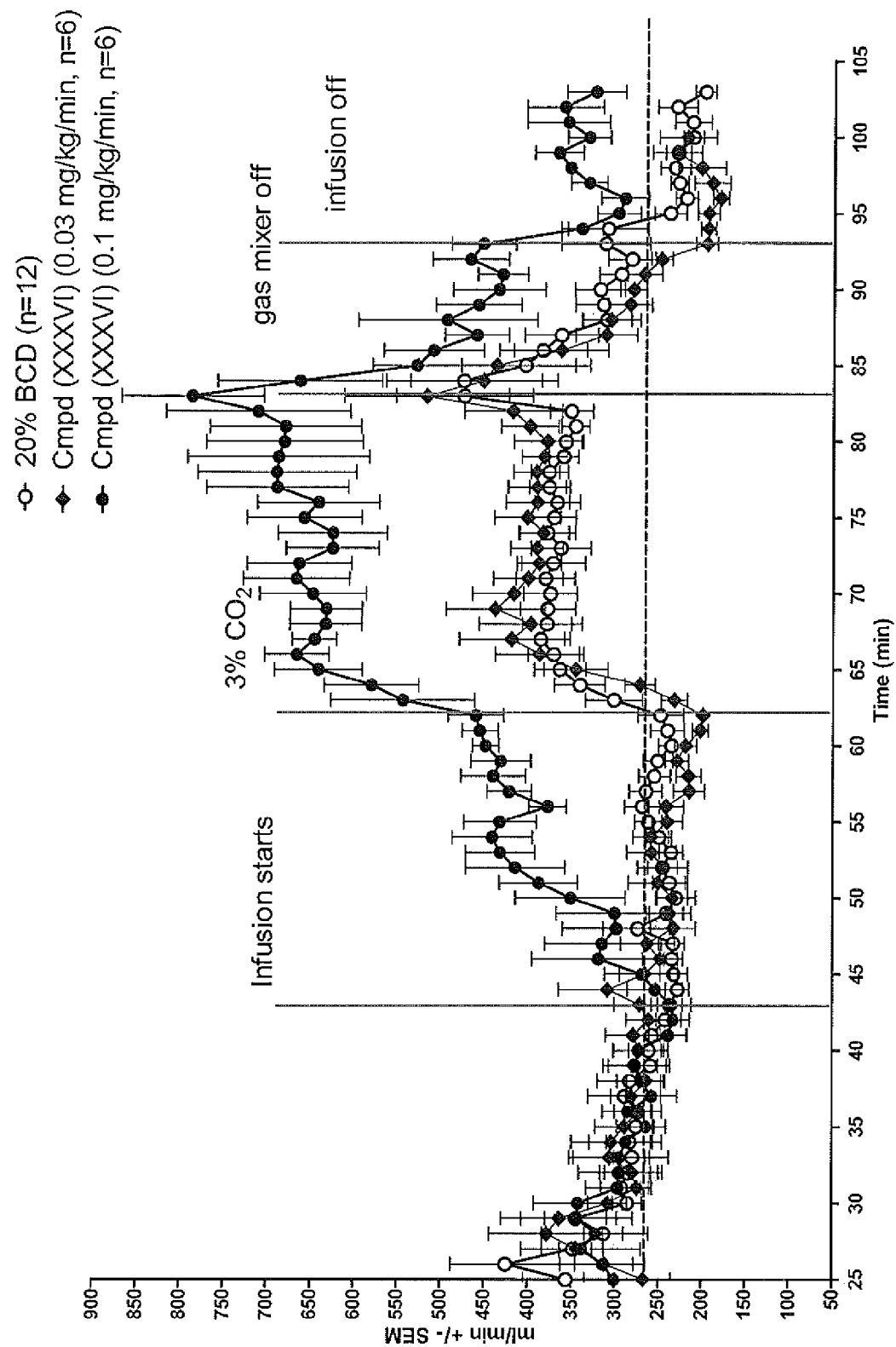
FIG. 18 is a graph illustrating the effect of Compound (XXXVI) infusion on the minute volume response to acute hypercapnia (3% $CO_2$).

Results:

Compound (XXXVI) (0.1 mg/kg/min) reversed the BIRD induced decrease in MV by 100 by the end of the infusion period (t=38). Compound (XXXVI) had an effect to reverse the effects of midazolam on MV (FIG. 15), TV (FIG. 16), AV, Te, PIF, PEF, and EEP, and had no obvious effect on f (FIG. 17), Ti, RT, EIP, dv, EF50, Rinx, Comp, Penh, PAU, Rpef, RH, and Temp. Small increases in minute ventilation in all groups were often seen during IV bolus injections which were treated as injection artifacts due to animal arousal, and had no other apparent impact on ventilation.

Potential adverse events were monitored, and there were no adverse behavioral effects observed following administration of compound (XXXVI) at the doses tested. The results of these experiments demonstrated that compound (XXXVI) reverses midazolam induced-respiratory depression and appears to be well tolerated in rats at the doses tested.

Example 106

Effect of Compound (XXXVI) on Hypercapnia

In one aspect, the objective of the study was to evaluate the effects of Compound (XXXVI), administered by intravenous infusion, on the hypercapnic ventilatory response (HCVR) in rats.

Vehicle, 20% hydroxypropyl-beta-cyclodextran in sterile water, was added to pre-weighed compound and mixed thoroughly, resulting in a clear solution. A 1.5 mg/mL stock was created to give an infusion dose of 0.10 mg/kg/min. A separate 0.45 mg/mL stock was created to give an infusion dose of 0.03 mg/kg/min. All compound solutions and vehicles were titrated to have a pH between 4-8, using a pH paper and titrating with NaOH or HCl solution.

Male Sprague-Dawley rats (Harlan, Inc.), 250-350 g at time of dosing, had been surgically prepared by Harlan to contain jugular vein cannulas. A 12 chamber plethysmography system with temperature/humidity compensation (Epstein et al., 1980, J. Apply Physiol. 49:1107-1115) from Buxco, Inc. (PLY 3223; Buxco, Inc, Wilmington, N.C., USA)

using Biosystem XA software, v2.11.1 and a customized 12 site automated infusion system (Harvard Apparatus, Instech, Inc). Gas mixer (CWE Inc.) was used for this experiment to give concentrations of hypercapnia (3% $CO_2$, 21% $O_2$, balance nitrogen). Three tanks containing 100% $O_2$, $CO_2$, and nitrogen were attached to the gas mixer, with the customized gas mixture fed to each plethysmograph at a rate of 2 L/min.

Rat whole body plethysmography was used to evaluate and quantify minute ventilation and the pattern of breathing. A respiratory waveform was generated from the exchange of air between the animal and the chamber. This exchange induced changes in air volume that were measured with a pressure transducer, constituting the respiratory waveform (Lomask M., 2005, "Respiration measurement in the whole body plethysmography," Buxco Inc., retrieved from http://www dot buxco dot com/downloads/LomaskWBP dot pdf). Atmospheric temperature and humidity were also measured using temperature and humidity probes that sampled chamber conditions. A compensation factor was then determined and applied to the respiratory waveform using a standardized algorithm (Epstein et al., 1980, J. Apply Physiol. 49:1107-1115) to compensate for respiratory conditioning, which was reported as the parameter COMP.

All animals were acclimated to plethysmography chambers for at least 1 hour, or until animals were no longer restless (up to 2 hours prior to data collection). Minute ventilation (MV) was calculated by the Biosystem XA software from direct measurements of tidal volume (TV) and respiratory frequency (f) using the formula MV=TV×f. Minute ventilation (mL/min) is a common endpoint for evaluating ventilatory performance. The protocol included compound (XXXVI) given as a 20 minute infusion, followed by a 20 minute exposure to 3% hypercapnia in addition to the compound (XXXVI) infusion. After 20 minutes of hypercapnia, the compound (XXXVI) infusion continued for an additional 10 minutes, resulting in a total compound (XXXVI) infusion time of 50 minutes. Each experiment included 6 animals receiving compound (XXXVI) (0.03 or 0.10 mg/kg/min) tested against 6 animals receiving vehicle, all of which were challenged with hypercapnia (3%). Animals were continuously monitored and observed for adverse behavioral effects. Such findings were recorded into laboratory notebooks for each individual animal tested.

Statistical Analysis

Respiratory data was collected on a breath-by-breath basis and averaged into 1 min time bins for data analysis. For each designated acquisition phase, which is the time between doses, AUC percent change from pre-treatment baseline values were calculated for each cohort on multiple ventilatory parameters including, respiratory frequency (f), tidal volume (TV), accumulated volume (AV), minute ventilation (MV), inspiratory time (Ti), expiratory time (Te), peak inspiratory flow (PIF), peak expiratory flow (PEF), relaxation time (RT), end inspiratory pause (EIP), end expiratory pause (EEP), delta volume (dV), expiratory flow at 50% TV (EF50), rejection index (Rinx), compensation (Comp), enhanced pause (Penh), pause (PAU), PEF rate (Rpef), relative humidity (RH), and atmospheric temperature (Temp). Each parameter was compared to vehicle in order to calculate percent difference, using area under the curve (AUC) and peak response values for each defined acquisition period using a customized visual basic restructure analysis macro (Lopotosky, S. Galleon Buxco Restructure tool, v5.2, 2008). All of the data analysis for the single, stand-alone studies was done using the restructure analysis macro (Lopotosky, S. Galleon Buxco Restructure tool, v5.2, 2008). All merged data analysis with both doses was performed in Graphpad Prism for MV, TV, and f only, for hypercapnia studies. Additionally, percent increase was calculated based on the cohort average immediately prior to the hypercapnic challenge to the group's peak response. For merged hypercapnia studies, t=62 to t=67 was used.

Results and Discussion:

Administration of compound (XXXVI) stimulated respiration in naive animals at 0.10 mg/kg/min, with little or no effect at 0.03 mg/kg/min. Furthermore, when animals received compound (XXXVI), exposure to hypercapnia (3% $CO_2$) resulted in an increased MV response in a dose dependent manner when compared to vehicle treatment alone. Compound (XXXVI), at 0.03 or 0.1 mg/kg/min IV, resulted in the augmentation of the hypercapnia ventilatory response (HCVR), at the higher dose of 0.10 mg/kg/min, with no effect at 0.03 mg/kg/min. The 0.03 mg/kg/min and vehicle groups resulted in a 60% facilitation of the HCVR, from t=62 to t=67. The 0.10 mg/kg/min demonstrated an increase of 44% in MV during the HCVR challenge at the same time points, in addition to an elevated MV due to compound (XXXVI) alone. Compound (XXXVI) at 0.03 mg/kg/min against HCVR resulted in an effect on PIF only, with no discernable change in f, TV, AV, MV, Ti, Te, PEF, RT, EIP, EEP, dv, EF50, Rinx, Comp, penh, PAU Rpef, RH, or Temp. The 0.10 mg/kg/min dose showed an effect on f, TV, AV, MV, Ti, Te, PIF, PEF, EIP, EF50, Comp, and RH, with no discernable change in EEP, dV, Rinx, Penh, PAU, Rpef, and Temp. These data suggest that compound (XXXVI), given as an infusion, may enhance the ventilatory effects of hypercapnia, resulting in facilitation of ventilation during acute hypoxemia. In addition, there were no adverse clinical observations associated with compound (XXXVI) at the doses tested.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A compound selected from the group consisting of
N-(4,6-Bis-methylamino-[1,3,5]triazin-2-yl)-N,O-dimethyl-hydroxylamine (XX),
N-(4,6-Bis-ethylamino-[1,3,5]triazin-2-yl)-N,O-dimethyl-hydroxylamine (XXII),
N-(4-Cyclopropylmethyl)-N-(6-n-propylamino) [1,3,5] triazin-2-yl)-N,O-dimethyl-hydroxylamine (XXV),
N-(4-Ethylamino)-N-(6-n-propylamino)-[1,3,5]triazin-2-yl)-N,O-dimethyl-hydroxylamine (XXVII),
N-(Bis-4,6-(2-methylpropylamino)) [1,3,5]triazin-2-yl)-N,O-dimethyl-hydroxylamine (XXIX),
N-(Bis-4,6-(2,2-dimethylpropylamino)) [1,3,5]triazin-2-yl)-O,N-dimethyl-hydroxylamine (XXXI),
N-(Bis-4,6-(cyclopropylamino))[1,3,5]triazin-2-yl)-O,N-dimethyl-hydroxylamine (XXXIII),
N-(4,6-Bis-n-propylamino-[1,3,5]triazin-2-yl)-O,N-dimethyl-hydroxylamine (XXXV),
O-Benzyl-N-(4,6-bis-propylamino-[1,3,5]triazin-2-yl)-N-methyl-hydroxylamine (LIII),
6-[1,2]Oxazinan-2-yl-N,N'-dipropyl-[1,3,5]triazine-2,4-diamine (LVII),
N-(4,6-Bis-propylamino-[1,3,5]triazin-2-yl)-O-isopropyl-N-methyl-hydroxylamine (LXIV),
O-Benzyl-N-(4,6-bis-propylamino-[1,3,5]triazin-2-yl)-N-ethyl-hydroxylamine (LXVIII), 6-((Benzyloxy)(isopropyl)amino)-$N^2,N^4$-dipropyl-1,3,5-triazine-2,4-diamine (LXXII), N-(4,6-Bis-propylamino-[1,3,5]triazin-2-yl)-N-ethyl-O-isopropyl-hydroxylamine (LXXVI), N-(4,6-Bis-propylamino-[1,3,5]triazin-2-yl)-O-isobutyl-N-methyl-hydroxylamine (LXXXII), 6-(Methyl(thiophen-2-ylmethoxy)amino)-N2,N4-dipropyl-1,3,5-triazine-2,4-diamine (LXXXIV), N-(4,6-Bis-propylamino-[1,3,5]triazin-2-yl)-O-cyclopropylmethyl-N-methyl-hydroxylamine (XCI), N-(4,6-Bis-propylamino-[1,3,5]triazin-2-yl)-O-ethyl-N-methyl-hydroxylamine (XCVI), 4-N-(2-Dimethylaminoethyl)amino-6-N-(n-propyl)amino-[1,3,5]triazin-2-yl)-N,O-dimethyl-hydroxylamine (CIII), 4-N-(3-(1-N-Methylimidazol-2-yl)-propyl)-amino-6-N-(n-propyl)amino-[1,3,5]triazin-2-yl)-N,O-dimethyl-hydroxylamine (CV), 4-N-(1-N-Methylimidazol-2-yl)-methylamino-6-N-(n-propyl)amino-[1,3,5]triazin-2-yl)-O,N-dimethyl-hydroxylamine (CVII), 4,6-Bis-(N-(2-dimethylaminoethyl)amino)-[1,3,5]triazin-2-yl)-N,O-dimethyl-hydroxylamine (CIX), 4,6-Bis-(N-(pyridin-4-ylmethyl)amino)-[1,3,5]triazin-2-yl)-N,O-dimethyl-hydroxylamine (CXI), 4,6-Bis-[N-(3-methoxy-n-propyl)amino]-[1,3,5]triazin-2-yl)-N,O-dimethyl-hydroxylamine (CXIII), 4,6-Bis-[N-(tetrahydropyran-4-ylmethyl)amino]-[1,3,5]triazin-2-yl)-N,O-dimethyl-hydroxylamine (CXV), N-(5,8,11-Trioxa-2,14,16,18,19-pentaazabicyclo[13.3.1]nonadeca-1(18),15(19),16(17)-trien-17-yl)-N,O-dimethylhydroxylamine (CXVII), a salt thereof and mixtures thereof.

2. The compound of claim 1, wherein the salt is hydrogen sulfate or hydrochloride.

3. The compound of claim 1, wherein the compound is part of a pharmaceutical composition further comprising at least one pharmaceutically acceptable carrier.

4. Compound (XXXV) (N-(4,6-Bis-n-propylamino-[1,3,5]triazin-2-yl)-O,N-dimethyl-hydroxylamine) or a salt thereof.

5. A pharmaceutical composition comprising a pharmaceutically acceptable carrier and compound (XXXV) (N-(4,6-Bis-n-propylamino-[1,3,5]triazin-2-yl)-O,N-dimethyl-hydroxylamine) or a salt thereof.

\* \* \* \* \*